US008753628B2

(12) United States Patent
Lazar et al.

(10) Patent No.: US 8,753,628 B2
(45) Date of Patent: Jun. 17, 2014

(54) OPTIMIZED FC VARIANTS

(71) Applicants: Gregory Alan Lazar, Indianapolis, IN (US); Wei Dang, Pasadena, CA (US); John Desjarlais, Pasadena, CA (US); Sher Bahadur Karki, Santa Monica, CA (US); Omid Vafa, Monrovia, CA (US); Robert Hayes, Paoli, PA (US); Jost Vielmetter, Altadena, CA (US)

(72) Inventors: Gregory Alan Lazar, Indianapolis, IN (US); Wei Dang, Pasadena, CA (US); John Desjarlais, Pasadena, CA (US); Sher Bahadur Karki, Santa Monica, CA (US); Omid Vafa, Monrovia, CA (US); Robert Hayes, Paoli, PA (US); Jost Vielmetter, Altadena, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 13/915,608

(22) Filed: Jun. 11, 2013

(65) Prior Publication Data

US 2013/0273043 A1 Oct. 17, 2013

Related U.S. Application Data

(60) Division of application No. 13/870,781, filed on Apr. 25, 2013, which is a continuation of application No. 12/896,610, filed on Oct. 1, 2010, which is a continuation of application No. 11/124,620, filed on May 5, 2005, now Pat. No. 8,188,231, which is a continuation-in-part of application No. 10/822,231, filed on Mar. 26, 2004, now Pat. No. 7,317,091, which is a continuation-in-part of application No. 10/672,280, filed on Sep. 26, 2003, now abandoned.

(60) Provisional application No. 60/627,774, filed on Nov. 12, 2004, provisional application No. 60/626,991, filed on Nov. 10, 2004, provisional application No. 60/627,026, filed on Nov. 9, 2004, provisional application No. 60/589,906, filed on Jul. 20, 2004, provisional application No. 60/477,839, filed on Jun. 12, 2003, provisional application No. 60/467,606, filed on May 2, 2003, provisional application No. 60/442,301, filed on Jan. 23, 2003, provisional application No. 60/414,433, filed on Sep. 27, 2002.

(51) Int. Cl.
*A61K 39/395* (2006.01)
*C07K 16/00* (2006.01)

(52) U.S. Cl.
USPC ............ 424/130.1; 424/133.1; 424/134.1; 424/141.1; 424/143.1; 424/144.1; 424/152.1; 424/153.1; 424/155.1

(58) Field of Classification Search
CPC . C07K 16/32; C07K 16/2887; C07K 16/2863
See application file for complete search history.

(56) References Cited

U.S. PATENT DOCUMENTS

| | | |
|---|---|---|
| 4,816,397 A | 3/1989 | Boss et al. |
| 5,225,348 A | 7/1993 | Nagata et al. |
| 5,266,491 A | 11/1993 | Nagata et al. |
| 5,328,987 A | 7/1994 | Maliszewski |
| 5,541,087 A | 7/1996 | Lo et al. |
| 5,576,184 A | 11/1996 | Better et al. |
| 5,623,053 A | 4/1997 | Gastinel et al. |
| 5,624,821 A | 4/1997 | Winter et al. |
| 5,633,162 A | 5/1997 | Keen et al. |
| 5,648,237 A | 7/1997 | Carter |
| 5,648,260 A | 7/1997 | Winter et al. |
| 5,821,337 A | 10/1998 | Carter et al. |
| 5,834,597 A | 11/1998 | Tso et al. |
| 5,885,573 A | 3/1999 | Bluestone et al. |
| 6,030,613 A | 2/2000 | Blumberg et al. |
| 6,086,875 A | 7/2000 | Blumberg et al. |
| 6,121,022 A | 9/2000 | Presta et al. |
| 6,165,745 A | 12/2000 | Ward et al. |
| 6,188,965 B1 | 2/2001 | Mayo et al. |
| 6,194,551 B1 | 2/2001 | Idusogie et al. |
| 6,242,195 B1 | 6/2001 | Idusogie et al. |
| 6,269,312 B1 | 7/2001 | Mayo et al. |
| 6,277,375 B1 | 8/2001 | Ward et al. |
| 6,284,536 B1 | 9/2001 | Morrison et al. |
| 6,331,415 B1 | 12/2001 | Cabilly et al. |
| 6,358,733 B1 | 3/2002 | Motwani et al. |
| 6,365,161 B1 | 4/2002 | Deo et al. |
| 6,403,312 B1 | 6/2002 | Dahiyat et al. |
| 6,444,789 B1 | 9/2002 | Luo |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,632,927 B2 | 10/2003 | Adair et al. |
| 6,649,165 B2 | 11/2003 | Schubert |
| 6,708,120 B1 | 3/2004 | Mayo et al. |
| 6,719,971 B1 | 4/2004 | Carter et al. |
| 6,737,056 B1 | 5/2004 | Presta et al. |

(Continued)

FOREIGN PATENT DOCUMENTS

| | | |
|---|---|---|
| EP | 0383799 | 8/1990 |
| EP | 0268636 | 1/1997 |

(Continued)

OTHER PUBLICATIONS

Aase, et al., "The Extended Hinge Region of IgG3 Is Not Required for High Phogocytic Capacity Mediated by Fc Gamma Receptors . . . " Eur. J. Immunol. 23(7) 1546-1551 (1993).
Abadeh, et al., "Remodeling the Oligosaccharide of Human IgG Antibodies: Effects on Biological Activities," Biochem. Soc. Trans. 25(4)S661 (1997).

(Continued)

*Primary Examiner* — Chun Dahle
(74) *Attorney, Agent, or Firm* — Robin M. Silva; Ada O. Wong; Morgan, Lewis & Bockius, LLP

(57) ABSTRACT

The present invention relates to Fc variants having decreased affinity for FcγRIIb, methods for their generation, Fc polypeptides comprising optimized Fc variants, and methods for using optimized Fc variants.

14 Claims, 92 Drawing Sheets

(56) References Cited

U.S. PATENT DOCUMENTS

| | | |
|---|---|---|
| 6,792,356 B2 | 9/2004 | Mayo et al. |
| 6,797,492 B2 | 9/2004 | Daugherty et al. |
| 6,801,861 B2 | 10/2004 | Mayo et al. |
| 6,804,611 B2 | 10/2004 | Mayo et al. |
| 6,821,505 B2 | 11/2004 | Ward et al. |
| 6,933,368 B2 | 8/2005 | Co et al. |
| 6,946,292 B2 | 9/2005 | Kanda et al. |
| 6,950,754 B2 | 9/2005 | Mayo et al. |
| 6,982,321 B2 | 1/2006 | Winter |
| 6,992,234 B2 | 1/2006 | Roopenian |
| 2001/0036459 A1 | 11/2001 | Ravetch |
| 2002/0004587 A1 | 1/2002 | Miller et al. |
| 2002/0048772 A1 | 4/2002 | Dahiyat et al. |
| 2002/0062010 A1 | 5/2002 | Arathoon et al. |
| 2002/0090648 A1 | 7/2002 | Dahiyat et al. |
| 2002/0142374 A1 | 10/2002 | Gallo et al. |
| 2002/0155537 A1 | 10/2002 | Carter et al. |
| 2002/0164328 A1 | 11/2002 | Shinkawa et al. |
| 2002/0192222 A1 | 12/2002 | Blumberg et al. |
| 2003/0012789 A1 | 1/2003 | Blumberg et al. |
| 2003/0049654 A1 | 3/2003 | Dahiyat et al. |
| 2003/0073164 A1 | 4/2003 | Simmons et al. |
| 2003/0078385 A1 | 4/2003 | Arathoon et al. |
| 2003/0105294 A1 | 6/2003 | Gilles et al. |
| 2003/0108548 A1 | 6/2003 | Bluestone et al. |
| 2003/0118592 A1 | 6/2003 | Ledbetter et al. |
| 2003/0130827 A1 | 7/2003 | Bentzien et al. |
| 2003/0133939 A1 | 7/2003 | Ledbetter et al. |
| 2003/0143682 A1 | 7/2003 | Nicolaides et al. |
| 2003/0157108 A1 | 8/2003 | Presta et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0235536 A1 | 12/2003 | Blumberg et al. |
| 2004/0002587 A1 | 1/2004 | Watkins et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0093621 A1 | 5/2004 | Shitara et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0228856 A1 | 11/2004 | Presta |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen et al. |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0064514 A1 | 3/2005 | Stavenhagen et al. |
| 2005/0118174 A1 | 6/2005 | Presta |
| 2005/0152894 A1 | 7/2005 | Krummen et al. |
| 2005/0175614 A1 | 8/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0019316 A1 | 1/2006 | Mayo et al. |
| 2006/0275283 A1 | 12/2006 | Van Vlijmen et al. |
| 2007/0148164 A1 | 6/2007 | Farrington et al. |
| 2007/0224188 A1 | 9/2007 | Allan et al. |
| 2007/0224192 A1 | 9/2007 | Lazar et al. |
| 2007/0238665 A1 | 10/2007 | Lazar et al. |
| 2008/0206867 A1 | 8/2008 | Desjarlais et al. |

FOREIGN PATENT DOCUMENTS

| | | |
|---|---|---|
| EP | 0753065 | 1/1997 |
| EP | 1176195 | 1/2002 |
| EP | 1229125 | 8/2002 |
| EP | 1255209 | 11/2002 |
| EP | 1255826 | 11/2002 |
| EP | 0805628 | 5/2003 |
| EP | 1323346 | 11/2003 |
| EP | 0888125 | 5/2004 |
| EP | 0904107 | 10/2004 |
| WO | WO 88/07089 | 9/1988 |
| WO | WO 91/06305 | 5/1991 |
| WO | WO 91/19515 | 12/1991 |
| WO | WO 92/04053 | 3/1992 |
| WO | WO 92/16562 | 10/1992 |
| WO | WO 92/22324 | 12/1992 |
| WO | WO 94/29351 | 12/1994 |
| WO | WO 95/05468 | 2/1995 |
| WO | WO 96/22024 | 7/1996 |
| WO | WO 97/28267 | 8/1997 |
| WO | WO 97/34631 | 9/1997 |
| WO | WO 98/02462 | 1/1998 |
| WO | WO 98/05787 | 2/1998 |
| WO | WO 98/23289 | 6/1998 |
| WO | WO 98/47089 | 11/1998 |
| WO | WO 99/04813 | 2/1999 |
| WO | WO 99/51642 | 10/1999 |
| WO | WO 99/54342 | 10/1999 |
| WO | WO 99/54484 | 10/1999 |
| WO | WO 99/58572 | 11/1999 |
| WO | WO 00/09560 | 2/2000 |
| WO | WO 00/23564 | 4/2000 |
| WO | WO 00/24782 | 5/2000 |
| WO | WO 00/42072 | 7/2000 |
| WO | WO 00/61739 | 10/2000 |
| WO | WO 01/29246 | 4/2001 |
| WO | WO 01/38490 | 5/2001 |
| WO | WO 01/57088 | 8/2001 |
| WO | WO 01/59066 | 8/2001 |
| WO | WO 02/30954 | 4/2002 |
| WO | WO 02/31140 | 4/2002 |
| WO | WO 02/44215 | 6/2002 |
| WO | WO 02/060919 | 8/2002 |
| WO | WO 02/061090 | 8/2002 |
| WO | WO 02/061093 | 8/2002 |
| WO | WO 02/066514 | 8/2002 |
| WO | WO 03/014325 | 2/2003 |
| WO | WO 03/016470 | 2/2003 |
| WO | WO 03/025154 | 3/2003 |
| WO | WO 03/035835 | 5/2003 |
| WO | WO 03/054213 | 7/2003 |
| WO | WO 03/059282 | 7/2003 |
| WO | WO 03/074679 | 9/2003 |
| WO | WO 03/089624 | 10/2003 |
| WO | WO 2004/004662 | 1/2004 |
| WO | WO 2004/004798 | 1/2004 |
| WO | WO 2004/016750 | 2/2004 |
| WO | WO 2004/022717 | 3/2004 |
| WO | WO 2004/024871 | 3/2004 |
| WO | WO 2004/024889 | 3/2004 |
| WO | WO 2004/029207 | 4/2004 |
| WO | WO 2004/035752 | 4/2004 |
| WO | WO 2004/056312 | 7/2004 |
| WO | WO 2004/063351 | 7/2004 |
| WO | WO 2004/063963 | 7/2004 |
| WO | WO 2004/074455 | 9/2004 |
| WO | WO 2004/092219 | 10/2004 |
| WO | WO 2004/099249 | 11/2004 |
| WO | WO 2004/103404 | 12/2004 |
| WO | WO 2004/110472 | 12/2004 |
| WO | WO 2005/000899 | 1/2005 |
| WO | WO 2005/001025 | 1/2005 |
| WO | WO 2005/007809 | 1/2005 |
| WO | WO 2005/011376 | 2/2005 |

(56) References Cited

FOREIGN PATENT DOCUMENTS

| | | |
|---|---|---|
| WO | WO 2005/012877 | 2/2005 |
| WO | WO 2005/013090 | 2/2005 |
| WO | WO 2005/018572 | 3/2005 |
| WO | WO 2005/023866 | 3/2005 |
| WO | WO 2005/027966 | 3/2005 |
| WO | WO 2005/037867 | 4/2005 |
| WO | WO 2005/040217 | 5/2005 |
| WO | WO 2005/047327 | 5/2005 |
| WO | WO 2005/056606 | 6/2005 |
| WO | WO 2005/056759 | 6/2005 |
| WO | WO 2005/060642 | 7/2005 |
| WO | WO 2005/063815 | 7/2005 |
| WO | WO 2005/070963 | 8/2005 |
| WO | WO 2005/116078 | 12/2005 |
| WO | WO 2005/123780 | 12/2005 |
| WO | WO 2006/012500 | 2/2006 |

OTHER PUBLICATIONS

Akewanlop et al.,"Phagocytosis of Breast Cancer Cells Mediated by Anti-MUC-1 Monoclonal Antibody, DF3 and Its Bispecific Antibody, " Cancer Res. (61) 4061-4065 (2001).
Alegre, et al., "A Non-Activatin "Humanized" Anti-CD3 Monoclonal Antibody Retains Immunosuppresive Properties in Vivo," Transplantation, (57)1537-1543 (1994).
Alegre, et al., "Effect of a Single Amino Acid Mutation on the Activating and Immunosuppresive Properties of a Humanized OKT3 Monoclonal Antibody," J. Immunol. (148) 3461-3468 (1992).
Amigorena, et al., "Fc Receptors for IgG and Antigen Presentation on MHC Class I and Class II Molecules," Immunol. (1)385-390 (1999).
Andreakos, et al., "Monoclonal Antibodies in Immune and Inflammatory Diseases" Curr. Opin. Biotech (13) 615-620 (2002).
Armour, et al., "Recombinant Human IgG Molecules Lacking Fcy Receptor I Binding and Monocyte Triggering Activities," Eur. J. Immunol., (29)2613-2624 (1999).
Armour, et al., "Differential Binding to Human FcyRIIa and FcyRIIb Receptors by Human IgG Wildtype and Mutant Antibodies," Mol. Immunol. (40)585-593 (2003).
Ashkenazi, et al., "Immunoadhesins As Research Tools and Therapeutic Agents," Curr. Opin. Immunol. (9)195-200 (1997).
Ashkenazi, et al., "Mapping the CD4 Binding Site for Human Immunodeficiency Virus by Alanine-Scanning Mutagenesis," PNAS, USA (87)7150-7154 (1990).
Bastida-Corcuera, et al., "Differential Complement Activation by Bovine IgG2 Allotypes," Veterinary Immunology and Immunopathology 71(2) 115-123 (1999).
Bolland, et al., A Newly Discovered Fc Receptor That Explains IgG—Isotype Disparities in Effector Responses, J. Immunol. (23) 2-4 (2005).
Boruchov, et al., "Activating and Inhibitory IgG Fc Receptors on Human DCs Mediate Opposing Functions," J. Clin. Invest. 115(10) 2914-2923 (2005).
Bowles, et al., "CD16 Polymorphisms and NK Activation Induced by Monoclonal Antibody-Coated Target Cells," J. Immunol. Methods (304:1-2)88-99 (2005).
Brekke, et al.,"Human IgG Isotype-Specific Amino Acid Residues Affecting Complement Mediated Cell Lysis and Phagocytosis," Eur. J. Immunol. 24(10) 2452-2547 (1994).
Brekke, et al.,"Human IgG3 Can Adopt the Disulfide Bond Pattern Characteristic for IgG1, Without Resembling It in Complement Mediated Cell Lysis," Mol. Immunol. 30(16) 1419-1425 (1993).
Bruggemann, et al., "Comparison of the Effector Functions of Human Immunoglobulins Using a Matched Set of Chimeric Antibodies," J. Exp. Med. (166) 1351-1361(1987).
Bruggemann, et al., "A Matched Set of Rat/Mouse Chimeric Antibodies Identification and Biological Properties of Rat H Chain Constant Regions Mu, Gamma1, Gamma 2a, Gamma 2b, Gamma 2c, Epsilon and Alpha," J. Imunol. 142(9) 3145-3150 (1989).
Burmeister, et al., "Crystal Structure of the Complex of Rat Neonatal Fc Receptor With Fc," Nature (372) 379-383 (1994).
Burton, et al., "Immunoglobulin G: Functional Sites," Mol. Immunol. 22(3) 161-206 (1985).
Canfield, et al., "The Binding Affinity of Human IgG for Its High Affinity Fc Receptor is Determined by Multiple Amino Acids in the CH2 Domain and is Modulated by the Hinge Region," J. Exp. Med., (173)1483-1491 (1991).
Caron, et al., "Engineered Humanized Dimeric Forms of IgG Are More Effective Antibodies," J. Exp. Med., (176) 1191-1195 9(1992).
Caron, et al., "Murine and Humanized Constructs of Monoclonal Antibody M19 (Anti-CD33) for the Therapy of Acute Myelogenous Leukemia," Cancer 73(3) Supp 1049-1056 (1994).
Carpenter, et al., "Non-Fc Receptor Binding Humanized Anti-CD3 Antibodies Reduce Apoptosis of Activated Human T-Cells," J. Immunol. (165) 6205-6213 (2000).
Carter, et al., "Humanization of an Anti-p185HER2 Antibody for Human Cancer Therapy," Proc. Natl. Acad. Sci. (89)4285-4289 (1992).
Carter, P., "Improving the Efficacy of Antibody-Based Cancer Therapies," Nature Reviews (1) 118-129 (2001).
Carton, et al., "Therapeutic Activity of Humanized Anti-CD20 Monoclonal Antibody and Polymorphism in IgG Fc Receptor FcyRIIIa Gene," Blood 99(3) 754-758 (2002).
Chadd, et al., "Therapeutic Antibody Expression Technology," Curr. Opin. Biotech (12)188-194 (2001).
Chamow, et al., "Immunoadhesins: Principles and Applications," TIBTECH (14)52-60 (1996).
Chan, et al., "Variable Region Domain Exchange in Human IgGs Promotes Antibody Complex Formation With Accompanying Structural Changes and Altered Effector Functions," Mol. Immunol. (21) 527-538 (2004).
Chapman, P.B., "T-Cell Chauvinists Versus Antibody Advocates—Can't We All Just Get Along?" J. Clin. Oncol. 22(22) 4446-4448 (2004).
Chappel, et al., "Identification of the Fcy Receptor Class I Binding Site in Human IgG Through the Use of Recombinant IgG1/IgG2 Hybrid and Point-Mutated Antibodies," Proc. Natl. Acad. Sci. (88) 9036-9040 (1991).
Chappel, et al., "Identification of A Secondary FcyRI Binding Site with a Genetically Engineered Human IgG Antibody," J. Biol. Chem., 268(33) 25124-25131 (1993).
Chintalacharuvu, et al., "Hybrid IgA2/IgG1 Antibodies With Tailor-Made Effector Functions," Clin. Immunol. 101(1) 21-31 (2001).
Chirino, et al. "Minimizing the Immunogenicity of Protein Therapeutics," Drug Discovery Today 9(2) 82-90 (2004).
Clark, et al, "Antibody Humanization: A Case of The "Emperor's New Clothes"?" Immuno. Today 21(8) 397-402 (2000).
Clark, M.R., "Chemical Immunology Antibody Engineering IgG Effector Mechanisms," Dissertation submitted to Immmunology Div of Dept of Pathology, Cambridge University, UK (J. Chem. Immunol. (65) 88-110 (1997)).
Clynes, et al., "Fc Receptors Are Required in Passive and Active Immunity to Melanoma," Proc. Natl. Acad. Sci., (95) 652-656 (1998).
Clynes, et al., "Inhibitory Fc Receptors Modulate in Vivo Cytotoxicity Against Tumor Targets," Nature Med., 6(4) 443-446 (2000).
Clynes, et al. "Modulation of Immune Complex-Induced Inflammation in Vivo by the Coordinate Expression of Activation and Inhibitory Fc Receptors," J. Exp. Med. 189(1) 179-185 (1999).
Clynes, R., "Immune Complexes As Therapy for Autoimmunity," J. Clin. Invest. (115)25-27 (2005).
Cohen-Sodal, et al.,"Review: FcY Receptors," Immunol. Lett. (92)199-205 (2004).
Cole, et al., "Human IgG2 Variants of Chimeric Anti-CD3 Are Nonmitogenic to T Cells," J. Immunol. 159(7) 3613-3621 (1997).
Cole, et al.,"HUM291, A Humanized Anti-CD3 Antibody, Is Immunosuppresive to T Cells While Exhibiting Reduced Mitogenicity in Vitro," Transplantation 68(4) 563-571 (1999).
Coloma, et al.,"The Hinge As a Spacer Contributes to Covalent Assembly and Is Required for Function of IgG," J. Immunol. 158(2) 733-740 (1997).
Cragg, et al., "Signaling Antibodies in Cancer Therapy," Curr. Opin. Immunol. (11) 541-547 (1999).

(56) References Cited

OTHER PUBLICATIONS

Dall'Acqua, et al., "Increasing the Affinity a Human IgG1 for the Neonatal Fc Receptor: Biological Consequences," J. Immunol. (169) 5171-5180 (2002).
Dall'Acqua, et al., "Modulation of the Effector Functions of a Human IgG1 Through Engineering of Its Hinge Region," J. Immunol. (177) 1129-1138 (2006).
Dall'Acqua, et al., "Antibody Engineering," Curr. Opin. Struct. Biol. (8) 443-450 (1998).
Dahiyat, et al.,"Protein Design Automation," Protein Science 5(5)895-903 (1996).
Da Silveira, et al., "Complement Activation Selectively Potentiates The Pathogenicity of the IgG2B and IgG3 Isotypes of a High Affinity Anti-Erythrocyte Autoantibody," J. Exp. Med. 195(6) 665-672 (2002).
Davies, et al., "Expression of Gntlll in a Recombinant Anti-CD20 CHO Production Cell Line: Expression of Antibodies With Altered Glycoforms Leads to an Increase in ADCC Through Higher Affinity to FcyRlll," Biotech and Bioeng 74(4) 288-294 (2001).
Davis, et al., "Identification of a Family of Fc Receptor Homologs With Preferential B Cell Expression," PNAS, USA 98(17)9772-9777 (2001).
Davis, et al., "Fc Receptor Homologs: Newest Members of a Remarkably Diverse Fc Receptor Gene Family," Immuno. Rev. (190) 123-136 (2002).
Delano, et al., "Convergent Solutions to Binding At a Protein-Protein Interface," Science (287) 1279-1283 (2000).
Dhodapkar, K.M. et al., "Selective Blockade of Inhibitory FcY Receptor Enables Human Dendritic Cell Maturation With IL-12p70 Production and Immunity to Antibody-Coated Tumor Cells," PNAS 102(8) 2910-2915 (2005).
Dhodapkar, K.M. et al., "Antitumor Monoclonal Antibodies Enhance Cross-Presentation of Cellular Antigens and the Generation of Myeloma-Specific Killer T-Cells by Dendritic Cells," J. Exp. Med. 195(1) 125-133 (2002).
Dhodapkar, K.M. et al., "Recruiting Dendritic Cells to Improve Antibody Therapy of Cancer," PNAS 102(18) 6243-6244 (2005).
Dhodapkar, M.V. et al., "T Cells From the Tumor Microenvironment of Patients With Progressive Myeloma Can Generate Strong Tumor-Specific Cytolytic Responses to Autologous, Tumor-Loaded Dendritic Cells," PNAS 99(20) 13009-13013 (2002).
Dillon, T., et al. "Structural and Functional Characterization of Disulfide Isoforms of the Human IgG2 Subclass" J. of Bio Chem vol. 283, No. 023, pp. 16206-16215, (2008).
Duncan, et al., "Localization of the Binding Site for the Human High-Affinity Fc Receptor on IgG," Nature, (332) 563-564 (1988).
Duncan, et al. "The Binding Site for C1q on IgG" Nature (332) 738-740 (1988).
D'Uscio, et al., "Cellular Cytotoxicity Mediated by Isotype-Switch Variants of a Monoclonal Antibody to Human Neuroblastoma," Br. J. Cancer 64(3)445-450 (1991).
Edelman, et al., "The Covalent Structure of an Entire yG Immunoglobulin Molecule," Biochemistry (63) 78-85 (1969).
Ehrhardt, et al., "The Inhibitory Potential of Fc Receptor Homolog 4 on Memory B Cells," PNAS, USA 100(23) 13489-13494 (2003).
Ellison, et al., "The Nucleotide Sequence of Human Immunoglobulin CY Gene," Nucleic Acids Research 10(13) 4071-4079 (1982).
Ernst, et al., "Molecular Characterization of Six Variant FcY Receptor Class 1 (CD64) Transcripts," Mol. Immunol. (35) 943-954 (1998).
Faccheti, et al., "An Unusual Fc Receptor-Related Protein Expressed in Human Centroblasts," PNAS, USA 99(6) 3776-3781 (2002).
Gaboriaud, et al., "The Crystal Structure of the Globular Head of Complement Protein C1q Provides a Basis for Its Versatile Recognition Properties," J. Biol. Chem. 278(47) 46974-46982 (2003).
Garman, et al., "Structure of the Fc Fragment of Human IgE Bound to Its High-Affinity Receptor FcεRIα," Nature (406)259-266 (2000).
Getahun, et al., "IgG2a-Mediated Enhancement of Antibody and T Cell Responses and Its Relation to Inhibitory and Activating FcY Receptors," J. Immunol. (172) 5269-5276 (2004).

Ghazizadeh, et al.,"Physical and Functional Association of Src-Related Protein Tyrosine Kinases With FcRII in Monocytic THP-1 Cells," J. Biol. Chem. 269(12) 8878-8884 (1994).
Ghetie, et al., "Multiple Roles for the Major Histocompatibility Complex Class I-Related Receptor FcRn," (18) 739-766 (2000).
Ghetie, et al.,"FcRn: The MHC Class-I-Related Receptor That Is More Than an IgG Transporter," Immunol. Today 18(12) 592-598 (1997).
Ghetie, et al., "Increasing the Serum Persistence of an IgG Fragment by Random Mutagenesis," Nature Biotech. (15) 637-640 (1997).
Glennie, et al., "Clinical Trials of Antibody Therapy," Immuno. Today 21(8) 403-410 (2001).
Glennie, et al., "Renaissance of Cancer Therapeutic Antibodies," Drug Discovery Today 8(11) 503-510 (2003).
Gonzales, et al., "SDR Grafting of a Murine Antibody Using Multiple Human Germline Templates to Minimize Its Immunogenicity," Mol. Immunol. (41) 863-872 (2004).
Greenwood, T., "Molecular Recognition in the Structure and Assembly of Filamentous Bacteriophages," Dissertation submitted to Cambridge Univ. (1989) 1-251.
Greenwood, et al., "Structural Motifs Involved in Human IgG Antibody Effector Functions," Eur. J. Immunol. 23(5)1098-1104 (1993).
Greenwood, et al., "Dual Importance of Positive Charge in the C-Terminal Region of Filamentous Bacteriophage Coat Protein for Membrane Insertion and DNA-Protein Interaction in Virus Assembly," Virology (171) 444-452 (1989).
Greenwood, T., "Effector Functions of Matched Sets of Recombinant Human IgG Subclass Antibodies," Dissertation submitted to Cambridge Univ. (1993) 1-23.
Greenwood, et al., "Engineering Multiple-Domain Forms of the Therapeutic Antibody CAMPATH-1H: Effects on Complement Lysis," Ther. Immunol. 1(5) 247-255 (1994).
Groh, et al., "Efficient Cross-Priming of Tumor Antigen Specific T Cells by Dendritic Cells Sensitized With Diverse Anti-MICA Opsonized Tumor Cells," PNAS 102(18) 6461-6466 (2005).
Harrison, et al., "Domain Swap Chimeras to Study the Binding of IgG by Fc Gamm RI, The High Affinity Receptor for IgG," Biochem. Soc. Trans. 24(1) 144S (1996).
Hayes, et al., "Combining Computational and Experimental Screening for Rapid Optimization of Protein Properties," PNAS 99(25) 15926-15931 (2002).
Hayhurst, et al., "High-Throughput Antibody Isolation," Curr. Opin. Chem. Biol. (5)683-689 (2001).
Hazenbos, et al., "Murine IgG1 Complexes Trigger Immune Effector Functions Predominantly Via FcYRlll (CD16)," J. Immunol. (161) 3026-3032 (1998).
Henry, et al.,"Participation of the N-Terminal of Cε3 in the Binding of Human IgE to Its High-Affinity Receptor FcεR1," Biochemistry (36)15568-15578 (1997).
Hezareh, et al., "Effector Function Activities of a Panel of Mutants of a Broadly Neutralizing Antibody Against Human Immunodeficiency Virus Type I," J. Virol. 75(24) 12161-12168 (2001).
Hinton, et al., "Engineering Human IgG Antibodies With Longer Serum Half-Lives in Primates," J. Biol. Chem., 279(8) 6213-6216 (2004).
Hogarth, et al., "Fc Receptors Are Major Mediators of Antibody Based Inflammation in Autoimmunity," Curr. Opin. Immunol. (14)798-802 (2002).
Holliger, et al., "Antibodies Come Back From the Brink," Nature Biotech. (16)1015-1016 (1998).
Hudson, P. "Recombinant Antibody Constructs in Cancer Therapy," Curr. Opin. Immunol. (11) 548-557 (1999).
Hudson, P. "Recombinant Antibody Fragments," Curr. Opin. Biotech. (9) 395-402 (1998).
Hutchins, et al., "Improved Biodistribution, Tumor Targeting and Reduced Immunogenicity in Mice With y4 Variants of CAMPATH-1H," Proc. Natl. Acad. Sci. (92) 11980-11984 (1995).
Idusogie, et al., "Mapping of the C1q Binding Site on Rituxan, A Chimeric Antibody With a Human IgG1 Fc," J. Immunol. (164) 4178-4184 (2000).
Idusogie, et al., "Engineered Antibodies With Increased Activity to Recruit Complement," J. Immunol. (166) 2571-2575 (2001).

(56) References Cited

OTHER PUBLICATIONS

Isaacs, J.D., "Improving Serotherapy With Monoclonal Antibodies," Dissertation submitted to Cambridge Univ. (1991) 1-209.
Isaacs, et al., "From Bench to Bedside: Discovering Rules for Antibody Design, and Improving Serotherapy With Monoclonal Antibodies," Rheumatology (40)724-738 (2001).
Isaacs, et al. "Therapy With Monoclonal Antibodies, II. The Contribution of FcY Receptor Binding and the Influence of $C_H1$ and $C_H3$ Domains on in Vivo Effector Function," J. Immunol. (161) 3862-3869 (1998).
Isaacs, et al.,"Therapy With Monoclonal Antibodies: An in Vivo Model for the Assessment of Therapeutic Potential," J. Immunol. 148(10) 3062-3071 (1992).
Jefferis, et al., "Recognition Sites on Human IgG for Fcy Receptors: The Role of Glycosylation," Immunol. Lett. (44) 111-117 (1995).
Jefferis, et al., "Modulation of FcyR and Human Complement Activation by IgG3-Core Oligosaccharide Interactions," Immunol. Lett. (54) 101-104 (1996) and errata at Immunol. Lett. 58:67 (1997).
Jefferis, et al., "Interaction Sites on Human IgG-Fc for FcyR: Current Models," Immunol. Lett. 82(1) 57-65 (2002).
Jefferis, et al., "Molecular Definition of Interaction Sites on Human IgG for Fc Receptors (huFc gamma R)" Mol. Immunol. 27(12) 1237-1240 (1990).
Jendenberg, et al., "Engineering of $Fc_1$ and $Fc_3$ From Human Immunoglobulin G to Analyse Subclass Specificity for Staphyloccocal Protein A," J. Immunol Methods (201) 25-34 (1997).
Johnson, et al., "Kabat Database and Its Applications: 30 Years After the First Variability Plot," Nucleic Acids Res. 28(1) 214-218 (2000).
Johnson, et al., "Kabat Database and Its Applications: Future Directions," Nucleic Acids Res. 29(1) 205-206 (2001).
Junghans, et al., "The Protection Receptor for IgG Catabolism Is the $\beta_2$- Microglobulin-Containing Neonatal Intestinal Transport Receptor," PNAS, (93) 5512-5516 (1996).
Kalergis, et al., "Inducing Tumor Immunity Through the Selective Engagement of Activating FcY Receptors on Dendritic Cells," J. Exp. Med. 195(12) 1653-1659 (2002).
Kan, et al., "Thioether-Bonded Constructs of Fab'y and Fcy Modules Utilizing Differential Reduction of Interchain Disulfide Bonds," J. Immunol. (166) 1320-1326 (2001).
Karassa, et al., "The Role of FcYRllA and IIIa Polymorphisms in Autoimmune Diseases," Biomedicine and Pharmacotherapy (58)286-291 (2004).
Kato, et al., "Analysis of IgG-FcgammaR Interactions in Solution: Mapping of The FcgammaR Binding Site and Evidence for a Conformational Change Occuring in the Fc Region," Immunol. Lett. 73(2-3) No. 409 (2000).
Kim, et al, "Mapping The Site on Human IgG for Binding of the MHC Class I-Related Receptor, FcRn," Eur. J. Immunol. (29) 2819-2825 (1999).
Kim, et al., "Analysis of FcyRlll and IgG Fc Polymorphism Reveals Functional and Evolutionary Implications of Protein-Protein Interaction," J. Mol. Evol. (53)1-9 (2001).
Kim, et al., "Localization of the Site of the Murine IgG1 Molecule That Is Involved in Binding to the Murine Intestinal Fc Receptor," Eur. J. Immunol. 24(10) 2429-2439 (1994).
Kim, et al., "Identifying Amino Acid Residues That Influence Plasma Clearance of Murine IgG1 Fragments by Site-Directed Mutagenesis," Eur. J. Immunol. 24(3) 542-548 (1994).
Krapp, et al., Structural Analysis of Human IgG-Fc Glycoforms Reveals A Correlation Between Glycosylation and Structural Integrity, J. Mol. Biol. (325) 979-989 (2003).
Kurucz, et al., "Bacterially Expressed Human FcYRllb Is Soluble and Functionally Active After in Vitro Refolding," Immunol. Lett. (75)33-40 (2000).
Lehrnbecher, et al., "Variant Genotypes of The Low-Affinity Fcy Receptors in Two Control Populations and a Review of Low Affinity Fcy Receptors Polymorphisms in Control and Disease Populations," Blood (94) 4220-4232 (1999).

Lund, et al., "Human FcyRl and FcyRll Interact With Distinct But Overlapping Sites on Human IgG," J. Immunol. (147) 2657-2662 (1991).
Lund, et al., "Multiple Binding Sites on The CH2 Domain for IgG for Mouse FcyRll," Mol. Immunol. (29) 53-59 (1992).
Lund, et al., "Oligosaccharide-Protein Interactions on IgG Can Modulate Recognition by Fcy Receptors," FASEB J. (9) 115-119 (1995).
Lund, et al., "Multiple Interactions of IgG With Its Core Oliogosaccharide Can Modulate Recognition by Complement and Human Fcy Receptor I and Influence the Synthesis of Its Oligosaccharide Chains," J. Immunol. 4963-4969 (1996).
Lund, et al., "A Protein Structural Change in Aglycosylated IgG3 Correlates With Loss of huFc gamma RI and huFc gamma RIll Binding and/or Activation," Mol. Immunol. 27(11) 1145-1153 (1990).
Lund, et al., "Control of IgG/Fc Glycosylation: A Comparison of Oligosaccharides From Chimeric Human/Mouse and Mouse Subclass Immunoglobulin Gs," Mol. Immunol. 30(8) 741-748 (1993).
Maenaka, et al., "The Human Low Affinity FcY Receptors IIa, IIb and III Bind IgG With Fast Kinetics and Distinct Thermodynamic Properties," J. Biol. Chem. 276(48) 44898-44904 (2001).
Martin, et al., "Crystal Structure At 2.8 A of An FcRn/Heterodimeric Fc Complex: Mechanism of pH-Dependent Binding," Mol. Cell (7) 867-877 (2001).
Martin, et al., "Characterization of the 2:1 Complex Between the Class I MHC-Related Fc Receptor and Its Fc Ligand in Solution," Biochemistry (38) 12639-12647 (1999).
Masztalerz, et al., "Mechanisms of Macrophage Cytotoxicity in II-2 and II-12 Mediated Tumor Regression," Cancer Immunol. Immunother. (52)235-242 (2003).
Maxwell, et al.,"Crystal Structure of the Human Leukocyte Fc Receptor, FcyRlla," Nature Struct. Biol. (6) 437-442 (1999).
Mayfield, et al., "Expression and Assembly of a Fully Active Antibody Algae," PNAS, 100(2) 438-442 (2003).
Maynard, et al., "Antibody Engineering," Ann. Rev. Biomed. Engin. (2) 339-376 (2000).
Mechetina, et al, "Identification of CD16-2, A Novel Mouse Receptor Homologous to CD16/FcyRlll," Immunogenetics (54) 463-468 (2002).
Medesan, et al.,"Comparative Studies of Rat IgG to Further Delineate The Fc:FcRn Interaction Site," Eur. J. Immunol. (28)2092-2100 (1998).
Merchant, et al.,"An Efficient Route to Human Bispecific IgG," Nat. Biotechnol. 16(7) 677-681 (1998).
Metes, et al., "Expression of Functional CD32 Molecules on Human NK Cells Is Determined by an Allelic Polymorphism of The FcY RllC Gene," Blood 91(7) 2369-2380 (1998).
Michaelsen, et al., "Antibody Dependent Cell-Mediated Cytotoxicity Induced by Chimeric Mouse-Human IgG Subclasses and IgG3 Antibodies With Altered Hinge Region," Mol. Immunol. 29(3) 319-326 (1992).
Michaelson, et al., "One Disulfide Bond in Front of the Second Heavy Chain Constant Region Is Necessary and Sufficient for Effector Functions of Human IgG3 Without a Genetic Hinge," PNAS (91) 9243-9247 (1994).
Michaelson, et al., "Primary Structure of the 'Hinge' Region of Human IgG3," J. Biol. Chem. 252(3) 883-889 (1977).
Miller, et al., "ITRAs: A New Family of Immunoglobulinlike Receptors Differentially Expressed in B Cells," Blood 99(8) 2662-2669 (2002).
Mimura, et al., "Role of Oligosaccharide Residues of IgG1-Fc in RcyRllB Binding," J. Biol. Chem. 276(49) 45539-45547 (2001).
Morea, et al., "Antibody Modeling: Implications for Engineering and Design," Methods (20) 267-279 (2000).
Morgan, et al., "The N-Terminal End of the $CH_2$ Domain of Chimeric Human IgG1 Anti-HLA-DR is Necessary for C1q Fc gamma R1 and Fc gamma RIII Binding," Immunol. 86(2) 319-324 (1995).
Morrison, et al., "Variable Region Domain Exchange Influences The Functional Properties of $IgG_1$," J. Immunol. (160) 2802-2808 (1998).
Nakamura, et al., "Dissection and Optimization of Immune Effector Functions of Humanized Anti-Ganglioside GM2 Monoclonal Antibody," Mol. Immunol. (37) 1035-1046 (2000).

(56) References Cited

OTHER PUBLICATIONS

Natsume, et al., "Engineered Antibodies of IgG1/IgG3 Mixed Isotype With Enhanced Cytotoxic Activities," Cancer Res. 68(10) 3863-3871 (2008).
Neidhardt-Berard, et al.,"Dendritic Cells Loaded With Killer Breast Cells Induce Differentiation of Tumor-Specific Cytotoxic T Lymphocytes," Breast Cancer Res. 6R322-R328 (2004).
Nimmerjahn, et al.., "Divergent Immunoglobulin-G Subclass Activity Through Selective Fc Receptor Binding," Science 310 (5753) 1510-1512 (2005).
Nimmerjahn, et al., "Supporting Online Material for: Divergent Immunoglobulin-G Subclass Activity Through Selective Fc Receptor Binding," Science (310) 1510 (2005).
Nimmerjahn, et al., "FcY RIV: A Novel FcR With Distinct IgG Subclass Specificity," Immunity (23) 41-51 (2005).
Niwa, et al.,"Defucosylated Chimeric Anti-CC Chemokine Receptor 4 IgG1 With Enhanced Antibody-Dependent Cellular Cytotoxicity Shows Potent Therapeutic Activity to T-Cell Leukemia and Lymphoma," Cancer Res. (64) 2127-2133 (2004).
Norderhaug, et al., "Chimeric Mouse Human IgG3 Antibodies With an IgG4-Like Hinge Region Induce Complement-Mediated Lysis More Efficienty Than IgG3 With Normal Hinge," Eur. J. Immunol. 21(10)2379-2384 (1991).
Ober, et al.,"Differences in Promiscuity for Antibody-FcRn Interactions Across Species: Implications for Therapeutic Antibodies,"Int'l Immunol. 13(12) 1551-1559 (2001).
Ober, et al.,"Exocytosis of IgG As Mediated by the Receptor, FcRn: An Analysis At the Single-Molecule Level," PNAS 101(30) 11076-11081 (2004).
O'Connor, et al., "Humanization of an Antibody Against Human Protein C and Calcium-Dependence Involving Framework Residues," Protein Eng. (11) 321-328(1998).
Okazaki, et al.,"Fucose Depletion From Human IgG1 Oligosaccharide Enhances Binding Enthalpy and Association Rate Between IgG1 and FcY RIlla," J. Mol. Biol. (336) 1239-1249 (2004).
Parren, et al., "Characterization of IgG FcR-Mediated Proliferation of Human T Cells Induced by Mouse and Human Anti-CD3 Monoclonal Antibodies Identification of a Functional Polymorphism to Human IgG2 Anti-CD3," J. Immunol. 148(3) 695-701 (1992).
Parren, et al., "On The Interaction of IgG Subclasses With the Low Affinity Fc Gamma RIIa (CD32) on Human Monocytes, Neutrophils, and Platelets: Analysis of a Functional Polymorphism to Human IgG2," J. Clin. Invest. 90(4) 1537-1546 (1992).
Pearce, et al.,"Mutational Analysis of Thrombopoietin for Identification of Receptor and Neutralizing Antibody Sites," J. Biol. Chem. 272(33) 20595-20602 (1997).
Pendley, et al., "Immunogenicity of Therapeutic Monoclonal Antibodies," Curr. Opin. In Mol. Therap. 5(2) 172-179 (2003).
Penichet, et al., "Antibody-Cytokine Fusion Proteins for the Therapy of Cancer," J. Immunol. Methods (248) 91-101 (2001).
Preithner, et al., "High Concentrations of Therapeutic IgG1 Antibodies Are Needed to Compensate for Inhibition of Antibody-Dependent Cellular Cytotoxicity by Excess Endogenous Immunoglobulin G," Mol. Immunol. 43(8) 1183-1193 (2006).
Presta, et al., "Engineering Therapeutic Antibodies for Improved Function," Biochem. Society (30) 487-490 (2002).
Radaev, et al., "The Structure of a Human Type III Fcy Receptor in Complex With Fc," J.Bio. Chem. (276) 16469-16477 (2001).
Radaev, et al., "Recognition of IgG by Fcy Receptor," J. Biol. Chem. 276(19) 16478-16483 (2001).
Radaev, et al., "Review: Recognition of Immunoglobulins by FcY Receptors," Mol. Immunol. (38) 1073-1083 16483 (2001).
Rafiq, et al., "Immune Complex-Mediated Antigen Presentation Induces Tumor Immunity," J. Clin. Invest. (110) 71-79 (2002).
Raghavan, et al., "Fc Receptors and Their Interactions With Immunoglobulins," Annu. Rev. Cell Dev. Biol. (12) 181-220 (1996).
Ravetch, et al., "IgG Fc Receptors," Annu. Rev. Immunol. (19) 275-290 (2001).
Ravetch, et al., "Immune Inhibitory Receptors," Science (290) 84-89 (2000).
Ravetch, et al., "Fc Receptors," Annu. Rev. Immunol. (9) 457-492 (1991).
Reddy, et al., "Elimination of the Fc Receptor-Dependent Effector Functions of a Modified IgG4 Monoclonal Antibody to Human CD4," J. Immunol. (164) 1925-1933 (2000).
Redpath, et al., "The Influence of The Hinge Region Length in Binding of Human IgG to Human Fcy Receptors," Human Immunol. (59) 720-727 (1998).
Reichert, et al., "Monoclonal Antibodies in The Clinic," Nature Biotech. (19) 819-822 (2001).
Rozsnyay, et al., "Distinctive Role of IgG1 and IgG3 Isotypes in FcR-Mediated Functions," Immunology 66(4) 491-498 (1989).
Sandlie, A.A., "The Extended Hinge Region of IgG3 Is Not Required for High Phogocytic Capacity Mediated by Fc Gamma Receptors, But the Heavy Chains Must Be Disulfide Bonded," Eur. J. Immunol. 23(7) 1546-1551 (1993).
Sarmay, et al., "Mapping and Comparison of the Interaction Sites on the Fc Region of IgG Responsible for Triggering Antibody Dependent Cellular Toxicity (ADCC) Through Different Types of Human FcY Receptor," Mol. Immunol. 29(5) 633-639 (1992).
Sautes-Fridman, et al., "Fc Gamma Receptors: A Magic Link With The Outside World," ASHI Quarterly, 148-151 (4Q 2003).
Sensel, et al., "Amino Acid Differences in The N-Terminus of CH2 Influence the Relative Abilities of IgG2 and IgG3 to Activate Complement," Mol. Immunol. 34(14)1019-1029 (1997).
Shields, et al., "High Resolution Mapping of the Binding Site on Human IgG1 for FcyRl, FcyRlll and FcRn and Design of IgG1 Variants With Improved Binding to the FcyR," J. Biol. Chem. 276(9) 6591-6604 (2001).
Shields, et al.,"Lack of Fucose on Human IgG1 N-Linked Oligosaccharide Improves Binding to Human FcyRIII and Antibody-Dependent Cellular Toxicity," J. Biol. Chem. 277(30) 26733-26740 (2002).
Shinkawa, et al., "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity," J. Biol. Chem. 278(5) 3466-3473 (2003).
Shitara, et al., "A New Vector for the High Level Expression of Chimeric Antibodies in Myeloma Cells," J. Immunol. Method (167) 271-278 (1994).
Shopes, et al., "A Genetically Engineered Human IgG Mutant With Enhanced Cytolytic Activity," J. Immunol. (148) 2918-2922 (1992).
Shopes, et al., "Recombinant Human IgG1-Murine IgE Chimeric Ig Construction Expression and Binding to Human Fc Gamma Receptors," J. Immunol. 145(11) 3842-3848 (1990).
Simmons, et al., "Expression of Full-Length Immunoglobulins in *Escherichia coli*: Rapid and Efficient Production of Aglycosylated Antibodies," J. Immunol. Methods (263) 133-147 (2002).
Smith, K.G. et al., "T Cell Activation by Anti-T3 Antibodies: Comparison of IgG1 and IgG2b Switch Variants and Direct Evidence for Accessory Function of Macrophage Fc Receptors," Eur. J. Immunol. 16(5) 478-486 (1986).
Smith, R.I. et al., "Addition of a μ-Tailpiece to IgG Results in Polymeric Antibodies With Enhanced Effector Functions Including Complement-Mediated Cytolysis by IgG4," J. Immunol. 154(5) 2226-2236 (1995).
Sondermann, et al., "The 3.2-A Crystal Structure of the Human IgG1 Fc Fragment-FcyRIII Complex," Nature (406) 267-273 (2000).
Sondermann, et al., "Molecular Basis for Immune Complex Recognition: A Comparison of Fc-Receptor Structures," J. Mol. Biol. (309) 737-749 (2001).
Sondermann, et al., "Crystal Structure of the Soluble Form of the Human Fcy—Receptor IIb: A New Member of the Immunoglobulin Superfamily At 1.7 A Resolution," EMBO J. 18(5) 1095-1103 (1999).
Sondermann, et al., "Human FcY Receptor IIb Expressed in *Escherichia coli* Reveals IgG Binding Capability," Biol. Chem. (380) 717-721 (1999).
Sorenson, et al., "Effect of the IgM and IgA Secretory Tailpieces on Polymerization and Secretion of IgM and IgG," J. Immunol. 156(8) 2858-2865 (1996).

(56) References Cited

OTHER PUBLICATIONS

Steplewski, et al., "Biological Activity of Human-Mouse IgG1, IgG2, IgG3 and IgG4 Chimeric Monoclonal Antibodies With Antitumor Specificity," PNAS USA (85) 4852-4856 (1988).
Stevenson, et al., "Preparation of FcY for Addition to Sulfhydryl-Expressing Ligands With Minimal Disturbance of the Hinge," J. Immunol. Methods (231) 169-175 (1999).
Tamm, et al., "IgG Binding Sites on Human FcY Receptors," Int'l Reviews of Immunology, 16(1) 57-85 (1997).
Tao, et al., "The Differential Ability of Human IgG1 and IgG4 to Active Complement Is Determined by the COOH-Terminal Sequence of The CH2 Domain," J. Exp. Med. (173) 1025-1028 (1991).
Tao, et al., "Structural Features of Human Immunoglobulin G That Determine Isotype-Specific Differences in Complement Activation," J. Exp. Med. (178) 661-667 (1993).
Thommesen, et al., "Lysine 322 in The Human IgG3 CH2 Domain Is Crucial for Antibody Dependent Complement Activation," Mol. Immunol. (37) 995-1014 (2000).
Thrush, et al.., "Immunotoxins: An Update," Ann. Rev. Immunol. (14) 49-71 (1996).
Torphy, et al., "Pharmaceutical Biotechnology Monoclonal Antibodies: Boundless Potential, Daunting Challenges—Editorial Overview," Curr. Opin. Biotech. (13) 589-591 (2002).
Trail, et al., "Monoclonal Antibody Drug Conjugates in the Treatment of Cancer," Curr. Opin. Immunol. (11) 584-588 (1999).
Trikha, M., "Monoclonal Antibodies As Therapeutics in Oncology," Curr. Opin. Biotech. (13) 609-614 (2002).
Tuijnman, et al., "A Flow Cytometric Rosetting Assay for the Analysis of IgG-Fc Receptor Interactions," J. Immunol. Methods 127(2) 207-214 (1990).
Uchide, et al., "The Innate Mononuclear Phagocyte Network Depletes B Lymphocytes Through Fc Receptor-Dependent Mechanisms During Anti-CD20 Antibody Immunotherapy," J. Exp. Med. 199(12) 1659-1669 (2004).
Umana, et al., "Engineered Glycoforms of an Antineuro-Blastoma IgG1 With Optimized Antibody-Dependent Cellular Cytotoxicity Activity," Nature (17) 176-180 (1999).
Valerius, et al., "FcAlpha RI (CD89) As a Novel Trigger Molecule for Bispecific Antibody Therapy," Blood (90) 4485-4492 (1997).
Van Dijk, et al., "Human Antibodies As Next Generation Therapeutics," Curr. Opin. Chem. Biol. (5) 368-374 (2001).
Van Royen-Kerkhof, et al., "Flow Cytometric Determination of FcY RIIa (CD32) Polymorphism," J. Immunol. Methods (294)135-144 (2004).
Van Schie, et al., "Evaluation of Human FcY RIIa (CD32) and FcY RIIIb (CD16) Polymorphisms in Caucasians and African-Americans Using Salivary DNA," Clin. and Diag. Lab Immunol. 7(4)676-681 (2000).
Van Sorge, et al., "FcY R Polymorphisms: Implications for Function, Disease Susceptibility and Immunotherapy," Tissue Antigens, (61) 189-202 (2003).
Vasserot, et al., "Optimization of Protein Therapeutics by Directed Evolution," Drug Discovery Today 8(3) 118-126 (2003).
Vidarte, et al., "Serine 132 Is The C3 Covalent Attachment Point of the $CH_1$ Domain of Human IgG1," J. Biol. Chem., 276(41) 38217-38223 (2001).
Waldmann, et al., "Emerging Therapies: Spectrum of Application of Monoclonal Antibody Therapy," (American Society of Hematology Program Book) 394-408 (Jan. 2000).
Ward, et al., "Evidence to Support the Cellular Mechanism Involved in Serum IgG Homeostasis in Humans," Int'l Immunol. 15(2) 187-195 (2003).
Warmerdam, et al., "Interaction of a Human Fc Gamma RIIb1 (CD32) Isoform With Murine and Human IgG Subclasses," Int'l Immunol. 5(3) 239-247 (1993).

Wawrzynczak, et al., "Recombinant Mouse Monoclonal Antibodies With Single Amino Acid Substitutions Affecting CLq and High Affinity Fc Receptor Binding Have Identical Serum Half-Lives in the BALB/c Mouse," Mol. Immunol. 29(2) 221-227 (1992).
Weiner, et al., "Tunable Antibodies," Nat. Biotech. 23(5) 556-557 (2005).
Weng, et al., "Two Immunoglobulin G Fragment C Receptor Polymorphisms Independently Predict Response to Rituximab in Patients With Follicular Lymphoma," J. Clin. Oncol. (21) 3940-3947 (2003).
Weng, et al., "Clinical Outcome of Lymphoma Patients After Idiotype Vaccination Is Correlated With Humoral Immune Response and Immunoglobulin G Fc Receptor Genotype," J. Clin. Oncol. 22(23) 1-8 (2004).
West, et al., "Crystal Structure and Immunoglobulin G Binding Properties of the Human Major Histocompatibility Complex-Related Fc Receptor," Biochemistry (39) 9698-9708 (2000).
White, et al., Antibody-Targeted Immunotherapy for Treatment of Malignancy, Annu. Rev. Med. (52) 125-145 (2001).
WHO Review of the Notation for The Allotypic and Related Markers of Human Immunoglobulins, J. Immunogen (3) 357-362 (1976).
WHO Review of the Notation for the Allotypic and Related Markers of Human Immunoglobulins, Eur. J. Immunol. (6) 599-601 (1976).
Wines, et al., "The IgG Fc Contains Distinct Fc Receptor (FcR) Binding Sites: The Leukocyte Receptors Fc[Gamma] Rile Bind to a Region in the Fc Distinct From That Recognized by Neonatal FcR and Protein A," J. Immunol. (164) 5313-5318 (2000).
Wing, et al., "Mechanism of First-Dose Cytokine-Release Syndrome of CAMPATH 1-H : Involvement of CD16 (FcYRIII) and CD11a/CD18 (LFA-1) on NK Cells," J. Clin. Invest. 98(12) 2819-2826 (1996).
Wolff, et al., "Monoclonal Antibody Homodimers: Enhanced Antitumor Activity in Nude Mice," Cancer Res. 53(11) 2560-2565 (1993).
Woof, et al., "Localisation of the Monocyte-Binding Region on Human Immunoglobulin G," Mol. Immunol. 23(3) 319-330 (1986).
Wright, A. et al., "Effect of C2-Associated Carbohydrate Structure on IgG Effector Function: Studies With Chimeric Mouse-Human IgG1 Antibodies in Glycosylation Mutants of Chinese Hamster Ovary Cells," J. Immunol. (160) 3393-3402 (1998).
Wright, A. et al., "In vivo Trafficking and Catabolism of IgG1 Antibodies With Fc Associated Carbohydrates of Differing Structure," Glycobiology 10(12) 1347-1355 (2000).
Xu, D. et al., "In Vitro Characterization of Five Humanized OKT3 Effector Function Variant Antibodies," Cell. Immunol. 200(1) 16-26 (2000).
Xu, M., et al., "Molecular Cloning and Characterization of SPAP1, An Inhibitory Receptor," Biochem and Biophys Res Comm (280) 768-775 (2001).
Xu, Y. et al., "Residue At Position 331 in The IgG1 and IgG4 CH2 Domains Contributes to Their Differential Ability to Bind and Activate Complement," J. Blol. Chem. 269(5) 3469-3474 (1994).
Yamane-Ohnuki, et al., "Establishment of FUT8 Knockout Chinese Hamster Ovary Cells: An Ideal Host Cell Line for Producing Completely Defucosylated Antibodies With Enhanced Antibody-Dependent Cellular Toxicity," Biotechnology and Bioengineering Interscience Publishers, London GB 87(5) No. 5 (2004).
Zelaschi, et al., "Human Immunoglobulin Allotypes: Previously Unrecognized Determinants and Alleles Defined With Monoclonal Antibodies," PNAS USA (80) 3762-3766 (1983).
Zhou, et al., "Generation of Mutated Variants of the Human Form of the MHC Class I-Related Receptor, FcRn, With Increased Affinity for Mouse Immunoglobulin G," J. Mol. Biol. (332) 901-913 (2003).
Zhou, et al."DNA-Based Vaccines Activate Innate and Adaptive Antitumor Immunity by Engaging the NKG2D Receptor," PNAS 102(31) 10846-10851 (2005).
Zhu, et al., "A Novel Human Immunoglobulin Fc Gamma Fc Epsilon Bifunctional Fusion Protein Inhibits Fc Epsilon RI-Mediated Degranulation," Nat. Med. 8(5) 518-521 (2002).

| EU Index | 118 | 119 | 120 | 121 | 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |

| EU Index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU Index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU Index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | S | L | G | T | K | T | Y | T | C | N |

Figure 3b

| Figure 3b-1 | Figure 3b-2 | Figure 3b-3 |

Figure 3b-1

| CH2 EU Index | 237 | 238 | 239 | 240 | 241 | 242 | 243 | 244 | 245 | 246 | 247 | 248 | 249 | 250 | 251 | 252 | 253 | 254 | 255 | 256 | 257 |
|---|---|---|---|---|---|---|---|---|---|---|---|---|---|---|---|---|---|---|---|---|---|
| IgG1 | G | P | S | V | F | L | F | P | P | K | P | K | D | T | L | M | I | S | R | T | P |
| IgG2 | G | P | S | V | F | L | F | P | P | K | P | K | D | T | L | M | I | S | R | T | P |
| IgG3 | G | P | S | V | F | L | F | P | P | K | P | K | D | T | L | M | I | S | R | T | P |
| IgG4 | G | P | S | V | F | L | F | P | P | K | P | K | D | T | L | M | I | S | R | T | P |

| EU Index | 258 | 259 | 260 | 261 | 262 | 263 | 264 | 265 | 266 | 267 | 268 | 269 | 270 | 271 | 272 | 273 | 274 | 275 | 276 | 277 | 278 |
|---|---|---|---|---|---|---|---|---|---|---|---|---|---|---|---|---|---|---|---|---|---|
| IgG1 | E | V | T | C | V | V | V | D | V | S | H | E | D | P | E | V | K | F | N | W | Y |
| IgG2 | E | V | T | C | V | V | V | D | V | S | H | E | D | P | E | V | Q | F | N | W | Y |
| IgG3 | E | V | T | C | V | V | V | D | V | S | H | E | D | P | E | V | Q | F | K | W | Y |
| IgG4 | E | V | T | C | V | V | V | D | V | S | Q | E | D | P | E | V | Q | F | N | W | Y |

| EU Index | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|
| IgG1 | V | D | G | V | E | V | H | N | A | K | T | K | P | R | E | E | Q | Y | N | S | T |
| IgG2 | V | D | G | V | E | V | H | N | A | K | T | K | P | R | E | E | Q | F | N | S | T |
| IgG3 | V | D | G | V | E | V | H | N | A | K | T | K | P | R | E | E | Q | Y | N | S | T |
| IgG4 | V | D | G | V | E | V | H | N | A | K | T | K | P | R | E | E | Q | F | N | S | T |

| EU Index | 300 | 301 | 302 | 303 | 304 | 305 | 306 | 307 | 308 | 309 | 310 | 311 | 312 | 313 | 314 | 315 | 316 | 317 | 318 | 319 | 320 |
|---|---|---|---|---|---|---|---|---|---|---|---|---|---|---|---|---|---|---|---|---|---|
| IgG1 | Y | F | R | V | S | V | L | T | V | L | H | Q | D | W | L | N | G | K | E | Y | K |
| IgG2 | F | R | V | S | V | L | T | V | V | H | Q | D | W | L | N | G | K | E | Y | K | |
| IgG3 | F | R | V | S | V | L | T | V | L | H | Q | D | W | L | N | G | K | E | Y | K | |
| IgG4 | Y | R | V | S | V | L | T | V | L | H | Q | D | W | L | N | G | K | E | Y | K | |

| EU Index | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|
| IgG1 | C | K | V | S | N | K | A | L | P | A | P | – | E | K | T | – | S | K | A | K |
| IgG2 | C | K | V | S | N | K | G | L | P | A | P | – | E | K | T | – | S | K | T | K |
| IgG3 | C | K | V | S | N | K | A | L | P | A | P | – | E | K | T | – | S | K | T | K |
| IgG4 | C | K | V | S | N | K | G | L | P | S | S | – | E | K | T | – | S | K | A | K |

CH3

| EU Index | 341 | 342 | 343 | 344 | 345 | 346 | 347 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|
| IgG1 | G | Q | P | R | E | P | Q | V | Y | T | L | P | P | S | R | D | E | L | T | K | N |
| IgG2 | G | Q | P | R | E | P | Q | V | Y | T | L | P | P | S | R | E | E | M | T | K | N |
| IgG3 | G | Q | P | R | E | P | Q | V | Y | T | L | P | P | S | R | E | E | M | T | K | N |
| IgG4 | G | Q | P | R | E | P | Q | V | Y | T | L | P | P | S | Q | E | E | M | T | K | N |

| EU Index | 362 | 363 | 364 | 365 | 366 | 367 | 368 | 369 | 370 | 371 | 372 | 373 | 374 | 375 | 376 | 377 | 378 | 379 | 380 | 381 | 382 |
|---|---|---|---|---|---|---|---|---|---|---|---|---|---|---|---|---|---|---|---|---|---|
| IgG1 | Q | V | S | L | T | C | L | V | K | G | F | Y | P | S | D | – | A | V | E | W | E |
| IgG2 | Q | V | S | L | T | C | L | V | K | G | F | Y | P | S | D | – | A | V | E | W | E |
| IgG3 | Q | V | S | L | T | C | L | V | K | G | F | Y | P | S | D | – | A | V | E | W | E |
| IgG4 | Q | V | S | L | T | C | L | V | K | G | F | Y | P | S | D | – | A | V | E | W | E |

| EU Index | 383 | 384 | 385 | 386 | 387 | 388 | 389 | 390 | 391 | 392 | 393 | 394 | 395 | 396 | 397 | 398 | 399 | 400 | 401 | 402 | 403 |
|---|---|---|---|---|---|---|---|---|---|---|---|---|---|---|---|---|---|---|---|---|---|
| IgG1 | S | N | G | Q | P | E | N | N | Y | K | T | T | P | P | V | L | D | S | D | G | S |
| IgG2 | S | N | G | Q | P | E | N | N | Y | K | T | T | P | P | M | L | D | S | D | G | S |
| IgG3 | S | S | G | Q | P | E | N | N | Y | N | T | T | P | P | M | L | D | S | D | G | S |
| IgG4 | S | N | G | Q | P | E | N | N | Y | K | T | T | P | P | V | L | D | S | D | G | S |

Figure 3b-2

| EU Index | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|
| IgG1 | F | F | L | Y | S | K | L | T | V | D | K | S | R | W | Q | Q | G | N | V | F | S |
| IgG2 | F | F | L | Y | S | K | L | T | V | D | K | S | R | W | Q | Q | G | N | V | F | S |
| IgG3 | F | F | L | Y | S | K | L | T | V | D | K | S | R | W | Q | Q | G | N | I | F | S |
| IgG4 | F | F | L | Y | S | R | L | T | V | D | K | S | R | W | Q | E | G | N | V | F | S |

| EU Index | 425 | 426 | 427 | 428 | 429 | 430 | 431 | 432 | 433 | 434 | 435 | 436 | 437 | 438 | 439 | 440 | 441 | 442 | 443 | 444 | 445 |
|---|---|---|---|---|---|---|---|---|---|---|---|---|---|---|---|---|---|---|---|---|---|
| IgG1 | C | S | V | M | H | E | A | L | H | N | H | Y | T | Q | K | S | L | S | L | S | P |
| IgG2 | C | S | V | M | H | E | A | L | H | N | H | Y | T | Q | K | S | L | S | L | S | P |
| IgG3 | C | S | V | M | H | E | A | L | H | N | R | F | T | Q | K | S | L | S | L | S | P |
| IgG4 | C | S | V | M | H | E | A | L | H | N | H | Y | T | Q | K | S | L | S | L | S | L |

| EU Index | 446 | 447 | |
|---|---|---|---|
| IgG1 | G | K | SEQ ID NO: 1 |
| IgG2 | G | K | SEQ ID NO: 2 |
| IgG3 | G | K | SEQ ID NO: 3 |
| IgG4 | G | K | SEQ ID NO: 4 |

Figure 3b-3

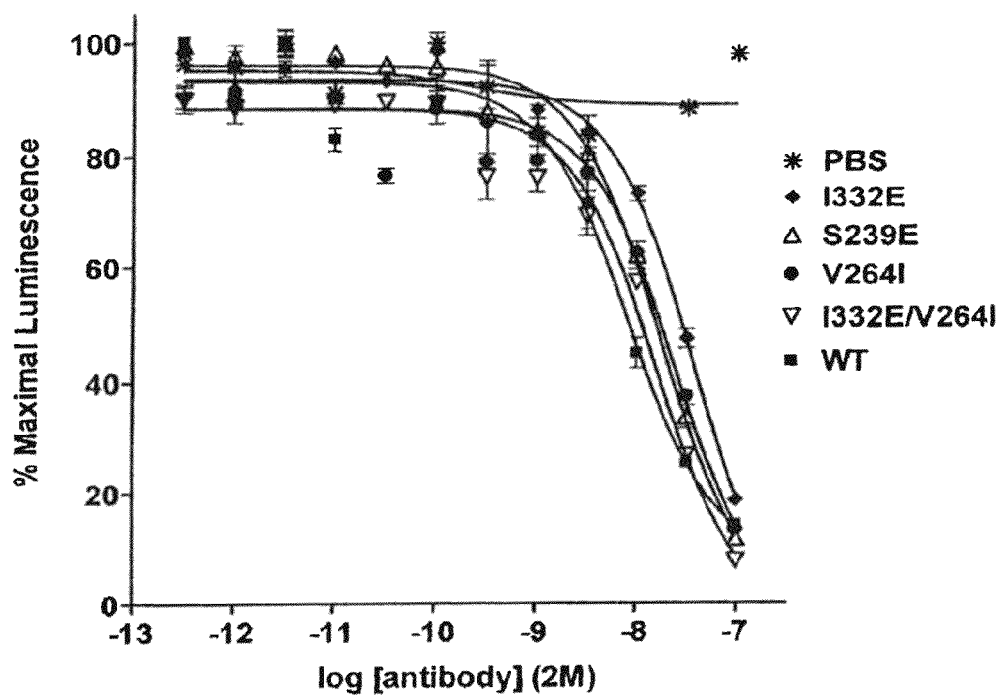

Anti-CD20 Heavy Chain Comprising Possible Fc Variants
QVQLQQPGAELVKPGASVKMSCKASGYTFTSYNMHWVKQTPGRGLEWIGAIYPGNGDTSYNQKFKGK
ATLTADKSSSTAYMQLSSLTSEDSAVYYCARSTYYGGDWYFNVWGAGTTVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKAEPKSCDKTHTCPPCPAPELLGGPX$_1$X$_2$FLFPPKPKDTLMISRTPEVTCV
VX$_3$DVSX$_4$EDPX$_5$VX$_6$FNWYVDGVEVHNAKTKPREEQYX$_7$Z$_1$TYRVVSVLTVLHQDWLNGKEYKCKVSN
Z$_2$ALPX$_8$PX$_9$EKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK
SEQ ID NO: 5

| Position | WT | Possible Substitutions |
|---|---|---|
| X$_1$ | S | D, E, N, Q, T |
| X$_2$ | V | I, M |
| X$_3$ | V | I, T, Y |
| X$_4$ | H | |
| X$_5$ | E | Y |
| X$_6$ | K | E |
| X$_7$ | N | D |
| X$_8$ | A | Y, L, I |
| X$_9$ | I | D, E, N, Q |
| Z$_1$ | S | A, D |
| Z$_2$ | K | E, T |

Figure 40a

Anti-CD20 Light Chain
QIVLSQSPAILSASPGEKVTMTCRASSSVSYIHWFQQKPGSSPKPWIYATSNLASGVPVRFSGSGSG
TSYSLTISRVEAEDAATYYCQQWTSNPPTFGGGTKLEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGLS
SPVTKSFNRGEC  SEQ ID NO: 6

Figure 40b

Anti-CD20 Heavy Chain
QVQLQQPGAELVKPGASVKMSCKASGYTFTSYNMHWVKQTPGRGLEWIGAIYPGNGDTSYNQKFKGK
ATLTADKSSSTAYMQLSSLTSEDSAVYYCARSTYYGGDWYFNVWGAGTTVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKAEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK  SEQ ID NO: 7

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 1 | V264A | a | 0.67 | 0.06 | 0.32 | 0.69 | 1.03 | 0.40 | 0.91 | 0.57 | 0.14 | 0.25 | 2.16 | 0.23 | 1.12 | 0.18 | 0.13 |
| 2 | V264L | a | 0.76 | 0.07 | 0.43 | 0.67 | 1.17 | 0.33 | 0.90 | 0.56 | 0.53 0.22 | 0.31 | 1.44 | 0.21 | 0.81 | 0.17 | 0.19 |
| 3 | V264I | a t r | 1.35 | 0.05 | 0.70 | 0.57 | 1.28 | 0.33 | 1.05 | 0.51 | 0.56 0.84 | 0.22 | 8.58 | 0.56 | 1.32 | 0.18 | 0.66 |
| 4 | F241W | a | 1.59 | 0.13 | 0.68 | 0.62 | 1.10 | 0.34 | 0.85 | 0.57 | 1.43 0.32 | 0.23 | 3.68 | 0.21 | 1.70 | 0.25 | 0.29 |
| 5 | F241L | a | 0.84 | 0.25 | 0.77 | 0.57 | 1.20 | 0.34 | 1.12 | 0.50 | 0.29 0.24 | 0.27 | 3.24 | 0.30 | 1.99 | 0.48 | 0.20 |
| 6 | F243W | a | 1.61 | 0.23 | 1.71 | 0.58 | 1.44 | 0.34 | 1.11 | 0.45 | 0.26 1.12 | 0.18 | 2.88 | 0.24 | 4.63 | 0.26 | 0.78 |
| 7 | F243L | a | 0.51 | 0.07 | 0.31 | 0.63 | 1.00 | 0.44 | 0.72 | 0.72 | 0.51 0.43 | 0.26 | 2.47 | 0.21 | 0.64 | 0.12 | 0.43 |
| 8 | F241L/F243L/V262I/V264I | a | 0.80 0.51 | 0.21 0.10 | 0.10 | 0.36 | 0.49 | 24.05 0.57 | 8.39 | 6.19 | 0.51 0.06 | 0.66 | 1.24 | 0.20 | 0.44 | 0.19 | 0.10 |
| 9 | F241W/F243W | a | 1.13 | 0.07 | 0.81 | 0.59 | 1.39 | 0.38 | 0.96 | 0.54 | 0.05 0.09 | 0.48 | 1.88 | 0.27 | 1.12 | 0.12 | 0.20 |
| 10 | F241W/F243W/V262A/V264A | a | 0.50 | 0.12 | 0.28 | 0.58 | 1.33 | 0.32 | 1.06 | 0.53 | 0.28 0.07 | 0.21 | 2.13 | 0.19 | 1.91 | 0.15 | 0.15 |
| 11 | F241L/V262I | a | 1.30 | 0.10 | 0.27 | 0.59 | 0.75 | 0.36 | | | 0.19 0.04 | 0.23 | 5.29 | 0.63 | 1.37 | 0.17 | 0.23 |
| 12 | F243L/V264I | a | 1.02 | 0.12 | 0.34 | 0.68 | 0.69 | 0.38 | | | 0.17 0.06 | 0.25 | 3.94 | 0.30 | 0.71 | 0.34 | 1.04 |
| 13 | F243L/V262I/V264W | a | 0.32 | 0.26 | 0.12 | 0.31 | | 24.05 | 15.82 | 5.78 | 0.72 1.23 | 0.21 | 3.72 | 0.62 | 1.35 | 0.42 | 0.60 |
|  |  |  | 0.30 | 0.18 | 0.24 | 195 | 0.91 | 0.44 | 1.05 | 28.03 | 0.03 0.02 | 0.51 |  |  |  |  |  |
| 14 | F241Y/F243Y/V262T/V264T | a | 0.58 | 0.19 | 0.18 | 0.32 | | 24.04 | 30.49 | 5.72 | 0.55 | 0.24 | 1.19 | 0.36 | 1.89 | 0.57 | 0.40 |
|  |  |  | 0.66 | 0.23 | 0.25 | 1.97 | 1.17 | 0.35 | 1.01 | 9.71 | 0.06 0.47 0.05 | 0.42 0.19 |  |  |  |  |  |

Figure 41B

| # | Mutation | | | | | | | | | | | | | | | | | |
|---|---|---|---|---|---|---|---|---|---|---|---|---|---|---|---|---|---|---|
| 15 | F241E/F243R/V262E/V264R | a | 0.05<br>0.06 | 0.39<br>0.11 | 0.04 | 0.61 | | | 24.05<br>0.52 | 10.73<br>0.67 | 5.99<br>1.52 | 0.48<br>0.05 | 0.24 | 1.51 | 0.18 | 0.28 | 0.16 | 0.70 |
| 16 | F241E/F243Q/V262T/V264E | a | 0.02<br>0.01 | 0.31<br>0.27 | 0.10 | 0.99 | | 0.36 | 24.07<br>0.67 | 5.62 | 6.06 | 0.07<br>0.07 | 0.30 | 1.34 | 0.24 | 0.24 | 0.23 | 0.19 |
| 17 | F241R/F243Q/V262T/V264R | a | 0.01<br>0.16 | 0.63<br>0.11 | 0.07<br>0.21 | 0.51<br>521 | 1.00 | | 24.06<br>0.35 | 17.05<br>0.71 | 5.77<br>0.80 | | 54.64 | 1.58 | 0.22 | 0.45 | 0.27 | 0.79 |
| 18 | F241E/F243Y/V262T/V264R | a | 0.17<br>0.12 | 0.24<br>0.18 | 0.08<br>0.18 | 0.30<br>63.41 | 0.94 | | 24.05<br>0.38 | 17.48<br>0.83 | 5.79<br>1.39 | 0.80<br>0.02 | 0.19 | 1.24 | 0.19 | 0.54 | 0.29 | 0.55 |
| 19 | L328M | a | 2.07<br>1.33 | 5407<br>0.07 | 0.47<br>0.85 | 0.35<br>0.56 | 1.90 | | 24.04<br>0.32 | 0.19<br>1.29 | 9.68<br>0.46 | 0.02 | 1.23 | 5.40 | 0.57 | 0.84 | 0.21 | 0.32 |
| 20 | L328E | a | 2.17<br>1.23 | 0.17<br>0.10 | 0.07<br>0.23 | 0.34<br>124 | 1.90 | | 24.04<br>0.33 | 1.07 | 0.54 | 0.51<br>0.05 | 0.19 | 2.55 | 0.36 | 0.73 | 0.31 | 0.38 |
| 21 | L328F | a | 1.38<br>0.99 | 0.17<br>0.18 | 0.13<br>0.25 | 0.30<br>2.89 | 5.14 | | 24.05<br>0.33 | 71.81<br>4.13 | 5.62<br>0.45 | 0.05<br>0.62<br>0.21 | 0.28<br>0.22 | | | | | |
| 22 | I332E | a t r p | 3.97<br>2.08 | 0.19<br>0.13 | 1.09<br>1.26 | 0.60<br>0.21 | 1.92<br>2.37<br>3.93 | | 0.33<br>0.37 | 1.27<br>2.64 | 0.49<br>0.34 | 0.07<br>0.72<br>0.12 | 0.34<br>0.21 | 2.48 | 0.35 | 2.06 | 0.46 | |
| 23 | L328M/I332E | a | 0.30 | 0.19 | 0.28 | 0.35 | 0.90 | | 0.12 | 0.82 | 0.12 | 0.00<br>0.24 | 4.94 | 4.28 | 0.56 | 1.32<br>0.78 | 0.44<br>0.41 | 1.86<br>0.52<br>1.71<br>0.24 |
| 24 | P244H | a | 1.05 | 0.34 | 0.53 | 0.67 | 1.02 | | 0.42 | 0.79 | 0.68 | 3.57<br>1.22<br>6.72<br>0.21<br>2.6 | 0.19<br>2.82 | 0.05 | 0.64 | 0.46 | 0.14 | 0.62 |
| 25 | P245A | a | 0.84 | 0.11 | 0.46 | 0.65 | 0.70 | | 0.52 | | | 0.64<br>0.83 | 0.15 | 1.42 | 0.26 | 0.44 | 0.27 | 0.64 |
| 26 | P247V | a | 1.06 | 0.12 | 0.99 | 0.58 | 1.34 | | 0.48 | 0.88 | 0.54 | 0.45<br>0.25 | 0.23 | 2.00 | 0.26 | 0.43 | 0.24 | 0.46 |
| 27 | W313F | a | 0.82 | 0.11 | 0.38 | 0.65 | 0.64 | | 0.39 | | | 0.62<br>0.53<br>0.24 | 0.22 | 1.45<br>1.36 | 0.31<br>0.19 | 0.47 | 0.25 | 0.38 |

Figure 41C

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 28 | P244H/P245A/P247V | a | 0.98 | 0.09 | 0.68 | 0.57 | 0.73 | 0.32 | | | 0.88 | | | | 0.52 | 0.25 | 0.71 |
| | | | | | | | | | | | 0.52 | 0.23 | 4.95 | 0.54 | | | |
| 29 | P247G | a | 1.57 | 0.20 | 0.35 | 0.70 | 0.69 | 0.40 | 0.83 | 8.15 | 0.93 | | 1.72 | 0.24 | 0.68 | 0.45 | 0.41 |
| | | | | | | | | | | | 0.28 | 0.22 | | | | | |
| | | | | | | | | | | | 0.54 | | | | | | |
| 30 | V264I/I332E | a t r c | 1.65 | 0.18 | 0.79 | 0.54 | 2.13 | 0.36 | 1.41 | 0.49 | 4.80 | 0.19 | 4.07 | 0.38 | 1.70 | 0.61 | 2.25 |
| | | | 4.58 | 0.20 | 0.89 | 0.23 | 5.08 | 0.40 | 2.80 | 0.31 | 3.00 | 2.82 | | | 0.89 | 0.38 | 0.59 |
| | | | | | | | 1.57* | | | | 12.49 | | | | | | 7.96 |
| 31 | F241E/F243R/V262E/ | a | | | | | | | | | 0.19 | | | | | | |
| 32 | V264R/I332E F241E/F243Q/V262T/ | a | | | | | | | | | | | | | | | |
| 33 | V264E/I332E F241R/F243Q/V 262T/ | a | | | | | | | | | | | | | | | |
| 34 | V264R/I332E F241E/F243Y/V262T/ | a | | | | | | | | | 0.1 | | | | | | |
| 35 | V264R/I332E S298A | a | | | | | | | | | 2.21 | | | | | | |
| 36 | S298A/I332E | a | | | | | | | | | 21.73 | | | | | | |
| 37 | S298A/E333A/K334A | a t r p | | | | | | | | | 2.56 | | | | | | |
| 41 | S239E/I332E | a | 3.64 | 0.21 | 3.22 | 0.13 | 8.73 | 0.11 | 8.29 | 0.17 | 88.98 | 0.33 | 0.76 | 0.29 | 1.34 | 0.31 | 10.19 |
| | | | | | | | 3.49 | | | | 5.8 | | | | | | 1.66 |
| 42 | S239Q/I332E | a | 2.08 | 0.23 | 1.91 | 0.14 | 3.68 | 0.13 | 3.64 | 0.18 | 13.85 | 0.42 | 1.67 | 0.20 | 1.33 | 0.37 | 3.77 |
| | | | | | | | 4.68 | | | | 6.6 | | | | | | 1.41 |
| 43 | S239E | a t | 2.17 | 0.23 | 1.38 | 0.15 | 2.18 | 0.11 | 3.01 | 0.23 | 51.22 | 0.47 | 0.95 | 0.21 | 1.47 | 0.85 | 23.47 |
| | | | | | | | | | | | 10.16 | | | | | | |
| 44 | D265G | a | 0.17 | 0.22 | 1.97 | 0.10 | 4.86 | 0.09 | 3.19 | 0.15 | 4.37 | 0.38 | 0.72 | 0.28 | 1.74 | 0.52 | 0.90 |
| | | | | | | | | | | | <0.02 | | | | | | |
| 45 | D265N | a | 0.02 | 0.31 | 0.95 | 0.14 | 0.90 | 0.14 | 0.58 | 0.18 | <0.02 | 1.30 | 0.55 | 0.31 | 0.48 | 0.28 | |

Figure 41D

| # | Mutation | | | | | | | | | | | | | | | |
|---|---|---|---|---|---|---|---|---|---|---|---|---|---|---|---|---|
| 46 | S239E/D265G | a | 0.11 | 0.42 | 0.75 | 0.12 | 0.93 | 0.11 | 0.95 | 0.22 | | | 1.15 | 0.22 | 0.50 | 0.34 | |
| 47 | S239E/D265N | a | 0.12 | 0.26 | 0.61 | 0.12 | 1.39 | 0.09 | 1.11 | 0.15 | <0.02 | 0.38 | 0.63 | 0.25 | 0.52 | 0.35 | 1.08 |
| | | | | | | | | | | | 1.51 | | | | | | |
| | | | | | | | | | | | 0.02 | | | | | | |
| 48 | S239E/D265Q | a | 0.65 | 0.23 | 0.53 | 0.15 | 0.99 | 0.12 | 1.00 | 0.18 | | | 1.74 | 0.19 | 0.37 | 0.55 | |
| 49 | Y296E | a | 1.56 | 0.22 | 1.09 | 0.13 | 1.28 | 0.12 | 1.66 | 0.19 | 0.05 | 0.49 | 1.85 | 0.18 | 1.23 | 0.60 | 0.81 |
| | | | | | | | 1.11 | | | | 1.04 | | | | | | 0.66 |
| | | | | | | | | | | | 0.73 | | | | | | 0.85 |
| 50 | Y296Q | a | 0.81 | 0.23 | 1.18 | 0.19 | 2.49 | 0.15 | 2.45 | 0.19 | 2.13 | 0.37 | 1.18 | 0.22 | 0.31 | 0.50 | 1.21 |
| | | | | | | | 0.43 | | | | 0.52 | | | | | | 1.41 |
| 51 | S298T | a | 1.33 | 0.23 | 1.15 | 0.15 | 1.44 | 0.10 | 1.63 | 0.19 | 2.04 | 0.35 | 1.90 | 0.19 | 2.13 | 0.76 | |
| | | | | | | | <0.02 | | | | 0.94 | | | | | | |
| 52 | S298N | a | 0.59 | 0.24 | 0.80 | 0.14 | 1.27 | 0.13 | 0.91 | 0.17 | 0.41 | | 1.28 | 0.21 | 0.94 | 0.31 | |
| 53 | T299I | a | 0.13 | 0.22 | 0.90 | 0.13 | <0.02 | 0.11 | 0.57 | 0.17 | | | 0.80 | 0.24 | 0.34 | 0.36 | |
| | | | | | | | 1.26 | | | | | | | | | | |
| 54 | A327S | a | 0.39 | 0.26 | 0.64 | 0.12 | 0.89 | 0.10 | 1.15 | 0.24 | <0.02 | 3.86 | 0.47 | 0.25 | 0.13 | 0.44 | 0.59 |
| | | | | | | | 0.39 | | | | 0.23 | | | | | | 0.57 |
| 55 | A327N | a | 1.25 | 0.32 | 0.77 | 0.16 | 1.07 | 0.10 | 1.31 | 0.17 | 0.61 | 0.40 | 0.66 | 0.32 | 0.88 | 0.38 | 0.17 |
| | | | | | | | 1.15 | | | | 0.19 | | | | | | |
| 56 | S267Q/A327S | a | 0.44 | 0.22 | 0.52 | 0.11 | 1.14 | 0.16 | 1.08 | 0.18 | | | 0.88 | 0.22 | 0.71 | 0.51 | |
| 57 | S267L/A327S | a | 0.35 | 0.23 | 0.64 | 0.14 | 1.23 | 0.13 | 0.97 | 0.19 | 0.03 | 0.35 | 1.93 | 0.20 | 1.05 | 0.35 | 0.22 |
| | | | | | | | | | | | 0.27 | | | | | | |
| | | | | | | | | | | | <0.02 | | | | | | |
| 58 | A327L | a | 0.53 | 0.28 | 0.55 | 0.21 | 1.21 | 0.19 | 0.97 | 0.29 | | | 0.89 | 0.25 | 1.55 | 0.52 | |
| 59 | P329F | a | 0.33 | 0.25 | 0.93 | 0.16 | 1.86 | 0.09 | 1.91 | 0.17 | 0.05 | 0.33 | 2.29 | 0.18 | 0.61 | 0.29 | 0.51 |
| | | | | | | | | | | | 0.96 | | | | | | |
| | | | | | | | | | | | <0.02 | | | | | | |
| 60 | A330L | a p | 1.37 | 0.23 | 1.27 | 0.13 | 1.23 | 0.10 | 1.20 | 0.18 | 1.08 | 0.41 | 0.83 | 0.24 | 0.96 | 0.47 | 0.87 |
| | | | | | | | 0.38 | | | | 0.73 | | | | | | 1.92 |
| 61 | A330Y | a p | 1.18 | 0.23 | 1.08 | 0.15 | 1.62 | 0.09 | 1.11 | 0.20 | 1.04 | 0.47 | 2.00 | 0.24 | 0.94 | 0.41 | 0.64 |
| | | | | | | | 0.75 | | | | 1.64 | | | | | | 2.19 |
| 62 | I332D | a | 2.70 | 0.26 | 5.41 | 0.11 | 3.76 | 0.11 | 3.69 | 0.17 | 9.03 | 0.36 | 2.73 | 0.20 | 0.42 | 0.36 | 2.40 |
| | | | 3.95 | 0.10 | 8.79 | 0.23 | 8.32 | 0.39 | 7.11 | 0.29 | 2.85 | 2.82 | | | 1.75 | 0.39 | 0.34 |
| | | | | | | | 3.34 | | | | 17.8 | | | | | | 5.33 |
| 63 | N297S | a | 0.03 | 0.26 | 0.68 | 0.12 | 0.65 | 0.11 | 0.68 | 0.23 | <0.02 | | 1.77 | 0.23 | 0.38 | 0.55 | |

Figure 41E

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 64 | N297D | a | 0.22 | 0.23 | 0.62 | 0.19 | 1.30 | 0.09 | 1.07 | 0.16 | 1.00 | 0.36 | 1.01 | 0.22 | 0.63 | 0.32 | 0.77 |
| 65 | N297S/I332E | a | 0.18 | 0.24 | 0.52 | 0.24 | 0.89 | 0.13 | 0.69 | 0.20 | <0.02 | | 0.89 | 0.19 | 0.19 | 0.52 | |
| 66 | N297D/I332E | a | 1.41 | 0.23 | 0.60 | 0.23 | 0.94 | 0.20 | 0.80 | 0.29 | <0.02 | | 0.97 | 0.23 | 0.96 | 0.82 | |
| 67 | N297E/I332E | a | 0.45 | 0.24 | 0.54 | 0.15 | <0.02 | 0.17 | 0.76 | 0.24 | 0.08 | | 0.65 | 0.22 | 0.58 | 0.31 | |
| 68 | D265Y/N297D/I332E | a | 0.09 | 0.24 | 0.65 | 0.14 | 1.16 | 0.11 | 0.83 | 0.16 | <0.02 | | 2.78 | 0.21 | 0.25 | 0.33 | 0.27 |
| 69 | D265Y/N297D/T299L/I332E | a | 0.33 | 0.22 | 1.63 | 0.13 | 1.99 | 0.09 | 1.30 | 0.15 | 0.31 | 0.38 | 1.33 | 0.21 | 0.63 | 0.57 | 1.58 |
| 70 | D265F/N297E/I332E | a | 0.01 | 0.29 | 0.79 | 0.13 | 0.65 | 0.13 | 0.87 | 0.20 | 3.15 | 0.40 | 1.56 | 0.18 | 0.31 | 0.47 | 3.37 |
|    |                 |   | 0.37 | 0.36 | 0.80 | 0.26 | 1.68 | 0.32 | 2.64 | 0.29 | <0.02 | | 1.00 | 0.46 | 1.38 | 0.75 | |
| 71 | L328I/I332E | a | 2.79 | 0.11 | 1.44 | 0.17 | 7.61 | 0.24 | 6.59 | 0.25 | 5.65 | 0.71 | 1.14 | 0.47 | 2.21 | 0.55 | 1.46 |
|    |             |   | 3.95 | 0.13 | 1.22 | 0.23 | 11.60 | 0.27 | 7.87 | 0.94 | <0.02 | | 2.63 | 0.31 | 0.82 | 0.34 | 1.09 |

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 72 | L328Q/I332E | a | 2.87 | 0.12 | 1.76 | 0.13 | 11.30 | 0.29 | 6.52 | 0.23 | 11.11 | 0.69 | 0.91 | 0.48 | 4.29 | 0.65 | 0.17 |
|    |             |   | 2.15 | 0.14 | 1.05 | 0.16 | 15.13 | 0.29 | 7.38 | 0.93 | 12.61 | 0.22 | 1.90 | 0.31 | 0.88 | 0.33 | 0.11 |
|    |             |   |      |      |      |      |       |      |      |      | 7.03  |      |      |      |      |      |      |
| 73 | I332N | a | 1.64 | 0.20 | 2.96 | 0.14 | 1.43 | 0.32 | 1.82 | 0.26 | 1.93 | 0.71 | 0.98 | 0.52 | 3.20 | 0.54 | 1.19 |
|    |       |   | 0.82 | 0.12 | 1.52 | 0.19 | 1.26 | 0.57 |      | 46.97 | 1.69 | 0.11 | 2.35 | 0.33 | 0.71 | 0.33 | 0.26 |
|    |       |   |      |      |      |      |      |      |      |      | 1.54 |      |      |      |      |      |      |
| 74 | I332Q | a | 1.49 | 0.33 | 2.70 | 0.16 | 1.10 | 0.28 | 1.10 | 0.29 | 1.70 | 0.70 | 1.10 | 0.49 | 1.07 | 0.51 | 0.61 |
|    |       |   | 1.29 | 0.15 | 2.08 | 0.19 | 1.46 | 0.29 | 1.11 | 1.34 | 0.33 | 0.14 | 1.82 | 0.36 | 1.20 | 0.32 | 0.45 |
|    |       |   |      |      |      |      |      |      |      |      | 0.39 |      |      |      |      |      |      |
|    |       |   |      |      |      |      |      |      |      |      | 0.67 |      |      |      |      |      |      |
|    |       |   |      |      |      |      |      |      |      |      | 0.65 |      |      |      |      |      |      |
|    |       |   |      |      |      |      |      |      |      |      | 0.37 |      |      |      |      |      |      |
| 75 | V264T | a | 1.36 | 0.21 | 2.82 | 0.15 | 2.94 | 0.20 | 2.86 | 0.24 | 1.30 | 0.69 | 1.08 | 0.49 | 1.00 | 0.47 | 0.44 |
|    |       |   | 1.25 | 0.15 | 2.50 | 0.16 | 4.84 | 0.21 | 6.12 | 1.16 | 1.73 | 0.10 | 1.42 | 0.33 | 1.66 | 0.35 | 0.36 |
|    |       |   |      |      |      |      |      |      |      |      | 2.73 |      |      |      |      |      |      |
| 76 | V264F | a | 0.35 | 0.17 | 0.14 | 0.43 | 0.96 | 0.56 | 0.47 | 0.82 | 0.16 | 0.79 | 1.16 | 0.50 | 0.82 | 0.51 | 0.17 |
|    |       |   | 0.43 | 0.22 | 0.05 | 0.23 | 0.22 | 0.46 |      |      | 0.06 | 0.13 | 1.87 | 0.29 | 1.07 | 0.36 | 0.29 |

Figure 41F

| | | | | | | | | | | | | | | |
|---|---|---|---|---|---|---|---|---|---|---|---|---|---|---|
| 77 | V240I | a | 0.95<br>1.17 | 0.12<br>0.14 | 1.19<br>0.38 | 0.16<br>22.08 | 1.02<br>1.04 | 0.28<br>0.22 | 1.06<br>0.86 | 0.25<br>0.91 | 0.16<br>1.37<br>0.87<br>3.25 | 0.69<br>0.10 | 2.02 | 0.33 | 1.21<br>1.28 | 0.51<br>0.34 | 1.34<br>0.84 |
| 78 | V263I | a | 1.39 | 0.31 | 0.61 | 0.21 | 0.68 | 0.60 | 0.94 | 0.42 | 0.15<br>0.1 | 0.71 | 1.11 | 0.49 | 2.71 | 0.73 | 0.22 |
| 79 | V266I | a | 1.64 | 0.12 | 1.63 | 0.24 | 3.66 | 0.36 | 3.85 | 1.17 | 1.41<br>1.86 | 0.15 | 1.25 | 0.31 | 1.17 | 0.32 | 0.39 |
| 80 | T299A | a | 0.01 | 0.18 | 0.10 | 0.25 | 0.56 | 0.48 | 72.84 | 6.18 | 0.06<br>0.03 | 0.37 | 2.31 | 0.32 | 0.82 | 0.33 | 0.11 |
| 81 | T299S | a | 0.80 | 0.19 | 0.16 | 0.24 | 2.01 | 0.81 | | | 0.19<br>0.15 | 0.20 | 1.52 | 0.32 | 0.86 | 0.31 | 0.09 |
| 82 | T299V | a | 0.02 | 0.20 | 0.14 | 0.20 | 0.21 | 0.50 | 19.44 | 7.11 | 0.21<br><0.02 | 0.14 | 1.92 | 0.41 | 0.35 | 0.31 | 1.03 |
| 83 | N325Q | a | 0.65 | 0.17 | 0.07 | 0.23 | 0.26 | 0.42 | 62.17 | 9.35 | 0.04<br><0.02 | 0.57 | 1.92 | 0.34 | 0.69 | 0.34 | 0.16 |
| 84 | N325L | a | 0.42 | 0.25 | 0.04 | 0.42 | 1.46 | 0.39 | | 18.73 | 0.03<br><0.02 | 0.93 | 2.18 | 0.28 | 0.91 | 0.33 | 0.02 |
| 85 | N325I | a | 0.35 | 0.12 | 0.05 | 0.31 | 0.86 | 0.26 | 0.97 | 1.09 | 0.09<br><0.02 | 0.13 | 2.05 | 0.33 | 0.89 | 0.33 | 0.11 |
| 86 | S239D | atp | 4.40<br>2.63<br>1.86 | 0.25<br>0.13<br>0.13 | 1.74<br>2.29<br>2.17 | 0.57<br>0.13<br>0.22 | 6.21<br>11.42<br>9.04<br>4.47* | 0.29<br>0.17<br>0.37 | 5.13<br>3.83<br>10.98 | 0.45<br>0.80<br>0.28 | 6.29<br>23.17<br>2.55<br>11.64 | 0.20<br>0.10<br>2.82 | 3.54<br>0.96 | 0.42<br>0.46 | 1.73<br>0.80<br>1.07 | 0.48<br>0.31<br>0.41 | 1.01<br>2.03<br>0.28<br>2.60 |
| 87<br>88 | S239N<br>S239F | a<br>a | 0.28 | 0.17 | 0.02 | 1.14 | 0.33<br><0.02 | 0.68 | 51.36 | | <0.02<br>0.10<br>0.22 | 0.24 | 0.95 | 0.43 | 0.85 | 0.34 | 0.30 |
| 89 | S239D/I332D | a | 2.33 | 0.11 | 2.68 | 0.16 | 41.43 | 0.18 | 18.96 | 0.78 | 25.53<br>14.1 | 0.11 | 1.53 | 0.29 | 1.12 | 0.33 | 0.62 |
| 90 | S239D/I332E | atrcp | 3.89<br>9.42 | 0.12<br>0.13 | 11.57<br>15.46 | 0.15<br>0.19 | 128<br>70.44<br>19.71* | 0.26<br>0.37 | 145<br>84.57 | 0.99<br>0.29 | 192<br>27.74<br>56.1 | 0.10<br>2.82 | 1.88 | 0.35 | 1.01<br>1.22 | 0.36<br>0.36 | 1.50<br>0.39<br>2.85 |
| 91 | S239D/I332N | a | 1.97 | 0.12 | 4.95 | 0.16 | 14.13 | 0.20 | 8.14 | 0.82 | 10.79<br>7.19 | 0.12 | 1.16 | 0.35 | 0.76 | 0.31 | 0.76 |
| 92 | S239D/I332Q | a | 1.81 | 0.21 | 3.05 | 0.33 | 15.24 | 0.19 | 9.75 | 0.91 | 9.41<br>9.28 | 0.09 | 1.28 | 0.32 | 0.64 | 0.35 | 0.62 |
| 93 | S239E/I332D | a | 4.52 | 0.18 | 1.72 | 0.15 | 10.87 | 0.29 | 30.32 | 1.31 | 21.77 | 0.10 | 2.42 | 0.31 | 1.00 | 0.37 | 2.00 |

Figure 41G

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 94 | S239E/I332N | a | 1.62 | 0.12 | 1.81 | 0.16 | 4.55 | 0.23 | 6.01 | 1.16 | 9.33 / 16.86 / 11.93 | 0.13 | 2.00 | 0.32 | 0.88 | 0.33 | 3.71 |
| 95 | S239E/I332Q | a | 1.66 | 0.19 | 0.93 | 0.11 | 2.52 | 0.34 | 1.41 | 0.97 | 3.21 / 3.8 | 0.10 | 1.78 | 0.29 | 0.64 | 0.31 | 1.28 |
| 96 | S239N/I332D | a | 2.01 | 0.21 | 2.40 | 0.16 | 11.11 | 0.32 | 8.21 | 0.91 | 9.89 / 3.08 | 0.12 | 2.09 | 0.27 | 0.73 | 0.34 | 0.89 |
| 97 | S239N/I332E | a | 1.93 | 0.12 | 1.64 | 0.16 | 29.42 | 0.24 | 8.44 | 0.81 | 19.80 / 14.21 | 0.12 | 1.38 | 0.29 | 0.73 | 0.33 | 0.67 |
| 98 | S239N/I332N | a | 0.55 | 0.18 | 0.67 | 0.21 | 1.88 | 0.46 | 13.55 | | 0.55 / 0.43 | 0.15 | 1.08 | 0.33 | 0.84 | 0.35 | 0.29 |
| 99 | S239N/I332Q | a | 0.73 | 0.13 | 0.72 | 0.17 | 2.55 | 0.35 | 2.16 | | 0.59 / 0.56 | 0.11 | 1.88 | 0.29 | 0.73 | 0.33 | 0.23 |
| 100 | S239Q/I332D | a | 1.40 | 0.13 | 1.08 | 0.14 | 5.76 | 0.36 | 5.26 | | 2.33 / 5.05 | 0.11 | 1.89 | 0.29 | 0.74 | 0.35 | 0.40 |
| 101 | S239Q/I332N | a | 0.52 | 0.25 | 0.80 | 0.15 | 1.55 | 0.50 | 10.71 | | 0.32 / 0.39 | 0.09 | 2.68 | 0.30 | 1.11 | 0.35 | 0.21 |
| 102 | S239Q/I332Q | a | 0.86 | 0.22 | 0.69 | 0.12 | 1.51 | 0.42 | | | 0.42 / 0.59 | 0.21 | 1.41 | 0.21 | 1.04 | 0.14 | 0.28 |
| 103 | K326E | a p | 3.17 / 3.41 | 0.17 / 0.11 | 1.55 / 0.79 | 0.13 / 0.24 | 4.15 / 4.99 | 0.47 / 0.41 | 3.68 | 0.31 | 8.07 / 0.25 / 3.85 | 0.34 / 2.82 | 0.96 | 0.18 | | | 1.95 / 0.05 |
| 104 | Y296D | a | 1.28 | 0.18 | 0.88 | 0.10 | 1.28 | 0.55 | | | 0.86 / 0.62 | 0.21 | 0.83 | 0.21 | 0.82 | 0.38 | 0.67 |
| 105 | Y296N | a | 0.84 | 0.23 | 0.68 | 0.13 | 1.30 | 0.41 | | | 0.21 / 0.29 | 0.21 | 0.67 | 0.20 | 0.50 | 0.09 | 0.16 |
| 106 | F241Y/F243Y/V262T/V264T/N297D/I332E | a | 0.38 | 0.25 | 0.11 | 0.23 | | | | | 0.25 | 0.23 | 1.35 | 0.22 | 0.25 | 0.09 | |
| 107 | A330Y/I332E | a | 4.49 | 0.18 | 4.81 | 0.13 | 10.81 / 4.4 | 0.36 | | | 0.15 / 68.79 / 12.02 | 0.20 | 0.74 | 0.18 | 1.53 | 0.09 | 6.37 / 2.73 |
| 108 | V264I/A330Y/I332E | a | 3.89 | 0.19 | 1.17 | 0.07 | 4.18 | 0.35 | | | 22.76 | 0.20 | 0.61 | 0.17 | 0.85 | 0.08 | 5.44 |

Figure 41H

| | | | | | | | | | | | | | |
|---|---|---|---|---|---|---|---|---|---|---|---|---|---|
| 109 | A330L/I332E | a | 4.94 | 0.17 | 1.28 | 0.09 | 3.54 3.15 2.03 | 0.35 | 12 55.42 10.34 | 0.20 | 0.72 | 0.18 | 1.50 | 0.20 |
| 110 | V264I/A330L/ I332E | a | 4.31 | 0.22 | 0.66 | 0.08 | 2.73 | 0.34 | 24.96 | 0.20 | 1.12 | 0.21 | 1.13 | 0.17 | 3.39 17.59 5.09 9.13 |
| 111 | L234D | a | 0.36 | 0.30 | 0.40 | 0.13 | 1.79 4.95 | 0.35 | 11.15 3.89 0.21 | 0.21 | 0.96 | 0.21 | 1.54 | 0.16 | 6.23 0.79 |
| 112 | L234E | a | 0.42 | 0.29 | 0.24 | 0.08 | 4.78 2.21 | 0.36 | 1.86 1.34 | 0.21 | 1.19 | 0.21 | 1.25 | 0.11 | 0.39 0.61 |
| 113 | L234N | a | 0.10 | 0.32 | 0.19 | 0.11 | 2.05 1.39 | 0.41 | 0.49 0.56 | 0.22 | 1.18 | 0.33 | 1.06 | 0.13 | 0.24 0.40 0.15 |
| 114 | L234Q | a | 0.28 | 0.27 | 0.28 | 0.09 | 3.53 | 0.38 | 0.52 0.37 | 0.20 | 0.94 | 0.18 | 0.97 | 0.11 | 0.14 |
| 115 | L234T | a | 0.49 | 0.26 | 0.20 | 0.10 | 1.79 | 0.43 | 0.26 0.35 | 0.22 | 0.56 | 0.21 | 0.99 | 0.08 | 0.18 |
| 116 | L234H | a | 0.11 | 0.34 | 0.29 | 0.08 | 1.56 | 0.49 | 0.27 0.33 | 0.21 | 0.65 | 0.19 | 1.48 | 0.08 | 0.41 1.31 |
| 117 | L234Y | a p | 1.45 | 0.24 | 0.51 | 0.09 | 1.93 1.08 | 0.39 | 0.80 1.42 | 0.21 | 0.99 | 0.22 | 1.90 | 0.21 | 0.50 1.36 |
| 118 | L234I | a | 1.20 | 0.27 | 0.78 | 0.08 | 2.57 1.14 | 0.40 | 1.30 1.55 | 0.21 | 1.28 | 0.28 | 1.26 | 0.12 | 0.41 |
| 119 | L234V | a | 1.66 | 0.26 | 0.78 | 0.08 | 3.94 | 0.35 | 1.61 0.38 | 0.22 | 0.64 | 0.18 | 1.45 | 0.13 | 0.15 |
| 120 | L234F | a | 0.74 | 0.26 | 0.47 | 0.07 | 2.36 | 0.37 | 0.37 0.3 | 0.21 | 0.72 | 0.21 | 1.46 | 0.13 | 0.29 0.46 0.32 |
| 121 | L235D | a p | | | 0.76 | 0.09 | 5.48 3.63 | 0.37 | 1.61 1.66 | 0.20 | 1.05 | 0.17 | 0.90 | 0.15 | 0.23 |
| 122 | L235S | a | | | 0.27 | 0.08 | 2.99 | 0.37 | 0.95 1.25 | 0.21 | 0.66 | 0.21 | 1.51 | 0.09 | 0.73 |
| 123 | L235N | a | 0.06 | 0.37 | 0.21 | 0.15 | 1.59 | 0.46 | 0.37 0.4 | 0.22 | 0.70 | 0.20 | 1.32 | 0.09 | 0.60 |
| 124 | L235Q | a | 0.09 | 0.28 | 0.30 | 0.10 | 1.40 | 0.44 | 1.02 0.51 | 0.21 | 0.85 | 0.22 | 1.67 | 0.14 | 0.17 |
| 125 | L235T | a | 0.13 | 0.26 | 0.53 | 0.11 | 3.55 | 0.34 | 2.15 0.52 | 0.21 | 1.06 | 0.23 | 1.65 | 0.38 | |
| 126 | L235H | a | 0.06 | 0.37 | 0.51 | 0.09 | 1.77 | 0.37 | 0.30 | 0.23 | 0.54 | 0.19 | 0.96 | 0.14 | |

Figure 41I

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 127 | L235Y | a / p | 0.24 / 0.02 | 0.31 / 0.55 | 3.32 / 0.70 | 0.08 / 0.20 | 4.44 / 1.39 | 0.35 / 0.64 |  |  | 0.41 / 1.74 | 0.23 / 2.82 |  |  | 1.02 / 0.78 | 0.10 / 0.39 | 0.39 / 0.04 |
| 128 | L235I | a | 0.16 | 0.26 | 0.67 | 0.10 |  |  | 1.15 | 0.38 | 0.05 / 1.19 | 0.26 | 0.68 | 0.21 | 0.81 | 0.10 | 0.12 |
| 129 | L235V | a | 0.16 / 0.11 | 0.31 / 0.21 | 0.43 / 0.23 | 0.10 / 0.22 | 10.15 / 1.24 / 0.94 | 0.55 | | | 1.47 / 1.1 | 0.22 | 0.94 | 0.26 | 1.31 / 0.86 | 0.17 / 0.45 | 1.18 / 1.17 |
| 130 | L235F | a |  |  | 1.25 | 0.17 | 1.62 / 3.53 / 1.47 | 0.45 / 0.52 |  |  | 0.58 / 0.05 / 0.48 | 0.22 / 2.82 | 0.71 | 0.21 | 0.80 | 0.11 | 0.07 |
| 131 | S239T | a | 0.88 | 0.17 | 0.91 | 0.13 |  |  | 0.57 | 1.26 | 0.56 / 0.73 | 0.22 | 0.84 | 0.25 | 1.12 | 0.10 | 0.35 |
| 132 | S239H | a | 0.08 | 0.10 | 0.11 | 0.38 | 0.20 | 0.65 |  |  | 0.90 / 1.34 | 0.21 | 0.88 | 0.24 | 0.72 | 0.11 | 0.21 |
| 133 | S239Y | a | 0.19 | 0.12 | 0.12 | 0.34 | 0.69 | 0.48 | 0.23 | 1.24 | 0.2 | 2.04 | 1.70 | 0.23 | 1.08 | 0.13 | 0.61 |
| 134 | V240A | a | 0.80 | 0.10 | 0.62 | 0.28 | 1.45 / 0.14 | 0.39 | 1.88 / 1.02 | 0.42 / 0.44 | 0.21 / 1.49 / 0.7 | 0.20 | 0.91 | 0.22 | 0.93 | 0.11 |  |
| 135 | V240T | a | 0.92 | 0.12 | 0.67 | 0.30 | 1.20 | 0.46 | 0.13 | 0.97 | 1.16 | 0.16 | 0.78 | 0.23 | 0.46 | 0.69 | 1.03 / 5.00 |
| 136 | V240M | a | 1.60 | 0.07 | 0.67 | 0.30 | 0.94 | 0.55 | 0.68 | 0.68 | 0.86 | 0.22 | 0.74 | 0.21 | 0.93 | 0.09 | 0.96 / 0.92 |
| 137 | V263A | a | 1.05 | 0.14 | 0.45 | 0.31 | 1.38 / 0.04 | 1.64 | 1.02 | 0.67 | 2.06 / 0.54 | 0.26 | 1.35 | 0.25 | 0.91 | 0.09 | 1.49 / 12.93 |
| 138 | V263T | a | 1.00 | 0.08 | 1.57 | 0.27 | 1.20 | 0.39 |  |  | 2.67 / 0.43 | 0.32 | 0.59 | 0.20 | 0.93 | 0.15 | 2.23 |

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 139 | V263M | a | 0.69 | 0.07 | 0.41 | 0.26 | 1.69 | 0.41 | 1.65 | 0.38 | 0.05 | 3.66 | 1.32 | 0.26 | 0.58 | 0.19 | 0.25 |
| 140 | V264M | a | 0.64 | 0.08 | 0.30 | 0.29 | 0.83 | 0.44 | 0.94 | 0.87 | 0.21 / 0.26 | 0.41 | 0.73 | 0.21 | 0.63 | 0.11 |  |
| 141 | V264Y | a | 0.51 | 0.08 | 0.32 | 0.29 | 0.57 / 0.27 | 0.44 | 0.81 | 0.59 | 0.30 / 1.02 | 0.29 | 1.19 | 0.22 | 0.75 | 0.12 | 0.52 / 3.78 |
| 142 | V266A | a | 0.61 | 0.12 | 0.30 | 0.28 | 0.76 | 0.64 | 0.06 | 1.67 | 0.61 / <0.02 | 0.25 | 0.95 | 0.22 | 0.71 | 0.12 | 0.80 |
| 143 | V266T | a | 0.28 | 0.12 | 0.10 | 0.32 | 1.16 | 0.48 | 0.18 | 1.05 | 0.45 |  | 1.21 | 0.24 | 0.53 | 0.14 |  |

Figure 41J

| # | Mutation | | | | | | | | | | | | | | | | |
|---|---|---|---|---|---|---|---|---|---|---|---|---|---|---|---|---|---|
| 144 | V266M | a | 1.32 / 1.11 | 0.09 / 0.15 | 0.43 / 0.19 | 0.29 / 0.23 | 16.45 / 2.63 | 0.45 / 0.40 | 3.32 / 2.57 | 0.45 / 0.30 | 0.01 / 0.62 | 7.83 / 2.84 | 0.83 | 0.21 | 0.71 / 0.86 | 0.11 / 0.45 | 0.01 |
| 145 | E269H | a | 0.16 | 0.13 | 0.18 | 0.31 | 0.07 | 1.25 | 0.28 | 0.92 | | 5.90 | 1.11 | 0.25 | 0.72 | 0.12 | 0.34 |
| 146 | E269Y | a | 0.51 | 0.07 | 0.48 | 0.30 | 0.79 | 0.54 | 0.37 | 0.94 | <0.02 | 0.25 | 0.79 | 0.29 | 0.76 | 0.11 | |
| 147 | E269F | a | 0.21 | 0.07 | 0.20 | 0.30 | 0.48 | 0.56 | 0.51 | 1.33 | 0.27 | | 0.94 | 0.26 | 0.74 | 0.15 | |
| 148 | E269R | a | 0.07 | 0.11 | 0.07 | 0.28 | 0.13 | 1.73 | 0.06 | 2.21 | 0.12 | 1.97 | 1.15 | 0.26 | 0.72 | 0.15 | |
| 149 | Y296S | a | 0.63 | 0.08 | 0.71 | 0.28 | 0.51 | 0.49 | 0.64 | 1.31 | 0.16 | | 1.21 | 0.26 | 0.67 | 0.13 | |
| 150 | Y296T | a | 0.72 | 0.09 | 0.71 | 0.25 | 0.97 | 0.39 | 0.58 | 0.80 | 0.05 | | 1.07 | 0.20 | 0.60 | 0.15 | 1.08 |
| 151 | Y296L | a | 0.81 | 0.10 | 0.41 | 0.29 | 1.15 | 0.43 | 0.17 | 1.20 | 0.12 | 3.07 | 0.53 | 0.26 | 0.62 | 0.12 | 0.67 |
| 152 | Y296I | a | 0.87 | 0.11 | 0.43 | 0.27 | 0.52 | 0.85 | 0.20 | 1.02 | <0.02 | 0.19 | 1.51 | 0.25 | 0.56 | 0.11 | |
| 153 | S298H | a | 0.58 | 0.10 | 0.23 | 0.31 | 0.09 | 1.22 | 0.18 | 0.86 | 1.24 / 0.22 | 0.24 | 1.22 | 0.22 | 0.60 | 0.10 | |
| 154 | T299H | a | 0.03 | 0.09 | 0.16 | 0.29 | 0.44 | 0.48 | 0.33 | 1.23 | 0.35 / 0.09 | 1.02 | 1.65 | 0.26 | 0.57 | 0.15 | 1.47 |
| 155 | A330V | a p | 1.12 | 0.09 | 0.41 | 0.28 | 0.37 | 0.58 | 0.79 | 1.13 | 0.27 | 0.20 | 0.81 | 0.28 | 0.75 | 0.16 | 1.90 |
| 156 | A330I | a p | 1.14 | 0.09 | 0.35 | 0.28 | 0.21 / 0.02 | 0.68 | 0.27 | 0.74 | <0.02 / 0.55 / 0.43 | 0.19 | 1.33 | 0.28 | 0.61 | 0.19 | 85.50 |
| 157 | A330F | a | 1.65 | 0.12 | 0.89 | 0.29 | 1.19 | 0.47 | 0.32 | 0.87 | 0.40 / 1.71 | 0.19 | 1.59 | 0.22 | 0.98 | 0.12 | 1.70 |
| 158 | A330R | a | 0.45 / 0.46 | 0.09 / 0.14 | 1.42 / 1.16 | 0.36 / 0.22 | 1.01 / 1.05 | 0.53 / 0.39 | 0.90 / 1.63 | 0.45 / 0.35 | 2.02 / 0.6 | 0.22 / 2.82 | 0.74 | 0.20 | 0.58 / 0.95 | 0.14 / 0.42 | 0.45 / 0.07 |
| 159 | A330H | a p | 1.09 | 0.12 | 1.16 | 0.33 | 2.09 | 0.99 | 1.62 | 0.48 | 0.45 / 0.07 / <0.02 / 1.41 | 0.16 | 0.81 | 0.24 | 0.91 | 0.14 | 0.67 |
| 160 | N325D | a | 1.20 / 0.87 | 0.11 / 0.12 | 0.14 / 0.14 | 0.34 / 3.34 | 0.38 / 1.62 | 0.99 / 0.44 | 0.63 | 0.54 | 0.02 / 0.41 / 0.52 | 2.82 | 0.79 | | 0.68 / 0.78 | 0.11 / 0.39 | 0.01 |

Figure 41K

| Variant | Substitution(s) | Context | FcyRI Fold | FcyRI Conf | FcyRIIa Fold | FcyRIIa Conf | FcyRIIb Fold | FcyRIIb Conf | FcyRIIc Fold | FcyRIIc Conf | FcyRIIIa Fold | FcyRIIIa Conf | C1q Fold | C1q Conf | FcRn Fold | FcRn Conf | IIIa:IIb |
|---|---|---|---|---|---|---|---|---|---|---|---|---|---|---|---|---|---|
| 161 | N325E | a | 1.34 | 0.10 | 0.09 | 0.38 | 0.05 | 1.35 | 0.03 | 2.06 | <0.02 | 7.72 | 0.86 | 0.23 | 0.55 | 0.11 | |
| 162 | N325A | a | 0.31 | 0.06 | | | | | 0.05 | 3.84 | 0.11 | | 1.27 | 0.14 | 0.74 | 0.08 | |
| 163 | N325T | a | 0.83 | 0.05 | 0.41 | 0.37 | | | 0.13 | 3.68 | 0.93 / 1.1 | 0.18 | 1.35 | 0.16 | 1.23 | 0.08 | |
| 164 | N325V | a | 0.61 | 0.08 | 0.42 | 0.36 | | | 0.16 | 3.68 | 0.66 / 0.48 | 0.17 | 1.24 | 0.15 | 1.29 | 0.08 | |
| 165 | N325H | a | 0.52 | 0.08 | 0.25 | 2.55 | | | 0.13 | 3.68 | 0.64 / 0.73 | 0.22 | 1.28 | 0.15 | 0.03 | 1.97 | |
| 166 | L328D/I332E | a | 3.56 | 0.05 | 1.64 | 0.29 | | | 1.38 | 3.69 | 2.01 / 1.34 | 0.37 | 1.97 | 0.20 | 1.54 | 0.10 | |
| 167 | L328E/I332E | a | 2.02 | 0.15 | 0.94 | 0.34 | | | 1.39 | 3.66 | 0.95 / 0.2 | 0.37 | 2.59 | 0.20 | 1.44 | 0.11 | |
| 168 | L328N/I332E | a | 2.69 | 0.05 | 0.32 | 0.33 | | | 2.29 | 3.69 | 10.24 / <0.02 / 0.7 | 0.24 | 1.12 | 0.16 | 1.18 | 0.14 | |
| 169 | L328Q/I332E | a | 3.12 | 0.07 | 0.91 | 0.32 | | | 8.43 | 3.69 | 17.20 / 2.06 | 0.23 | 1.34 | 0.15 | 0.93 | 0.10 | |
| 170 | L328V/I332E | a | | | | | | | 14.23 | 3.66 | 19.76 / 1.1 | 10.55 | 2.36 | 0.39 | 0.99 | 0.15 | |
| 171 | L328T/I332E | a | 2.70 | 0.07 | 1.46 | 0.35 | | | 0.44 | 3.67 | 1.63 / <0.02 | 0.20 | 1.39 | 0.15 | 1.16 | 0.09 | |
| 172 | L328H/I332E | a | 1.26 | 0.08 | 0.32 | 0.36 | | | | | | | | | | | |
| 173 | L328I/I332E | a | | | | | | | | | 3.49 | | | | | | |
| 174 | L328A | a | 0.86 | 0.05 | 10.48 | 0.34 | | | 0.49 | 3.67 | 3.81 / 0.2 | 0.30 | 1.23 | 0.19 | 1.32 | 0.09 | |
| 175 | I332T | a | 1.58 | 0.05 | 2.82 | 0.30 | | | 0.74 | 3.66 | 3.18 / 0.72 | 0.38 | 1.15 | 0.22 | 1.02 | 0.09 | |
| 176 | I332H | a | 1.19 | 0.06 | 2.12 | 0.34 | | | 0.73 | 3.71 | 1.05 / 0.46 | 0.14 | 2.13 | 0.14 | 1.24 | 0.17 | |
| 177 | I332Y | a | 1.88 | 0.07 | 4.18 | 0.29 | | | 0.63 | 3.68 | 2.14 / 0.76 | 0.16 | 1.53 | 0.21 | 1.43 | 0.17 | |
| 178 | I332A | a | 1.60 | 0.10 | 3.01 | 0.31 | | | 0.48 | 3.67 | 1.97 / 0.89 | 0.20 | 1.57 | 0.17 | 0.96 | 0.13 | |

Figure 41L

| | | | | | | | | | | | | | | |
|---|---|---|---|---|---|---|---|---|---|---|---|---|---|---|
| 179 | S239E/V264I/I332E | a | 4.75 | 0.06 | 1.73 | 0.40 | 2.58 | 3.66 | 142 | 1.57 | 1.45 | 0.18 | 1.07 | 0.24 |
| 180 | S239Q/V264I/I332E | a | 2.44 | 0.07 | 0.50 | 0.41 | 0.45 | 3.66 | 15.46 | 0.24 | 1.07 | 0.16 | 0.97 | 0.16 |
| 181 | S239E/V264I/A330Y/I332E | a | 7.52 | 0.12 | 1.80 | 0.32 | 4.69 | 3.66 | 21.84 2.14 | 0.27 | 2.05 | 2309 | 2.36 | 0.85 |
| 182 | S239E/V264I/S298A/A330Y/I332E | a | 6.80 | 0.11 | 0.32 | 0.35 | 0.73 | 3.67 | 318 8.53 | 0.24 | 1.98 | 0.23 | 1.22 | 0.10 |
| 183 | S239D/N297D/I332E | a | 2.82 | 0.09 | | | 0.06 | 3.67 | 862 | 0.37 | 3.14 | 0.29 | 0.76 | 0.07 |
| 184 | S239E/N297D/I332E | a | 2.27 | 0.06 | | | | | 0.28 | 0.18 | 2.48 | 0.25 | 0.76 | 0.20 |
| 185 | N297D/I332E/S239D/D265V | a | 0.11 | 0.11 | | | 0.31 | 4.45 | 0.28 0.06 0.03 | 0.13 | 7.68 | 0.24 | 0.45 | 0.15 |
| 186 | S239D/D265I/N297D/I332E | a | 0.10 | 0.09 | | | 0.05 | 3.74 | 0.44 0.01 | 0.24 | 2.78 | 0.20 | 0.47 | 0.09 |
| 187 | S239D/D265L/N297D/I332E | a | 0.20 | 0.09 | | | 0.17 | 3.67 | 0.10 <0.02 | 0.35 | 1.47 | 0.13 | 0.62 | 0.08 |
| 188 | S239D/D265F/N297D/I332E | a | 0.19 | 0.09 | | | 0.08 | 3.69 | 0.54 <0.02 | 0.14 | 2.96 | 0.24 | 0.52 | 0.13 |
| 189 | S239D/D265Y/N297D/I332E | a | 0.09 | 0.09 | | | 0.12 | 3.68 | 0.39 0.02 | 0.23 | 2.16 | 0.23 | 1.26 | 0.24 |
| 190 | S239D/D265H/N297D/I332E | a | 0.35 | 0.07 | 0.24 | 0.85 | 0.11 | 3.70 | 0.51 0.04 | 0.42 | 8.28 | 0.25 | 0.59 | 0.07 |
| 191 | S239D/D265T/N297D/I332E | a | | | | | | | 0.51 | | | | | |

Figure 41N

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 209 | S239D/A330L/I332E | a t r c p | 5.54 | 0.21 | 2.52 | 0.33 | 25.98 | | 31.11 | 5.64 | | 6.50 | | | | | 18.48 |
| 210 | S239N/I332E/A330L | a | | | | | 7.5 | | | | 139 | | | | | | |
| 211 | I332E/V264I/S298A | t | | | | | | | | | 12.95 | | | | | | |
| 212 | I332E/S239D/S298A | t p | | | | | 6.16 | | | | 16.5 | | | | | | 47.92 |
| 213 | I332E/S239N/S298A | t | | | | | 5.15 | | | | 295 | | | | | | 6.24 |
| 214 | S239D/I332E/V264I | t | | | | | 14.39 | | | | 32.14 | | | | | | 2.54 |
| 215 | S239D/I332E/V264I/S298A | t | | | | | | | | | 36.58 | | | | | | |
| 216 | S239D/I332E/V264I/A330L | t | | | | | | | | | | | | | | | |
| 217 | L328N | a | | | | | | | | | 0.59 | | | | | | |
| 218 | L328H | a | | | | | | | | | <0.02 | | | | | | |
| 219 | S239D/I332E/A330I | a p | | | | | | | | | 59.1 | | | | | | |
| 220 | N297D/I332E/S239D/A330L | a | | | | | | | | | | | | | | | |
| 221 | P230A | t | 1.28 | 0.13 | 0.99 | 0.18 | 1.13 | 39.94 | | | 0.55 | 0.20 | 2.53 | 0.25 | 0.77 | 0.19 | 0.49 |
|     |       |   |      |      |      |      |      |       | | | 1.09 | | | | | | |
| 222 | E233D | t | 0.85 | 0.15 | 0.81 | 0.16 | 1.05 | 1.12 | | | 0.64 | 0.18 | 2.66 | 0.36 | 0.76 | 0.23 | 0.61 |
|     |       |   |      |      |      |      |      |      | | | 0.85 | | | | | | |
| 223 | P230A/E233D | t | 2.03 | 0.22 | 0.76 | 0.13 | | | | | 0.54 | 0.17 | 2.04 | 0.27 | 0.84 | 0.18 | |
|     |       |   |      |      |      |      |      |      | | | 0.92 | | | | | | |
| 224 | P230A/E233D/I332E | t | 4.92 | 0.16 | 0.97 | 0.16 | 2.01 | 0.90 | 1.36 | 75.92 | 7.81 | 0.14 | 3.64 | 0.35 | 0.78 | 0.16 | 3.88 |
|     |       |   |      |      |      |      |      |      |      |       | 1.87 | | | | | | |
| 225 | S267T | t | 0.93 | 0.14 | 0.15 | 0.32 | 1.06 | 1.26 | 1.01 | 450 | 0.86 | 0.18 | 3.09 | 0.28 | 0.75 | 0.19 | 0.81 |
| 226 | S267H | t | 0.34 | 0.15 | 0.16 | 0.23 | 0.93 | 14.97 | 4.78 | 75.92 | 0.34 | 0.23 | 3.26 | 0.28 | 0.57 | 0.23 | 0.36 |
| 227 | S267D | t p | 1.41 | 0.13 | 0.75 | 0.09 | 5.02 | 0.89 | | | 1.45 | 0.11 | 2.88 | 0.18 | 1.00 | 0.20 | 0.29 |

Figure 41O

| | | | | | | | | | | | | | | |
|---|---|---|---|---|---|---|---|---|---|---|---|---|---|---|
| 228 | S267N | t | 0.72 | 0.20 | 0.08 | 0.71 | | | | 0.27 | 0.19 | 3.18 | 0.34 | 0.85 | 0.16 |
| 229 | E269T | t | 0.32 | 0.16 | 0.20 | 0.31 | | | | 0.14 | 0.60 | 1.17 | 0.20 | 0.92 | 0.18 |
| 230 | E269L | t | 0.28 | 0.15 | 0.16 | 0.24 | | | | <0.02 | | 1.83 | 0.29 | 0.75 | 0.21 |
| 231 | E269N | t | 0.19 | 0.15 | 0.12 | 0.38 | | | | <0.02 | | 1.36 | 0.27 | 0.65 | 0.22 |
| 232 | D270Q | t | 0.51 | 0.22 | 0.42 | 0.19 | | | | 0.30 | 0.19 | 2.41 | 0.24 | 0.76 | 0.18 |
| 233 | D270T | t | 0.33 | 0.22 | 0.16 | 0.23 | | | | <0.02 | | 2.50 | 0.27 | 0.84 | 0.17 |
| 234 | D270H | t | 0.33 | 0.18 | 0.24 | 0.17 | | | | 0.16 | 1.68 | 1.45 | 0.28 | 0.85 | 0.19 |
| 235 | E272S | t | 1.04 | 0.20 | 0.53 | 0.25 | 1.15 | 4.37 | 1.07 | 6.40 | <0.02 | 1.28 | 0.31 | 0.90 | 0.23 | 0.34 |
| 236 | E272K | t | 0.79 | 0.19 | 0.55 | 0.10 | 1.85 | 0.30 | 1.33 | 0.35 | 0.39 | 0.20 | 1.09 | 0.30 | 0.96 | 0.18 | 1.84 |
| 237 | E272I | tp | 0.83 | 0.16 | 0.72 | 0.12 | 1.04 | 0.40 | 1.11 | 2.20 | 3.41 | 0.19 | 1.48 | 0.31 | 1.05 | 0.20 | 4.79 |
| 238 | E272Y | t | 0.58 | 0.16 | 0.80 | 0.09 | | | | | 4.96 | 0.16 | 1.68 | 0.32 | 2.08 | 0.26 | |
| | | | | | | | | | | 0.78 | 0.17 | | | | | |
| 239 | V273I | t | 0.98 | 0.17 | 0.55 | 0.09 | 2.20 | 0.31 | 1.62 | 0.34 | 8.7 | 0.17 | 1.11 | 0.37 | 0.95 | 0.28 | 0.27 |
| | | | | | | | | | | 0.60 | | | | | | |
| 240 | K274T | t | 1.01 | 0.24 | 0.82 | 0.08 | | | | | 0.79 | | | | | | |
| | | | | | | | | | | 0.90 | 0.19 | 1.55 | 0.33 | 1.08 | 0.42 | |
| 241 | K274E | tp | 1.46 | 0.13 | 0.86 | 0.11 | 1.17 | 0.29 | 1.10 | 13.52 | 1.41 | | | | | |
| | | | | | | | | | | 1.00 | 0.12 | 2.73 | 0.37 | 1.05 | 0.27 | 0.86 |
| 242 | K274R | tp | 0.95 | 0.16 | 0.77 | 0.11 | | | 1.07 | 0.50 | 6.11 | | | | | |
| | | | | | | | | | | 0.71 | 0.17 | 2.22 | 0.35 | 0.65 | 0.23 | |
| 243 | K274L | t | 1.17 | 0.15 | 0.91 | 0.11 | 1.71 | 0.30 | 0.85 | 0.56 | 1.41 | | | | | |
| | | | | | | | | | | 4.35 | 0.15 | 1.15 | 0.30 | 0.51 | 0.24 | 2.54 |
| 244 | K274Y | tp | 1.02 | 0.16 | 0.79 | 0.11 | 1.09 | 0.37 | 1.41 | 0.37 | 1.09 | | | | | |
| | | | | | | | | | | 0.93 | 0.13 | 1.42 | 0.33 | 0.63 | 0.25 | 0.85 |
| 245 | F275W | t | 1.16 | 0.17 | 0.57 | 0.10 | 1.15 | 0.37 | 1.16 | 10.90 | 1.06 | | | | | |
| | | | | | | | | | | 1.51 | 0.14 | 1.49 | 0.34 | 0.90 | 0.23 | 1.31 |
| 246 | N276S | tp | 0.84 | 0.15 | 0.62 | 0.09 | 0.97 | 0.46 | 1.09 | 0.48 | 1.11 | | | | | |
| | | | | | | | | | | 0.71 | 0.19 | 2.00 | 0.32 | 0.67 | 0.21 | 0.74 |
| 247 | N276E | t | 2.07 | 0.15 | | | 1.29 | 2.40 | 1.24 | 25.25 | 0.41 | 0.19 | | | | | 0.19 |
| | | | | | | | | | | 0.24 | | | | | | |
| 248 | N276R | t | 0.84 | 0.22 | 0.64 | 0.11 | 0.87 | 0.50 | 1.26 | 21.80 | 0.87 | 0.19 | 1.43 | 0.35 | 1.19 | 0.31 | 0.59 |
| | | | | | | | | | | 0.51 | | | | | | |

Figure 41P

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 249 | N276L | t p | 0.65 | 0.29 | 0.66 | 0.10 | 0.94 | 0.41 | 1.10 | 10.72 | 0.66 / 0.52 / 1.07 | 0.22 | 1.37 | 0.36 | 1.21 | 0.43 | 0.56 |
| 250 | N276Y | t | 1.23 | 0.16 | 1.18 | 0.09 | 3.02 | 0.29 | 2.97 | 0.31 | 3.47 / 0.56 | 0.10 | 1.34 | 0.31 | 0.74 | 0.18 | 1.15 |
| 251 | Y278T | t | 0.73 | 0.17 | 0.35 | 0.10 | 0.71 | 0.55 | 1.08 | 2.80 | 0.34 / 1.87 | 0.18 | 1.55 | 0.30 | 0.55 | 0.18 | 0.48 |
| 252 | Y278E | t p | 2.11 | 0.15 | 0.59 | 0.14 | 1.09 | 0.35 | 1.04 | 0.76 | 0.54 / 0.9 | 0.13 | 1.43 | 0.33 | 0.61 | 0.30 | 0.49 |
| 253 | Y278K | t | 0.63 | 0.24 | 0.45 | 0.14 | 1.12 | 4.55 | 1.02 | 5.44 | 0.37 | 0.17 | 1.18 | 0.30 | 0.78 | 0.20 | 0.34 |
| 254 | Y278W | t | 0.65 | 0.15 | 0.45 | 0.10 | 0.83 | 0.93 | 1.06 | 15.47 | 0.31 / 0.41 | 0.16 | 1.40 | 0.35 | 0.74 | 0.22 | 0.38 |
| 255 | E283R | t | 0.67 | 0.14 | 0.62 | 0.08 | 0.91 | 0.70 | 1.11 | 3.27 | 0.49 / 0.67 | 0.14 | 1.36 | 0.32 | 1.86 | 0.18 | 0.54 |
| 256 | V302I | t | 0.75 | 0.20 | 0.66 | 0.11 | 1.20 | 0.41 | 1.08 | 0.44 | 0.81 / 1.01 | 0.15 | 1.13 | 0.35 | 2.44 | 0.24 | 0.68 |
| 257 | E318R | t | 0.71 | 0.35 | 0.57 | 0.13 | 1.14 | 6.22 |  |  | 0.50 / 1.06 | 0.19 | 1.83 | 0.34 | 1.17 | 0.36 | 0.44 |
| 258 | K320T | t p | 1.37 | 0.41 | 1.10 | 0.16 | 1.23 | 0.29 | 0.91 | 0.33 | 1.53 | 0.13 | 1.12 | 0.34 | 0.56 | 0.19 | 1.25 |
| 259 | K320D | t | 2.29 | 0.14 | 0.79 | 0.19 | 1.37 | 0.29 | 1.06 | 0.35 | 0.70 | 0.21 | 1.80 | 0.35 | 0.58 | 0.19 | 0.51 |
| 260 | K320I | t p | 1.87 | 0.13 | 0.99 | 0.15 | 1.65 | 0.27 | 1.21 | 0.37 | 1.84 | 0.20 | 1.69 | 0.36 | 0.72 | 0.25 | 1.12 |
| 261 | K322T | t p | 1.64 | 0.16 | 0.56 | 0.16 | 1.14 | 0.32 | 1.08 | 1.26 | 0.94 | 0.18 | 1.48 | 0.31 | 0.83 | 0.21 | 0.83 |
| 262 | K322H | t p | 1.20 | 0.17 | 0.66 | 0.14 | 0.92 | 0.52 | 1.20 | 3.35 | 0.71 | 0.13 | 1.32 | 0.36 | 0.77 | 0.22 | 0.77 |
| 263 | V323I | t | 0.90 | 0.13 | 0.74 | 0.13 | 1.64 | 0.33 | 1.29 | 0.35 | 0.97 / 0.83 | 0.12 | 1.81 | 0.31 | 0.99 | 0.22 | 0.59 |
| 264 | S324T | t p | 2.07 | 0.28 | 1.29 | 0.09 | 1.15 | 0.08 | 1.15 | 0.06 | 2.37 | 0.36 | 2.15 | 0.09 |  |  | 2.07 |
| 265 | S324D | t p | 1.03 | 0.23 | 0.89 | 0.09 | 1.00 | 0.42 | 1.13 | 1.80 | 1.11 / 1.54 / 0.75 / 1.07 | 0.19 | 1.60 | 0.40 | 1.07 | 0.26 | 1.12 |
|  |  |  | 3.36 | 0.25 | 1.71 | 0.11 | 1.25 | 0.08 | 1.31 | 0.07 |  | 0.35 | 1.71 | 0.08 | 1.27 | 0.44 | 1.23 |
|  |  |  | 0.94 | 0.20 | 1.03 | 0.10 | 0.93 | 0.67 |  |  |  | 0.18 | 1.46 | 0.33 |  |  | 0.80 |
| 266 | S324R | t | 2.67 | 0.27 | 1.18 | 0.15 | 1.39 | 0.10 | 2.52 | 0.33 | 1.86 / 0.56 / 0.71 | 0.38 | 1.23 | 0.08 | 0.61 | 0.37 | 1.34 |
|  |  |  | 0.64 | 0.16 | 0.73 | 0.17 |  |  |  |  |  | 0.17 | 2.06 | 0.19 |  |  |  |
| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
| 267 | S324I | t p | 9.07 | 0.25 | 1.98 | 0.15 | 6.71 | 0.34 | 7.80 | 0.30 | 1.88 | 0.30 | 0.69 | 0.12 | 0.90 | 0.20 | 0.28 |
|  |  |  | 1.43 | 0.17 | 0.69 | 0.10 |  |  |  |  | 0.54 | 0.16 | 2.02 | 0.21 |  |  |  |

Figure 41Q

| | | | | | | | | | | | | | | | |
|---|---|---|---|---|---|---|---|---|---|---|---|---|---|---|---|
| 268 | S324V | t<br>p | 2.47<br>2.12 | 0.24<br>0.16 | 1.96<br>1.32 | 0.08<br>0.23 | 1.88<br>1.01 | 0.09<br>0.98 | 1.94<br>1.03 | 0.07<br>76.44 | 1.15<br>2.25 | 0.36<br>0.19 | 0.90<br>1.66 | 0.10<br>0.19 | 0.90 0.19 | 1.19<br>1.05 |
| 269 | S324L | t<br>p | 2.01<br>0.93 | 0.26<br>0.14 | 1.95<br>0.96 | 0.07<br>0.13 | 1.22<br>0.93 | 0.08<br>1.00 | 1.24<br>0.90 | 0.06<br>79.37 | 1.06<br>1.17 | 0.38<br>0.14 | 0.62<br>1.71 | 0.08<br>0.19 | 0.82 0.22 | 1.86<br>0.79 |
| 270 | S324Y | t | 1.89<br>1.51 | 0.25<br>0.13 | 1.53<br>0.86 | 0.06<br>0.09 | 1.48<br>0.97 | 0.07<br>1.05 | 1.40 | 0.06 | 2.28<br>0.74<br><0.02 | 0.44<br>0.14 | 1.83<br>2.25 | 0.10<br>0.23 | 0.76 0.21 | 1.26<br>0.91 |
| 271 | K326L | t<br>p | 2.19<br>2.66 | 0.26<br>0.19 | 1.50<br>0.70 | 0.09<br>0.18 | 1.40<br>1.55 | 0.08<br>0.91 | 1.37<br>1.79 | 0.04<br>75.92 | 1.86<br>0.89 | 0.28<br>0.17 | 1.13<br>1.64 | 0.08<br>0.20 | 0.70 0.19 | 2.29<br>1.00 |
| 272 | K326I | t | 2.79<br>2.10 | 0.25<br>0.17 | 1.62<br>0.67 | 0.09<br>0.17 | 1.39<br>1.79 | 0.07<br>0.92 | 1.41<br>1.69 | 0.05<br>75.92 | 3.20<br>1.54<br>3.12<br>1.68<br>0.98 | 0.31<br>0.15 | 1.06<br>2.49 | 0.09<br>0.21 | 0.65 0.20 | 2.24<br>0.94 |
| 273 | K326T | t<br>p | 4.10<br>2.92 | 0.26<br>0.19 | 2.07<br>1.26 | 0.12<br>0.13 | 1.95<br>1.33 | 0.07<br>0.91 | 2.05<br>1.06 | 0.06<br>75.92 | 2.75<br>1.79<br>1.88<br>1.43 | 0.36<br>0.14 | 2.25<br>2.65 | 0.11<br>0.21 | 0.68 0.22 | 1.41<br>1.34 |
| 274 | A327D | t | 15.80<br>2.55 | 0.25<br>0.13 | 2.09<br>0.73 | 0.19<br>0.16 | 7.30<br>1.62 | 0.36<br>0.89 | 11.30<br>1.11 | 0.39<br>75.92 | 3.34<br>0.51 | 0.24<br>0.14 | 0.62<br>3.00 | 0.17<br>0.21 | 1.01 0.18 | 0.46<br>0.32 |
| 275 | A327T | t | 1.13<br>0.19 | 0.25<br>0.19 | 0.82<br>0.13 | 0.15<br>1.18 | 1.06 | 0.08 | 1.15 | 0.06 | <0.02<br>0.65 | 0.27 | 2.64<br>2.63 | 0.08<br>0.29 | 0.67 0.17 | 0.62 |
| 276 | A330S | t<br>p | 4.00<br>2.38 | 0.25<br>0.19 | 1.58<br>0.80 | 0.13<br>0.21 | 1.91<br>0.97 | 0.09<br>1.11 | 1.84 | 0.11 | <0.02<br>1.56<br>0.67 | 0.36<br>0.18 | 1.88<br>1.64 | 0.07<br>0.24 | 0.91 0.21 | 0.81<br>0.69 |
| 277 | A330W | t | 3.94<br>2.14 | 0.25<br>0.16 | 1.33<br>0.37 | 0.07<br>0.17 | 1.45<br>1.00 | 0.08<br>8.31 | 1.49 | 0.06 | 1.37<br>0.76 | 0.38<br>0.19 | 1.96<br>2.44 | 0.08<br>0.23 | 1.02 0.19 | 0.94<br>0.76 |
| 278 | A330M | t | 2.30<br>2.01 | 0.25<br>0.15 | 1.36<br>0.53 | 0.09<br>0.14 | 1.26<br>1.15 | 0.07<br>17.59 | 1.09 | 0.05 | 1.79<br>1.00 | 0.38<br>0.15 | 1.91<br>2.31 | 0.08<br>0.22 | 0.77 0.24 | 1.42<br>0.87 |
| 279 | P331V | t | 2.52<br>1.43 | 0.24<br>0.13 | 1.01<br>0.34 | 0.06<br>0.18 | 1.30<br>0.88 | 0.07<br>1.06 | 1.36<br>0.93 | 0.05<br>76.26 | 1.19<br>0.26 | 0.29<br>0.22 | 2.12<br>3.49 | 0.08<br>0.18 | 0.83 0.19 | 0.92<br>0.29 |
| 280 | P331H | t | 2.28<br>2.09 | 0.26<br>0.46 | 1.40<br>0.43 | 0.18<br>0.09 | 1.27<br>1.24 | 0.08<br>0.93 | 1.34<br>0.95 | 0.05<br>76.55 | 1.12<br>0.35 | 0.29<br>0.18 | 2.24<br>2.86 | 0.07<br>0.25 | 0.90 0.22 | 0.88<br>0.28 |
| 281 | E333T | t | 2.46<br>1.21 | 0.26<br>0.16 | 1.43<br>0.68 | 0.11<br>0.12 | 1.27<br>1.05 | 0.08<br>1.34 | 1.22<br>0.98 | 0.05<br>454 | 1.77<br>0.72<br>0.78 | 0.34<br>0.15 | 1.68<br>3.17 | 0.75<br>0.21 | 0.85 0.18 | 1.39<br>0.68 |

Figure 41R

| | | | | | | | | | | | | | | | | |
|---|---|---|---|---|---|---|---|---|---|---|---|---|---|---|---|---|
| 282 | E333H | t | 2.91 | 0.25 | 1.23 | 0.09 | 1.24 | 0.11 | 1.30 | 0.06 | 1.77 | 0.34 | 2.21 | 0.12 | 0.84 | 0.29 | 1.43 |
| | | | 0.40 | 0.06 | 0.59 | 0.33 | 1.19 | 0.46 | 0.73 | 0.32 | 0.46 | 0.17 | 1.06 | 0.73 | | | 0.39 |
| 283 | E333I | | | | | | | | | | 0.75 | | | | | | |
| | | | 2.60 | 0.26 | 1.53 | 0.11 | 1.78 | 0.09 | 2.10 | 0.07 | 1.94 | 0.34 | 2.55 | 0.07 | 0.84 | 0.26 | 1.09 |
| | | | 0.34 | 0.13 | 0.58 | 0.40 | 1.72 | 0.30 | 0.93 | 0.23 | 0.38 | 0.11 | 1.52 | 0.60 | | | 0.22 |
| 284 | E333Y | t | 7.61 | 0.25 | 2.51 | 0.10 | 10.60 | 0.17 | 11.60 | 0.21 | 8.70 | 0.23 | 1.10 | 0.14 | 0.83 | 0.27 | 0.82 |
| | | | 0.45 | 0.11 | 0.64 | 0.32 | 1.93 | 0.31 | 0.88 | 0.29 | 0.90 | 0.15 | 0.81 | 0.94 | | | 0.47 |
| 285 | K334I | t | 3.99 | 0.25 | 1.82 | 0.07 | 1.67 | 0.05 | 1.60 | 0.05 | 10.32 | 0.28 | 1.84 | 0.08 | 0.64 | 0.27 | 6.18 |
| | | | 0.97 | 0.15 | 0.85 | 0.36 | 1.89 | 0.33 | 1.00 | 0.28 | 2.47 | 0.11 | 1.16 | 0.72 | | | 1.31 |
| 286 | K334T | t p | 3.63 | 0.26 | 2.15 | 0.07 | 0.93 | 0.38 | 0.96 | 0.06 | 5.35 | 0.36 | 1.03 | 0.10 | 0.82 | 0.29 | 5.75 |
| | | | 1.24 | 0.25 | 0.98 | 0.31 | 2.28 | 0.30 | 1.39 | 0.23 | 1.69 | 0.13 | 1.06 | 0.80 | | | 0.74 |
| 287 | K334F | t | 4.03 | 0.25 | 1.57 | 0.10 | 1.26 | 0.07 | 1.15 | 0.05 | 5.47 | 0.42 | 2.70 | 0.08 | 0.77 | 0.26 | 4.33 |
| | | | 1.54 | 0.11 | 0.75 | 0.29 | 1.77 | 0.32 | 0.92 | 0.23 | 1.46 | 0.12 | 1.01 | 1.00 | | | 0.83 |
| 288 | T335D | t p | 3.52 | 0.28 | 1.68 | 0.13 | 1.21 | 0.07 | 1.13 | 0.07 | 3.03 | 0.33 | 1.93 | 0.09 | 0.99 | 0.24 | 2.51 |
| | | | 1.37 | 0.07 | 0.82 | 0.26 | 1.37 | 0.30 | 0.66 | 0.32 | 0.96 | 0.14 | 1.25 | 0.67 | | | 0.70 |
| 289 | T335R | t | 2.72 | 0.26 | 1.28 | 0.09 | 1.23 | 0.10 | 1.22 | 0.07 | 2.79 | 0.33 | 2.06 | 0.15 | 0.74 | 0.26 | 1.19 |
| | | | 0.38 | 0.07 | 0.66 | 0.26 | 1.23 | 0.31 | 0.66 | 0.30 | 1.47 | 0.12 | 1.00 | 0.70 | | | 0.31 |
| | | | | | | | | | | | 0.38 | | | | | | |
| | | | | | | | | | | | 2.58 | | | | | | |
| 290 | T335Y | t p | 2.72 | 0.28 | 1.48 | 0.09 | 1.23 | 0.06 | 1.19 | 0.05 | 2.29 | 0.37 | 3.22 | 0.11 | 0.86 | 0.26 | 1.86 |
| | | | 0.46 | 0.10 | 0.70 | 0.37 | 0.81 | 0.62 | 0.62 | 0.41 | 0.52 | 0.12 | 1.31 | 0.69 | | | 0.64 |
| | | | | | | | | | | | | 1.56 | | | | | |
| 291 | L234I/L235D | t | 0.81 | 0.32 | 2.20 | 0.09 | 0.96 | 0.10 | 0.89 | 0.06 | 3.68 | 0.37 | 0.60 | 0.12 | 1.03 | 0.25 | 3.82 |
| | | | 0.04 | 0.15 | 0.25 | 2.73 | 1.14 | 0.34 | 0.52 | 0.25 | 0.57 | 0.12 | 2.07 | 0.60 | | | 0.50 |
| | | | | | | | | | | | | 0.07 | | | | | |
| 292 | V240I/V266I | t | 3.99 | 0.24 | 1.86 | 0.09 | 1.99 | 0.11 | 1.90 | 0.06 | 3.42 | 0.35 | 3.08 | 0.07 | 0.81 | 0.25 | 1.71 |
| | | | 0.60 | 0.12 | 0.46 | 0.32 | 1.91 | 0.37 | 1.05 | 0.27 | 0.52 | 0.14 | 1.16 | 0.73 | | | 0.27 |
| | | | | | | | | | | | 1.72 | | | | | | |
| 293 | S239D/A330Y/I332E | t | | | | | | | | | 22.39 | | | | | | |
| 294 | L235D/S239D/A330Y/I332E | t | 5.43 | 0.28 | 1.62 | 0.06 | 1.59 | 0.06 | 1.35 | 0.06 | 65.84 | 0.29 | 1.16 | 0.09 | 0.78 | 0.28 | 41.38 |
| | | | 0.15 | 0.12 | 0.34 | 0.35 | 7.07 | 0.30 | 3.66 | 0.26 | 80.04 | 0.11 | 1.11 | 0.83 | | | 11.33 |
| | | | | | | | | | | | 7.04 | | | | | | |
| 295 | S239D/V240I/A330Y/I332E | t | 2.64 | 0.13 | 2.78 | 0.25 | 21.68 | 0.29 | 13.70 | 0.22 | 115 | 0.13 | 0.99 | 0.90 | 0.71 | 0.27 | 5.33 |
| | | | | | | | | | | | 27.97 | | | | | | |

Figure 41S

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 296 | S239D/V264T/A330Y/I332E | t | 1.64 | 0.10 | 4.85 | 0.26 | 22.14 | 0.30 | 14.88 | 0.23 | 59.09 | 0.11 | 0.89 | 1.07 | 0.98 | 0.25 | 2.67 |
| 297 | S239D/A330Y/I332E/V266I | t | | | | | | | | | 17.72 | | | | | | |
| 298 | S239D/K326E/A330Y/I332E | t p | 3.21 | 0.08 | 3.00 | 0.26 | 48.74 | 0.30 | 27.56 | 0.23 | 298 / 64.14 | 0.12 | 1.20 | 0.66 | 0.39 | 0.27 | 6.12 |
| 299 | S239D/K326T/A330Y/I332E | t | 1.83 | 0.08 | 8.89 | 0.22 | 41.48 | 0.29 | 22.59 | 0.22 | 185 | 0.10 | 1.27 | 0.60 | 0.40 | 0.28 | 4.47 |
| 300 | S239D/N297D/A330Y/I332E | t | 0.10 | 0.13 | | | 0.23 | 1.70 | 0.85 | 11.57 | 59.03 | 0.33 | 1.27 | 0.62 | 0.19 | 0.81 | 0.32 |
| 301 | S239D/F241S/F243H/V264T/N297D/A330Y/I332E | t | 0.08 | 0.11 | | | 0.90 | 0.87 | 0.84 | 9.38 | 0.08 / 0.03 | 0.41 | 1.65 | 0.59 | 0.23 | 0.64 | 0.03 |
| 302 | L235D/S239D/N297D/I332E | t | 0.02 | 0.20 | | | 0.81 | 0.68 | 0.57 | 0.34 | <0.02 / 0.08 | 0.48 | 1.10 | 0.78 | 0.19 | 0.59 | 0.45 |
| 303 | S239D/N297D/K326E/I332E | t | 0.23 | 0.10 | | | | | | | 0.36 | 0.13 | 1.33 | 0.66 | 0.19 | 0.63 | 0.95 |
| 321 | P232E | a | 2.97 | 0.14 | 0.80 | 0.14 | 1.59 | 0.21 | 0.99 | 0.23 | 1.51 | 0.36 | 1.18 | 0.16 | 0.76 | 0.23 | 1.19 |
|  |  |  | 0.18 | 0.19 | 0.06 | 0.38 | 0.27 | 0.20 | 0.30 | 0.16 | 0.32 | 0.16 | 0.08 | 0.59 |  |  | 0.91 |
| 322 | P232K | a | 0.70 | 0.14 | 0.87 | 0.16 | 0.85 | 0.17 | 0.61 | 0.24 | 0.77 | 0.39 | 0.78 | 0.18 | 1.56 | 0.30 | 0.72 |
|  |  |  | 0.07 | 0.25 | 0.05 | 0.45 | 0.27 | 0.17 | 0.33 | 0.20 | 0.20 | 0.15 | 0.07 | 0.60 |  |  | 0.66 |
| 323 | P232Y | a | 1.91 | 0.21 | 1.51 | 0.12 | 1.49 | 0.19 | 0.96 | 0.28 | 0.99 | 0.34 | 0.87 | 0.18 | 0.68 | 0.26 | 0.40 |
|  |  |  | 0.15 | 0.16 | 0.22 | 0.32 | 0.54 | 0.14 | 0.74 | 0.19 | 0.21 | 0.13 | 0.16 | 0.61 |  |  | 0.74 |
| 324 | P232G | a | 1.31 | 0.18 | 0.49 | 0.13 | 0.69 | 0.18 | 0.42 | 0.23 | 0.51 | 0.31 | 0.84 | 0.15 | 0.70 | 0.26 | 0.36 |
|  |  |  | 0.10 | 0.19 | 0.05 | 0.41 | 0.11 | 0.30 | 0.01 | 1.67 | 0.04 | 0.22 | 0.14 | 0.60 |  |  | 1.44 |
| 325 | S239Q | a | 0.98 | 0.15 | 1.05 | 0.12 | 1.11 | 0.25 | 0.59 | 0.24 | 1.59 | 0.31 | 0.81 | 0.15 | 0.57 | 0.22 | 1.35 |
|  |  |  | 0.07 | 0.21 | 0.09 | 0.34 | 0.68 | 0.16 | 0.91 | 0.21 | 0.92 | 0.11 | 0.17 | 0.59 |  |  | 1.58 |
| 326 | S239K | a | 0.18 | 0.12 | 0.94 | 0.11 | 0.76 | 0.22 | 0.43 | 0.23 | 1.20 | 0.36 | 0.98 | 0.15 | 0.86 | 0.27 | 1.12 |
|  |  |  | 0.02 | 0.16 | 0.14 | 0.29 | 0.78 | 0.17 | 0.94 | 0.17 | 0.88 | 0.14 | 0.49 | 0.86 |  |  |  |

Figure 41T

|  |  |  |  |  |  |  |  |  |  |  |  |  |  |  |
|---|---|---|---|---|---|---|---|---|---|---|---|---|---|---|
| 327 | S239R | a | 0.05 | 0.14 | 0.41 | 0.14 | 0.51 | 0.16 | 0.19 | 0.37 | 0.11 | 0.28 | 1.29 | 0.18 | 1.04 | 0.20 | 0.22 |
| 328 | S239V | a | 0.01 | 0.15 |  |  | 0.08 | 0.63 | 0.00 | 2.30 |  |  | 0.12 | 0.58 |  |  |  |
| 329 | S239L | a p | 0.08 | 0.19 | 0.36 | 0.26 | 2.49 | 0.16 | 1.98 | 0.15 | 1.10 | 0.14 | 0.36 | 0.65 | 1.17 | 0.36 | 0.44 |
| 330 | S239I | a | 1.28 | 0.19 | 0.29 | 0.22 | 1.92 | 0.49 | 1.23 | 0.32 | 0.05 | 2.82 |  |  | 4.60 | 0.25 | 0.02 |
| 331 | S239M | a | 0.99 | 0.16 | 3.98 | 0.13 | 6.06 | 0.22 | 3.69 | 0.22 | 4.49 | 0.25 | 6.30 | 0.19 |  |  | 0.74 |
| 332 | S239W | a | 0.00 | 0.20 |  |  | 0.10 | 0.35 | 0.14 | 0.27 |  |  | 0.06 | 0.58 |  |  |  |
| 333 | S239P | a | 0.06 | 0.18 | 0.57 | 0.17 | 1.47 | 0.19 | 0.87 | 0.26 | 0.13 | 0.25 | 1.28 | 0.16 | 0.71 | 0.29 | 0.09 |
| 334 | S239G | a | 0.14 | 0.15 | 0.10 | 0.35 | 0.16 | 0.24 | 0.07 | 0.62 | 0.05 | 0.14 | 0.11 | 0.60 |  |  | 0.34 |
| 335 | F241D | a | 0.90 | 0.12 | 0.81 | 0.16 | 1.02 | 0.17 | 0.91 | 0.33 | 0.64 | 0.29 | 1.36 | 0.16 | 1.03 | 0.26 | 0.63 |
| 336 | F241E | a | 0.05 | 0.16 | 0.05 | 25.50 | 0.01 | 2.15 | 0.03 | 5.02 | 0.03 | 0.17 | 0.20 | 0.61 |  |  | 6.26 |
| 337 | F241Y | a | 0.43 | 0.13 | 0.52 | 0.16 | 0.49 | 0.17 | 0.38 | 0.23 | 0.45 | 0.28 | 1.53 | 0.15 | 0.57 | 0.27 | 0.92 |
| 338 | S267E | a p | 0.04 | 0.16 | 0.04 | 13.71 | 0.11 | 0.40 | 0.02 | 1.84 | 0.02 | 0.22 | 0.15 | 0.59 |  |  | 0.16 |
| 339 | S267Q | a p | 0.27 | 0.16 | 0.63 | 0.15 | 0.91 | 0.18 | 0.73 | 0.23 | 0.19 | 0.30 | 0.96 | 0.15 | 0.30 | 0.30 | 0.21 |
| 340 | S267K | a | 0.15 | 0.15 | 0.16 | 0.30 | 0.82 | 0.15 | 0.55 | 0.30 | 0.04 | 0.19 | 0.13 | 0.58 |  |  | 0.05 |
| 341 | S267R | a | 1.20 | 0.14 | 0.97 | 0.14 | 1.80 | 0.14 | 1.31 | 0.23 | 0.47 | 0.30 | 0.91 | 0.16 | 1.16 | 0.38 | 0.26 |
| 342 | S267V | a | 0.08 | 0.16 | 0.05 | 0.33 | 0.05 | 0.50 | 0.09 | 0.58 | 0.03 | 0.18 | 0.30 | 0.81 |  |  | 0.69 |
| 343 | S267L | a | 1.76 | 0.18 | 1.37 | 0.12 | 1.36 | 0.14 | 0.86 | 0.21 | 0.60 | 0.29 | 0.78 | 0.16 | 0.69 | 0.26 | 0.45 |
| 344 | S267I | a | 0.15 | 0.16 | 0.08 | 0.33 | 0.09 | 0.50 | 0.11 | 0.63 | 0.03 | 0.13 | 0.13 | 0.60 |  |  | 0.34 |
|  |  |  | 0.96 | 0.15 | 1.90 | 0.11 | 1.18 | 0.17 | 1.02 | 0.23 | 0.57 | 0.33 | 1.10 | 0.16 | 1.09 | 0.19 | 0.48 |
|  |  |  | 0.14 | 0.16 | 0.16 | 0.28 | 0.33 | 0.17 | 0.29 | 0.13 | 0.09 | 0.15 | 0.07 | 0.63 |  |  | 0.29 |
|  |  |  | 1.33 | 0.15 | 1.15 | 0.13 | 2.04 | 0.17 | 1.51 | 0.22 | 1.04 | 0.28 | 1.23 | 0.23 | 0.74 | 0.27 | 0.51 |
|  |  |  | 0.15 | 0.17 | 0.05 | 152 | 0.68 | 0.16 | 0.55 | 0.17 | 0.27 | 0.13 | 0.06 | 0.58 |  |  | 0.40 |
|  |  |  | 4.43 | 0.16 | 4.76 | 0.18 | 337 | 0.42 | 248 | 0.39 | 1.30 | 0.33 | 21.33 | 0.17 | 0.20 | 0.28 | 0.00 |
|  |  |  | 2.39 | 0.21 | 5.92 | 0.13 | 97.52 | 0.21 | 438 | 0.49 | 1.18 | 0.39 | 30.15 | 0.14 | 1.09 | 0.19 | 0.01 |
|  |  |  | 3.50 | 0.16 | 11.50 | 0.20 | 335 | 0.37 | 1321 | 0.28 | 0.65 | 2.82 |  |  | 2.24 | 0.39 | 0.00 |
|  |  |  | 1.01 | 0.12 | 0.67 | 0.21 | 2.03 | 0.17 | 1.50 | 0.23 | 0.74 | 0.40 | 1.14 | 0.17 | 0.65 | 0.27 | 0.36 |
|  |  |  | 0.02 | 0.14 |  |  | 0.14 | 0.24 | 0.05 | 0.84 |  |  | 0.19 | 0.61 |  |  |  |
|  |  |  | 0.32 | 0.19 | 1.65 | 0.14 | 1.25 | 0.23 | 0.69 | 0.25 | 0.30 | 3.25 | 0.96 | 0.18 | 1.70 | 0.35 | 0.24 |
|  |  |  | 0.02 | 0.16 |  |  | 0.01 | 1.29 | 0.02 | 79.64 |  |  | 0.14 | 0.60 |  |  |  |
|  |  |  | 0.15 | 0.15 | 0.45 | 0.19 | 0.36 | 0.17 | 0.17 | 0.24 | 0.16 | 0.24 | 1.03 | 0.15 | 0.75 | 0.30 | 0.44 |
|  |  |  | 0.12 | 0.18 | 0.05 | 283 | 1.18 | 0.19 | 1.38 | 0.22 |  |  | 0.14 | 0.60 |  |  |  |
|  |  |  | 1.21 | 0.16 | 0.81 | 0.13 | 3.26 | 0.16 | 2.35 | 0.45 | 0.17 | 0.25 | 1.38 | 0.16 | 0.50 | 0.33 | 0.05 |
|  |  |  | 0.09 | 0.14 |  |  | 0.35 | 0.33 | 0.24 | 0.22 | 0.01 | 0.72 | 0.15 | 0.62 |  |  | 0.04 |
|  |  |  | 0.82 | 0.15 | 0.90 | 0.12 | 1.29 | 0.18 | 1.22 | 0.22 | 0.16 | 0.25 | 0.90 | 0.15 | 0.96 | 0.27 | 0.13 |
|  |  |  | 0.10 | 0.12 |  |  | 0.92 | 0.17 | 1.18 | 0.14 | 0.02 | 5.05 | 0.39 | 0.84 |  |  | 0.02 |
|  |  |  | 0.76 | 0.15 | 0.55 | 0.13 | 2.81 | 0.18 | 2.07 | 0.22 | 0.13 | 0.28 | 1.23 | 0.16 | 0.63 | 0.29 | 0.04 |
|  |  |  | 0.03 | 0.13 |  |  | 0.04 | 0.63 | 0.03 | 1.06 |  |  | 6.12 | 0.60 |  |  |  |

Figure 41U

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 345 | S267F | a | 0.40 | 0.17 | 0.54 | 0.13 | 0.71 | 0.16 | 0.61 | 0.25 | 0.22 | 0.24 | 0.87 | 0.23 | 0.42 | 0.34 | 0.30 |
|  |  |  | 0.18 | 0.16 |  |  | 0.51 | 0.17 | 0.66 | 0.19 | 0.02 | 0.23 | 0.09 | 0.65 |  |  | 0.04 |
| 346 | S267M | a | 2.16 | 0.12 | 0.91 | 0.13 | 2.46 | 0.23 | 1.73 | 0.28 | 0.44 | 0.26 | 1.11 | 0.18 | 0.48 | 0.33 | 0.18 |
|  |  |  | 0.03 | 0.14 |  |  | 0.07 | 0.44 | 0.09 | 0.74 |  |  | 0.07 | 0.63 |  |  |  |
| 347 | S267Y | a | 0.37 | 0.13 | 1.28 | 0.20 | 0.95 | 0.23 | 0.60 | 0.30 | 0.35 | 0.28 | 1.10 | 0.18 | 0.93 | 0.33 | 0.37 |
|  |  |  | 0.05 | 0.15 |  |  | 0.12 | 0.33 | 0.01 | 1.75 |  |  | 0.10 | 0.61 |  |  |  |
| 348 | S267W | a | 0.48 | 0.16 | 0.48 | 0.28 | 1.09 | 0.17 | 0.38 | 0.27 | 0.18 | 0.24 | 1.36 | 0.16 | 0.36 | 0.33 | 0.17 |
|  |  |  | 0.02 | 0.16 |  |  | 0.00 | 1.59 | 0.00 | 5.22 | 0.02 | 0.18 | 0.12 | 0.62 |  |  | 7.37 |
| 349 | S267P | a | 0.27 | 0.14 | 0.58 | 0.14 | 0.97 | 0.15 | 0.50 | 0.24 | 0.49 | 2.27 | 1.42 | 0.16 | 0.35 | 0.35 | 0.50 |
|  |  |  | 0.51 | 0.16 | 0.79 | 0.29 | 2.99 | 0.16 | 3.81 | 0.15 | 0.56 | 0.14 | 0.11 | 0.62 |  |  | 0.19 |
| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
| 350 | H268D | a | 3.92 | 0.13 | 7.02 | 0.12 | 12.81 | 0.17 | 9.43 | 0.22 | 4.97 | 0.29 | 1.89 | 0.17 | 0.43 | 0.48 | 0.39 |
| 351 | H268E | a p | 0.29 | 0.13 | 0.71 | 0.23 | 4.42 | 0.14 | 5.80 | 0.20 | 0.80 | 0.13 | 0.29 | 0.60 |  |  | 0.18 |
| 352 | H268Q | a | 3.25 | 0.14 | 5.03 | 0.14 | 7.91 | 0.19 | 6.42 | 0.25 | 4.42 | 0.27 | 1.40 | 0.15 | 1.71 | 0.39 | 0.56 |
| 353 | H268K | a | 2.13 | 0.43 | 1.26 | 0.12 | 1.70 | 0.15 | 2.05 | 0.14 | 1.38 | 0.49 | 0.79 | 0.42 | 0.98 | 0.22 | 0.81 |
| 354 | H268R | a | 0.87 | 0.40 | 0.58 | 0.13 | 0.38 | 0.17 | 0.37 | 0.11 | 0.47 | 0.49 | 0.50 | 0.32 | 0.54 | 0.25 | 1.25 |
| 355 | H268T | a | 0.80 | 0.43 | 0.55 | 0.13 | 0.51 | 0.12 | 0.32 | 0.17 | 0.41 | 0.54 | 0.64 | 0.39 | 0.67 | 0.21 | 0.79 |
| 356 | H268V | a | 2.20 | 0.45 | 0.78 | 0.09 | 0.57 | 0.14 | 0.39 | 0.15 | 0.57 | 0.68 | 0.49 | 1314 | 0.68 | 0.29 | 1.00 |
| 357 | H268L | a | 2.61 | 0.44 | 1.03 | 0.10 | 0.85 | 0.15 | 0.51 | 0.14 | 0.58 | 0.49 | 0.38 | 0.49 | 0.63 | 0.26 | 0.68 |
| 358 | H268I | a | 1.33 | 0.40 | 0.46 | 0.13 | 0.45 | 0.13 | 0.31 | 0.11 | 0.65 | 0.49 | 1.12 | 0.39 | 0.39 | 0.26 | 1.46 |
|  |  |  | 3.69 | 0.43 | 0.49 | 0.08 | 0.61 | 0.12 | 0.37 | 0.13 | 0.53 | 0.48 | 0.52 | 0.34 | 0.93 | 0.23 | 0.86 |
|  |  |  | 0.43 | 0.23 |  |  | 1.04 | 0.85 | 0.72 | 15.94 | 0.07 | 2.82 |  |  | 0.54 | 0.42 | 0.07 |
| 359 | H268F | a | 2.70 | 0.41 | 2.13 | 0.09 | 0.98 | 0.12 | 0.86 | 0.12 | 1.44 | 0.49 | 2.12 | 0.42 | 0.40 | 0.25 | 1.48 |
| 360 | H268M | a | 1.15 | 0.13 | 0.50 | 0.24 | 1.08 | 0.46 | 0.73 | 0.36 | 0.43 | 2.82 |  |  | 1.88 | 0.40 | 0.40 |
| 361 | H268W | a | 1.41 | 0.43 | 0.88 | 0.11 | 2.63 | 0.35 | 1.29 | 0.14 | 0.56 | 0.66 | 1.41 | 0.40 | 0.35 | 0.23 | 0.21 |
| 362 | H268P | a | 1.78 | 0.40 | 0.35 | 0.14 | 0.91 | 0.14 | 0.71 | 0.12 | 0.57 | 0.49 | 0.67 | 0.41 | 0.68 | 0.16 | 0.63 |
| 363 | H268G | a p | 2.41 | 0.42 | 0.99 | 0.14 | 1.38 | 0.13 | 1.58 | 0.08 | 0.84 | 0.50 | 1.11 | 0.40 | 0.38 | 0.19 | 0.61 |
| 364 | S298D | a | 2.96 | 0.40 | 0.20 | 0.21 | 0.30 | 0.12 | 0.15 | 0.16 | 0.66 | 0.50 | 1.06 | 0.42 | 0.55 | 0.18 | 2.24 |
| 365 | S298E | a | 3.36 | 0.39 | 0.25 | 0.19 | 0.26 | 0.14 | 0.17 | 0.27 | 0.19 | 0.50 | 0.97 | 0.43 | 0.31 | 0.18 | 0.74 |
|  |  |  | 1.90 | 0.21 | 0.09 | 3.80 | 0.58 | 0.44 | 0.63 | 0.53 | 0.04 | 2.83 |  |  | 1.54 | 0.37 | 0.06 |
| 366 | S298Q | a | 1.82 | 0.40 | 0.49 | 0.08 | 0.87 | 0.09 | 0.78 | 0.10 | 0.59 | 0.49 | 0.66 | 0.48 | 0.45 | 0.19 | 0.68 |
| 367 | S298K | a | 0.33 | 0.39 | 0.21 | 0.16 | 0.39 | 0.15 | 0.29 | 0.16 | 0.14 | 0.48 | 0.78 | 0.28 | 0.54 | 0.17 | 0.36 |
| 368 | S298R | a | 0.86 | 0.40 | 0.30 | 0.12 | 0.17 | 0.24 | 0.13 | 0.26 | 0.24 | 0.48 | 0.92 | 0.41 | 0.48 | 0.16 | 1.38 |
| 369 | S298I | a | 3.25 | 0.40 | 0.44 | 0.22 | 0.69 | 0.16 | 0.56 | 0.16 | 0.94 | 0.49 | 1.54 |  | 0.13 | 0.23 | 1.36 |
| 370 | S298F | a | 3.35 | 0.39 | 1.05 | 0.15 | 2.57 | 0.10 | 1.48 | 0.13 | 1.50 | 0.48 | 1.20 | 0.28 | 0.25 | 0.16 | 0.58 |
|  |  |  | 2.42 | 0.10 | 0.16 | 0.29 | 0.93 | 0.42 | 0.55 | 0.72 | 0.08 | 2.82 |  |  | 1.15 | 0.38 | 0.09 |

Figure 41V

| | | | | | | | | | | | | | | |
|---|---|---|---|---|---|---|---|---|---|---|---|---|---|---|
| 371 | S298M | a | 3.34 | 0.42 | 1.76 | 0.13 | 2.53 | 0.12 | 1.73 | 0.11 | 1.24 | 0.49 | 1.40 | 0.62 | 0.60 | 0.21 | 0.49 |
| 372 | S298Y | a | 2.51 | 0.41 | 0.54 | 0.15 | 0.68 | 0.11 | 0.49 | 0.19 | 0.98 | 0.50 | 0.91 | 0.49 | 0.50 | 0.19 | 1.43 |
| 373 | S298W | a | 2.46 | 0.40 | 0.31 | 0.16 | 0.32 | 0.21 | 0.22 | 0.19 | 0.32 | 0.48 | 0.80 | 0.46 | 0.23 | 0.25 | 0.98 |
| 374 | T299D | a | 0.12 | 0.41 | 0.26 | 0.16 | 0.26 | 0.19 | 0.22 | 0.12 | 0.18 | 0.50 | 1.50 | 1.25 | 0.44 | 0.34 | 0.67 |
| 375 | T299E | a | 0.24 | 0.40 | 0.39 | 0.08 | 0.37 | 0.14 | 0.28 | 0.15 | 0.28 | 0.48 | 1.07 | 0.29 | 0.47 | 0.18 | 0.76 |
| 376 | T299N | a | 0.22 | 0.42 | 0.33 | 0.21 | 0.36 | 0.15 | 0.27 | 0.18 | 0.21 | 0.48 | 1.90 | 0.39 | 0.61 | 0.26 | 0.60 |
| 377 | T299Q | a | 0.15 | 0.40 | 0.19 | 0.39 | 0.11 | 0.22 | 0.16 | 0.22 | 0.17 | 0.48 | 1.16 | 0.39 | 0.25 | 0.27 | 1.50 |
| 378 | T299K | a | 0.04 | 0.54 | 0.58 | 0.29 | 0.30 | 0.18 | 0.27 | 0.16 | 0.10 | 0.48 | 0.50 | 0.31 | 0.49 | 0.15 | 0.35 |
| 379 | T299R | a | 0.02 | 0.99 | 0.23 | 0.41 | 0.20 | 0.36 | 0.08 | 0.42 | 0.00 | 0.49 | 0.61 | 0.41 | 0.44 | 0.21 | 0.00 |
| 380 | T299L | a | 0.26 | 0.44 | 0.18 | 0.30 | 0.58 | 0.22 | 0.43 | 0.09 | 0.06 | 24.61 | 0.60 | 12.53 | 0.34 | 0.19 | 0.11 |
| 381 | T299F | a | 0.61 | 0.43 | 1.77 | 0.26 | 0.95 | 0.17 | 0.33 | 0.20 | 0.06 | 0.59 | 1.31 | 0.47 | 1.86 | 0.20 | 0.12 |
| 382 | T299M | a | 0.17 | 0.44 | 0.21 | 0.24 | 0.85 | 0.13 | 0.46 | 0.12 | 0.12 | 0.49 | 0.85 | 0.33 | 0.36 | 0.23 | 0.08 |
| 383 | T299Y | a | 0.03 | 0.38 | 0.77 | 0.26 | 0.86 | 0.27 | 0.62 | 0.21 | 0.06 | 0.66 | 1.66 | 0.38 | 3.85 | 0.13 | 0.13 |
| 384 | T299W | a | 0.09 | 0.32 | 0.31 | 0.20 | 0.85 | 0.18 | 0.59 | 0.12 | 0.11 | 0.20 | 1.46 | 0.33 | 1.09 | 0.10 | 0.24 |
| 385 | T299P | a | 0.02 | 0.36 | 0.20 | 0.16 | 0.34 | 0.17 | 0.26 | 0.17 | 0.20 | 0.13 | 2.60 | 0.36 | 0.72 | 0.11 | 0.29 |
| 386 | T299G | a | 0.02 | 0.45 | 0.15 | 0.29 | 0.24 | 0.21 | 0.09 | 0.23 | 0.10 | 0.23 | 1.94 | 0.52 | | | 0.12 |
| 387 | Y300D | a p | 1.58 | 0.32 | 0.67 | 0.08 | 1.68 | 0.15 | 1.37 | 0.16 | 0.03 | 0.61 | 3.22 | 0.46 | 0.97 | 0.10 | 0.71 |
| 388 | Y300E | a | 0.12 | 0.37 | 0.10 | 0.33 | 0.22 | 0.17 | 0.11 | 0.20 | 1.19 | 0.15 | 2.51 | 0.37 | 0.82 | 0.12 | 0.26 |
| | | | | | | | | | | | | 0.24 | | | 1.27 | 0.41 | 0.04 |
| 389 | Y300N | a | 1.53 | 0.17 | 1.00 | 0.23 | 3.51 | 0.40 | 2.95 | 0.30 | 0.06 | 2.82 | | | | | |
| 390 | Y300Q | a | 1.87 | 0.44 | 0.98 | 0.08 | 11.42 | 2509 | 0.56 | 0.12 | 0.14 | 0.14 | 0.88 | 0.38 | 1.14 | 0.10 | 0.06 |
| 391 | Y300K | a | 0.86 | 0.31 | 1.02 | 0.07 | 1.71 | 0.15 | 1.88 | 0.12 | 0.63 | 0.14 | 2.29 | 0.42 | 1.11 | 0.12 | 0.71 |
| 392 | Y300R | a | 0.42 | 0.29 | 0.48 | 0.11 | 0.54 | 0.17 | 0.50 | 0.13 | 1.22 | 0.13 | 1.14 | 0.34 | 1.01 | 0.18 | 1.08 |
| 393 | Y300S | a | 0.41 | 0.38 | 0.35 | 0.10 | 0.57 | 0.16 | 0.57 | 0.14 | 0.58 | 0.14 | 2.12 | 0.32 | 0.86 | 0.13 | 0.72 |
| 394 | Y300T | a p | 0.72 | 0.31 | 0.73 | 0.10 | 0.48 | 0.15 | 0.46 | 0.14 | 0.41 | 0.15 | 2.79 | 0.41 | 0.80 | 0.14 | 1.25 |
| 395 | Y300H | a | 1.16 | 0.27 | 0.87 | 0.11 | 1.31 | 0.16 | 1.18 | 0.13 | 0.59 | 0.15 | 17.00 | 0.51 | | | 2.14 |
| | | | | | | | | | | | | 2.80 | 0.14 | 3.90 | 0.45 | | | 0.34 |
| 396 | Y300A | a | 1.23 | 0.31 | 1.23 | 0.08 | 3.85 | 0.13 | 3.86 | 0.12 | 1.31 | 0.14 | | | | | 0.04 |
| 397 | Y300V | a | 1.64 | 0.13 | 0.78 | 0.25 | 1.47 | 0.46 | 0.92 | 0.36 | 0.06 | 2.82 | 1.64 | 0.26 | 0.81 | 0.14 | 1.01 |
| 398 | Y300M | a | 1.16 | 0.32 | 0.63 | 0.08 | 0.74 | 0.12 | 0.55 | 0.12 | 0.75 | 0.13 | 1.72 | 0.42 | 0.80 | 0.38 | 1.02 |
| 399 | Y300W | a | 0.80 | 0.38 | 1.19 | 0.10 | 0.83 | 0.12 | 1.07 | 0.12 | 0.84 | 0.14 | 1.85 | 0.48 | 1.04 | 0.14 | 1.13 |
| 400 | Y300P | a | 1.32 | 0.30 | 1.22 | 0.11 | 0.89 | 0.14 | 0.84 | 0.13 | 1.00 | 0.19 | 1.55 | 0.36 | 1.09 | 0.19 | 0.93 |
| 401 | Y300G | a | 0.68 | 0.31 | 0.82 | 0.10 | 1.10 | 0.13 | 0.99 | 0.15 | 1.01 | 0.14 | 1.93 | 0.30 | 1.10 | 0.14 | 1.48 |
| 402 | A330E | a p | 0.11 | 0.28 | 0.54 | 0.13 | 0.61 | 0.17 | 0.47 | 0.13 | 0.90 | 0.12 | 2.96 | 0.41 | 0.96 | 0.15 | 1.20 |
| | | | 0.83 | 0.33 | 0.62 | 0.16 | 0.67 | 0.12 | 0.64 | 0.12 | 0.80 | 0.13 | 2.14 | 0.53 | 0.61 | 0.14 | 3.25 |
| | | | 3.27 | 0.30 | 0.58 | 0.08 | 0.59 | 0.15 | 0.51 | 0.20 | 1.92 | 0.18 | | | 1.07 | 0.12 | 0.08 |
| | | | 2.18 | 0.14 | 0.26 | 0.25 | 1.35 | 0.55 | 0.55 | 0.71 | 0.11 | 2.82 | | | | | |
| 403 | A330N | a p | 1.44 | 0.34 | 0.39 | 0.11 | 0.47 | 0.19 | 0.22 | 0.21 | 0.58 | 0.17 | 2.03 | 0.37 | 0.86 | 0.39 | 1.23 |
| 404 | A330T | a | 0.94 | 0.32 | 0.74 | 0.08 | 0.71 | 0.14 | 0.53 | 0.15 | 0.91 | 0.15 | 1.06 | 0.31 | 0.80 | 0.13 | 1.27 |
| | | | | | | | | | | | | | | | | 0.96 | 0.12 | |

Figure 41W

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 405 | A330P |  | 0.33 | 0.35 | 0.40 | 0.35 | 1.26 | 0.23 | 0.79 | 0.23 | 0.12 | 0.17 | 0.72 | 0.31 | 5.48 | 0.15 | 0.09 |
| 406 | A330G |  | 0.38 | 0.21 | 0.13 | 22.81 | 1.86 | 0.63 | 1.44 | 0.31 | 0.00 | 2.84 |  |  | 1.37 | 0.35 | 0.00 |
| 407 | I332K | a p | 0.91 | 0.31 | 1.27 | 0.11 | 1.14 | 0.16 | 1.34 | 0.12 | 1.32 | 0.19 | 1.54 | 0.37 | 1.01 | 0.15 | 1.16 |
| 408 | I332R | a | 0.15 | 0.29 | 0.47 | 0.11 | 0.59 | 0.13 | 0.60 | 0.15 | 0.40 | 0.13 | 1.52 | 0.34 | 0.90 | 0.17 | 0.68 |
| 409 | I332S | a | 0.14 | 0.33 | 0.39 | 0.07 | 0.58 | 0.16 | 0.37 | 0.17 | 0.27 | 0.14 | 1.25 | 0.33 | 0.79 | 0.13 | 0.47 |
| 410 | I332V | a | 1.63 | 0.35 | 1.83 | 0.12 | 1.11 | 0.20 | 1.00 | 0.13 | 1.05 | 0.13 | 2.45 | 0.41 | 0.98 | 0.15 | 0.94 |
| 411 | I332L | a | 1.91 | 0.37 | 1.18 | 0.11 | 0.78 | 0.20 | 0.51 | 0.21 | 1.05 | 0.21 | 5.94 | 0.50 | 59.27 | 0.70 | 1.35 |
| 412 | I332F | a | 1.76 | 0.31 | 0.86 | 0.07 | 0.99 | 0.18 | 0.76 | 0.17 | 0.97 | 0.14 | 3.98 | 0.56 | 0.73 | 0.19 | 0.98 |
| 413 | I332M | a | 1.56 | 0.32 | 1.66 | 0.09 | 1.55 | 0.16 | 1.26 | 0.16 | 1.13 | 0.14 | 3.32 | 0.34 | 0.78 | 0.18 | 0.73 |
| 414 | I332W | a |  |  |  |  |  |  |  |  |  |  |  |  |  |  |  |
| 415 | I332P | a |  |  |  |  |  |  |  | 20.57 |  |  |  |  |  |  |  |
| 417 | L234K | a | 0.43 | 0.34 | 0.65 | 0.50 | 1.42 | 0.32 | 1.09 | 0.12 | 0.53 | 0.75 | 2.02 | 0.07 | 0.62 | 0.14 | 0.38 |
| 418 | L234R | a | 0.38 | 0.36 | 0.87 | 0.57 | 1.49 | 0.37 | 1.52 | 0.14 | 0.73 | 0.59 | 1.72 | 0.10 | 1.19 | 0.12 | 0.49 |
| 419 | L234S | a | 0.49 | 0.20 | 1.01 | 0.41 | 1.40 | 0.26 | 1.30 | 0.14 | 0.69 | 0.32 | 1.10 | 9.38 | 0.93 | 0.10 | 0.49 |
| 420 | L234A | a | 0.44 | 0.09 | 0.80 | 0.30 | 0.85 | 0.19 | 0.62 | 0.09 | 0.35 | 0.24 | 0.88 | 0.04 | 0.58 | 0.10 | 0.32 |
| 421 | L234M | a | 0.64 | 0.08 | 0.89 | 0.24 | 0.90 | 0.17 | 0.65 | 0.10 | 0.49 | 0.16 | 0.88 | 0.26 | 0.55 | 0.10 | 0.54 |
| 422 | L234W | a |  |  |  |  |  |  |  |  |  |  |  |  |  |  |  |
| 423 | L234P | a |  |  |  |  |  |  |  |  |  |  |  |  |  |  |  |
| 424 | L234G | a | 0.70 | 0.47 | 3.26 | 0.53 | 3.62 | 0.34 | 3.48 | 0.26 | 2.17 | 0.61 | 1.91 | 0.08 | 2.54 | 0.11 | 0.60 |
| 425 | L235E | a | 0.08 | 0.20 |  |  | 0.62 | 0.68 | 0.69 | 26.67 | 0.01 | 2.83 |  |  | 1.75 | 0.37 | 0.02 |
| 426 | L235K | a | 0.34 | 0.28 | 0.63 | 0.31 | 0.83 | 0.19 | 0.80 | 0.08 | 1.06 | 0.18 | 0.93 | 0.04 | 0.78 | 0.14 | 1.28 |
| 427 | L235R | a | 0.42 | 0.64 | 0.56 | 0.55 | 1.28 | 0.35 | 1.34 | 0.13 | 0.63 | 0.71 | 1.55 | 0.13 | 0.96 | 0.17 | 0.49 |
| 428 | L235A | a | 0.35 | 0.69 | 0.71 | 0.52 | 1.93 | 0.29 | 1.15 | 0.11 | 0.62 | 0.68 | 1.73 | 0.07 | 0.53 | 0.17 | 0.32 |
| 429 | L235M | a | 0.34 | 0.22 | 0.62 | 0.35 | 0.84 | 0.21 | 0.78 | 0.10 | 0.41 | 0.30 | 1.00 | 0.04 | 0.97 | 0.15 | 0.49 |
| 430 | L235W | a | 0.38 | 0.09 | 0.79 | 0.26 | 0.89 | 0.19 | 0.64 | 0.09 | 0.46 | 0.23 | 1.05 | 0.05 | 0.69 | 0.11 | 0.51 |
| 431 | L235P | a | 0.11 | 0.34 | 0.90 | 0.19 | 0.77 | 0.17 | 0.50 | 0.08 | 0.32 | 0.24 | 0.83 | 0.04 | 0.46 | 0.11 | 0.42 |
| 432 | L235G | a | 0.13 | 0.62 | 1.16 | 0.27 | 1.16 | 0.18 | 0.89 | 0.10 | 0.78 | 0.23 | 1.31 | 0.05 | 0.86 | 0.12 | 0.67 |
| 433 | V264D | a |  | 579 | 0.99 | 0.31 | 1.02 | 0.19 | 0.74 | 0.11 | 0.43 | 0.34 | 1.12 | 0.06 | 0.68 | 0.11 | 0.42 |
| 434 | V264E | a | 0.56 | 0.20 | 0.19 | 0.22 | 0.24 | 0.49 | 0.54 | 0.38 | 0.93 | 0.69 | 0.54 | 0.67 | 7.67 | 0.51 | 3.92 |
| 435 | V264N | a | 0.67 | 0.06 | 0.37 | 0.44 | 0.74 | 0.26 | 0.94 | 0.09 | 0.44 | 0.67 | 0.60 | 0.07 | 0.93 | 0.17 | 0.60 |
| 436 | V264Q | a | 0.93 | 0.15 | 1.04 | 0.17 | 1.63 | 0.28 | 1.60 | 0.25 | 0.34 | 0.69 |  |  | 3.39 | 0.56 | 0.21 |
| 437 | V264K | a | 0.62 | 0.08 | 0.48 | 0.25 | 0.68 | 0.20 | 0.61 | 0.09 | 0.38 | 0.20 | 0.73 | 0.13 | 0.72 | 0.14 | 0.55 |
| 438 | V264R | a | 0.48 | 0.13 | 0.46 | 0.39 | 0.77 | 0.24 | 0.67 | 0.09 | 0.36 | 0.45 | 0.97 | 0.05 | 0.50 | 0.11 | 0.47 |
|  |  |  | 0.31 | 1.12 | 1.21 | 0.66 | 2.37 | 0.30 | 2.01 | 0.13 | 7.42 | 11.18 | 3.05 | 0.04 | 0.67 | 0.10 | 3.13 |

Figure 41X

| | | | | | | | | | | | | | | | | |
|---|---|---|---|---|---|---|---|---|---|---|---|---|---|---|---|---|
| 439 | V264S | a | 1.15 | 0.23 | 0.69 | 0.17 | 1.37 | 0.51 | 0.81 | 0.37 | 0.35 | 0.69 | 0.83 | 0.72 | 5.13 | 0.52 | 0.26 |
| 440 | V264H | a | 0.34 | 0.09 | 0.27 | 0.25 | 0.30 | 0.20 | 0.22 | 0.13 | 0.16 | 0.22 | 0.58 | 0.05 | 0.55 | 0.18 | 0.52 |
| 441 | V264W | a | 0.59 | 0.06 | 0.81 | 0.27 | 0.81 | 0.18 | 0.67 | 0.09 | 0.39 | 0.27 | 0.86 | 0.03 | 0.87 | 0.15 | 0.48 |
| 442 | V264P | a | 0.41 | 0.19 | 0.26 | 0.19 | 1.11 | 0.26 | 1.14 | 0.33 | 0.21 | 0.70 | 1.13 | 0.53 | 0.93 | 0.57 | 0.19 |
| 443 | V264G | a | 0.33 | 0.23 | 0.94 | 0.30 | 0.89 | 0.19 | 0.71 | 0.11 | 0.51 | 0.45 | 1.04 | 0.13 | 0.76 | 0.14 | 0.57 |
| 444 | D265Q | a | 0.20 | 1.32 | 1.72 | 0.42 | 2.15 | 0.23 | 1.46 | 0.13 | 1.00 | 1.01 | 2.12 | 0.05 | 0.87 | 0.19 | 0.47 |
| 445 | D265K | a | 0.71 | 1.23 | 0.77 | 0.79 | 2.55 | 0.45 | 2.18 | 0.14 | 1.50 | 1.54 | 2.98 | 0.04 | 1.16 | 0.13 | 0.59 |
| 446 | D265R | a | 0.29 | 0.47 | 0.50 | 0.44 | 1.07 | 0.27 | 0.89 | 0.10 | 0.49 | 0.65 | 1.47 | 0.07 | 0.53 | 0.11 | 0.46 |
| 447 | D265S | a | 0.41 | 0.39 | 0.64 | 0.46 | 1.41 | 0.26 | 1.04 | 0.12 | 0.61 | 0.67 | 1.66 | 0.07 | 0.74 | 0.13 | 0.43 |
| 448 | D265T | a | 0.33 | 0.23 | 0.48 | 0.53 | 0.86 | 0.23 | 0.74 | 0.09 | 0.40 | 0.52 | 1.24 | 0.04 | 0.72 | 0.10 | 0.47 |
| 449 | D265H | a | 0.11 | 0.76 | 0.72 | 0.38 | 0.93 | 0.22 | 0.92 | 0.11 | 0.47 | 0.60 | 1.39 | 0.06 | 0.44 | 0.11 | 0.50 |
| 450 | D265V | a | 0.14 | 0.58 | 0.86 | 0.34 | 0.90 | 0.19 | 0.78 | 0.10 | 0.53 | 0.52 | 0.92 | 0.04 | 0.55 | 0.11 | 0.59 |
| 451 | D265L | a | 0.24 | 1.08 | 1.70 | 0.36 | 1.63 | 0.20 | 1.44 | 0.11 | 0.90 | 0.65 | 1.60 | 0.06 | 0.49 | 0.12 | 0.55 |
| 452 | D265I | a | 0.12 | 0.67 | 1.00 | 0.32 | 0.98 | 0.19 | 0.88 | 0.11 | 0.67 | 0.75 | 0.97 | 0.04 | 0.55 | 0.09 | 0.68 |
| 453 | D265F | a | 0.49 | 0.28 | 0.56 | 0.34 | 0.80 | 0.18 | 0.74 | 0.09 | 0.59 | 0.32 | 0.63 | 0.08 | 0.61 | 0.13 | 0.74 |
| 454 | D265M | a | 0.01 | 1.21 | | 13.21 | 0.58 | 0.40 | 0.30 | 1.04 | 0.02 | 1.09 | | | 0.43 | 0.46 | 0.03 |
| 455 | D265Y | a | 0.52 | 0.43 | 0.72 | 0.34 | 0.99 | 0.17 | 0.98 | 0.09 | 0.84 | 0.42 | 1.02 | 0.09 | 0.67 | 0.13 | 0.85 |
| 456 | D265W | a | 0.74 | 0.43 | 1.13 | 0.41 | 1.94 | 0.20 | 1.56 | 0.10 | 1.19 | 0.56 | 1.92 | 0.10 | 1.18 | 0.12 | 0.61 |
| 457 | D265P | a | | | | | | | | | | | | | | | |
| 458 | K326P | a | 0.99 | 0.11 | 0.71 | 0.17 | 0.54 | 0.12 | 0.45 | 0.07 | 0.64 | 0.20 | 0.59 | 0.08 | 0.91 | 0.15 | 1.18 |
| 459 | A327E | a | 0.93 | 0.17 | 1.19 | 0.29 | 1.25 | 0.15 | 0.96 | 0.09 | 1.01 | 0.46 | 1.21 | 0.10 | 1.01 | 0.14 | 0.81 |
| 460 | A327K | a | 0.91 | 0.17 | 1.20 | 0.27 | 1.36 | 0.15 | 0.95 | 0.10 | 0.98 | 0.51 | 1.29 | 0.10 | 0.80 | 0.12 | 0.72 |
| 461 | A327R | ap | 1.36 | 0.14 | 0.52 | 0.47 | 1.01 | 0.23 | 0.97 | 0.13 | 0.75 | 0.54 | 1.39 | 0.11 | 1.29 | 0.15 | 0.74 |
| 462 | A327H | ap | | | | | | | | | | | | | | | |
| 463 | A327V | a | 0.65 | 0.07 | 0.26 | 0.26 | 0.44 | 0.21 | 0.33 | 0.11 | 0.27 | 0.25 | 0.56 | 0.09 | 0.71 | 0.20 | 0.60 |
| 464 | A327I | a | 0.69 | 0.07 | 0.45 | 0.27 | 0.64 | 0.17 | 0.51 | 0.09 | 0.37 | 0.27 | 0.60 | 0.08 | 1.08 | 0.14 | 0.58 |
| 465 | A327F | a | 0.82 | 0.07 | 0.64 | 0.26 | 0.78 | 0.16 | 0.67 | 0.09 | 0.51 | 0.24 | 0.75 | 0.08 | 1.23 | 0.13 | 0.66 |
| 466 | A327M | a | 1.04 | 0.09 | 0.70 | 0.31 | 0.86 | 0.18 | 0.76 | 0.10 | 0.61 | 0.30 | 0.86 | 0.08 | 0.90 | 0.12 | 0.71 |
| 467 | A327Y | a | 0.76 | 0.09 | 0.66 | 0.25 | 0.70 | 0.14 | 0.59 | 0.08 | 0.47 | 0.28 | 0.68 | 0.08 | 0.86 | 0.14 | 0.67 |
| 468 | A327W | a | 1.06 | 0.09 | 0.78 | 0.23 | 0.76 | 0.13 | 0.63 | 0.08 | 0.47 | 0.22 | 0.80 | 0.07 | 0.89 | 0.15 | 0.61 |
| 469 | A327P | a | 0.95 | 0.15 | 0.64 | 0.19 | 0.54 | 0.12 | 0.51 | 0.09 | 0.51 | 0.31 | 0.43 | 0.09 | 0.89 | 0.16 | 0.95 |
| 470 | L328D | a | 1.15 | 0.07 | 0.70 | 0.22 | 0.86 | 0.14 | 0.77 | 0.07 | 0.67 | 0.22 | 0.79 | 0.10 | 0.95 | 0.19 | 0.78 |
| 471 | L328Q | ap | 0.77 | 0.22 | 0.51 | 0.38 | 0.99 | 0.20 | 0.91 | 0.09 | 0.87 | 0.32 | 1.13 | 0.09 | 1.82 | 0.46 | 0.88 |
| 472 | L328K | a | 0.07 | 0.27 | 0.10 | 0.82 | 0.88 | 0.58 | 0.37 | 1.05 | 0.11 | 0.93 | 1.21 | 0.52 | 0.66 | 0.20 | 0.12 |
| 473 | L328R | a | 0.96 | 0.08 | 1.14 | 0.17 | 0.90 | 0.13 | 0.70 | 0.07 | 0.59 | 0.19 | 0.76 | 0.08 | 0.66 | 0.20 | 0.65 |
| 474 | L328S | a | 0.60 | 0.07 | 0.62 | 0.23 | 0.61 | 0.12 | 0.44 | 0.07 | 0.46 | 0.24 | 0.59 | 0.08 | 0.74 | 0.14 | 0.76 |
| 475 | L328T | a | | | | | | | | | | | | | | | |

Figure 41Y

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 476 | L328V | a | 0.70 | 0.06 | 0.54 | 0.18 | 0.60 | 0.13 | 0.43 | 0.08 | 0.49 | 0.22 | 0.57 | 0.09 | 0.52 | 0.12 | 0.82 |
| 477 | L328I | a | 0.79 | 0.08 | 0.69 | 0.19 | 0.67 | 0.12 | 0.55 | 0.07 | 0.58 | 0.20 | 0.60 | 0.08 | 0.77 | 0.14 | 0.86 |
| 478 | L328Y | a | 1.05 | 0.09 | 0.88 | 0.19 | 0.75 | 0.12 | 0.63 | 0.08 | 0.47 | 0.30 | 0.71 | 0.07 | 0.92 | 0.13 | 0.63 |
| 479 | L328W | a | 1.01 | 0.06 | 1.16 | 0.19 | 0.90 | 0.13 | 0.82 | 0.09 | 0.73 | 0.30 | 0.63 | 0.09 | 1.35 | 0.13 | 0.81 |
| 480 | L328P | a | 0.72 | 0.07 | 0.38 | 0.29 | 0.61 | 0.17 | 0.52 | 0.08 | 0.42 | 0.33 | 0.56 | 0.09 | 0.76 | 0.19 | 0.68 |
| 481 | L328G | a | 1.18 | 0.10 | 0.71 | 0.34 | 0.90 | 0.16 | 0.93 | 0.08 | 0.64 | 0.41 | 0.80 | 0.08 | 1.16 | 0.24 | 0.70 |
| 482 | P329D | a | 0.72 | 0.12 | 0.55 | 0.32 | 0.82 | 0.17 | 0.80 | 0.09 | 0.62 | 0.29 | 0.80 | 0.09 | 0.79 | 0.26 | 0.76 |
| 483 | P329E | a | | | | | | | | | | | | | | | |
| 484 | P329N | a | 0.76 | 0.08 | 0.65 | 0.54 | 0.98 | 0.15 | 0.86 | 0.08 | 0.97 | 0.21 | 0.97 | 0.08 | 1.00 | 0.13 | 0.99 |
| 485 | P329Q | a | 0.72 | 0.15 | 0.70 | 0.33 | 0.84 | 0.17 | 0.81 | 0.09 | 0.68 | 0.41 | 0.91 | 0.08 | | | 0.80 |
| 486 | P329K | a | 0.20 | 2.88 | | | 0.16 | 0.47 | 0.57 | 0.42 | 0.02 | 0.90 | 1.17 | 0.53 | 0.72 | 0.12 | 0.10 |
| 487 | P329R | a | 1.83 | 0.18 | 2.06 | 0.33 | 2.38 | 0.17 | 2.03 | 0.10 | 1.52 | 0.43 | 2.23 | 0.07 | 1.64 | 0.16 | 0.64 |
| 488 | P329S | a | 0.60 | 0.13 | 0.77 | 0.25 | 0.76 | 0.14 | 0.75 | 0.52 | 0.62 | 0.36 | 0.87 | 0.07 | 0.77 | 0.13 | 0.82 |
| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
| 489 | P329T | a | 0.34 | 0.11 | 0.49 | 0.21 | 0.47 | 0.14 | 0.33 | 0.10 | 0.41 | 0.32 | 0.52 | 0.09 | 0.70 | 0.13 | 0.88 |
| 490 | P329H | a | 0.09 | 0.21 | 0.24 | 0.57 | 0.24 | 0.15 | 0.30 | 0.23 | 0.03 | 0.25 | 1.05 | 0.12 | 0.64 | 0.41 | 0.12 |
| 491 | P329V | a | 0.51 | 0.19 | 0.33 | 0.49 | 0.31 | 0.21 | 0.28 | 0.26 | 0.04 | 0.27 | 1.62 | 0.12 | 0.64 | 0.39 | 0.12 |
| 492 | P329L | a | 0.17 | 0.21 | 0.24 | 0.58 | 0.22 | 0.13 | 0.22 | 0.17 | 0.04 | 0.19 | 2.78 | 0.16 | 0.56 | 0.42 | 0.18 |
| 493 | P329I | a | 0.40 | 0.15 | 0.31 | 0.54 | 0.27 | 0.21 | 0.27 | 0.21 | 0.03 | 0.18 | 2.57 | 0.14 | 0.48 | 0.36 | 0.12 |
| 494 | P329M | a | 0.21 | 0.16 | 0.23 | 0.57 | 0.21 | 0.21 | 0.16 | 0.18 | 0.03 | 0.21 | 4.36 | 0.15 | 0.62 | 0.43 | 0.13 |
| 495 | P329Y | a | | | | | | | | | | | | | | | |
| 496 | P329W | a | 0.54 | 0.55 | | | 0.09 | 1.39 | 0.61 | 0.76 | 0.02 | 1.47 | 1.04 | 0.49 | 3.16 | 0.72 | 0.25 |
| 497 | P329G | a | 1.03 | 0.14 | 0.30 | 0.47 | 0.25 | 0.16 | 0.29 | 0.14 | 0.06 | 0.19 | 4.72 | 0.13 | 0.45 | 0.40 | 0.23 |
| 498 | P331D | a p | 3.14 | 0.18 | 0.92 | 0.49 | 1.18 | 0.12 | 1.23 | 0.19 | 0.74 | 0.18 | 5.89 | 0.12 | 0.79 | 0.40 | 0.63 |
| | | | 1.65 | 0.12 | 0.32 | 0.19 | 1.00 | 0.50 | 0.86 | 4.39 | 0.05 | 2.82 | | | 0.80 | 0.42 | 0.05 |
| 499 | P331Q | a | 1.71 | 0.14 | 0.60 | 0.40 | 0.63 | 0.13 | 0.77 | 0.17 | 0.64 | 0.12 | 2.46 | 0.12 | 0.60 | 0.46 | 1.01 |
| 500 | P331R | a | 2.29 | 0.19 | 0.39 | 0.42 | 0.54 | 0.22 | 0.32 | 0.22 | 0.29 | 0.09 | 0.96 | 0.15 | 0.89 | 0.37 | 0.54 |
| 501 | P331T | a | 1.67 | 0.13 | 0.53 | 0.41 | 0.71 | 0.17 | 0.88 | 0.23 | 0.57 | 0.10 | 3.25 | 0.14 | 0.57 | 0.37 | 0.81 |
| 502 | P331L | a p | 1.95 | 0.33 | 0.53 | 0.45 | 0.92 | 0.12 | 0.99 | 0.24 | 0.50 | 0.12 | 6.07 | 0.15 | 0.54 | 0.40 | 0.54 |
| | | | 0.64 | 0.16 | 0.68 | 0.14 | 1.14 | 0.11 | 1.37 | 0.36 | 0.35 | 0.36 | 5.28 | 0.12 | 1.77 | 0.13 | 0.31 |
| 503 | P331I | a | 1.63 | 0.15 | 0.41 | 0.41 | 0.71 | 0.18 | 0.78 | 0.19 | 0.22 | 0.19 | 3.81 | 0.16 | 0.56 | 0.41 | 0.32 |
| 504 | P331F | a | 1.02 | 0.13 | 0.51 | 0.18 | 0.67 | 0.41 | 0.97 | 0.26 | 0.29 | 0.69 | 0.96 | 0.48 | 3.91 | 0.90 | 0.44 |
| 505 | P331M | a | 1.74 | 0.12 | 0.60 | 0.47 | 1.13 | 0.18 | 0.94 | 0.16 | 0.77 | 0.12 | 2.50 | 0.12 | 0.53 | 0.37 | 0.68 |
| 506 | P331Y | a | 1.20 | 0.13 | 1.24 | 0.16 | 0.47 | 0.47 | 0.82 | 0.35 | 0.69 | 0.69 | 0.95 | 0.55 | 6.06 | 0.75 | 1.47 |
| 507 | P331W | a | 1.95 | 0.13 | 0.79 | 0.41 | 1.46 | 0.14 | 1.32 | 0.18 | 0.76 | 0.12 | 2.41 | 0.13 | 0.87 | 0.46 | 0.52 |
| 508 | E333L | a | 1.03 | 0.14 | 0.56 | 0.44 | 0.93 | 0.15 | 0.94 | 0.23 | 0.90 | 0.10 | 3.06 | 0.16 | 1.03 | 0.49 | 0.97 |

Figure 41Z

| | | | | | | | | | | | | | | |
|---|---|---|---|---|---|---|---|---|---|---|---|---|---|---|
| 509 | E333F | a p | 2.22 | 0.14 | 0.69 | 0.45 | 0.93 | 0.18 | 1.55 | 0.30 | 1.69 | 0.15 | 6.96 | 0.16 | 0.82 | 0.42 | 1.82 |
| 510 | E333M | a | 0.91 | 0.17 | 0.86 | 0.14 | 1.58 | 0.18 | 1.66 | 0.39 | 1.22 | 0.40 | 5.83 | 0.20 | 1.96 | 0.15 | 0.77 |
| 511 | E333P | a | 1.17 | 0.18 | 0.86 | 0.15 | 1.20 | 1.87 | 0.21 | 0.76 | 0.74 | 0.70 | 0.96 | 0.53 | 5.46 | 0.78 | 0.62 |
| 512 | K334P | a | 1.77 | 0.13 | 1.26 | 0.41 | 1.04 | 0.16 | 1.22 | 0.20 | 1.51 | 0.14 | 1.23 | 0.15 | 0.64 | 0.38 | 1.44 |
| 513 | K222E | a | 0.77 | 0.14 | 0.48 | 0.51 | 0.50 | 0.15 | 0.34 | 0.26 | 0.34 | 0.10 | 1.06 | 0.12 | 0.66 | 0.41 | 0.68 |
| 514 | K222Y | a | 1.92 | 0.22 | 1.28 | 0.28 | 1.69 | 0.42 | 1.33 | 0.44 | 0.11 | 2.86 | | | 1.31 | 0.39 | 0.07 |
| 515 | F243E | a | 0.93 | 0.13 | 0.18 | 0.33 | 1.24 | 0.49 | 0.63 | 0.52 | 0.14 | 2.84 | | | 1.14 | 0.40 | 0.11 |
| 516 | D270R | a | 0.60 | 0.32 | 0.37 | 0.56 | 0.94 | 0.12 | 0.36 | 0.19 | 0.14 | 0.13 | 0.47 | 0.16 | 0.82 | 0.43 | 0.14 |
| 517 | D270S | a | 0.81 | 0.16 | 0.69 | 0.44 | 1.80 | 0.14 | 0.61 | 0.18 | 0.19 | 0.13 | 0.81 | 0.19 | 1.03 | 0.49 | 0.10 |
| 518 | D270L | a | 1.03 | 0.18 | 0.59 | 0.47 | 0.35 | 0.19 | 0.31 | 0.16 | 0.40 | 0.11 | 0.72 | 0.12 | 0.54 | 0.43 | 1.15 |
| 519 | D270I | a | 0.58 | 0.15 | 0.15 | 0.30 | 0.76 | 0.60 | | | 0.02 | 2.83 | | | 1.23 | 0.38 | 0.03 |
| 520 | D270F | a | 0.66 | 0.18 | 0.64 | 0.40 | 0.39 | 0.17 | 0.21 | 0.15 | 0.19 | 0.14 | 0.70 | 0.13 | 0.70 | 0.40 | 0.49 |
| 521 | D270M | a | 0.74 | 0.19 | 0.43 | 0.49 | 0.21 | 0.18 | 0.37 | 0.19 | 0.36 | 0.09 | 1.11 | 0.12 | 0.99 | 0.44 | 1.72 |
| 522 | D270Y | a | 0.51 | 0.22 | 0.54 | 0.48 | 0.34 | 0.14 | 0.37 | 0.16 | 0.28 | 0.11 | 0.62 | 0.18 | 0.93 | 0.37 | 0.83 |
| 523 | D270W | a | 0.84 | 0.20 | 0.49 | 0.44 | 0.25 | 0.20 | 0.38 | 0.21 | 0.17 | 0.10 | 0.62 | 0.21 | 0.92 | 0.43 | 0.68 |
| 524 | D270P | a | 0.37 | 0.21 | 0.32 | 0.60 | 0.25 | 0.19 | 0.32 | 0.22 | 0.04 | 0.23 | 0.91 | 0.27 | 0.55 | 0.34 | 0.15 |
| 525 | D270G | a | 0.52 | 0.24 | 0.42 | 0.50 | 0.38 | 0.12 | 0.22 | 0.23 | 0.08 | 0.18 | 0.63 | 0.30 | 0.97 | 0.46 | 0.21 |
| 526 | D271D | a p | 1.48 | 0.15 | 0.77 | 0.43 | 1.20 | 0.13 | 1.02 | 0.14 | 1.12 | 0.13 | 1.80 | 0.14 | 0.52 | 0.42 | 0.93 |
| 527 | P271E | a | 1.87 | 0.14 | 0.65 | 0.46 | 0.95 | 0.15 | 0.72 | 0.17 | 0.75 | 0.17 | 0.72 | 0.14 | 0.41 | 0.50 | 0.79 |
| 528 | P271N | a | 1.61 | 0.13 | 0.78 | 0.41 | 0.98 | 0.11 | 0.79 | 0.12 | 0.63 | 0.14 | 1.17 | 0.13 | 0.54 | 0.41 | 0.64 |
| 529 | P271Q | a | 0.55 | 0.24 | 0.71 | 0.09 | 1.07 | 0.79 | 0.66 | 0.30 | 0.60 | 0.23 | 0.86 | 0.18 | 0.56 | 0.12 | 0.56 |
| 530 | P271K | a | 0.63 | 0.27 | 0.67 | 0.09 | 0.90 | 0.87 | 0.36 | 0.29 | 0.71 | 0.17 | 0.71 | 0.20 | 0.87 | 0.16 | 0.79 |
| 531 | P271R | a | 0.60 | 0.30 | 0.67 | 0.08 | 1.68 | 1.14 | 0.28 | 0.31 | 0.51 | 0.19 | 0.52 | 0.20 | 0.78 | 0.14 | 0.31 |
| 532 | P271S | a | 0.55 | 0.24 | 0.73 | 0.08 | 1.71 | 1.10 | 0.61 | 0.27 | 0.70 | 0.21 | 0.71 | 0.16 | 1.14 | 0.14 | 0.41 |
| 533 | P271T | a | 0.77 | 0.22 | 0.97 | 0.07 | 2.73 | 0.90 | 0.83 | 0.30 | 0.53 | 0.19 | 0.95 | 0.17 | 3.88 | 0.12 | 0.19 |
| 534 | P271H | a p | 0.56 | 0.30 | 0.63 | 0.13 | 0.37 | 0.66 | 0.45 | 0.31 | 0.67 | 0.20 | 0.88 | 0.18 | 0.74 | 0.13 | 1.80 |
| 535 | P271A | a | 0.85 | 0.24 | 0.70 | 0.07 | 1.05 | 0.87 | 0.93 | 0.27 | 0.73 | 0.23 | 1.02 | 0.17 | 1.01 | 0.21 | 0.70 |
| 536 | P271V | a | 0.33 | 0.30 | 0.43 | 0.14 | 1.73 | 0.95 | 0.15 | 0.33 | 0.17 | 0.18 | 0.50 | 0.18 | 0.54 | 0.15 | 0.10 |
| 537 | P271L | | 1.52 | 0.15 | 0.35 | 0.27 | 0.84 | 0.43 | 0.75 | 0.42 | 0.06 | 2.82 | | | 1.06 | 0.38 | 0.07 |
| 538 | P271I | a p | 1.77 | 0.27 | 0.73 | 0.09 | 1.09 | 0.79 | 1.17 | 0.30 | 0.46 | 0.22 | 1.56 | 0.16 | 0.43 | 0.23 | 0.42 |
| 539 | P271F | a | 0.99 | 0.22 | 2.13 | 0.08 | 1.42 | 0.71 | 1.09 | 0.27 | 1.28 | 0.19 | 1.51 | 0.16 | 1.99 | 0.20 | 0.90 |
| 540 | P271M | a | 0.64 | 0.25 | 0.54 | 0.12 | 1.66 | 0.92 | 0.45 | 0.29 | 0.44 | 0.20 | 0.89 | 0.19 | 0.68 | 0.12 | 0.26 |
| 541 | P271Y | a | 0.91 | 0.30 | 0.62 | 0.08 | 2.37 | 1.38 | 0.67 | 0.28 | 0.52 | 0.20 | 0.91 | 0.20 | 0.54 | 0.14 | 0.22 |
| 541b | P271Y | | 0.71 | 0.31 | 0.70 | 0.12 | 3.65 | 1.10 | 0.21 | 0.36 | 0.37 | 0.21 | 0.64 | 0.17 | 1.48 | 0.14 | 0.10 |
| 542 | P271W | a | 0.60 | 0.24 | 0.63 | 0.47 | 0.52 | 0.73 | 0.25 | 0.32 | 0.72 | 0.22 | 1.06 | 0.18 | 0.98 | 0.15 | 1.37 |

Figure 41AA

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 543 | P271G | a | 0.88 | 0.21 | 2.33 | 0.04 | 1.79 | 0.86 | 5.03 | 0.27 | 1.09 | 0.27 | 0.96 | 0.17 | 0.57 | 0.22 | 0.61 |
| 544 | D280K | a | 2.07 | 0.14 | 1.50 | 0.25 | 4.50 | 0.37 | 4.02 | 0.34 | 0.07 | 2.82 |  |  | 0.79 | 0.37 | 0.02 |
| 545 | D280L | a | 1.99 | 0.32 | 0.68 | 0.08 | 1.54 | 0.83 | 0.51 | 0.32 | 0.59 | 0.17 | 0.68 | 0.20 | 0.38 | 0.17 | 0.38 |
| 546 | D280W | a | 0.62 | 0.25 | 0.84 | 0.06 | 1.33 | 0.78 | 0.39 | 0.29 | 0.65 | 0.29 | 0.86 | 0.19 | 0.45 | 0.16 | 0.49 |
| 547 | D280P | a | 0.47 | 0.26 | 0.83 | 0.07 | 1.30 | 0.78 | 0.33 | 0.30 | 0.57 | 0.24 | 0.76 | 0.18 | 0.38 | 0.16 | 0.44 |
| 548 | D280G | a | 0.81 | 0.12 |  |  | 0.91 | 0.34 |  |  | 0.28 | 0.17 |  |  |  |  | 0.31 |
| 549 | K290D | a | 1.75 | 0.15 | 0.92 | 0.25 | 2.12 | 0.63 | 1.71 | 0.31 | 0.15 | 2.82 | 2.20 | 0.20 | 0.98 | 0.38 | 0.07 |
| 550 | K290N | a | 0.91 | 0.31 | 1.42 | 0.07 | 1.36 | 1.07 | 1.87 | 0.28 | 1.81 | 0.23 | 1.97 | 0.19 | 0.33 | 0.15 | 1.33 |
| 551 | K290H | a | 0.85 | 0.30 | 1.26 | 0.07 | 0.76 | 0.90 | 1.31 | 0.28 | 1.48 | 0.21 | 1.88 | 0.17 | 0.39 | 0.14 | 1.93 |
| 552 | K290L | a | 1.14 | 0.34 | 1.13 | 0.06 | 1.66 | 0.86 | 0.83 | 0.30 | 1.50 | 0.23 |  |  | 0.41 | 0.16 | 0.90 |
| 553 | K290W | a | 1.07 | 0.10 |  |  | 0.86 | 0.29 |  |  | 0.30 | 0.18 |  |  |  |  | 0.35 |
| 554 | E293N | a | 0.76 | 0.19 | 1.00 | 0.15 | 0.38 | 0.66 | 1.44 | 0.29 | 1.37 | 0.28 | 1.53 | 0.19 | 0.68 | 0.13 | 3.63 |
|  |  |  | 1.24 | 0.25 | 0.83 | 0.08 | 1.43 | 0.91 | 0.62 | 0.30 | 0.67 | 0.18 | 1.06 | 0.21 | 0.71 | 0.24 | 0.47 |
| Variant | Substitution(s) | Context | Fold | Conf | Fold | Conf | Fold | Conf | Fold | Conf | Fold | Conf | Fold | Conf | Fold | Conf | IIIa:IIb |
| 555 | E293R | a p | 172 | 0.64 | 0.66 | 0.20 | 1.75 | 0.82 | 0.40 | 0.46 | 68.81 | 2.94 | 3.16 | 0.48 | 0.67 | 0.15 | 39.28 |
| 556 | E293S | a | 18.03 | 0.43 | 0.93 | 0.16 | 2.22 | 0.28 | 0.88 | 0.31 | 2.90 | 1.26 | 1.77 | 0.36 | 0.38 | 0.31 | 1.31 |
| 557 | E293T | a | 2.69 | 0.25 | 0.91 | 0.17 | 1.61 | 0.76 | 0.57 | 0.34 | 0.86 | 0.22 | 1.01 | 0.21 | 0.53 | 0.20 | 0.53 |
| 558 | E293H | a | 1.50 | 0.38 | 0.73 | 0.09 | 2.11 | 0.91 | 0.55 | 0.27 | 0.69 | 0.21 | 0.91 | 0.24 | 0.58 | 0.15 | 0.33 |
| 559 | E293V | a | 2.26 | 0.21 | 0.59 | 0.09 | 1.85 | 1.06 | 0.29 | 0.26 | 0.61 | 0.18 | 1.05 | 0.28 | 0.48 | 0.13 | 0.33 |
| 560 | E293L | a | 2.23 | 0.30 | 0.77 | 0.13 | 4.03 | 0.97 | 0.55 | 0.28 | 0.90 | 0.19 | 1.08 | 0.22 | 0.63 | 0.14 | 0.22 |
| 561 | E293I | a | 1.66 | 0.28 | 0.85 | 0.14 | 2.79 | 0.83 | 0.56 | 0.30 | 0.51 | 0.18 | 1.02 | 0.26 | 0.77 | 0.15 | 0.18 |
| 562 | E293F | a | 1.28 | 0.22 | 0.79 | 0.16 | 0.47 | 0.68 | 0.33 | 0.29 | 0.61 | 0.19 | 0.77 | 0.23 | 0.60 | 0.13 | 1.29 |
| 563 | E293M | a | 0.74 | 0.13 | 0.51 | 0.09 | 1.27 | 0.95 | 0.31 | 0.31 | 0.23 | 0.25 | 0.64 | 0.12 | 0.61 | 0.20 | 0.18 |
| 564 | E293Y | a | 1.30 | 0.21 | 1.06 | 0.09 | 0.60 | 0.95 | 1.01 | 0.29 | 0.39 | 0.26 | 0.53 | 0.14 | 0.90 | 0.21 | 0.65 |
| 565 | E293W | a | 0.84 | 0.14 | 0.59 | 0.13 | 0.91 | 1.15 | 0.28 | 0.33 | 0.24 | 0.24 | 0.61 | 0.13 | 0.66 | 0.20 | 0.26 |
| 566 | E293P | a | 0.92 | 0.21 | 0.68 | 0.12 | 4.93 | 1.73 | 0.21 | 0.56 | 0.24 | 0.23 | 0.45 | 0.14 | 0.65 | 0.23 | 0.05 |
| 567 | E293G | a | 0.34 | 0.28 | 0.26 | 0.14 | 9.25 | 1.72 | 0.10 | 0.31 | 0.10 | 0.23 | 0.66 | 0.14 | 0.44 | 0.17 | 0.01 |
| 568 | E294K | a | 1.25 | 0.26 | 0.68 | 0.09 | 1.00 | 1.38 | 0.24 | 0.31 | 0.31 | 0.25 | 0.77 | 0.13 | 0.59 | 0.18 | 0.31 |
|  |  |  | 0.70 | 0.29 | 0.57 | 0.13 | 1.44 | 1.19 | 0.45 | 0.34 | 1.02 | 0.25 | 0.50 | 0.14 | 0.74 | 0.23 | 0.71 |
| 569 | E294R | a | 0.68 | 0.19 | 0.36 | 0.27 | 1.57 | 0.64 | 0.61 | 0.81 | 0.07 | 2.82 |  |  | 1.16 | 0.40 | 0.04 |
| 570 | E294S | a | 0.71 | 0.10 | 0.60 | 0.14 | 0.98 | 0.98 | 0.65 | 0.22 | 0.86 | 0.25 | 0.58 | 0.13 | 0.92 | 0.28 | 0.89 |
| 571 | E294T | a | 0.87 | 0.11 |  |  | 0.84 | 0.72 |  |  | 0.30 | 0.18 |  |  |  |  | 0.36 |
| 572 | E294H | a | 1.28 | 0.11 | 1.37 | 0.10 | 0.68 | 0.98 | 1.16 | 0.26 | 0.45 | 0.25 | 1.07 | 0.15 | 0.71 | 0.33 | 0.66 |
| 573 | E294V | a | 1.50 | 0.27 | 1.11 | 0.13 | 0.58 | 0.92 | 0.55 | 0.22 | 0.45 | 0.27 | 0.81 | 0.12 | 0.76 | 0.20 | 0.77 |
| 574 | E294L | a | 0.86 | 0.21 | 0.74 | 0.10 | 0.39 | 1.28 | 0.87 | 0.22 | 0.43 | 0.49 | 0.87 | 0.13 | 0.70 | 0.17 | 1.11 |
|  |  |  | 0.43 | 0.26 | 0.35 | 0.15 | 0.42 | 1.14 | 0.45 | 0.24 | 0.35 | 0.58 | 0.93 | 0.12 | 0.45 | 0.19 | 0.83 |

Figure 41BB

| | | | | | | | | | | | | | | | |
|---|---|---|---|---|---|---|---|---|---|---|---|---|---|---|---|
| 575 | E294I | a | 1.23 | 0.26 | 0.70 | 0.32 | 1.30 | 0.20 | 1.26 | 0.30 | 1.65 | 0.16 | 1.05 | 0.13 | 0.98 | 0.47 | 1.26 |
| 576 | E294F | a | 1.70 | 0.25 | 0.95 | 0.14 | 3.65 | 1.09 | 0.83 | 0.26 | 0.71 | 0.23 | 0.72 | 0.16 | 1.09 | 0.22 | 0.19 |
| 577 | E294M | a | 1.08 | 0.35 | 0.89 | 0.16 | 0.56 | 0.95 | 0.58 | 0.22 | 0.43 | 0.31 | 1.17 | 0.14 | 0.90 | 0.18 | 0.78 |
| 578 | E294Y | a | 0.96 | 0.15 | 0.84 | 0.09 | 1.70 | 1.26 | 0.65 | 0.27 | 0.67 | 0.28 | | | 0.78 | 0.21 | 0.39 |
| 579 | E294W | a | 0.70 | 0.12 | | | 0.68 | 0.49 | | | 1.32 | 0.17 | | | | | 1.95 |
| 580 | E294P | a | 0.74 | 0.18 | 0.93 | 0.10 | 0.99 | 1.08 | 0.77 | 0.22 | 1.70 | 0.38 | 1.37 | 0.15 | 0.80 | 0.20 | 1.73 |
| 581 | E294G | a | 1.00 | 0.20 | 1.09 | 0.12 | 1.34 | 0.97 | 0.50 | 0.23 | 0.67 | 0.24 | 0.50 | 0.12 | 0.77 | 0.26 | 0.50 |
| 582 | Q295D | a | 1.55 | 0.20 | 1.18 | 0.09 | 0.55 | 0.97 | 1.45 | 0.21 | 0.61 | 0.25 | 0.94 | 0.14 | 1.25 | 0.27 | 1.10 |
| 583 | Q295E | a | 1.73 | 0.24 | 0.57 | 0.10 | 3.31 | 1.54 | 0.67 | 0.30 | 0.54 | 0.26 | 2.41 | 0.27 | 0.55 | 0.17 | 0.16 |
| | | | 4.42 | 0.12 | 1.49 | 0.14 | 1.91 | 1.40 | 0.88 | 0.22 | 1.03 | 0.24 | 0.84 | 0.17 | 0.96 | 0.23 | 0.54 |
| | | | 1.36 | 0.26 | 1.37 | 0.26 | 0.80 | 0.27 | 0.72 | 0.20 | 0.89 | 0.15 | | | 0.81 | 0.49 | 1.10 |
| 584 | Q295N | a | 2.09 | 0.18 | 0.81 | 0.12 | 5.76 | 1.58 | 0.50 | 0.34 | 0.45 | 0.25 | 0.69 | 0.15 | 0.93 | 0.17 | 0.08 |
| 585 | Q295R | a | 1.30 | 0.19 | 0.78 | 0.11 | 0.51 | 0.87 | 0.45 | 0.30 | 0.35 | 0.28 | 1.43 | 0.22 | 0.67 | 0.16 | 0.69 |
| 586 | Q295S | a | 1.27 | 0.12 | 0.74 | 0.13 | 0.95 | 1.07 | 0.77 | 0.31 | 0.55 | 0.24 | 1.89 | 0.13 | 0.72 | 0.23 | 0.57 |
| 587 | Q295T | a | 1.46 | 0.12 | 1.84 | 0.11 | 1.09 | 1.04 | 1.54 | 0.23 | 1.36 | 0.24 | 1.48 | 0.21 | 3.82 | 0.20 | 1.25 |
| 588 | Q295H | a | 1.14 | 0.20 | 1.01 | 0.11 | 4.39 | 1.62 | 0.79 | 0.31 | 0.43 | 0.25 | 1.39 | 0.20 | 0.76 | 0.32 | 0.10 |
| 589 | Q295V | a | 2.12 | 0.19 | 1.63 | 0.10 | 0.99 | 1.15 | 1.56 | 0.24 | 0.61 | 0.25 | 1.35 | 0.18 | 1.19 | 0.20 | 0.62 |
| 590 | Q295I | a | 1.42 | 0.17 | 1.99 | 0.12 | 1.94 | 1.00 | 1.04 | 0.21 | 0.53 | 0.27 | 1.28 | 0.15 | 0.68 | 0.37 | 0.27 |
| 591 | Q295F | a | 1.38 | 0.27 | 0.87 | 0.13 | 1.79 | 1.17 | 0.28 | 0.28 | 0.33 | 0.26 | 1.73 | 0.12 | 0.83 | 0.24 | 0.19 |
| 592 | Q295M | a | 2.88 | 0.26 | 1.69 | 0.11 | 1.50 | 1.00 | 0.66 | 0.40 | 0.81 | 0.27 | 2.93 | 0.17 | 0.70 | 0.25 | 0.54 |
| 593 | Q295Y | a | 0.94 | 0.22 | 0.61 | 0.11 | 0.18 | 0.86 | 0.56 | 0.22 | 0.27 | 0.29 | 2.30 | 0.14 | 0.62 | 0.34 | 1.47 |
| 594 | Q295W | a | 0.12 | 0.24 | 0.43 | 0.48 | 0.38 | 0.42 | 0.50 | 0.33 | 0.27 | 0.24 | 3.15 | 0.16 | 0.32 | 0.38 | 0.71 |
| 595 | Q295P | a | 0.38 | 0.30 | 0.94 | 0.28 | 0.57 | 0.37 | 0.71 | 0.20 | 0.48 | 0.32 | 3.14 | 0.14 | 0.49 | 0.36 | 0.83 |
| 596 | Q295G | a | 0.19 | 0.23 | 0.62 | 0.35 | 0.35 | 0.51 | 0.47 | 0.25 | 0.54 | 0.25 | 4.08 | 0.12 | 0.35 | 0.37 | 1.54 |
| 597 | Y296K | ap | 0.21 | 0.26 | 0.40 | 0.36 | 0.33 | 0.53 | 0.54 | 0.30 | 0.35 | 0.16 | 2.67 | 0.14 | 0.58 | 0.34 | 1.07 |
| 598 | Y296R | a | 0.26 | 0.41 | 0.58 | 0.28 | 0.41 | 0.48 | 0.74 | 0.20 | 0.54 | 0.15 | 2.51 | 0.13 | 0.49 | 0.34 | 1.33 |
| 599 | Y296A | a | 0.56 | 0.35 | 0.44 | 0.27 | 0.48 | 0.39 | 0.68 | 0.33 | 1.06 | 0.23 | 4.09 | 0.14 | 0.42 | 0.40 | 2.20 |
| 600 | Y296V | a | 0.41 | 0.29 | 1.08 | 0.51 | 0.58 | 0.31 | 0.88 | 0.14 | 0.72 | 0.26 | 6.49 | 0.13 | 0.48 | 0.41 | 1.25 |
| 601 | Y296M | a | 0.21 | 0.33 | 0.94 | 0.36 | 0.64 | 0.34 | 0.90 | 0.17 | 0.65 | 0.28 | 3.02 | 0.19 | 0.53 | 0.36 | 1.01 |
| 602 | Y296G | a | 0.63 | 0.82 | 1.65 | 0.42 | 0.58 | 0.32 | 1.01 | 0.21 | 0.33 | 0.27 | 5.51 | 0.13 | 0.59 | 0.38 | 0.56 |
| 603 | S324H | a | 0.99 | 0.33 | 0.84 | 0.25 | 0.74 | 0.29 | 0.57 | 0.17 | 0.73 | 0.36 | 3.54 | 0.15 | 0.57 | 0.34 | 0.98 |
| 604 | S324F | a | 1.17 | 0.40 | 0.94 | 0.29 | 0.65 | 0.33 | 0.74 | 0.23 | 0.92 | 0.30 | 4.10 | 0.13 | 0.50 | 0.33 | 1.43 |
| 605 | S324M | a | 0.76 | 0.80 | 1.13 | 0.28 | 0.88 | 0.23 | 1.07 | 0.12 | 1.46 | 0.24 | 2.02 | 0.13 | 0.61 | 0.33 | 1.66 |
| 606 | S324W | a | | | | | | | | | | | | | | | |
| 607 | S324P | a | 0.28 | 0.30 | 0.42 | 0.29 | 1.23 | 0.26 | 1.01 | 0.15 | 1.38 | 0.29 | 1.68 | 0.14 | 0.63 | 0.34 | 1.12 |
| 608 | S324G | a | 1.61 | 0.33 | 2.07 | 0.27 | 1.92 | 0.27 | 1.89 | 0.34 | 6.18 | 0.22 | 3.22 | 0.16 | 1.70 | 0.36 | 3.22 |
| | | | 0.60 | 0.15 | 3.06 | 0.11 | 2.56 | 0.18 | 2.18 | 0.30 | 3.93 | 0.30 | 2.14 | 0.13 | 2.74 | 0.18 | 1.53 |

Figure 41CC

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 609 | P230E |   | 1.46 | 0.20 | 1.55 | 0.23 | 1.07 | 0.20 | 0.89 | 0.27 | 1.88 | 0.10 | 2.70 | 0.13 | 1.25 | 0.50 | 1.77 |
| 610 | P230Y | a | 2.07 | 0.52 | 1.25 | 0.31 | 2.34 | 0.45 | 1.47 | 0.15 | 1.40 | 0.24 | 2.00 | 0.12 | 1.01 | 0.34 | 0.60 |
| 611 | P230G | a | 0.44 | 0.52 | 0.40 | 0.30 | 0.85 | 0.34 | 1.22 | 0.20 | 0.56 | 0.33 | 1.27 | 0.16 | 0.65 | 0.33 | 0.66 |
| 612 | A231E | a | 1.04 | 0.45 | 0.99 | 0.38 | 1.13 | 0.36 | 0.75 | 0.21 | 0.48 | 0.22 |   |   | 1.16 | 0.34 | 0.42 |
| 613 | A231K | a | 0.50 | 0.36 | 0.62 | 0.34 | 0.41 | 0.61 | 0.58 | 0.24 | 0.58 | 0.49 | 1.40 | 0.16 | 0.52 | 0.33 | 1.39 |
| 614 | A231Y | a |   |   |   |   |   |   |   |   |   |   |   |   |   |   |   |
| 615 | A231P | a | 1.17 | 0.15 |   |   | 0.81 | 0.43 |   |   | 0.31 | 0.17 |   |   |   |   | 0.38 |
| 616 | A231G | a |   |   |   |   |   |   |   |   |   |   |   |   |   |   |   |
| 617 | E233N | a | 0.16 | 0.28 | 0.50 | 0.44 | 0.34 | 0.79 | 0.46 | 0.22 | 0.48 | 0.17 | 1.28 | 0.15 | 0.74 | 0.33 | 1.42 |
| 618 | E233Q | a | 0.19 | 0.22 | 0.52 | 0.42 | 0.27 | 0.62 | 0.39 | 0.25 | 0.51 | 0.17 | 1.17 | 0.16 | 0.61 | 0.34 | 1.88 |
| 619 | E233K | a |   |   |   |   |   |   |   |   |   |   |   |   |   |   |   |
| 620 | E233R | a | 0.14 | 0.26 | 0.75 | 0.27 | 0.36 | 0.68 | 0.60 | 0.19 | 0.35 | 0.16 | 1.13 | 0.18 | 1.05 | 0.33 | 0.97 |
| 621 | E233S | a | 0.17 | 0.18 | 0.62 | 0.35 | 0.31 | 0.59 | 0.37 | 0.35 | 0.36 | 0.19 | 1.18 | 0.16 | 1.10 | 0.33 | 1.14 |
| 622 | E233T | a | 0.15 | 0.35 | 1.28 | 0.39 | 0.78 | 0.40 | 0.83 | 0.13 | 0.42 | 0.19 | 0.99 | 0.17 | 1.19 | 0.35 | 0.54 |
| 623 | E233H | a | 0.17 | 0.32 | 0.74 | 0.27 | 0.58 | 0.40 | 0.78 | 0.14 | 0.32 | 0.27 | 1.05 | 0.15 | 0.99 | 0.33 | 0.55 |
| 624 | E233A | a | 0.10 | 0.31 | 1.23 | 0.33 | 0.60 | 0.44 | 0.71 | 0.20 | 0.46 | 0.21 | 1.02 | 0.13 | 0.93 | 0.38 | 0.75 |
| 625 | E233V | a | 0.25 | 0.48 | 0.71 | 0.31 | 0.37 | 0.61 | 0.61 | 0.17 | 0.50 | 0.21 | 0.70 | 0.15 | 0.91 | 0.33 | 1.34 |
| 626 | E233L | a | 0.53 | 0.40 | 0.55 | 0.29 | 0.26 | 0.53 | 0.54 | 0.27 | 0.52 | 0.19 | 2.24 | 0.17 | 0.60 | 0.34 | 1.99 |
| 627 | E233I | a p | 0.30 | 0.28 | 1.09 | 0.29 | 1.69 | 0.27 | 1.80 | 0.14 | 0.88 | 0.27 | 2.30 | 0.14 | 0.95 | 0.34 | 0.52 |
| 628 | E233F | a | 0.23 | 0.34 | 0.64 | 0.31 | 0.73 | 0.38 | 0.84 | 0.27 | 0.58 | 0.20 | 1.27 | 0.15 | 0.90 | 0.35 | 0.79 |
| 629 | E233M | a | 0.29 | 0.27 | 0.67 | 0.27 | 0.49 | 0.48 | 0.85 | 0.15 | 0.70 | 0.18 | 1.56 | 0.14 | 1.13 | 0.43 | 1.42 |
| 630 | E233Y | a | 0.31 | 0.14 | 0.96 | 0.10 | 0.97 | 0.16 | 0.55 | 0.14 | 0.37 | 0.09 | 0.70 | 410 | 1.86 | 0.27 | 0.38 |
| 631 | E233W | a | 0.28 | 0.17 | 0.86 | 0.12 | 0.82 | 0.14 | 0.70 | 0.15 | 0.35 | 0.13 | 0.91 | 0.34 | 1.64 | 0.24 | 0.43 |
| 632 | E233G | a | 0.36 | 0.14 | 1.21 | 0.11 | 0.94 | 0.22 | 0.74 | 0.13 | 1.21 | 0.10 | 1.03 | 0.29 | 2.09 | 0.25 | 1.29 |
| 633 | E272D | a | 1.26 | 0.24 | 1.25 | 0.10 | 1.12 | 0.13 | 1.41 | 0.12 | 1.49 | 0.16 | 1.48 | 0.18 | 1.37 | 0.22 | 1.33 |
| 634 | E272R | a p | 66.62 | 0.43 | 0.84 | 0.11 | 0.80 | 0.17 | 1.91 | 0.27 | 41.60 | 2.06 | 26.26 | 2.58 | 1.83 | 0.22 | 51.94 |
| 635 | E272T | a | 98.41 | 0.98 | 0.94 | 0.21 | 1.26 | 0.31 | 0.47 | 0.30 | 0.67 | 0.35 | 0.69 | 0.23 | 1.62 | 0.25 | 0.53 |
|   |   |   | 3.32 | 0.22 | 1.24 | 0.11 | 1.74 | 0.31 | 1.34 | 0.18 | 3.04 | 0.25 |   |   | 2.46 | 0.21 | 1.75 |
| 636 | E272H | a p | 0.96 | 0.23 | 0.44 | 0.26 | 0.75 | 0.23 | 0.74 | 0.17 | 0.31 | 0.17 | 0.55 | 0.20 | 0.79 | 0.48 | 0.41 |
|   |   |   | 7.21 | 0.20 | 0.84 | 0.09 | 1.92 | 0.10 | 0.83 | 0.13 | 28.57 | 0.15 | 1.42 | 0.25 | 1.45 | 0.27 | 14.86 |
|   |   |   | 4.09 | 0.51 | 0.88 | 0.15 | 1.70 | 0.15 | 1.18 | 0.26 | 9.83 | 0.37 |   |   | 0.90 | 0.23 | 5.77 |
|   |   |   | 1.02 | 0.26 | 0.49 | 0.29 | 0.43 | 0.39 | 0.26 | 0.47 | 0.35 | 0.10 | 0.67 | 0.20 | 0.92 | 0.43 | 0.80 |
| 637 | E272V | a | 2.80 | 0.28 | 0.96 | 0.10 | 0.72 | 0.13 | 0.50 | 0.17 | 1.19 | 0.23 | 0.67 | 0.20 | 1.77 | 0.25 | 1.64 |
| 638 | E272L | a | 2.07 | 0.22 | 1.10 | 0.10 | 0.83 | 0.13 | 0.62 | 0.13 | 1.07 | 0.19 | 0.75 | 0.21 | 1.81 | 0.21 | 1.29 |

Figure 41DD

| | | | | | | | | | | | | | | |
|---|---|---|---|---|---|---|---|---|---|---|---|---|---|---|
| 639 | E272F | a | 1.61 | 0.32 | 1.06 | 0.11 | 1.09 | 0.12 | 0.68 | 0.15 | 2.59 | 0.15 | 0.62 | 0.23 | 1.82 | 0.23 | 2.38 |
| 640 | E272M | a | 5.27 | 0.21 | 1.14 | 0.14 | 2.99 | 0.14 | 3.36 | 0.22 | 0.67 | 0.11 | 0.55 | 0.30 | 2.17 | 0.21 | 0.23 |
| 641 | E272W | a | 1.73 | 0.23 | 0.37 | 0.30 | 3.46 | 0.17 | 4.31 | 0.13 | 0.32 | 0.11 | | | 0.67 | 0.62 | 0.09 |
| 642 | E272P | a | 1.25 | 0.11 | | | 0.46 | 0.45 | | | 0.24 | 0.18 | | | | | 0.52 |
| 643 | E272G | a | | | 1.37 | 0.10 | 1.17 | 0.13 | 1.42 | 0.13 | 1.18 | 0.09 | 1.55 | 0.21 | 1.26 | 0.25 | 1.01 |
| 644 | K274D | a | 1.25 | 0.17 | | | 1.21 | 0.30 | | | 0.27 | 0.24 | | | | | 0.22 |
| 645 | K274N | a | 1.02 | 0.22 | | | | | | | | | | | | | |
| 646 | K274H | a | 1.83 | 0.16 | 1.42 | 0.08 | 1.51 | 0.14 | 2.20 | 0.13 | 1.47 | 0.16 | 2.03 | 0.19 | 1.08 | 0.28 | 0.98 |
| 647 | K274V | a | 1.98 | 0.15 | 1.22 | 0.09 | 1.04 | 0.14 | 1.89 | 0.16 | 1.25 | 0.09 | 3.52 | 0.18 | 1.02 | 0.22 | 1.20 |
| 648 | K274I | a | 1.42 | 0.14 | 1.65 | 0.09 | 1.28 | 0.10 | 1.18 | 0.12 | 1.42 | 0.08 | 1.89 | 0.21 | 1.01 | 0.22 | 1.11 |
| 649 | K274F | a | | | | | | | | | | | | | | | |
| 650 | K274M | a | | | | | | | | | | | | | | | |
| 651 | K274W | a | | | | | | | | | | | | | | | |
| 652 | K274P | ap | 1.57 | 0.14 | 1.70 | 0.11 | 1.06 | 0.11 | 0.92 | 0.14 | 1.44 | 0.08 | 1.20 | 0.25 | 1.04 | 0.22 | 1.36 |
| 653 | K274G | a | 1.54 | 0.13 | 1.34 | 0.13 | 1.21 | 0.11 | 1.04 | 0.11 | 0.88 | 0.05 | 1.10 | 0.26 | 1.18 | 0.21 | 0.72 |
| 654 | N276D | a | | | | | | | | | | | | | | | |
| 655 | N276T | a | 2.78 | 0.18 | 0.98 | 0.09 | 1.10 | 0.10 | 0.72 | 0.14 | 0.71 | 0.15 | 0.79 | 2.83 | 1.19 | 0.21 | 0.64 |
| 656 | N276H | a | 1.25 | 0.15 | 1.06 | 0.12 | 1.03 | 0.13 | 1.12 | 0.15 | 1.04 | 0.07 | 0.91 | 0.21 | 1.27 | 0.24 | 1.01 |
| 657 | N276V | a | | | | | | | | | | | | | | | |
| 658 | N276I | a | 1.34 | 0.30 | 1.16 | 0.10 | 1.30 | 0.15 | 1.57 | 0.14 | 1.53 | 0.15 | 2.20 | 0.17 | 1.18 | 0.21 | 1.17 |
| 659 | N276F | a | 1.20 | 0.26 | | | 0.99 | 0.36 | | | 0.26 | 0.24 | | | | | 0.26 |
| 660 | N276M | a | 2.53 | 0.26 | 1.24 | 0.11 | 1.32 | 0.16 | 2.06 | 0.14 | 1.21 | 0.09 | 1.57 | 0.26 | 2.00 | 0.21 | 0.92 |
| 661 | N276W | a | | | | | | | | | | | | | | | |
| 662 | N276P | ap | | | | | | | | | | | | | | | |
| 663 | N276G | ap | 2.17 | 0.12 | 1.25 | 0.09 | 1.38 | 0.10 | 1.19 | 0.14 | 1.25 | 0.12 | 2.00 | 0.17 | 1.79 | 0.22 | 0.91 |
| 664 | Y278D | ap | 1.54 | 0.18 | 0.88 | 0.10 | 0.78 | 0.12 | 0.66 | 0.12 | 0.82 | 0.08 | 0.74 | 9.38 | 1.33 | 0.22 | 1.05 |
| 665 | Y278N | a | | | | | | | | | | | | | | | |
| 666 | Y278Q | a | 1.98 | 0.25 | 0.92 | 0.12 | 0.62 | 0.11 | 0.58 | 0.15 | 0.54 | 0.10 | 0.82 | 0.25 | 1.23 | 0.22 | 0.87 |
| 667 | Y278R | a | 2.19 | 0.18 | 0.97 | 0.10 | 1.10 | 0.13 | 0.99 | 0.12 | 0.79 | 0.07 | 2.24 | 0.18 | 1.23 | 0.22 | 0.72 |
| 668 | Y278S | a | | | | | | | | | | | | | | | |
| 669 | Y278H | a | | | | | | | | | | | | | | | |
| 670 | Y278V | a | 1.64 | 0.15 | 1.37 | 0.09 | 1.82 | 0.11 | 1.73 | 0.14 | 0.97 | 0.10 | 2.21 | 0.18 | 1.27 | 0.23 | 0.53 |
| 671 | Y278L | a | 2.57 | 0.20 | 1.05 | 0.13 | 1.32 | 0.12 | 0.94 | 0.12 | 2.92 | 0.09 | 0.44 | 0.21 | 1.74 | 0.21 | 2.21 |
| 672 | Y278I | a | 1.25 | 0.34 | 1.09 | 0.10 | 0.94 | 0.13 | 1.03 | 0.11 | 0.97 | 0.12 | 1.18 | 0.19 | 1.52 | 0.22 | 1.04 |
| 673 | Y278M | a | 1.49 | 0.16 | 0.94 | 0.09 | 0.71 | 0.11 | 1.02 | 0.15 | 0.55 | 0.15 | 1.22 | 0.20 | 1.28 | 0.21 | 0.77 |
| 674 | Y278P | a | | | | | | | | | | | | | | | |

Figure 41EE

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 676 | Y278G | a | 2.63 | 0.13 | 1.33 | 0.10 | 1.45 | 0.11 | 1.42 | 0.12 | 1.64 | 0.11 | 1.89 | 0.18 | 2.01 | 0.22 | 1.13 |
| 677 | K320N | a | 0.80 | 0.18 | 1.12 | 0.14 | 1.32 | 0.13 | 2.45 | 0.31 | 1.21 | 0.35 | 2.24 | 0.12 | 1.13 | 0.21 | 0.92 |
| 678 | K320S | a | 0.66 | 0.15 | 1.18 | 0.12 | 1.13 | 0.11 | 1.83 | 0.30 | 1.83 | 0.37 | 2.45 | 0.13 | 0.83 | 0.18 | 1.61 |
| 679 | K320H | a | 0.97 | 0.13 | 0.95 | 0.11 | 1.20 | 0.14 | 1.19 | 0.36 | 1.84 | 0.38 | 4.14 | 0.10 | 1.07 | 0.16 | 1.53 |
| 680 | K320V | a | 0.79 | 0.15 | 1.18 | 0.11 | 1.16 | 0.15 | 1.18 | 0.32 | 1.23 | 0.37 | 1.64 | 0.13 | 0.76 | 0.21 | 1.06 |
| 681 | K320L | a | 0.87 | 0.14 | 0.95 | 0.11 | 1.00 | 0.20 | 1.01 | 0.32 | 1.11 | 0.37 | 1.88 | 0.14 | 0.80 | 0.20 | 1.11 |
| 682 | K320F | a | 0.98 | 0.18 | 1.19 | 0.13 | 1.10 | 0.15 | 1.39 | 0.30 | 1.31 | 0.33 | 1.70 | 0.29 | 1.11 | 0.19 | 1.20 |
| 683 | K320Y | a p | | | | | | | | | | | | | | | |
| 684 | K320W | a | | | | | | | | | | | | | | | |
| 685 | K320P | a | | | | | | | | | | | | | | | |
| 686 | K320G | a | 0.73 | 0.20 | 1.11 | 0.12 | 1.06 | 0.14 | 1.19 | 0.37 | 1.21 | 0.36 | 1.53 | 0.12 | 0.69 | 0.22 | 1.13 |
| 687 | K322D | a | 1.11 | 0.15 | 0.80 | 0.12 | 0.78 | 0.10 | 1.43 | 0.31 | 0.80 | 0.36 | 1.69 | 0.11 | 0.48 | 0.25 | 1.03 |
| 688 | K322S | a | 0.93 | 0.43 | 0.94 | 0.11 | 0.97 | 0.11 | 1.99 | 0.31 | 1.14 | 0.36 | 1.86 | 0.11 | 0.87 | 0.20 | 1.17 |
| 689 | K322V | a | 0.69 | 0.14 | 1.07 | 0.11 | 1.25 | 0.14 | 2.00 | 0.31 | 1.16 | 0.39 | 1.51 | 0.11 | 0.72 | 0.18 | 0.92 |
| 690 | K322I | a | 0.69 | 0.28 | 0.90 | 0.11 | 1.33 | 0.15 | 1.54 | 0.32 | 0.92 | 0.36 | 1.61 | 0.11 | 0.75 | 0.24 | 0.69 |

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 691 | K322F | a p | 0.79 | 0.15 | 0.95 | 0.11 | 1.33 | 0.13 | 1.30 | 0.29 | 0.86 | 0.38 | 1.15 | 0.15 | 0.75 | 0.19 | 0.65 |
| 692 | K322Y | a p | 0.77 | 0.14 | 0.95 | 0.11 | 1.11 | 0.17 | 1.18 | 0.37 | 1.03 | 0.34 | 2.10 | 0.11 | 0.87 | 0.22 | 0.93 |
| 693 | K322W | a | 0.65 | 0.17 | 0.87 | 0.13 | 0.73 | 0.18 | 0.77 | 0.35 | 0.95 | 0.32 | 1.48 | 0.11 | 0.66 | 0.18 | 1.31 |
| 694 | K322P | a | | | | | | | | | | | | | | | |
| 695 | K322G | a | 0.86 | 0.18 | 0.64 | 0.14 | 0.73 | 0.11 | 0.69 | 0.40 | 0.57 | 0.39 | 1.86 | 0.11 | 0.62 | 0.18 | 0.78 |
| 696 | N325K | a | 0.06 | 0.14 | 0.59 | 0.14 | 0.76 | 0.13 | 0.43 | 0.45 | 0.67 | 0.29 | 1.09 | 0.15 | 0.77 | 0.13 | 0.88 |
| 697 | N325R | a | 2.02 | 0.36 | 0.47 | 0.15 | 0.81 | 0.16 | 0.58 | 0.38 | 0.43 | 0.35 | 1.15 | 0.42 | 0.72 | 0.22 | 0.53 |
| 698 | N325S | a | 0.43 | 0.17 | 0.60 | 0.15 | 1.05 | 0.12 | 1.21 | 0.30 | 0.84 | 0.33 | 0.49 | 0.14 | 0.79 | 0.16 | 0.80 |
| 699 | N325F | a | 0.32 | 0.17 | 0.71 | 0.13 | 2.87 | 0.17 | 3.26 | 0.27 | 0.62 | 0.27 | 0.60 | 0.13 | 1.22 | 0.21 | 0.21 |
| 700 | N325M | a | 0.39 | 0.15 | 0.82 | 0.11 | 1.54 | 0.14 | 1.92 | 0.29 | 1.03 | 0.28 | 1.61 | 0.13 | 1.43 | 0.19 | 0.67 |
| 701 | N325Y | a | 0.27 | 0.14 | 0.54 | 0.13 | 0.73 | 0.23 | 0.65 | 0.35 | 0.57 | 0.30 | 1.72 | 0.13 | 0.91 | 0.24 | 0.77 |
| 702 | N325W | a | 0.23 | 0.19 | 0.45 | 0.17 | 0.57 | 0.25 | 0.40 | 0.49 | 0.51 | 0.30 | 1.35 | 0.12 | 0.86 | 0.23 | 0.89 |
| 703 | N325P | a | 0.06 | 0.21 | | | 0.37 | 2.05 | | | 0.03 | 0.53 | | | | | 0.07 |
| 704 | N325G | a | 0.18 | 0.21 | 0.46 | 0.16 | 0.76 | 0.16 | 0.70 | 0.34 | 0.75 | 0.27 | 0.69 | 0.66 | 0.53 | 0.15 | 0.99 |
| 705 | P227E | a | 1.47 | 0.23 | 1.55 | 0.32 | 1.55 | 0.19 | 1.67 | 0.12 | 2.10 | 0.10 | | | 1.49 | 0.49 | 1.36 |
| 706 | P227K | a | 0.44 | 0.37 | 0.64 | 0.17 | 0.84 | 0.27 | 3.04 | 0.28 | 0.38 | 0.24 | 0.92 | 0.46 | | | 0.46 |
| | | | 0.97 | 0.10 | 1.00 | 0.42 | 0.79 | 0.53 | 0.94 | 0.56 | 0.26 | 0.25 | 2.21 | 0.28 | | | 0.33 |
| 707 | P227Y | a | 0.92 | 0.20 | 0.85 | 0.29 | 0.89 | 0.22 | 0.77 | 0.22 | 1.03 | 0.13 | | | 1.45 | 0.39 | 1.16 |
| 708 | P227G | a | 1.06 | 0.27 | 0.89 | 0.33 | 0.79 | 0.21 | 0.73 | 0.27 | 0.44 | 0.15 | 0.59 | 0.37 | 1.16 | 0.51 | 0.56 |
| | | | 0.70 | 0.38 | 1.39 | 0.16 | 1.93 | 0.22 | 6.56 | 0.26 | 15.77 | 0.20 | | | 0.80 | 0.49 | 8.18 |

Figure 41FF

| | | 1.67 | 0.15 | 0.91 | 0.37 | 1.98 | 0.24 | 3.47 | 0.32 | 12.61 | 0.37 | 1.16 | 0.32 | 1.67 | 0.40 | 6.36 |
|---|---|---|---|---|---|---|---|---|---|---|---|---|---|---|---|---|
| 709 | P228E | | 0.37 | 1.42 | 0.17 | 0.72 | 0.38 | 1.23 | 0.33 | 1.86 | 0.18 | 0.73 | 0.36 | 1.55 | 0.39 | 2.58 |
| 710 | P228K | | 0.28 | 1.31 | 0.58 | 1.14 | 0.25 | 1.13 | 0.54 | 1.28 | 0.25 | 1.62 | 0.29 | 1.29 | 0.53 | 1.12 |
| | | 1.91 | 0.29 | 2.65 | 0.26 | 1.67 | 0.20 | 1.94 | 0.18 | 1.73 | 0.14 | | | | | 1.04 |
| | | 0.48 | 0.39 | 1.10 | 0.17 | 0.60 | 0.31 | 2.04 | 0.29 | 0.71 | 0.21 | 1.11 | 0.34 | | | 1.18 |
| 711 | P228Y | 0.62 | 0.11 | 1.68 | 0.64 | 1.59 | 0.29 | 1.61 | 0.43 | 0.75 | 0.19 | 2.25 | 0.31 | 1.45 | 0.35 | 0.47 |
| | | 1.15 | 0.49 | 0.70 | 0.17 | 0.66 | 0.25 | 1.14 | 0.30 | 0.98 | 0.45 | 0.99 | 0.41 | | | 1.49 |
| 712 | P228G | 1.69 | 0.19 | 2.60 | 0.68 | 0.96 | 0.24 | 0.54 | 0.54 | 0.98 | 0.18 | 1.89 | 0.42 | 1.77 | 0.37 | 1.01 |
| | | 1.00 | 0.57 | 1.31 | 0.16 | 3.39 | 0.21 | 7.15 | 0.54 | 0.19 | 9.45 | 1.08 | 0.38 | | | 0.05 |
| 713 | G236D | 0.42 | 0.16 | 5.01 | 0.70 | 3.77 | 0.19 | 4.74 | 0.34 | 0.11 | 0.23 | 1.64 | 0.32 | 1.53 | 0.37 | 0.03 |
| | | 0.15 | 0.42 | 4.88 | 0.20 | 1.53 | 0.22 | 3.39 | 0.30 | 1.41 | 0.19 | 0.48 | 0.39 | | | 0.92 |
| 714 | G236E | 0.06 | 0.10 | 3.04 | 0.39 | 1.68 | 0.22 | 2.15 | 0.29 | 1.05 | 0.19 | 1.58 | 0.25 | 1.46 | 0.39 | 0.62 |
| | | 0.22 | 0.34 | 1.65 | 0.24 | 0.98 | 0.18 | 0.67 | 0.21 | 0.47 | 0.13 | | | 0.56 | 0.52 | 0.48 |
| | | 0.07 | 0.34 | 0.26 | 0.29 | 0.69 | 0.21 | 0.79 | 0.26 | 0.07 | 0.44 | | | 1.89 | 0.47 | 0.10 |
| 715 | G236N | 0.07 | 0.44 | 0.83 | 0.14 | 0.49 | 0.72 | 1.28 | 0.34 | 0.21 | 0.39 | 0.99 | 0.35 | | | 0.43 |
| 716 | G236Q | 0.03 | 0.15 | 0.60 | 0.34 | 0.89 | 7.57 | 0.26 | 0.53 | 0.17 | 0.20 | 1.89 | 0.33 | 1.46 | 0.40 | 0.18 |
| | | 0.12 | 0.40 | 0.27 | 11.52 | 45.05 | 8.94 | 1.38 | 0.29 | 0.48 | 0.28 | 1.15 | 0.35 | | | 0.01 |
| 717 | G236K | 0.01 | 0.29 | 3.21 | 4.73 | 0.90 | 3.50 | 0.55 | 0.69 | 0.46 | 0.25 | 2.18 | 0.37 | 1.38 | 0.35 | 0.01 |
| | | 0.11 | 0.40 | | | | | 0.06 | 0.70 | 0.01 | 1.89 | | | 0.73 | 0.46 | 0.51 |
| | | 0.02 | 0.38 | 0.29 | 0.23 | 0.63 | 0.33 | 0.62 | 0.69 | 0.20 | 0.72 | 1.04 | 0.34 | | | 0.32 |
| 718 | G236R | 0.01 | 0.09 | 0.31 | 0.56 | 0.98 | 16.50 | 0.19 | 0.55 | 0.10 | 0.27 | 2.03 | 0.35 | 1.99 | 0.36 | 0.10 |
| 719 | G236S | 0.10 | 0.38 | 28.92 | 0.14 | 2.23 | 0.29 | 7.98 | 0.26 | 6.10 | 0.21 | 0.68 | 0.36 | 1.77 | 0.38 | 2.73 |
| 720 | G236T | 0.12 | 0.12 | 22.71 | 0.37 | 2.77 | 0.21 | 3.68 | 0.45 | 5.77 | 0.26 | 1.82 | 0.29 | 1.56 | 0.35 | 2.08 |
| | | 0.55 | 0.42 | 1.58 | 0.16 | 0.36 | 0.55 | 1.35 | 0.28 | 0.21 | 0.91 | 0.99 | 0.33 | 0.43 | 0.58 | 0.59 |
| | | 0.02 | 0.13 | 1.89 | 0.39 | 0.95 | 0.32 | 0.48 | 0.57 | 0.11 | 0.22 | 3.25 | 0.34 | | | 0.12 |
| 721 | G236H | 0.11 | 0.36 | 0.56 | 0.26 | 0.34 | 0.47 | 0.15 | 0.35 | 0.04 | 0.85 | | | 1.48 | 0.37 | 0.10 |
| | | 0.06 | 0.47 | 0.69 | 0.20 | 0.36 | 1.36 | 0.46 | 0.39 | | | 0.87 | 0.36 | 0.52 | 0.51 | 0.07 |
| | | 0.05 | 0.16 | 2.02 | 0.51 | 0.87 | 15.81 | 0.28 | 0.97 | 0.07 | 0.33 | 2.32 | 0.47 | | | 0.26 |
| 722 | G236A | 0.19 | 0.40 | 0.37 | 0.31 | 0.31 | 0.49 | 0.21 | 0.45 | 0.08 | 0.13 | 1.05 | 0.36 | 1.75 | 0.35 | 0.61 |
| 723 | G236V | 0.03 | 0.43 | 45.05 | 0.19 | 1.20 | 0.22 | 1.58 | 0.32 | 0.73 | 0.22 | 1.64 | 0.27 | | | 0.62 |
| | | 0.37 | 0.16 | 44.99 | 0.28 | 1.05 | 0.24 | 1.45 | 0.50 | 0.65 | 0.18 | 0.99 | 0.37 | | | 1.02 |
| | | 0.48 | 0.52 | 2.06 | 0.15 | 0.23 | 0.88 | 0.96 | 0.36 | 0.24 | 0.37 | 1.59 | 0.28 | 1.35 | 0.39 | 0.33 |
| 724 | G236L | 0.03 | 0.15 | 1.52 | 0.36 | 0.82 | 0.46 | 0.47 | 0.38 | 0.27 | 0.19 | | | | | 0.17 |
| 725 | G236I | 0.14 | 0.28 | | | 1.07 | 0.48 | | | 0.18 | 0.25 | | | | | |
| | | 0.04 | 0.40 | 1.95 | 0.15 | 0.11 | 2.97 | 1.10 | 0.38 | | | 1.04 | 0.34 | | | |
| | | 0.02 | 0.18 | 1.33 | 0.30 | 0.75 | 2.41 | 0.12 | 0.69 | 0.02 | 0.87 | 1.96 | 0.26 | 1.33 | 0.37 | 0.02 |
| | | 0.11 | | | | | | | | | | | | | | |

Figure 41GG

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 726 | G236F | a | 0.06 | 0.41 | 0.43 | 0.17 | 0.55 | 0.43 | 0.88 | 0.34 | 0.18 | 0.64 | 1.19 | 0.34 | | | 0.33 |
| | | | 0.21 | 0.23 | 0.44 | 0.54 | 0.92 | 46.70 | 0.08 | 1.29 | 0.05 | 0.76 | 2.56 | 0.48 | 1.75 | 0.36 | 0.06 |
| 727 | G236M | a | 0.03 | 0.38 | 0.29 | 0.19 | 0.43 | 0.37 | 1.22 | 0.42 | 0.21 | 0.44 | 0.67 | 0.34 | | | 0.49 |
| 728 | G236Y | a | 0.14 | 0.12 | 0.34 | 0.44 | 0.79 | 0.83 | 0.40 | 0.67 | 0.19 | 0.20 | 1.40 | 0.55 | 1.60 | 0.35 | 0.24 |
| | | | 0.04 | 0.39 | 0.83 | 0.16 | 0.44 | 1.15 | 0.91 | 0.44 | 0.22 | 1.31 | 0.77 | 0.36 | | | 0.50 |
| | | | 0.17 | 0.13 | 0.78 | 0.58 | 0.85 | 1.07 | 0.44 | 1.38 | 0.14 | 0.26 | 1.34 | 0.33 | 1.52 | 0.35 | 0.16 |
| 729 | G236W | a | 0.10 | 0.38 | 0.37 | 0.31 | 0.41 | 1.22 | 0.00 | 2.84 | 0.04 | 0.88 | | | 0.56 | 0.52 | 0.09 |
| | | | 0.32 | 0.39 | 1.71 | 0.18 | 0.52 | 0.55 | 0.67 | 0.30 | 0.33 | 0.33 | 0.98 | 0.34 | 1.52 | 0.36 | 0.63 |
| | | | 0.78 | 0.17 | 2.13 | 0.40 | 0.70 | 0.51 | 0.29 | 0.69 | 0.29 | 0.20 | 1.40 | 0.26 | 0.56 | 0.51 | 0.41 |
| 730 | G236P | a | 0.68 | 0.27 | 1.23 | 0.27 | 0.83 | 0.21 | 1.56 | 0.15 | 0.34 | 0.13 | | | | | 0.40 |
| | | | 0.04 | 0.48 | 0.25 | 0.30 | 0.27 | 1.53 | 0.42 | 0.41 | 0.19 | 28.37 | 1.25 | 0.35 | 1.41 | 0.37 | 0.70 |
| | | | 0.15 | 0.16 | | 7.93 | 0.90 | 10.17 | 0.15 | 0.68 | 0.10 | 0.23 | 1.38 | 0.86 | 0.66 | 0.52 | 0.11 |
| 731 | G236D | a | 0.04 | 0.47 | | 0.72 | 0.24 | 0.76 | 0.10 | 1.03 | 0.07 | 0.21 | | | | | 0.30 |
| | | | 0.18 | 0.55 | 0.11 | 2.59 | 54.08 | 9.16 | 2.51 | 0.27 | | | 1.50 | 0.37 | 1.84 | 0.36 | 0.13 |
| | | | 0.10 | 0.25 | 0.21 | 8.65 | 1.00 | 0.27 | 1.13 | 0.52 | 0.13 | 0.19 | 2.86 | 0.27 | 0.80 | 0.50 | |
| | | | 0.08 | 0.33 | | | 1.04 | 0.19 | 0.74 | 0.17 | | | | | | | |

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 732 | G237E | a | 0.01 | 0.48 | 0.26 | 9.34 | 0.88 | 0.24 | 1.03 | 0.32 | 0.21 | 12.54 | 0.89 | 0.36 | | | 0.24 |
| | | | 0.09 | 0.13 | 0.70 | 0.95 | 0.88 | 0.45 | 0.42 | 0.48 | 0.02 | 0.60 | 1.16 | 0.24 | 1.36 | 0.42 | 0.02 |
| 733 | G237N | a | 0.02 | 0.40 | 0.27 | 13.28 | 0.65 | 0.38 | 2.79 | 0.26 | 0.18 | 5.37 | 0.71 | 0.36 | | | 0.27 |
| | | | 0.08 | 0.24 | 0.10 | 0.62 | 0.98 | 0.26 | 0.73 | 0.43 | 0.02 | 1.05 | 1.29 | 0.24 | 1.39 | 0.36 | 0.02 |
| 734 | G237Q | a | 0.01 | 0.39 | 0.26 | 14.91 | 0.85 | 8.46 | 1.20 | 0.30 | | | 0.84 | 0.34 | | | |
| | | | 0.07 | 0.32 | 0.46 | 4.47 | 0.78 | 17.18 | 1.80 | 5.62 | 0.00 | 3.01 | 1.33 | 0.31 | 1.39 | 0.37 | 0.00 |
| 735 | G237K | a | 0.01 | 0.39 | 0.22 | 0.34 | 0.32 | 0.81 | 1.29 | 0.38 | 0.17 | 0.73 | 0.81 | 0.35 | | | 0.54 |
| | | | 0.09 | 0.18 | 0.32 | 0.63 | 0.74 | 0.73 | 0.32 | 0.56 | 0.10 | 0.28 | 1.52 | 0.29 | 1.47 | 0.36 | 0.13 |
| 736 | G237R | a | 0.02 | 0.56 | | | 0.46 | 0.27 | 0.11 | 0.85 | 0.07 | 2.82 | | | 1.28 | 0.48 | 0.15 |
| | | | 0.01 | 0.38 | 0.21 | 0.32 | 0.48 | 0.83 | | | 0.21 | 0.66 | 0.73 | 0.35 | | | 0.43 |
| | | | 0.08 | 0.20 | | 41.28 | | | | | 0.16 | 0.28 | 1.01 | 0.34 | 1.36 | 0.36 | |
| 737 | G237S | a | 0.03 | 0.42 | 0.17 | 1.31 | 0.75 | 0.34 | 0.39 | 1.04 | | | 1.04 | 0.33 | | | 0.06 |
| | | | 0.12 | 0.15 | | 6.61 | 1.02 | 0.24 | 1.94 | 0.26 | 0.07 | 0.49 | 1.86 | 0.34 | 1.29 | 0.36 | |
| 738 | G237T | a | 0.05 | 0.54 | | | 0.50 | 0.68 | 0.78 | 0.53 | | | 0.69 | 0.35 | | | |
| | | | 0.13 | 0.18 | | 5.66 | | | 0.77 | 0.29 | | | 1.08 | 0.35 | 1.32 | 0.38 | 0.15 |
| 739 | G237H | a | 0.06 | 0.25 | 0.24 | 0.38 | 0.59 | 0.29 | 0.21 | 0.72 | 0.09 | 0.21 | 0.97 | 0.36 | 1.48 | 0.36 | 0.06 |
| 740 | G237V | a | 0.03 | 0.26 | | | 1.07 | 0.83 | 1.76 | 1.61 | 0.09 | 0.24 | 2.03 | 0.24 | 1.00 | 0.19 | 0.06 |
| 741 | G237L | a | 0.01 | 0.35 | | | 0.54 | 0.81 | 1.81 | 0.40 | 0.06 | 0.41 | 1.88 | 0.29 | 1.21 | 0.25 | 0.06 |
| 742 | G237I | a | | | | | 0.29 | 0.84 | 1.19 | 0.46 | 0.03 | 0.56 | | 0.28 | 0.60 | 0.70 | 1.18 |
| | | | | | | | | | 0.43 | 0.56 | 0.35 | 0.21 | 1.51 | | | | |

Figure 41HH

| | | | | | | | | | | | | | | |
|---|---|---|---|---|---|---|---|---|---|---|---|---|---|---|
| 743 | G237F | a | 0.02 | 0.22 | | | 0.41 | 0.73 | 1.08 | 0.45 | 0.40 | 0.15 | 1.65 | 0.29 | 1.01 | 0.27 | 0.11 |
| 744 | G237M | a | 0.07 | 0.36 | | | 0.30 | 0.58 | 1.06 | 0.49 | 0.04 | 0.56 | 1.80 | 0.27 | 0.81 | 0.28 | 0.18 |
| 745 | G237Y | a | 0.04 | 0.32 | | | 0.57 | 0.26 | 0.66 | 0.27 | 0.06 | 0.65 | | | 0.94 | 0.25 | 0.17 |
| 746 | G237W | a | 0.07 | 0.37 | 0.14 | 0.35 | 0.37 | 0.58 | 0.67 | 0.71 | 0.10 | 0.15 | | | 1.74 | 0.45 | 0.21 |
| 747 | G237P | a | 0.21 | 0.44 | | | 2.62 | 0.83 | 1.92 | 0.38 | 0.08 | 0.22 | 2.06 | 0.32 | 1.00 | 0.21 | |
| 748 | P238D | a | 0.04 | 1.92 | | | 0.52 | 0.90 | 0.52 | 0.51 | 0.01 | 0.69 | 0.85 | 0.24 | 1.20 | 0.21 | 0.02 |
| | | | 0.02 | 0.18 | | | 13.02 | 1.16 | 5.89 | 0.39 | 0.72 | 0.25 | 1.17 | 0.25 | 1.21 | 0.21 | 0.06 |
| 749 | P238E | a | 0.26 | 0.32 | | | | | | | 0.58 | 0.13 | 1.03 | 0.24 | 0.63 | 0.89 | |
| | | | 0.07 | 0.24 | | | 1.18 | 0.86 | 1.46 | 0.41 | | | | | 1.03 | 0.21 | |
| 750 | P238N | a | 0.95 | 0.29 | | | | | | | 0.04 | 3.53 | 1.20 | 0.25 | 3.71 | 1.18 | 0.12 |
| | | | 0.30 | 0.14 | | | 0.42 | 0.33 | 0.36 | 0.19 | 0.05 | 0.32 | | | 0.68 | 0.28 | |
| 751 | P238Q | a | 0.19 | 0.34 | | | 0.53 | 0.91 | 1.11 | 0.49 | | 0.61 | | | 1.43 | 0.62 | |
| 752 | P238K | a | 0.21 | 0.31 | | | | | | | 0.01 | 1.23 | 0.99 | 0.22 | 1.15 | 0.99 | |
| | | | 0.09 | 0.16 | | | 0.24 | 0.59 | 0.20 | 0.85 | | | | | 1.01 | 0.28 | |
| 753 | P238R | a | | 1.05 | | 3.96 | | | | | 0.00 | 3.28 | 1.00 | 0.25 | 5.01 | 0.83 | 1.78 |
| | | | 0.04 | 8.30 | | | 0.35 | 0.58 | 0.54 | 0.67 | 0.62 | 0.20 | | | 0.77 | 0.29 | |
| 754 | P238S | a | 0.17 | 0.32 | 0.31 | | 0.31 | 0.55 | 0.75 | 0.77 | 0.50 | 0.16 | 1.18 | 0.24 | 0.83 | 0.66 | |
| | | | 0.25 | 0.21 | | | | | | | 0.08 | 3.07 | 0.97 | 0.27 | 0.92 | 0.26 | |
| 755 | P238T | a | 0.29 | 0.31 | 0.15 | 0.38 | 0.63 | 0.40 | 1.08 | 0.22 | 0.23 | 0.17 | | | 0.42 | 0.60 | 0.37 |
| | | | 0.44 | 0.12 | | | 0.60 | 0.66 | 0.78 | 0.54 | | 0.13 | | | 0.93 | 0.22 | |
| 756 | P238H | a | 0.57 | 0.26 | 0.26 | 277 | | | | | 0.02 | 3.34 | 1.51 | 0.30 | 1.12 | 0.51 | |
| | | | 0.21 | 0.35 | | | 1.89 | 0.85 | 1.35 | 0.41 | 1.51 | 0.64 | | | 0.91 | 0.61 | |
| 757 | P238V | a | 0.11 | 0.22 | 0.32 | 2638 | | | | | 1.12 | 0.18 | 1.32 | 0.24 | 1.12 | 0.19 | 0.80 |
| | | | 0.44 | 0.35 | | | 2.24 | 0.91 | 1.99 | 0.38 | | 0.13 | | | 0.90 | 0.53 | |
| 758 | P238L | a | 0.26 | 0.09 | 0.38 | 0.37 | | | | | 0.06 | 2.80 | 1.55 | 0.28 | 1.46 | 0.22 | |
| | | | 1.09 | 0.28 | | | 2.54 | 0.95 | 3.64 | 0.41 | 0.79 | 0.43 | | | 1.43 | 0.57 | |
| 759 | P238I | a | 1.22 | 0.18 | 0.31 | 12.20 | | | | | 0.69 | 0.22 | 2.34 | 0.29 | 1.09 | 0.19 | 0.31 |
| | | | 1.78 | 0.31 | | | 0.40 | 0.82 | 0.38 | 0.73 | | 0.15 | | | 1.71 | 0.54 | |
| 760 | P238F | a | 1.17 | 0.14 | | | | | | | 0.02 | 0.77 | 1.79 | 0.29 | 1.40 | 0.30 | |
| | | | 1.32 | 0.29 | | | | | 3.72 | 0.38 | | 2.56 | | | 1.06 | 0.52 | |
| 761 | P238M | a | 0.62 | 0.21 | | | 0.44 | 0.66 | 1.27 | 0.44 | 0.02 | 0.84 | 2.32 | 0.32 | 1.44 | 0.26 | |
| | | | 1.70 | 0.31 | | | | | | | | 2.89 | 3.23 | 0.35 | 2.41 | 0.55 | |
| 762 | P238Y | a | 2.60 | 0.12 | | | | | | | 0.03 | 0.55 | | | 1.09 | 0.26 | |
| | | | 1.38 | 0.27 | | | 0.43 | 0.62 | 0.99 | 0.56 | | 6.35 | 1.16 | 0.29 | 2.33 | 1.22 | |
| | | | 1.39 | 0.09 | | | | | | | | | | | 0.91 | 0.24 | |
| | | | 0.66 | 0.26 | | | | | | | | | | | 0.80 | 0.54 | |

Figure 41II

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 763 | P238W |   | 3.05 | 0.20 |   |   |   |   |   |   |   |   |   |   | 0.92 | 0.21 |   |
|   |   |   | 1.27 | 0.27 |   |   |   |   |   |   |   |   |   |   | 0.10 | 0.54 |   |
|   |   |   | 0.73 | 0.21 |   |   |   |   |   |   |   |   |   |   | 1.30 | 0.20 |   |
| 764 | P238G | a | 0.33 | 0.35 |   |   | 0.73 | 0.69 | 1.12 | 0.53 |   | 2.95 | 1.92 | 0.31 | 0.12 | 0.53 | 0.30 |
|   |   |   | 0.11 | 0.16 |   |   |   |   |   |   | 0.39 | 0.21 |   |   | 1.53 | 0.22 |   |
|   |   |   | 0.14 | 0.36 |   |   |   |   |   |   | 0.36 | 0.20 |   |   |   |   |   |
| 765 | E269K | a | 0.08 | 0.17 | 0.34 | 0.27 | 1.30 | 0.86 | 0.84 | 0.41 |   |   | 1.41 | 0.26 | 0.13 | 0.20 |   |
|   |   |   | 0.31 | 0.30 |   |   | 1.00 | 0.79 | 0.95 | 0.44 | 0.14 | 0.12 | 1.46 | 0.26 | 1.23 | 0.55 |   |
| 766 | E269S | a | 0.21 | 0.15 |   |   |   |   |   |   | 0.30 | 0.20 |   |   | 0.13 | 0.33 |   |
|   |   |   | 0.30 | 0.29 |   |   | 0.74 | 0.77 | 1.19 | 0.44 | 0.21 | 0.20 |   |   | 1.31 | 0.52 | 0.41 |
| 767 | E269V | a | 0.24 | 0.17 | 0.29 | 8.99 | 0.35 | 0.80 | 0.32 | 0.68 |   | 4.69 | 0.93 | 0.28 | 0.13 | 0.28 |   |
|   |   |   | 0.35 | 0.29 |   |   |   |   |   |   | 0.19 | 0.54 |   |   | 1.38 | 0.52 |   |
| 768 | E269I | a | 0.41 | 0.22 | 0.26 | 34.19 | 0.29 | 0.63 | 0.40 | 0.42 |   |   | 1.48 | 0.28 | 0.13 | 0.30 |   |
|   |   |   | 0.38 | 0.25 |   |   |   |   |   |   | 0.12 | 0.24 |   |   | 1.26 | 0.52 |   |
| 769 | E269M | a | 0.51 | 0.14 | 0.28 | 1372 | 0.37 | 0.58 | 0.66 | 0.58 |   | 14.73 | 2.10 | 0.40 | 0.14 | 0.24 |   |
|   |   |   | 0.20 | 0.29 |   |   |   |   |   |   | 0.12 | 0.16 |   |   | 1.11 | 0.52 |   |
| 770 | E269W | a | 0.37 | 0.19 |   |   | 0.34 | 0.55 | 0.92 | 0.62 |   | 1.83 | 2.66 | 0.34 | 0.08 | 0.30 |   |
|   |   |   |   |   |   |   |   |   |   |   | 0.06 | 0.38 | 1.43 | 0.32 | 1.19 | 0.22 |   |

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 771 | E269P | a | 0.36 | 0.16 | 0.13 | 0.41 | 0.73 | 0.25 | 1.33 | 0.66 | 0.02 | 0.70 | 0.00 | 12605 | 1.23 | 0.21 | 0.02 |
| 772 | E269G | a |   |   | 0.58 | 0.54 | 0.51 | 0.28 | 1.11 | 0.66 | 0.03 | 0.63 | 0.00 | 7.64 | 1.34 | 0.18 | 0.05 |
|   |   |   |   |   | 0.23 | 0.37 | 0.58 | 0.28 | 0.44 | 0.51 | 0.23 | 0.16 |   |   | 1.18 | 0.50 | 0.39 |
| 773 | H285D |   | 0.39 | 0.29 | 1.57 | 0.54 | 1.18 | 0.33 | 2.56 | 0.72 | 1.22 | 0.64 | 0.00 | 7.64 | 2.40 | 0.27 | 1.03 |
| 774 | H285E |   | 1.81 | 0.16 | 1.39 | 0.32 | 0.98 | 0.29 | 1.53 | 0.35 | 1.46 | 0.19 |   |   | 1.93 | 0.50 | 1.50 |
| 775 | H285Q |   | 1.67 | 0.25 | 1.68 | 0.55 | 0.66 | 0.45 | 1.45 | 0.67 | 0.33 | 0.60 | 0.00 | 7.64 | 1.25 | 0.27 | 0.50 |
|   |   |   | 2.42 | 0.16 | 1.41 | 0.29 | 1.81 | 0.22 | 2.15 | 0.17 | 1.59 | 0.16 |   |   | 1.38 | 0.49 | 0.88 |
| 776 | H285K |   | 1.28 | 0.22 | 2.04 | 0.50 | 1.37 | 0.37 | 2.89 | 0.80 | 2.46 | 0.66 | 0.00 | 7.64 | 1.76 | 0.30 | 1.79 |
| 777 | H285Y | a p | 1.80 | 0.20 | 1.95 | 0.56 | 0.95 | 0.49 | 4.24 | 1.43 | 1.77 | 0.97 |   |   | 1.25 | 0.24 | 1.87 |
| 778 | H285W | a | 2.68 | 0.31 | 0.84 | 0.41 | 1.31 | 0.23 | 2.37 | 0.66 | 0.69 | 0.48 | 0.00 | 7.65 | 1.33 | 0.17 | 0.53 |
| 779 | N286E | a | 1.32 | 0.14 | 0.07 | 0.40 | 0.38 | 0.25 | 0.37 | 0.94 | 0.01 | 1.71 | 0.00 | 7.65 | 2.12 | 0.18 | 0.03 |
| 780 | N286Y | a |   | 3.40 |   | 0.07 | 0.44 | 0.42 | 0.22 | 1.16 | 0.66 | 0.02 | 0.62 | 0.00 | 7.66 | 1.45 | 0.17 | 0.05 |
| 781 | N286P | a |   | 2.92 |   | 1.80 | 0.40 | 2.35 | 0.23 | 5.43 | 0.62 | 1.18 | 0.51 | 0.17 | 8.96 | 2.31 | 0.18 | 0.50 |
|   |   |   | 2.62 | 0.15 | 1.05 | 0.32 | 2.50 | 0.21 | 3.86 | 0.13 | 0.71 | 0.11 |   |   | 2.90 | 0.49 | 0.29 |
|   |   |   | 1.16 | 0.28 |   |   |   |   |   |   |   |   |   |   |   |   |   |
| 782 | N286G | a | 2.19 | 0.10 |   |   | 1.85 | 0.21 | 8.05 | 0.63 | 1.78 | 0.18 | 0.00 | 7.64 | 0.89 | 0.19 | 0.96 |
| 783 | K288D | a | 2.76 | 0.14 | 1.72 | 0.41 | 3.27 | 0.26 | 2.71 | 0.64 | 2.77 | 0.52 | 0.00 | 7.64 | 1.10 | 0.19 | 0.85 |
| 784 | K288E | a | 2.17 | 0.13 | 1.80 | 0.53 | 1.14 | 0.27 |   |   | 0.69 | 0.54 |   |   |   |   | 0.61 |
| 785 | K288Y | a |   |   |   |   |   |   |   |   |   |   |   |   |   |   |   |

Figure 41JJ

| | | | | | | | | | | | | | | |
|---|---|---|---|---|---|---|---|---|---|---|---|---|---|---|
| 786 | R292D | a | 2.38 | 0.17 | 5.10 | 0.39 | 1.12 | 0.25 | 2.81 | 0.68 | 0.51 | 0.50 | 0.00 | 7.64 | 1.67 | 0.22 | 0.46 |
| 787 | R292E | a | 1.56 | 0.13 | 1.00 | 0.44 | 0.73 | 0.41 | 4.46 | 4.23 | 0.34 | 0.50 | 0.00 | 7.64 | 1.45 | 0.22 | 0.47 |
| 788 | R292T | a | 1.30 | 0.15 | 1.11 | 0.40 | 0.95 | 0.24 | 1.11 | 0.75 | 0.41 | 0.51 | 0.25 | 8.57 | 0.85 | 0.18 | 0.43 |
| 789 | R292Y | a | 1.59 | 0.13 | 0.35 | 0.40 | 0.86 | 0.27 | 2.24 | 0.60 | 0.40 | 0.50 | 0.00 | 7.65 | 1.36 | 0.16 | 0.47 |
| 790 | T335N | a | 1.89 | 0.12 | 1.21 | 0.40 | 1.27 | 0.22 | 2.14 | 0.64 | 0.85 | 0.51 | 0.00 | 7.65 | 1.23 | 0.16 | 0.67 |
| 791 | T335S | a | 2.02 | 0.14 | 6.31 | 0.38 | 1.27 | 0.22 | 2.70 | 0.68 | 1.43 | 0.58 | | | 1.42 | 0.16 | 1.12 |
| 792 | T335H | a | 2.26 | 0.19 | 1.31 | 0.45 | 1.07 | 0.24 | 1.67 | 0.67 | 1.25 | 0.61 | 0.00 | 7.65 | 1.16 | 0.21 | 1.17 |
| 793 | T335V | a | 2.33 | 0.13 | 1.80 | 0.53 | 0.97 | 0.27 | 2.53 | 0.72 | 1.41 | 0.63 | 0.00 | 7.64 | 1.25 | 0.17 | 1.46 |
| 794 | T335L | a | 2.48 | 0.18 | 1.96 | 0.51 | 2.62 | 0.32 | 14.39 | 0.70 | 2.22 | 0.50 | 0.00 | 2101 | 1.50 | 0.26 | 0.85 |
| 795 | T335I | a | 2.25 | 0.15 | 2.47 | 0.50 | 1.16 | 0.36 | 1.76 | 1.04 | 1.51 | 0.70 | 0.00 | 7.64 | 1.41 | 0.22 | 1.30 |
| 796 | T335F | a | 1.21 | 0.11 | 0.71 | 0.41 | 1.21 | 0.24 | 1.70 | 0.76 | 0.49 | 0.54 | 0.25 | 9.47 | 1.19 | 0.17 | 0.40 |
| 797 | T335M | a | 2.06 | 0.12 | 0.60 | 0.41 | 1.13 | 0.26 | 1.98 | 0.64 | 0.52 | 0.51 | 0.00 | 7.65 | 0.79 | 0.19 | 0.46 |
| | | | 1.31 | 0.24 | 1.14 | 0.26 | 1.13 | 0.24 | 1.46 | 0.13 | 1.18 | 0.10 | | | 1.35 | 0.48 | 1.04 |
| 798 | T335W | a | 2.11 | 0.13 | 0.68 | 0.40 | 1.16 | 0.22 | 2.08 | 0.66 | 0.59 | 0.51 | | | 1.35 | 0.17 | 0.51 |
| 799 | T335P | a | 2.80 | 0.12 | 2.42 | 0.46 | 0.93 | 0.26 | 1.75 | 0.65 | 1.35 | 0.60 | | | 1.45 | 0.17 | 1.45 |
| 800 | T335G | a | 1.99 | 0.16 | 0.93 | 0.46 | 0.77 | 0.25 | 1.47 | 0.66 | 0.32 | 0.51 | | | 0.90 | 0.24 | 0.42 |
| 801 | D221K | a | 4.53 | 0.19 | 4.32 | 0.39 | 3.50 | 0.28 | 17.75 | 0.61 | 65.60 | 0.48 | 0.00 | 7.64 | 5.66 | 0.18 | 18.72 |
| | | | 0.97 | 0.25 | 1.01 | 0.30 | 0.68 | 0.40 | 1.04 | 0.17 | 2.82 | 0.09 | | | 1.84 | 0.46 | 4.17 |
| 802 | D221Y | a | 2.43 | 0.19 | 2.62 | 0.44 | 2.41 | 0.28 | 10.01 | 0.67 | 0.56 | 0.48 | 0.00 | 7.64 | 2.74 | 0.21 | 0.23 |
| 803 | T223E | a | 2.12 | 0.14 | 2.37 | 0.42 | 1.74 | 0.23 | 3.70 | 0.69 | 0.75 | 0.49 | 0.00 | 0.30 | 2.04 | 0.22 | 0.43 |
| 804 | T223K | a | 1.61 | 0.17 | 2.18 | 0.29 | 1.81 | 0.25 | | 11.88 | 9.37 | 0.36 | 1.31 | | 2.97 | 0.36 | 5.19 |
| | | | 1.15 | 0.27 | 0.55 | 0.27 | 0.60 | 0.23 | 0.41 | 0.26 | 0.67 | 0.12 | | | 0.78 | 0.60 | 1.11 |
| 805 | H224E | a | 1.91 | 0.13 | 3.67 | 0.31 | 2.18 | 0.25 | | 11.88 | 14.28 | 0.36 | 2.80 | | 5.11 | 0.38 | 6.54 |
| | | | 0.54 | 0.09 | 0.27 | 0.21 | 0.21 | 0.36 | 0.66 | 0.71 | 0.58 | 1.31 | | | 0.43 | 0.23 | 2.73 |
| 806 | H224Y | a | 1.74 | 0.20 | 1.17 | 0.30 | 1.29 | 0.31 | 97.09 | 11.88 | 0.86 | 0.37 | 2.01 | 0.31 | 1.68 | 0.44 | 0.66 |
| 807 | T225E | a | 2.28 | 0.16 | 2.75 | 0.30 | 2.38 | 0.25 | 1.21 | 11.88 | 9.84 | 0.36 | 1.96 | 0.31 | 4.89 | 0.47 | 4.14 |
| | | | 0.46 | 0.14 | 0.35 | 0.19 | 0.44 | 0.44 | 95.70 | 0.66 | 0.76 | 1.31 | | | 0.41 | 0.16 | 1.71 |
| 808 | T225K | a | 0.30 | 0.17 | 0.37 | 0.32 | 0.45 | 0.34 | 1.01 | 11.88 | 0.22 | 0.44 | 1.12 | 0.28 | 5.68 | 0.68 | 0.48 |
| | | | 0.53 | 0.27 | 0.31 | 0.23 | 0.45 | 0.26 | 93.33 | 0.65 | 0.68 | 1.31 | | | 0.50 | 0.20 | 1.51 |
| 809 | T225W | a | 2.30 | 0.29 | 1.04 | 0.42 | 1.44 | 0.24 | 67.73 | 11.88 | 0.59 | 0.37 | 1.92 | 0.29 | 6.89 | 0.75 | 0.41 |
| 810 | K246D | a | 1.78 | 0.13 | 0.92 | 0.30 | 1.36 | 0.24 | 35.41 | 11.90 | 0.56 | 0.39 | 1.22 | 0.33 | 0.93 | 0.41 | 0.41 |
| 811 | K246E | a | 1.58 | 0.15 | 1.25 | 0.28 | 0.98 | 0.32 | | 11.89 | 2.86 | 0.40 | 1.86 | 0.33 | 0.51 | 0.38 | 2.91 |
| 812 | K246H | a | 1.67 | 0.15 | 1.66 | 0.29 | 1.24 | 0.26 | | 11.88 | 14.37 | 0.36 | 1.49 | 0.29 | 4.02 | 0.36 | 11.56 |
| | | | 0.35 | 0.17 | 0.26 | 0.21 | 0.16 | 0.76 | 0.24 | 0.83 | 0.36 | 1.31 | | | 0.38 | 0.14 | 2.22 |
| 813 | K246Y | a | 1.53 | 0.13 | 1.16 | 0.28 | 1.18 | 0.28 | 49.45 | 11.89 | 5.25 | 0.36 | 1.87 | 0.32 | 2.47 | 0.40 | 4.46 |
| 814 | D249Q | a | 0.30 | 0.20 | 0.22 | 0.33 | 0.61 | 0.82 | 74.56 | 11.89 | 0.36 | 0.36 | 2.13 | 0.33 | 2.06 | 0.37 | 0.59 |
| | | | 0.46 | 0.17 | 0.52 | 0.22 | 0.46 | 0.32 | 1.07 | 0.74 | 1.06 | 1.31 | | | 0.49 | 0.15 | 2.30 |

Figure 41KK

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 815 | D249H | a | 0.39 | 0.14 | 0.37 | 0.23 | 0.28 | 0.46 | 0.64 | 0.78 | 0.86 | 1.32 | | | 0.41 | 0.19 | 3.04 |
| 816 | D249Y | a | 1.80 | 0.14 | 1.87 | 0.29 | 1.13 | 0.28 | | 11.88 | 3.92 | 0.37 | | | 2.57 | 0.45 | 3.47 |
| 817 | R255E | a | 0.47 | 0.17 | 0.37 | 0.39 | 0.55 | 0.34 | 0.79 | 1.42 | 749 | 42.72 | | | 0.41 | 0.22 | 0.76 |
| 818 | R255Y | a | 1.80 | 0.13 | 1.38 | 0.31 | 0.95 | 0.28 | 89.36 | 11.89 | 0.72 | 0.36 | 2.09 | 0.30 | 1.16 | 0.41 | 14.80 |
|  |  |  | 3.21 | 0.28 | 5.87 | 0.31 | 2.30 | 0.23 |  | 11.88 | 34.11 | 0.39 |  |  | 12.88 | 0.52 | 1.33 |
|  |  |  | 0.38 | 0.23 | 0.35 | 0.33 | 0.33 | 0.46 | 0.79 | 0.75 | 0.43 | 1.32 | 1.50 | 0.30 | 0.36 | 0.21 | 0.47 |
| 819 | E258S | a | 2.79 | 0.30 | 1.13 | 0.34 | 1.39 | 0.27 | 40.92 | 11.92 | 0.65 | 0.56 | 2.07 | 0.34 | 0.54 | 0.52 | 6.25 |
| 820 | E258H | a | 2.62 | 0.23 | 2.92 | 0.40 | 1.77 | 0.29 | 48.21 | 11.89 | 11.08 | 0.58 |  |  | 0.89 | 0.39 | 4.96 |
| 821 | E258Y | a | 2.62 | 0.18 | 1.28 | 0.36 | 2.12 | 0.27 |  | 11.88 | 10.52 | 0.43 | 1.36 | 0.32 | 1.07 | 0.49 | 0.91 |
|  |  |  | 0.56 | 0.27 | 0.30 | 0.24 | 0.39 | 0.30 | 0.95 | 0.66 | 0.36 | 1.31 | 1.69 | 0.28 | 0.31 | 0.28 | 0.47 |
| 822 | T260D | a | 1.79 | 0.16 | 0.58 | 0.32 | 0.65 | 0.29 |  |  | 0.31 | 0.37 | 1.66 | 0.29 | 1.71 | 0.53 | 1.41 |
| 823 | T260E | a | 2.21 | 0.14 | 1.00 | 0.31 | 1.21 | 0.44 | 94.92 | 11.88 | 1.70 | 0.41 | 4.06 | 0.32 | 5.49 | 0.61 | 6.61 |
| 824 | T260H | a | 2.03 | 0.20 | 1.85 | 0.34 | 1.70 | 0.29 |  | 11.88 | 11.25 | 0.43 | 2.89 | 0.34 | 7.30 | 0.53 | 3.40 |
|  |  |  | 0.52 | 0.16 | 0.27 | 0.19 | 0.16 | 0.93 | 0.50 | 0.77 | 0.53 | 1.32 | 1.63 | 0.28 | 0.50 | 0.16 | 0.47 |
| 825 | T260Y | a | 1.59 | 0.16 | 0.84 | 0.37 | 1.03 | 0.27 | 1.08 | 11.88 | 0.48 | 0.38 |  |  | 7.51 | 0.93 | 2.73 |
|  |  |  | 0.38 | 0.32 | 0.59 | 0.29 | 0.51 | 0.26 |  | 0.65 | 1.40 | 1.31 | 1.62 | 0.27 | 0.69 | 0.18 |  |
| 826 | V262E | a | 1.03 | 0.34 | 0.16 | 0.43 | 0.92 | 0.24 | 36.47 | 11.91 |  |  | 2.85 | 0.29 | 9.27 | 0.52 |  |
| 827 | V262F | a | 1.04 | 0.15 | 0.43 | 0.28 | 1.23 | 0.26 |  |  |  |  | 5.20 | 0.39 | 0.50 | 0.38 |  |
| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
| 828 | F275L | a | 1.85 | 0.15 | 0.83 | 0.31 | 1.43 | 0.31 | 97.71 | 11.88 | 1.17 | 0.38 | 3.58 | 0.37 | 0.89 | 0.35 | 0.82 |
| 829 | G281D | a p | 2.19 | 0.17 | 1.81 | 0.29 | 2.15 | 0.23 |  | 11.88 | 4.55 | 0.38 | 6.23 | 0.38 | 1.33 | 0.36 | 2.11 |
| 830 | G281K | a | 1.25 | 0.15 | 1.01 | 0.26 | 1.20 | 0.29 |  | 11.88 | 0.79 | 0.39 | 1.92 | 0.30 | 0.95 | 0.35 | 0.66 |
| 831 | G281Y | a | 1.89 | 0.14 | 2.08 | 0.52 | 2.47 | 0.34 | 1.17 | 11.88 | 0.89 | 0.39 | 2.87 | 0.35 | 1.46 | 0.35 | 0.36 |
|  |  |  | 0.42 | 0.18 | 0.80 | 0.21 | 0.73 | 0.27 |  | 0.64 | 1.31 | 1.31 |  |  | 0.69 | 0.14 | 1.79 |
| 832 | G281P | a | 1.89 | 0.23 | 1.10 | 0.33 | 1.43 | 0.28 | 85.43 | 11.88 | 0.49 | 0.36 | 5.37 | 0.30 | 1.91 | 0.40 | 0.34 |
| 833 | V282E | a | 1.50 | 0.23 | 0.58 | 0.31 | 0.65 | 0.28 | 82.37 | 11.89 | 0.54 | 0.39 | 2.23 | 0.37 | 1.44 | 0.44 | 0.83 |
| 834 | V282K | a | 0.40 | 0.20 | 0.85 | 0.19 | 1.26 | 0.23 | 1.76 | 0.64 | 2.97 | 1.31 |  |  | 1.11 | 0.17 | 2.37 |
| 835 | V282Y | a | 2.34 | 0.26 | 1.43 | 0.29 | 1.41 | 0.24 |  | 11.88 | 1.10 | 0.37 | 2.38 | 0.36 | 1.92 | 0.37 | 0.78 |
|  |  |  | 0.37 | 0.16 | 0.53 | 0.22 | 0.49 | 0.40 | 0.86 | 0.72 | 0.89 | 1.32 |  |  | 0.65 | 0.18 | 1.83 |
| 836 | V282P | a | 1.41 | 0.19 | 1.58 | 0.18 | 1.12 | 0.39 | 1.08 | 0.70 | 0.98 | 0.26 | 8.93 | 0.45 | 1.16 | 0.18 | 0.34 |
| 837 | V282G | a p | 2.47 | 0.14 | 1.20 | 0.16 | 2.81 | 0.28 | 3.63 | 0.64 | 3.26 | 0.22 | 1.25 | 0.35 | 2.74 | 0.94 | 1.16 |
| 838 | E283K | a | 4.36 | 0.41 | 3.56 | 0.24 | 3.85 | 0.36 | 2.13 | 0.71 | 27.06 | 0.35 | 3.62 | 0.40 | 6.25 | 1.29 | 7.04 |
| 839 | E283H | a | 0.78 | 0.16 | 0.50 | 0.41 | 0.32 | 0.39 | 0.66 | 1.13 |  | 28.71 |  |  | 1.18 | 0.16 |  |
| 840 | E283L | a | 1.44 | 0.15 | 4.67 | 0.12 | 6.05 | 0.28 | 9.30 | 0.65 | 22.32 | 0.26 | 3.95 | 0.40 | 9.25 | 0.69 | 3.69 |

Figure 41LL

| | | | | | | | | | | | | | | | |
|---|---|---|---|---|---|---|---|---|---|---|---|---|---|---|---|
| 841 | E283Y | a | 0.42 | 0.24 | 0.34 | 0.34 | 0.67 | 0.46 | 1.06 | 0.79 | 0.52 | 1.32 | | | 0.82 | 0.20 | 0.78 |
| 842 | E283P | a | 1.68 | 0.16 | 1.19 | 0.15 | 1.51 | 0.30 | 0.85 | 0.71 | 1.43 | 0.23 | | | 1.42 | 0.68 | 0.94 |
| 843 | E283G | a | 1.56 | 0.18 | 0.95 | 0.23 | 2.51 | 0.32 | 1.14 | 0.71 | 1.65 | 0.26 | | | 1.33 | 0.41 | 0.66 |
| 844 | V284E | a | 0.47 | 0.11 | 0.33 | 0.24 | 0.45 | 0.27 | 0.89 | 0.68 | 0.43 | 1.31 | | | 0.77 | 0.20 | 0.97 |
| 845 | V284N | a | 1.45 | 0.17 | 5.92 | 0.13 | 4.86 | 0.30 | 2.89 | 0.66 | 18.48 | 0.28 | | | 25.76 | 0.15 | 3.80 |
| 846 | V284T | a p | 0.59 | 0.10 | 0.41 | 0.22 | 0.57 | 0.61 | 0.97 | 0.67 | 0.89 | 1.32 | | | 1.11 | 0.14 | 1.55 |
| 847 | V284L | a | 0.45 | 0.29 | 0.43 | 0.27 | 0.60 | 0.28 | 1.13 | 0.66 | 0.73 | 1.32 | | | 0.77 | 0.17 | 1.21 |
| 848 | V284Y | a | 0.25 | 0.18 | 0.41 | 0.17 | 1.26 | 0.47 | 1.08 | 0.67 | 1.16 | 0.23 | | | 1.15 | 0.16 | 0.92 |
| 849 | P291D | a | 0.37 | 0.11 | 0.45 | 0.19 | 0.53 | 0.34 | 0.95 | 0.68 | 0.78 | 1.31 | | | 0.79 | 0.16 | 1.47 |
| 850 | P291E | a | 1.56 | 0.16 | 1.90 | 0.16 | 3.13 | 0.32 | 1.32 | 0.70 | 2.71 | 0.23 | | | 1.51 | 0.20 | 0.87 |
| 851 | P291Q | a | 1.11 | 0.18 | 1.19 | 0.14 | 1.07 | 0.32 | 1.89 | 0.65 | 0.72 | 0.22 | 1.06 | 0.37 | 0.89 | 0.86 | 0.67 |
| 852 | P291T | a | 1.82 | 0.28 | 1.00 | 0.30 | 1.24 | 0.44 | 0.68 | 0.98 | 0.92 | 0.28 | 1.08 | 0.44 | 0.76 | 0.94 | 0.74 |
| 853 | P291H | a | 1.06 | 0.17 | 1.40 | 0.16 | 1.81 | 0.32 | 1.33 | 0.65 | 0.80 | 0.31 | 1.26 | 0.40 | 1.24 | 0.51 | 0.44 |
| 854 | P291I | a | 0.55 | 0.18 | 0.49 | 0.14 | 1.00 | 0.34 | 0.67 | 0.73 | 0.53 | 0.25 | 1.44 | 0.40 | 0.94 | 0.44 | 0.53 |
| 855 | P291G | a | 1.85 | 0.18 | 2.66 | 0.23 | 1.47 | 0.29 | 1.35 | 0.73 | 2.40 | 0.28 | 0.75 | 0.39 | 2.56 | 0.57 | 1.63 |
| 856 | N297Q | a | 1.24 | 0.25 | 1.20 | 0.13 | 1.19 | 0.34 | 2.15 | 0.67 | 0.52 | 0.25 | 1.30 | 0.41 | 1.15 | 0.17 | 0.44 |
| 857 | N297K | a | 0.08 | 0.29 | 0.35 | 0.22 | 1.26 | 0.37 | 0.68 | 0.75 | 0.31 | 0.24 | 2.19 | 0.41 | 0.81 | 0.18 | 0.24 |
| 858 | N297R | a | 0.46 | 0.17 | 0.64 | 0.20 | 0.98 | 0.26 | 1.66 | 0.65 | 1.14 | 1.31 | | | 0.78 | 0.14 | 1.17 |
| 859 | N297T | a | | | | | | | | | | | | | | | |
| 860 | N297H | a | 0.01 | 0.20 | 0.01 | 0.80 | 0.01 | 2.77 | 0.06 | 1.66 | 0.01 | 3.89 | | | 0.45 | 0.17 | 1.03 |
| 861 | N297V | a | | | | | | | | | | | | | | | |
| 862 | N297L | a | | | | | | | | | | | | | | | |
| 863 | N297I | a | | | | | | | | | | | | | | | |
| 864 | N297F | a | | | | | | | | | | | | | | | |
| 865 | N297M | a | | | | | | | | | | | | | | | |
| 866 | N297Y | a | | | | | | | | | | | | | | | |
| 867 | N297W | a | | | | | | | | | | | | | | | |
| 868 | N297P | a | | | | | | | | | | | | | | | |
| 869 | N297G | a | | | | | | | | | | | | | | | |
| 870 | R301D | a | 0.87 | 0.16 | 0.11 | 0.60 | 0.06 | 2.49 | 0.04 | 2.89 | 0.03 | 1.45 | 1.58 | 0.43 | 0.50 | 0.24 | 0.47 |
| 871 | R301E | a | 0.62 | 0.23 | 0.36 | 0.15 | 0.84 | 0.43 | 0.44 | 0.73 | 0.69 | 0.24 | 2.71 | 0.49 | 2.92 | 0.99 | 0.82 |
| 872 | R301H | a | 1.65 | 0.25 | 0.37 | 0.24 | 0.97 | 0.64 | 0.74 | 0.93 | 0.41 | 0.30 | 1.58 | 0.48 | 0.76 | 0.98 | 0.42 |
| 873 | R301Y | a | 0.72 | 0.15 | 0.64 | 0.17 | 1.27 | 0.35 | 0.95 | 0.68 | 0.17 | 0.31 | 1.49 | 0.44 | 0.78 | 0.51 | 0.13 |

Figure 41MM

| Variant | Substitution(s) | Context | FcγRI Fold | FcγRI Conf | FcγRIIa Fold | FcγRIIa Conf | FcγRIIb Fold | FcγRIIb Conf | FcγRIIc Fold | FcγRIIc Conf | FcγRIIIa Fold | FcγRIIIa Conf | C1q Fold | C1q Conf | FcRn Fold | FcRn Conf | IIIa:IIb |
|---|---|---|---|---|---|---|---|---|---|---|---|---|---|---|---|---|---|
| 874 | V303D | a | 0.69 | 0.18 | 0.67 | 0.15 | 0.55 | 0.64 | 0.53 | 0.75 | 0.29 | 0.30 | 1.45 | 0.45 | 0.91 | 0.33 | 0.52 |
| 875 | V303E | a | 2.29 | 0.23 | 1.02 | 0.19 | 1.41 | 0.28 | 1.31 | 0.68 | 1.43 | 0.25 | 1.43 | 0.40 | 1.63 | 0.35 | 1.02 |
| 876 | V303Y | a | 0.78 | 0.18 | 2.56 | 0.21 | 1.43 | 0.33 | 1.26 | 0.73 | 0.44 | 0.25 | 1.02 | 0.42 | 1.15 | 0.16 | 0.31 |
| 877 | S304D | a | 1.12 | 0.19 | 0.53 | 0.29 | 1.17 | 0.57 | | | 0.14 | 0.28 | 2.17 | 0.52 | 0.61 | 0.20 | 0.12 |
| 878 | S304N | a | 0.95 | 0.18 | 0.69 | 0.19 | 0.81 | 0.42 | 0.90 | 0.90 | 1.08 | 0.25 | 1.32 | 0.41 | 1.19 | 0.19 | 1.34 |
| 879 | S304T | a | 1.00 | 0.15 | 2.86 | 0.18 | 1.61 | 0.31 | 0.73 | 0.80 | 6.13 | 0.21 | 3.30 | 0.48 | 2.86 | 1.08 | 3.80 |
| 880 | S304H | a | 1.11 | 0.29 | 0.32 | 0.31 | 0.79 | 0.97 | 1.65 | 15.76 | 0.18 | 0.28 | 1.59 | 0.50 | 0.38 | 0.97 | 0.23 |
| 881 | S304L | a | | | | | | | | | | | | | | | |
| 882 | V305E | a | 0.89 | 0.16 | 0.90 | 0.16 | 1.45 | 0.31 | 1.14 | 0.76 | 0.65 | 0.24 | 1.99 | 0.49 | 0.67 | 0.51 | 0.45 |
| 883 | V305T | a | 1.17 | 0.22 | 0.91 | 0.16 | 1.23 | 0.33 | 0.07 | 1.74 | 0.68 | 0.25 | | | | | 0.55 |
| 884 | V305Y | a | 1.59 | 0.22 | 0.98 | 0.24 | 0.95 | 0.31 | 0.22 | 1.23 | 0.66 | 0.30 | 1.12 | 0.49 | 0.74 | 0.30 | 0.70 |
| 885 | K317E | a | 0.85 | 0.18 | 0.79 | 0.22 | 0.48 | 0.55 | 0.29 | 0.95 | 0.39 | 0.72 | | | 0.45 | 0.56 | 0.81 |
| 886 | K317Q | a | 1.22 | 0.10 | | | 0.98 | 0.42 | | | 1.25 | 0.17 | | | | | 1.27 |
| 887 | E318Q | a | 0.62 | 0.14 | 0.80 | 0.18 | 0.35 | 0.37 | 0.72 | 0.33 | 0.40 | 0.70 | 0.99 | 0.55 | 0.56 | 0.66 | 1.17 |
| 888 | E318H | a | 0.49 | 0.15 | 0.46 | 0.35 | 0.38 | 0.45 | | | 0.26 | 1.71 | | | 0.61 | 0.21 | 0.69 |
| 889 | E318L | a | 1.05 | 0.37 | 0.67 | 0.23 | 0.18 | 1.28 | 0.87 | 0.45 | 0.38 | 0.71 | | | 3.61 | 1.60 | 2.12 |
| 890 | E318Y | a | 0.67 | 0.16 | 0.63 | 0.14 | 0.22 | 0.83 | 0.51 | 0.80 | 0.25 | 0.69 | 1.07 | 0.52 | 6.14 | 1.63 | 1.13 |
| 891 | I336E | a | 0.36 | 0.27 | 0.08 | 0.77 | 0.05 | 0.95 | 0.17 | 1.59 | 0.06 | 0.82 | | | 8.11 | 1.03 | 1.10 |
|  |  |  | 0.70 | 0.44 | 0.38 | 0.29 | 0.34 | 0.59 | 1.02 | 0.86 | 1.79 | 1.33 | | | 0.64 | 0.21 | 5.20 |
| Variant | Substitution(s) | Context | Fold | Conf | Fold | Conf | Fold | Conf | Fold | Conf | Fold | Conf | Fold | Conf | Fold | Conf | IIIa:IIb |
| 892 | I336K | a | 1.11 | 0.21 | 0.94 | 0.20 | 1.05 | 1.26 | 0.47 | 1.27 | 0.73 | 0.71 | 1.13 | 0.40 | 12.12 | 0.94 | 0.69 |
| 893 | I336Y | a | 0.45 | 0.15 | 0.28 | 0.19 | 0.59 | 0.50 | 0.64 | 0.68 | 0.21 | 0.71 | | | 0.49 | 0.50 | 0.36 |
| 894 | S337E | a | 0.71 | 0.17 | 1.15 | 0.18 | 1.13 | 0.27 | 0.95 | 0.24 | 0.74 | 0.69 | | | 0.39 | 0.47 | 0.65 |
| 895 | S337N | a | 0.77 | 0.20 | 1.45 | 0.24 | 1.50 | 0.37 | 0.93 | 0.50 | 0.58 | 0.75 | | | 0.52 | 0.48 | 0.39 |
| 896 | S337H | a | 0.66 | 0.14 | 0.78 | 0.14 | 0.64 | 0.29 | 0.85 | 0.25 | 0.35 | 0.69 | | | 0.56 | 0.51 | 0.55 |
| 912 | S239D/E272Y/ I332E | tr | 1.98 | 0.18 | 3.33 | 0.30 | 12.09 | 0.30 | 9.89 | 0.23 | 43.67 | 0.12 | 0.88 | 0.96 | 1.31 | 0.27 | 3.61 |
| 913 | S239D/E272S/ I332E | tr | 1.23 | 0.09 | 3.11 | 0.24 | 14.47 | 0.29 | 12.02 | 0.23 | 18.57 | 0.11 | 0.87 | 1.07 | 1.49 | 0.25 | 1.28 |
| 914 | S239D/E272K/ I332E | tr | | | | | | | | | | | | | | | |
| 915 | S239D/E272I/ I332E | tr | 3.23 | 0.07 | 7.99 | 0.24 | 22.11 | 0.30 | 18.91 | 0.23 | 64.80 | 0.10 | 1.07 | 0.75 | 1.81 | 0.23 | 2.93 |
| 916 | S239D/E272Y/ A330L/I332E | tr | 1.83 | 0.12 | 0.89 | 0.28 | 2.92 | 0.34 | 3.04 | 0.23 | 46.36 | 0.12 | | | 1.00 | 0.25 | 15.90 |

Figure 41NN

| # | Mutation | | | | | | | | | | | | | | | |
|---|---|---|---|---|---|---|---|---|---|---|---|---|---|---|---|---|
| 917 | S239D/E272S/A330L/I332E | tr | 1.83 | 0.09 | 2.34 | 0.30 | 11.04 | 0.32 | 9.15 | 0.23 | 70.29 | 0.10 | 0.88 | 0.75 | 0.98 | 0.27 | 6.37 |
| 918 | S239D/E272K/A330L/I332E | tr | 3.20 | 0.09 | 3.66 | 0.31 | 26.79 | 0.34 | 14.88 | 0.23 | 86.88 | 0.10 | 1.23 | 0.70 | 0.60 | 0.27 | 3.24 |
| 919 | S239D/E272I/A330L/I332E | tr | 0.04 | 0.15 | 0.26 | 16.94 | 1.36 | 1.57 | 0.75 | 0.38 | 0.60 | 0.14 | 1.12 | 0.74 | 0.21 | 0.51 | 0.44 |
| 920 | S239D/K274E/I332E | tr | 5.76 | 0.13 | 20.99 | 0.23 | 122 | 0.31 | 78.15 | 0.22 | 332 | 0.11 | 0.70 | 1.34 | 2.22 | 0.26 | 2.71 |
| 921 | S239D/Y278T/I332E | tr p | 2.87 | 0.18 | 4.08 | 0.29 | 59.31 | 0.29 | 35.60 | 0.22 | 184 | 0.11 | 0.89 | 1.20 | 0.64 | 0.27 | 3.10 |
| 922 | S239D/K326T/I332E | tr p | 1.94 | 0.10 | 1.26 | 0.29 | 10.27 | 0.29 | 7.71 | 0.22 | 84.23 | 0.10 | 0.92 | 2.08 | 0.72 | 0.30 | 8.20 |
| 923 | S239D/K326E/I332E | tr | | | | | | | | | | | | | | | |
| 924 | S239D/K274E/A330L/I332E | tr | | | | | | | | | | | | | | | |
| 925 | S239D/Y278T/A330L/I332E | tr | | | | | | | | | | | | | | | |
| 926 | S239D/K326E/A330L/I332E | tr | | | | | | | | | | | | | | | |
| 927 | S267E | r | | | | | | | | | | | | | | | |
| 928 | S239D/S267E/I332E | r | | | | | | | | | | | | | | | |
| 929 | S239D/S267E/A330L/I332E | r | | | | | | | | | | | | | | | |
| 930 | Y278W | r | | | | | | | | | | | | | | | |
| 931 | E283R/V302I | r | | | | | | | | | | | | | | | |
| | Y278W/E283R | r | | | | | | | | | | | | | | | |
| 934 | Y278W/V302I | r | | | | | | | | | | | | | | | |
| 935 | Y278W/E283R/V302I | r | | | | | | | | | | | | | | | |
| 1145 | S239D/I332E/G236S | t | | | | | | | | | | | | | | | |
| 1146 | S239D/I332E/G236A | t | | | | | | | | | | | | | | | |
| 1147 | S239D/I332E/K246H | t | | | | | | | | | | | | | | | |

Figure 4100

| | | |
|---|---|---|
| 1148 | S239D/I332E/ R255Y | |
| 1149 | S239D/I332E/ S267E | t |
| 1150 | S239D/I332E/ E272R | t |
| 1151 | S239D/I332E/ E272H | t |
| 1152 | I332E/G281D | t |
| 1153 | S239D/I332E/ E283H | t |
| 1154 | S239D/I332E/ E283L | t |
| 1155 | I332E/V284E | t |
| 1156 | S239D/I332E/ V284E | t |
| 1157 | S267E/S324I | t |
| 1158 | S267E/A327D | t |
| 1159 | S324I/A327D | t |
| 1160 | S267E/P331D | t |
| 1161 | S267E/V282G | t |
| 1162 | G281D/V282G | t |
| 1163 | V282G/P331D | t |
| 1164 | G281E | t |
| 1165 | G281N | t |
| 1166 | G281Q | t |
| 1167 | V284D | t |
| 1168 | V284Q | t |
| 1169 | S298A/K326E | t |
| 1170 | S298A/K334L | t |
| 1171 | S298A/K326E/ K334L | t |
| 1608 | S239D/S298A/K 326E/I332E | t p |
| 1609 | S239D/S298A/K 326T/I332E | t |
| 1877 | I332E/H268E | p |

Figure 41PP

| | |
|---|---|
| 1878 | I332E/H268D p |
| 1879 | S239D/H268E p |
| 1880 | S239D/H268D p |
| 1881 | S239D/I332E/ p |
| | H268E |
| 1882 | S239D/I332E/H2 p |
| | 68D |
| 1883 | S239D/I332E/ p |
| | A327D |
| 1884 | S239D/I332E/ p |
| | V284D |
| 1885 | S239D/I332E/ p |
| | V284E |

Figure 42

SEQ ID NO:8

Xaa Xaa Xaa Xaa Xaa Cys Xaa Xaa Cys Xaa Xaa Xaa Xaa Xaa Xaa
221              225              230              235

Xaa Xaa Xaa Xaa Xaa Leu Xaa Xaa Xaa Xaa Xaa Lys Xaa Thr Leu Met
                240              245              250

Ile Ser Xaa Thr Pro Xaa Val Xaa Cys Xaa Xaa Xaa Xaa Xaa Xaa Xaa
        255              260              265

Xaa Xaa Xaa Xaa Xaa Xaa Xaa Xaa Trp Xaa Val Xaa Xaa Xaa Xaa Xaa
    270              275              280

Xaa Xaa Ala Xaa Thr Xaa Xaa Xaa Xaa Xaa Xaa Xaa Xaa Xaa Xaa
285              290              295              300

Xaa Xaa Xaa Xaa Xaa Leu Thr Val Leu His Gln Asp Xaa Leu Asn Gly
                305              310              315

Xaa Xaa Tyr Xaa Cys Xaa Xaa Xaa Xaa Xaa Xaa Xaa Xaa Xaa Xaa
        320              325              330

Xaa Xaa Xaa Xaa Xaa
        335

OPTIMIZED FC VARIANTS

This application is a divisional application of U.S. application Ser. No. 13/870,781, filed Apr. 25, 2013, which is continuation application of U.S. application Ser. No. 12/896,610, filed Oct. 1, 2010, which is a continuation of U.S. application Ser. No. 11/124,620, filed May 5, 2005, (now U.S. Pat. No. 8,188,231, issued May 29, 2012) which claims benefit under 35 U.S.C. §119(e) to U.S. Ser. Nos. 60/589,906 filed Jul. 20, 2004; 60/627,026 filed Nov. 9, 2004; 60/626,991 filed Nov. 10, 2004; 60/627,774 filed Nov. 12, 2004; U.S. application Ser. No. 11/124,620 is a continuation-in-part of U.S. Ser. No. 10/822,231, filed Mar. 26, 2004, now issued as U.S. Pat. No. 7,317,091, and U.S. Ser. No. 10/822,231 is a continuation in part of U.S. application Ser. No. 10/672,280, filed Sep. 26, 2003, (abandoned), and U.S. Ser. No. 10/672,280 is a nonprovisional application of U.S. Provisional Application Ser. Nos. 60/477,839, filed Jun. 12, 2003; 60/467,606, filed May 2, 2003; 60/442,301, filed Jan. 23, 2003; and 60/414,433, filed Sep. 27, 2002, all of which are incorporated by reference in their entirety.

FIELD OF THE INVENTION

The present invention relates to novel optimized Fc variants, engineering methods for their generation, and their application, particularly for therapeutic purposes.

BACKGROUND OF THE INVENTION

Antibodies are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the variable region. FIG. 1 shows an IgG1 antibody, used here as an example to describe the general structural features of immunoglobulins. IgG antibodies are tetrameric proteins composed of two heavy chains and two light chains. The IgG heavy chain is composed of four immunoglobulin domains linked from N- to C-terminus in the order $V_H$-$C_H1$-$C_H2$-$C_H3$, referring to the variable heavy domain, constant heavy domain 1, constant heavy domain 2, and constant heavy domain 3. The IgG $C_H1$, $C_H2$, and $C_H3$ domains are also referred to as constant gamma 1 domain (Cγ1), constant gamma 2 domain (Cγ2), and constant gamma 3 domain (Cγ3) respectively. The IgG light chain is composed of two immunoglobulin domains linked from N- to C-terminus in the order $V_L$-$C_L$, referring to the light chain variable domain and the light chain constant domain respectively.

The variable region of an antibody contains the antigen binding determinants of the molecule, and thus determines the specificity of an antibody for its target antigen. The variable region is so named because it is the most distinct in sequence from other antibodies within the same class. The majority of sequence variability occurs in the complementarity determining regions (CDRs). There are 6 CDRs total, three each per heavy and light chain, designated $V_H$ CDR1, $V_H$ CDR2, $V_H$ CDR3, $V_L$ CDR1, $V_L$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. The sequence and structural features of antibody variable regions are well characterized (Morea et al., 1997, Biophys Chem 68:9-16; Morea et al., 2000, Methods 20:267-279, incorporated by reference), and the conserved features of antibodies have enabled the development of a wealth of antibody engineering techniques (Maynard et al., 2000, Annu Rev Biomed Eng 2:339-376, incorporated by reference). For example, it is possible to graft the CDRs from one antibody, for example a murine antibody, onto the framework region of another antibody, for example a human antibody. This process, referred to in the art as "humanization", enables generation of less immunogenic antibody therapeutics from nonhuman antibodies. Fragments comprising the variable region can exist in the absence of other regions of the antibody, including for example the antigen binding fragment (Fab) comprising $V_H$-Cγ1 and $V_H$-$C_L$, the variable fragment (Fv) comprising $V_H$ and $V_L$, the single chain variable fragment (scFv) comprising $V_H$ and $V_L$ linked together in the same chain, as well as a variety of other variable region fragments (Little et al., 2000, Immunol Today 21:364-370, incorporated by reference).

The Fc region of an antibody interacts with a number of Fc receptors and ligands, imparting an array of important functional capabilities referred to as effector functions. For IgG the Fc region, as shown in FIG. 1, comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). A number of structures have been solved of the extracellular domains of human FcγRs, including FcγRIIa (pdb accession code 1H9V) (Sondermann et al., 2001, J Mol Biol 309:737-749) (pdb accession code 1FCG) (Maxwell et al., 1999, Nat Struct Biol 6:437-442), FcγRIIb (pdb accession code 2FCB) (Sondermann et al., 1999, Embo J 18:1095-1103); and FcγRIIIb (pdb accession code 1E4J) (Sondermann et al., 2000, Nature 406:267-273, incorporated by reference). All FcγRs bind the same region on Fc, at the N-terminal end of the Cγ2 domain and the preceding hinge, shown in FIG. 2. This interaction is well characterized structurally (Sondermann et al., 2001, J Mol Biol 309:737-749 incorporated by reference), and several structures of the human Fc bound to the extracellular domain of human FcγRIIIb have been solved (pdb accession code 1E4K) (Sondermann et al., 2000, Nature 406:267-273) (pdb accession codes 1IIS and 1IIX) (Radaev et al., 2001, J Biol Chem 276:16469-16477, incorporated by reference), as well as has the structure of the human IgE Fc/FcεRIα complex (pdb accession code 1F6A) (Garman et al., 2000, Nature 406:259-266, incorporated by reference).

The different IgG subclasses have different affinities for the FcγRs, with IgG1 and IgG3 typically binding substantially better to the receptors than IgG2 and IgG4. All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758, incorporated by reference). Approximately 10-20% of humans are V158/V158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758, incorporated by reference). Thus 80-90% of humans are poor responders, that is they have at least one allele of the F158 FcγRIIIa.

An overlapping but separate site on Fc, shown in FIG. 1, serves as the interface for the complement protein C1q. In the same way that Fc/FcγR binding mediates ADCC, Fc/C1q binding mediates complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4. There is currently no structure available for the Fc/C1q complex; however, mutagenesis studies have mapped the binding site on human IgG for C1q to a region involving residues D270, K322, K326, P329, and P331, and E333 (Idusogie et al., 2000, J Immunol 164:4178-4184; Idusogie et al., 2001, J Immunol 166:2571-2575, incorporated by reference).

A site on Fc between the Cγ2 and Cγ3 domains, shown in FIG. 1, mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. Thus the fidelity of this region on Fc is important for both the clinical properties of antibodies and their purification. Available structures of the rat Fc/FcRn complex (Martin et al., 2001, Mol Cell 7:867-877, incorporated by reference), and of the complexes of Fc with proteins A and G (Deisenhofer, 1981, Biochemistry 20:2361-2370; Sauer-Eriksson et al., 1995, Structure 3:265-278; Tashiro et al., 1995, Curr Opin Struct Biol 5:471-481, incorporated by reference) provide insight into the interaction of Fc with these proteins.

A key feature of the Fc region is the conserved N-linked glycosylation that occurs at N297, shown in FIG. 1. This carbohydrate, or oligosaccharide as it is sometimes referred, plays a critical structural and functional role for the antibody, and is one of the principle reasons that antibodies must be produced using mammalian expression systems. While not wanting to be limited to one theory, it is believed that the structural purpose of this carbohydrate may be to stabilize or solubilize Fc, determine a specific angle or level of flexibility between the Cγ3 and Cγ2 domains, keep the two Cγ2 domains from aggregating with one another across the central axis, or a combination of these. Efficient Fc binding to FcγR and C1q requires this modification, and alterations in the composition of the N297 carbohydrate or its elimination affect binding to these proteins (Umaña et al., 1999, Nat Biotechnol 17:176-180; Davies et al., 2001, Biotechnol Bioeng 74:288-294; Mimura et al., 2001, J Biol Chem 276:45539-45547.; Radaev et al., 2001, J Biol Chem 276:16478-16483; Shields et al., 2001, J Biol Chem 276:6591-6604; Shields et al., 2002, J Biol Chem 277:26733-26740; Simmons et al., 2002, J Immunol Methods 263:133-147, incorporated by reference). Yet the carbohydrate makes little if any specific contact with FcγRs (Radaev et al., 2001, *J Biol Chem* 276:16469-16477, incorporated by reference), indicating that the functional role of the N297 carbohydrate in mediating Fc/FcγR binding may be via the structural role it plays in determining the Fc conformation. This is supported by a collection of crystal structures of four different Fc glycoforms, which show that the composition of the oligosaccharide impacts the conformation of Cγ2 and as a result the Fc/FcγR interface (Krapp et al., 2003, *J Mol Biol* 325:979-989, incorporated by reference).

The features of antibodies discussed above—specificity for target, ability to mediate immune effector mechanisms, and long half-life in serum—make antibodies powerful therapeutics. Monoclonal antibodies are used therapeutically for the treatment of a variety of conditions including cancer, inflammation, and cardiovascular disease. There are currently over ten antibody products on the market and hundreds in development. In addition to antibodies, an antibody-like protein that is finding an expanding role in research and therapy is the Fc fusion (Chamow et al., 1996, *Trends Biotechnol* 14:52-60; Ashkenazi et al., 1997, *Curr Opin Immunol* 9:195-200, incorporated by reference). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends directly to Fc fusions.

There are a number of possible mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, *Curr Opin Immunol* 11:541-547; Glennie et al., 2000, *Immunol Today* 21:403-410. incorporated by reference). Anti-tumor efficacy may be due to a combination of these mechanisms, and their relative importance in clinical therapy appears to be cancer dependent. Despite this arsenal of anti-tumor weapons, the potency of antibodies as anti-cancer agents is unsatisfactory, particularly given their high cost. Patient tumor response data show that monoclonal antibodies provide only a small improvement in therapeutic success over normal single-agent cytotoxic chemotherapeutics. For example, just half of all relapsed low-grade non-Hodgkin's lymphoma patients respond to the anti-CD20 antibody rituximab (McLaughlin et al., 1998, *J Clin Oncol* 16:2825-2833. incorporated by reference). Of 166 clinical patients, 6% showed a complete response and 42% showed a partial response, with median response duration of approximately 12 months. Trastuzumab (Herceptin®, a registered trademark of Genentech), an anti-HER2/neu antibody for treatment of metastatic breast cancer, has less efficacy. The overall response rate using trastuzumab for the 222 patients tested was only 15%, with 8 complete and 26 partial responses and a median response duration and survival of 9 to 13 months (Cobleigh et al., 1999, *J Clin Oncol* 17:2639-2648, incorporated by reference). Currently for anti-cancer therapy, any small improvement in mortality rate defines success. Thus there is a significant need to enhance the capacity of antibodies to destroy targeted cancer cells.

The role of FcγR-mediated effector functions in the anti-cancer activity of antibodies has been demonstrated in mice (Clynes et al., 1998, *Proc Natl Acad Sci USA* 95:652-656; Clynes et al., 2000, *Nat Med* 6:443-446, incorporated by reference), and the affinity of interaction between Fc and certain FcγRs correlates with targeted cytotoxicity in cell-based assays (Shields et al., 2001, *J Biol Chem* 276:6591-6604; Presta et al., 2002, *Biochem Soc Trans* 30:487-490; Shields et al., 2002, *J Biol Chem* 277:26733-26740, incorporated by reference). Additionally, a correlation has been observed between clinical efficacy in humans and their allotype of high (V158) or low (F158) affinity polymorphic forms of FcγRIIIa (Cartron et al., 2002, *Blood* 99:754-758, incorporated by reference).

Mutagenesis studies have been carried out on Fc towards various goals, with substitutions typically made to alanine (referred to as alanine scanning) or guided by sequence homology substitutions (Duncan et al., 1988, *Nature* 332:563-564; Lund et al., 1991, *J Immunol* 147:2657-2662; Lund et al., 1992, *Mol Immunol* 29:53-59; Jefferis et al., 1995, *Immunol Lett* 44:111-117; Lund et al., 1995, *Faseb J* 9:115-119; Jefferis et al., 1996, *Immunol Lett* 54:101-104; Lund et al., 1996, *J Immunol* 157:4963-4969; Armour et al., 1999, *Eur J Immunol* 29:2613-2624; Shields et al., 2001, *J Biol Chem* 276:6591-6604) (U.S. Pat. No. 5,624,821; U.S. Pat. No. 5,885,573; PCT WO 00/42072; PCT WO 99/58572), all incorporated by reference. The majority of substitutions reduce or ablate binding with FcγRs. However some success has been achieved at obtaining Fc variants with higher FcγR affinity. (See for example U.S. Pat. No. 5,624,821 and PCT WO 00/42072). For example, Winter and colleagues substituted the human amino acid at position 235 of mouse IgG2b antibody (a glutamic acid to leucine mutation) that increased binding of the mouse antibody to human FcγRI by 100-fold (Duncan et al., 1988, *Nature* 332:563-564) (U.S. Pat. No. 5,624,821). Shields et al. used alanine scanning mutagenesis to map Fc residues important to FcγR binding, followed by substitution of select residues with non-alanine mutations (Shields et al., 2001, *J Biol Chem* 276:6591-6604; Presta et al., 2002, *Biochem Soc Trans* 30:487-490) (PCT WO 00/42072), incorporated by reference.

Enhanced affinity of Fc for FcγR has also been achieved using engineered glycoforms generated by expression of antibodies in engineered or variant cell lines (Umaña et al., 1999, *Nat Biotechnol* 17:176-180; Davies et al., 2001, *Biotechnol Bioeng* 74:288-294; Shields et al., 2002, *J Biol Chem* 277:26733-26740; Shinkawa et al., 2003, *J Biol Chem* 278:3466-3473, incorporated by reference). This approach has generated enhancement of the capacity of antibodies to bind FcγRIIIa and to mediate ADCC.

Another major shortcoming of antibodies is their demanding production requirements (Garber, 2001, *Nat Biotechnol* 19:184-185; Dove, 2002, *Nat Biotechnol* 20:777-779, incorporated by reference). Antibodies must be expressed in mammalian cells, and the currently marketed antibodies together with other high-demand biotherapeutics consume essentially all of the available manufacturing capacity. With hundreds of biologics in development, the majority of which are antibodies, there is an urgent need for more efficient and cheaper methods of production. The downstream effects of insufficient antibody manufacturing capacity are three-fold. First, it dramatically raises the cost of goods to the producer, a cost that is passed on to the patient. Second, it hinders industrial production of approved antibody products, limiting availability of high demand therapeutics to patients. Finally, because clinical trials require large amounts of a protein that is not yet profitable, the insufficient supply impedes progress of the growing antibody pipeline to market.

Alternative production methods have been explored in attempts at alleviating this problem. Transgenic plants and animals are being pursued as potentially cheaper and higher capacity production systems (Chadd et al., 2001, *Curr Opin Biotechnol* 12:188-194, incorporated by reference). Such expression systems, however, can generate glycosylation patterns significantly different from human glycoproteins. This may result in reduced or even lack of effector function because, as discussed above, the carbohydrate structure can significantly impact FcγR and complement binding. A potentially greater problem with nonhuman glycoforms may be immunogenicity; carbohydrates are a key source of antigenicity for the immune system, and the presence of nonhuman glycoforms has a significant chance of eliciting antibodies that neutralize the therapeutic, or worse cause adverse immune reactions. Thus the efficacy and safety of antibodies produced by transgenic plants and animals remains uncertain. Bacterial expression is another attractive solution to the antibody production problem. Expression in bacteria, for example *E. coli*, provides a cost-effective and high capacity method for producing proteins. For complex proteins such as antibodies there are a number of obstacles to bacterial expression, including folding and assembly of these complex molecules, proper disulfide formation, and solubility, stability, and functionality in the absence of glycosylation because proteins expressed in bacteria are not glycosylated. Full length unglycosylated antibodies that bind antigen have been successfully expressed in *E. coli* (Simmons et al., 2002, *J Immunol Methods* 263:133-147, incorporated by reference), and thus, folding, assembly, and proper disulfide formation of bacterially expressed antibodies are possible in the absence of the eukaryotic chaperone machinery. However the ultimate utility of bacterially expressed antibodies as therapeutics remains hindered by the lack of glycosylation, which results in lack effector function and may result in poor stability and solubility. This will likely be more problematic for formulation at the high concentrations for the prolonged periods demanded by clinical use.

In summary, there is a need for antibodies with enhanced therapeutic properties.

SUMMARY OF THE INVENTION

The present invention provides Fc variants that are optimized for a number of therapeutically relevant properties. These Fc variants are generally contained within a variant protein, that preferably comprises an antibody or a Fc fusion protein.

It is an object of the present invention to provide novel Fc positions at which amino acid modifications may be made to generate optimized Fc variants. Said Fc positions include 230, 240, 244, 245, 247, 262, 263, 266, 273, 275, 299, 302, 313, 323, 325, 328, and 332, wherein the numbering of the residues in the Fc region is that of the EU index as in Kabat. The present invention describes any amino acid modification at any of said novel Fc positions in order to generate an optimized Fc variant.

It is a further object of the present invention to provide Fc variants that have been characterized herein. In one embodiment, said Fc variants comprise at least one amino acid substitution at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein the numbering of the residues in the Fc region is that of the EU index as in Kabat. In a preferred embodiment, said Fc variants comprise at least one substitution selected from the group consisting of D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239E, S239F, S239G, S239H, S239I, S239K, S239L, S239M, S239N, S239P, S239Q, S239R, S239T, S239V, S239W, S239Y, V240A, V240I, V240M, V240T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264Q, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291E, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat. This set of variants is sometimes referenced to as "the single variant set" of the invention.

It is an additional aspect of the invention to provide Fc variants (and proteins containing these variants) that have at least 1, 2, 3, 4, 5, 6, 7, 8, 9 and 10 or more amino acid substitutions as compared to the parent Fc polypeptide, for example the Fc region SEQ ID NO:1. In some embodiments, 1, 2, 3 and 4 substitutions find particular use.

It is a further aspect of the invention to provide Fc variants (and proteins containing these variants) that exhibit altered Fc ligand binding as compared to the parent Fc polypeptide, for example the Fc region of SEQ ID NO:1, and that are encoded by nucleic acids that hybridize under high stringency conditions to a gene that encodes a human Fc polypeptide. High stringency conditions are known in the art; see for example U.S. Pat. No. 6,875,846, hereby incorporated by reference, particularly for high stringency conditions. Genes that encode human Fc polypeptides are usually fragments of larger genes, and are also known in the art, as well as genes that due to the degeneracy of the genetic code will encode a naturally occurring Fc polypeptide even if not naturally occurring themselves.

It is an additional aspect of the invention to provide Fc variants (and proteins containing these variants) that have at least 1, 2, 3, 4, 5, 6, 7, 8, 9 and 10 or more amino acid substitutions as compared to the parent Fc polypeptide, for example the Fc region SEQ ID NO:1. In some embodiments, 1, 2, 3 and 4 substitutions find particular use.

It is a further aspect of the invention to provide Fc variants (and proteins containing these variants) that exhibit altered Fc ligand binding as compared to the parent Fc polypeptide, for example the Fc region of SEQ ID NO:1, and that are encoded by nucleic acids that hybridize under high stringency conditions to a gene that encodes a human Fc polypeptide. High stringency conditions are known in the art; see for example U.S. Pat. No. 6,875,846, hereby incorporated by reference, particularly for high stringency conditions. Genes that encode human Fc polypeptides are usually fragments of larger genes, and are also known in the art, as well as genes that due to the degeneracy of the genetic code will encode a naturally occurring Fc polypeptide even if not naturally occurring themselves.

It is an additional aspect of the invention to provide for variant Fc polypeptides that exhibit altered ADCC activity, particularly increased ADCC activity. In some aspects, these variants comprise an amino acid substitution at position 239, optionally amino acid substitutions at positions 239 and 332, and optionally can include any other substitutions outlined in the single variant set above, to create variants comprising multiple substitutions.

It is a further object of the present invention to provide Fc variants that have been characterized herein, wherein said Fc variants are selected from the group consisting of D221K, D221Y, K222E, K222Y, T223E, T223K, H224E, H224Y, T225E, T225K, T225W, P227E, P227G, P227K, P227Y, P228E, P228G, P228K, P228Y, P230A, P230A/E233D, P230A/E233D/I332E, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234I/L235D, L234K, L234M, L234N, L234P, L234Q, L234R, L234S, L234T, L234V, L234W, L234Y, L235A, L235D, L235D/S239D/ A330Y/I332E, L235D/S239D/N297D/I332E, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239D/A330L/ I332E, S239D/A330Y/I332E/L234I, S239D/A330Y/I332E/ V266I, S239D/D265F/N297D/I332E, S239D/D265H/ N297D/I332E, S239D/D265I/N297D/I332E, S239D/ D265L/N297D/I332E, S239D/D265T/N297D/I332E, S239D/D265Y/N297D/I332E, S239D/E272I/A330L/I332E, S239D/E272I/I332E, S239D/E272K/A330L/I332E, S239D/ E272K/I332E, S239D/E272S/A330L/I332E, S239D/E272S/ I332E, S239D/E272Y/A330L/I332E, S239D/E272Y/I332E, S239D/F241S/F243H/V262T/V264T/N297D/A330Y/ I332E, S239D/H268D, S239D/H268E, S239D/I332D, S239D/I332E, S239D/I332E/A327D, S239D/I332E/A330I, S239D/I332E/A330Y, S239D/I332E/E272H, S239D/I332E/ E272R, S239D/I332E/E283H, S239D/I332E/E283L, S239D/I332E/G236A, S239D/I332E/G236S, S239D/I332E/ H268D, S239D/I332E/H268E, S239D/I332E/K246H, S239D/I332E/R255Y, S239D/I332E/S267E, S239D/I332E/ V264I, S239D/I332E/V264I/A330L, S239D/I332E/V264I/ S298A, S239D/I332E/V284D, S239D/I332E/V284E, S239D/I332E/V284E, S239D/I332N, S239D/I332Q, S239D/K274E/A330L/I332E, S239D/K274E/I332E, S239D/K326E/A330L/I332E, S239D/K326E/A330Y/ I332E, S239D/K326E/I332E, S239D/K326T/A330Y/I332E, S239D/K326T/I332E, S239D/N297D/A330Y/I332E, S239D/N297D/I332E, S239D/N297D/K326E/I332E, S239D/S267E/A330L/I332E, S239D/S267E/I332E, S239D/ S298A/K326E/I332E, S239D/S298A/K326T/I332E, S239D/V240I/A330Y/I332E, S239D/V264T/A330Y/ I332E, S239D/Y278T/A330L/I332E, S239D/Y278T/I332E, S239E, S239E/D265G, S239E/D265N, S239E/D265Q, S239E/I332D, S239E/I332E, S239E/I332N, S239E/I332Q, S239E/N297D/I332E, S239E/V264I/A330Y/I332E, S239E/ V264I/I332E, S239E/V264I/S298A/A330Y/I332E, S239F, S239G, S239H, S239I, S239K, S239L, S239M, S239N, S239N/I332D, S239N/I332E, S239N/I332E/A330L, S239N/ I332E/A330Y, S239N/I332N, S239N/I332Q, S239P, S239Q, S239Q/I332D, S239Q/I332E, S239Q/I332N, S239Q/I332Q, S239Q/V264I/I332E, S239R, S239T, S239V, S239W, S239Y, V240A, V240I, V240I/V266I, V240M, V240T, F241D, F241E, F241E/F243Q/V262T/V264E/I332E, F241E/F243Q/V262T/V264E, F241E/F243R/V262E/ V264R/I332E, F241E/F243R/V262E/V264R, F241E/ F243Y/V262T/V264R/I332E, F241E/F243Y/V262T/ V264R, F241L, F241L/F243L/V262I/V264I, F241L/V262I, F241R/F243Q/V262T/V264R/I332E, F241R/F243Q/ V262T/V264R, F241W, F241W/F243W, F241W/F243W/ V262A/V264A, F241Y, F241Y/F243Y/V262T/V264T/ N297D/I332E, F241Y/F243Y/V262T/V264T, F243E, F243L, F243L/V262I/V264W, F243L/V264I, F243W, P244H, P244H/P245A/P247V, P245A, K246D, K246E, K246H, K246Y, P247G, P247V, D249H, D249Q, D249Y, R255E, R255Y, E258H, E258S, E258Y, T260D, T260E, T260H, T260Y, V262E, V262F, V263A, V263I, V263M, V263T, V264A, V264D, V264E, V264E/N297D/I332E, V264F, V264G, V264H, V264I, V264I/A330L/I332E, V264I/A330Y/I332E, V264I/I332E, V264K, V264L, V264M, V264N, V264P, V264Q, V264R, V264S, V264T, V264W, V264Y, D265F, D265F/N297E/I332E, D265G, D265H, D265I, D265K, D265L, D265M, D265N, D265P, D265Q, D265R, D265S, D265T, D265V, D265W, D265Y, D265Y/N297D/I332E, D265Y/N297D/T299L/I332E, V266A, V266I, V266M, V266T, S267D, S267E, S267E, S267E/A327D, S267E/P331D, S267E/S324I, S267E/ V282G, S267F, S267H, S267I, S267K, S267L, S267L/ A327S, S267M, S267N, S267P, S267Q, S267Q/A327S, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278F, Y278G, Y278H, Y278I, Y278K, Y278L, Y278M, Y278N, Y278P, Y278Q, Y278R, Y278S, Y278T, Y278V, Y278W, Y278W, Y278W/E283R/V302I, Y278W/V302I, D280G, D280K, D280L, D280P, D280W, G281D, G281D/V282G, G281E, G281K, G281N, G281P, G281Q, G281Y, V282E, V282G, V282G/P331D, V282K, V282P, V282Y, E283G, E283H, E283K, E283L, E283P, E283R, E283R/V302I/Y278W/E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296I, Y296K, Y296L, Y296M, Y296N, Y296Q, Y296R, Y296S, Y296T, Y296V, N297D, N297D/I332E, N297D/I332E/A330Y, N297D/I332E/S239D/A330L, N297D/I332E/S239D/ D265V, N297D/I332E/S298A/A330Y, N297D/I332E/ T299E, N297D/I332E/T299F, N297D/I332E/T299H, N297D/I332E/T299I, N297D/I332E/T299L, N297D/I332E/ T299V, N297D/I332E/Y296D, N297D/I332E/Y296E, N297D/I332E/Y296H, N297D/I332E/Y296N, N297D/ I332E/Y296Q, N297D/I332E/Y296T, N297E/I332E, N297F, N297G, N297H, N297I, N297K, N297L, N297M, N297P, N297Q, N297R, N297S, N297S/I332E, N297T, N297V, N297W, N297Y, S298A/I332E, S298A/K326E, S298A/K326E/K334L, S298A/K334L, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324I/A327D, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328D/I332E, L328E, L328E/I332E, L328F, L328G, L328H, L328H/I332E, L328I, L328I/I332E, L328I/ I332E, L328K, L328M, L328M/I332E, L328N, L328N/ I332E, L328P, L328Q, L328Q/I332E, L328Q/I332E, L328R, L328S, L328T, L328T/I332E, L328V, L328V/I332E, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330L/I332E, A330M, A330N, A330P, A330R, A330S, A330T, A330V, A330W, A330Y, A330Y/I332E, P331D, P331F, P331H, P331I, P331L, P331M, P331Q, P331R, P331T, P331V, P331W, P331Y, I332A, I332D, I332E, I332E/G281D, I332E/H268D, I332E/H268E, I332E/S239D/S298A, I332E/S239N/S298A, I332E/V264I/S298A, I332E/V284E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat.

It is a further object of the present invention to provide an Fc variant that binds with greater affinity to one or more FcγRs. In one embodiment, said Fc variants have affinity for an FcγR that is more than 1-fold greater than that of the parent Fc polypeptide. In an alternate embodiment, said Fc variants have affinity for an FcγR that is more than 5-fold greater than that of the parent Fc polypeptide. In a preferred embodiment, said Fc variants have affinity for an FcγR that is between about 5-fold and 300-fold greater than that of the parent Fc polypeptide.

It is a further object of the present invention to provide Fc variant that have a FcγRIIIa-fold:FcγRIIb-fold ratio greater than 1:1. In one embodiment, said Fc variants have a FcγRIIIa-fold:FcγRIIb-fold ratio greater than 11:1. In a preferred embodiment, said Fc variants have a FcγRIIIa-fold:FcγRIIb-fold ratio between 11:1 and 86:1.

It is a further object of the present invention to provide Fc variants that mediate effector function more effectively in the presence of effector cells. In one embodiment, said Fc variants mediate ADCC that is greater than that mediated by the parent Fc polypeptide.

In a preferred embodiment, said Fc variants mediate ADCC that is more than 5-fold greater than that mediated by the parent Fc polypeptide. In a mostly preferred embodiment, said Fc variants mediate ADCC that is between 5-fold and 1000-fold greater than that mediated by the parent Fc polypeptide.

It is a further object of the present invention to provide Fc variants that bind with weaker affinity to one or more FcγRs. It is a further object of the present invention to provide Fc variants that mediate ADCC in the presence of effector cells less effectively.

It is a further object of the present invention to provide Fc variants that have improved function and/or solution properties as compared to the aglycosylated form of the parent Fc polypeptide. Improved functionality herein includes but is not limited to binding affinity to an Fc ligand. Improved solution properties herein includes but is not limited to stability and solubility. In an one embodiment, said Fc variants bind to an FcγR with an affinity that is within about 0.5-fold of the glycosylated form of the parent Fc polypeptide. In an alternate embodiment, said aglycosylated Fc variants bind to an FcγR with an affinity that is comparable to the glycosylated parent Fc polypeptide. In an alternate embodiment, said Fc variants bind to an FcγR with an affinity that is greater than the glycosylated form of the parent Fc polypeptide.

The present invention also provides methods for engineering optimized Fc variants. It is a further object of the present invention to provide experimental production and screening methods for obtaining optimized Fc variants.

The present invention provides isolated nucleic acids encoding the Fc variants described herein. The present invention provides vectors comprising said nucleic acids, optionally, operably linked to control sequences. The present invention provides host cells containing the vectors, and methods for producing and optionally recovering the Fc variants.

The present invention provides novel Fc polypeptides, including antibodies, Fc fusions, isolated Fc, and Fc fragments, that comprise the Fc variants disclosed herein. Said novel Fc polypeptides may find use in a therapeutic product.

The present invention provides compositions comprising Fc polypeptides that comprise the Fc variants described herein, and a physiologically or pharmaceutically acceptable carrier or diluent.

The present invention contemplates therapeutic and diagnostic uses for Fc polypeptides that comprise the Fc variants disclosed herein.

BRIEF DESCRIPTION OF THE DRAWINGS

FIGS. 3a-3b. Alignment of the amino acid sequences of the human IgG immunoglobulins IgG1, IgG2, IgG3, and IgG4 (SEQ ID NOs. 1-4]. FIG. 3a provides the sequences of the CH1 (Cγ1) and hinge domains, and FIG. 3b provides the sequences of the CH2 (Cγ2) and CH3 (Cγ3) domains. Positions are numbered according to the EU index of the IgG1 sequence, and differences between IgG1 and the other immunoglobulins IgG2, IgG3, and IgG4 are shown in grey. Polymorphisms exist at a number of positions (Kim et al., 2001, J. Mol. Evol. 54:1-9), and thus slight differences between the presented sequences and sequences in the prior art may exist. The possible beginnings of the Fc region are labeled, defined herein as either EU position 226 or 230.

FIGS. 21a and 21b show the correlation between SPR Kd's and AlphaScreen IC50's from binding of select alemtuzumab Fc variants to V158 FcγRIIIa (FIG. 21a) and F158 FcγRIIIa (FIG. 21b). FIGS. 21c and 21d show the correlation between SPR and AlphaScreen fold-improvements over WT for binding of select alemtuzumab Fc variants to V158 FcγRIIIa (FIG. 21c) and F158 FcγRIIIa (FIG. 21d). Binding data are presented in Table 3. The lines through the data represent the linear fits of the data, and the $r^2$ values indicate the significance of these fits.

FIG. 23a is a bar graph showing the raw fluorescence data for the indicated alemtuzumab antibodies at 10 ng/ml. The PBMC bar indicates basal levels of cytotoxicity in the absence of antibody. FIG. 23b shows the dose-dependence of ADCC on antibody concentration for the indicated alemtuzumab antibodies, normalized to the minimum and maximum fluorescence signal for each particular curve, provided by the baselines at low and high antibody concentrations respectively. The curves represent the fits of the data to a sigmoidal dose-response model using nonlinear regression.

FIG. 24a is a bar graph showing the raw fluorescence data for the indicated trastuzumab antibodies at 1 ng/ml. The PBMC bar indicates basal levels of cytotoxicity in the absence of antibody. FIGS. 24b and 24c show the dose-dependence of ADCC on antibody concentration for the indicated trastuzumab antibodies, normalized to the minimum and maximum fluorescence signal for each particular curve, provided by the baselines at low and high antibody concentrations respectively. The curves represent the fits of the data to a sigmoidal dose-response model using nonlinear regression.

FIG. 25a is a bar graph showing the raw fluorescence data for the indicated rituximab antibodies at 1 ng/ml. The PBMC bar indicates basal levels of cytotoxicity in the absence of antibody. FIGS. 25b and 25c show the dose-dependence of ADCC on antibody concentration for the indicated rituximab antibodies, normalized to the minimum and maximum fluorescence signal for each particular curve, provided by the baselines at low and high antibody concentrations respectively. The curves represent the fits of the data to a sigmoidal dose-response model using nonlinear regression.

FIG. 29a provides a western blot showing the Her2 expression level for each cell line; equivalent amounts of cell lysate were loaded on an SDS-PAGE gel, and Her2 was detected using trastuzumab. Human PBMCs allotyped as homozygous F158/F158 FcγRIIIa were used at 25-fold excess to target cells. The bar graph in FIG. 29b provides ADCC data for WT and Fc variant against the indicated cell lines, normalized to the minimum and maximum fluorescence signal provided by minimal lysis (PBMCs alone) and maximal lysis (Triton X1000).

FIGS. 32a-32c. Capacity of select Fc variants to mediate binding and activation of complement. FIG. 32a shows an AlphaScreen assay measuring binding of select alemtuzumab Fc variants to C1q. The binding data were normalized to the upper and lower baselines for each particular antibody, and the curves represent the fits of the data to a one site competition model. FIGS. 32b and 31c show a cell-based assay measuring capacity of select rituximab Fc variants to mediate CDC. CDC assays were performed using Alamar Blue to monitor lysis of Fc variant and WT rituximab-opsonized WIL2-S lymphoma cells by human serum complement (Quidel, San Diego, Calif.). The dose-dependence on antibody concentration of complement-mediated lysis is shown for the indicated rituximab antibodies, normalized to the minimum and maximum fluorescence signal for each particular curve, provided by the baselines at low and high antibody concentrations respectively. The curves represent the fits of the data to a sigmoidal dose-response model using nonlinear regression.

FIG. 33a shows the percent B cells remaining in *Macaca Fascicularis* monkeys during treatment with anti-CD20 WT and S239D/I332E rituximab antibodies, measured using markers CD20+ and CD40+. FIG. 33b shows the percent natural killer (NK) cells remaining in the monkeys during treatment, measured using markers CD3−/CD16+ and CD3−/CD8+. FIG. 33c shows the dose response of CD20+B cell levels to treatment with S239D/I332E rituximab. Data are presented as the average of 3 monkeys/sample.

FIG. 37a presents an AlphaScreen assay showing V158 FcγRIIIa binding by WT and Fc variant (V209, S239/I332E/A330L) trastuzumab expressed in 293T, CHO, and Lec-13 CHO cells. The data were normalized to the upper and lower baselines for each antibody, and the curves represent the fits of the data to a one site competition model. PBS was used as a negative control. FIG. 37b presents a cell-based ADCC assay showing the ability of 239T, CHO, and Lec-13 CHO expressed WT and V209 trastuzumab to mediate ADCC. ADCC was measured using the DELFIA® EuTDA-based cytotoxicity assay as described previously, with Sk-Br-3 breast carcinoma target cells. The data show the dose-dependence of ADCC on antibody concentration for the indicated trastuzumab antibodies, normalized to the minimum and maximum fluorescence signal for each particular curve, provided by the baselines at low and high antibody concentrations respectively. The curves represent the fits of the data to a sigmoidal dose-response model using nonlinear regression.

FIGS. 40a-40c. Sequences showing improved anti-CD20 antibodies. The light and heavy chain sequences of rituximab are presented in FIG. 40a (SEQ ID NO: 5) and FIG. 40b (SEQ ID NO: 6) respectively, and are taken from translated Sequence 3 of U.S. Pat. No. 5,736,137. Relevant positions in FIG. 40b are bolded, including S239, V240, V264I, H268, E272, K274, N297, S298, K326, A330, and I332. FIG. 40c (SEQ ID NO: 7) shows the improved anti-CD20 antibody heavy chain sequences, with variable positions designated in bold as X1, X2, X3, X4, X5, X6, X7, X8, X9, Z1, and Z2. The table below the sequence provides possible substitutions for these positions. The improved anti-CD20 antibody sequences comprise at least one non-WT amino acid selected from the group of possible substitutions for X1, X2, X3, X4, X5, X6, X7, X8, and X9. These improved anti-CD20 antibody sequences may also comprise a substitution Z1 and/or Z2. These positions are numbered according to the EU index as in Kabat, and thus do not correspond to the sequential order in the sequence.

FIG. 42 depicts SEQ ID NO:8; the particular Xaa residues are as shown in Table 10.

DETAILED DESCRIPTION OF THE INVENTION

Figure 1:
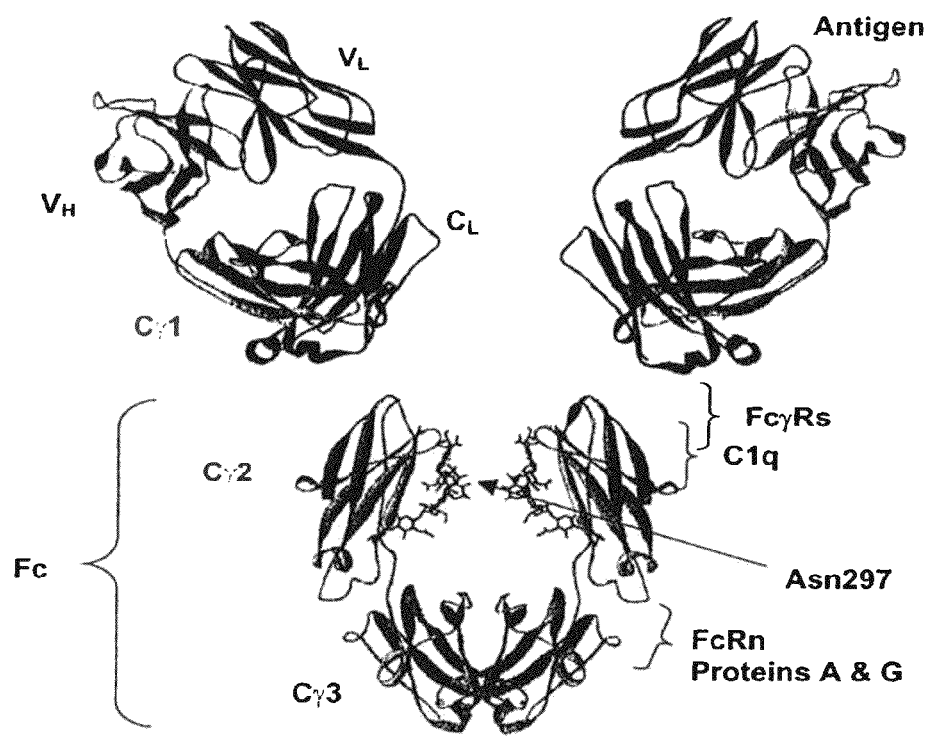
FIG. 1. Antibody structure and function. Shown is a model of a full length human IgG1 antibody, modeled using a humanized Fab structure from pdb accession code 1CE1 (James et al., 1999, J Mol Biol 289:293-301) and a human IgG1 Fc structure from pdb accession code 1DN2 (DeLano et al., 2000, Science 287:1279-1283). The flexible hinge that links the Fab and Fc regions is not shown. IgG1 is a homodimer of heterodimers, made up of two light chains and two heavy chains. The Ig domains that comprise the antibody are labeled, and include $V_L$ and $C_L$ for the light chain, and $V_H$, Cgamma1 (Cγ1), Cgamma2 (Cγ2), and Cgamma3 (Cγ3) for the heavy chain. The Fc region is labeled. Binding sites for relevant proteins are labeled, including the antigen binding site in the variable region, and the binding sites for FcγRs, FcRn, C1q, and proteins A and G in the Fc region.
Figure 2:
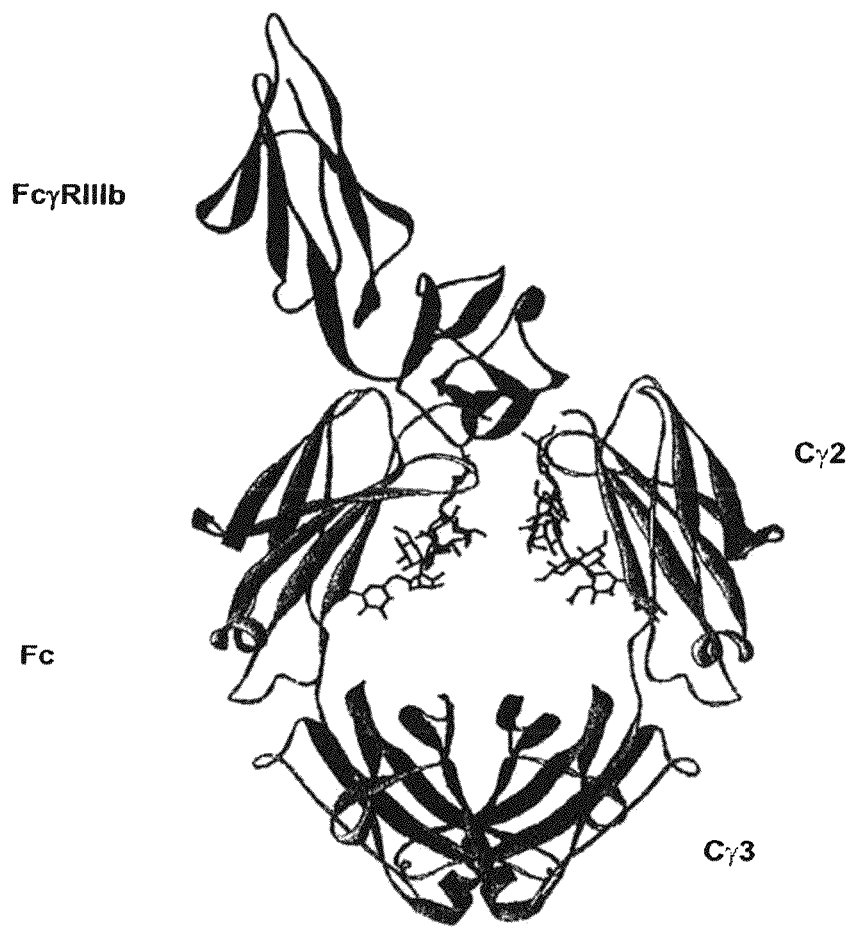
FIG. 2. The Fc/FcγRIIIb complex structure 1IIS. Fc is shown as a gray ribbon diagram, and FcγRIIIb is shown as a black ribbon. The N297 carbohydrate is shown as black sticks.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. The preferred amino acid modification herein is a substitution. By "amino acid substitution" or "substitution" herein is meant the replacement of an amino acid at a particular position in a parent polypeptide sequence with another amino acid. For example, the substitution I332E refers to a variant polypeptide, in this case an Fc variant, in which the isoleucine at position 332 is replaced with a glutamic acid. In some embodiments, the WT identity need not be defined. For example, the substitution 332E refers to a variant polypeptide in which position 332 is mutated to glutamic acid.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. The term "antibody" includes antibody fragments, as are known in the art, such as Fab, Fab', F(ab')₂, Fv, scFv, or other antigen-binding subsequences of antibodies, either produced by the modification of whole antibodies or those synthesized de novo using recombinant DNA technologies. Particularly preferred are full length antibodies that comprise Fc variants as described herein. The term "antibody" comprises monoclonal and polyclonal antibodies. Antibodies can be antagonists, agonists, neutralizing, inhibitory, or stimulatory. The antibodies of the present invention may be nonhuman, chimeric, humanized, or fully human, as described below in more detail.

Specifically included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, that is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or residues that encode the glycosylation pattern or by expression in an organism that does not attach carbohydrates to proteins, for example bacteria.

Specifically included within the definition of "antibody" are full-length antibodies that contain an Fc variant portion. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, C$\gamma$1 ($C_H1$), C$\gamma$2 ($C_H2$), and C$\gamma$3 ($C_H3$). In some mammals, for example in camels and llamas, IgG antibodies may consist of only two heavy chains, each heavy chain comprising a variable domain attached to the Fc region. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

By "amino acid" and "amino acid identity" as used herein is meant one of the 20 naturally occurring amino acids or any non-natural analogues that may be present at a specific, defined position. By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids (see Simon et al., 1992, *Proc Natl Acad Sci USA* 89(20):9367, incorporated by reference) particularly when LC peptides are to be administered to a patient. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "effector function" as used herein is meant a biochemical event that results from the interaction of an antibody Fc region with an Fc receptor or ligand. Effector functions include but are not limited to ADCC, ADCP, and CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and $\gamma\gamma$ T cells, and may be from any organism including but not limited to humans, mice, rats, rabbits, and monkeys. By "library" herein is meant a set of Fc variants in any form, including but not limited to a list of nucleic acid or amino acid sequences, a list of nucleic acid or amino acid substitutions at variable positions, a physical library comprising nucleic acids that encode the library sequences, or a physical library comprising the Fc variant proteins, either in purified or unpurified form.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cgamma2 and Cgamma3 (C$\gamma$2 and C$\gamma$3) and the hinge between Cgamma1 (C$\gamma$1) and Cgamma2 (C$\gamma$2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "Fc fusion" as used herein is meant a protein wherein one or more polypeptides or small molecules is operably linked to an Fc region or a derivative thereof. Fc fusion is herein meant to be synonymous with the terms "immunoadhesin", "Ig fusion", "Ig chimera", and "receptor globulin" (sometimes with dashes) as used in the prior art (Chamow et al., 1996, *Trends Biotechnol* 14:52-60; Ashkenazi et al., 1997, *Curr Opin Immunol* 9:195-200. incorporated by reference). An Fc fusion combines the Fc region of an immunoglobulin with a fusion partner, which in general can be any protein or small molecule. The role of the non-Fc part of an Fc fusion, i.e. the fusion partner, may be to mediate target binding, and thus it is functionally analogous to the variable regions of an antibody.

By "Fc gamma receptor" or "Fc$\gamma$R" as used herein is meant any member of the family of proteins that bind the IgG antibody Fc region and are substantially encoded by the Fc$\gamma$R genes. In humans this family includes but is not limited to Fc$\gamma$RI (CD64), including isoforms Fc$\gamma$RIa, Fc$\gamma$RIb, and Fc$\gamma$RIc; Fc$\gamma$RII (CD32), including isoforms Fc$\gamma$RIIa (including allotypes H131 and R131), Fc$\gamma$RIIb (including Fc$\gamma$RIIb-1 and Fc$\gamma$RIIb-2), and Fc$\gamma$RIIc; and Fc$\gamma$RIII (CD16), including isoforms Fc$\gamma$RIIIa (including allotypes V158 and F158) and Fc$\gamma$RIIIb (including allotypes Fc$\gamma$RIIIb-NA1 and Fc$\gamma$RIIIb-NA2), as well as any undiscovered human Fc$\gamma$Rs or Fc$\gamma$R isoforms or allotypes. An Fc$\gamma$R may be from any organism, including but not limited to humans, mice, rats, rabbits, and monkeys. Mouse Fc$\gamma$Rs include but are not limited to Fc$\gamma$RI (CD64), Fc$\gamma$RII (CD32), Fc$\gamma$RIII (CD16), and Fc$\gamma$RIII-2 (CD16-2), as well as any undiscovered mouse Fc$\gamma$Rs or Fc$\gamma$R isoforms or allotypes.

By "Fc ligand" or "effector ligand" as used herein is meant a molecule, preferably a polypeptide, from any organism that binds to the Fc region of an antibody to form an Fc/Fc ligand complex. Binding of an Fc ligand to Fc preferably elicits or more effector functions. Fc ligands include but are not limited to Fc receptors, FcγRs, FcαRs, FcεRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, *Immunological Reviews* 190:123-136, incorporated by reference). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "parent polypeptide" or "precursor polypeptide" (including Fc parent or precursors) as used herein is meant a polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant a Fc polypeptide that is modified to generate a variant, and by "parent antibody" as used herein is meant an antibody that is modified to generate a variant antibody.

As outlined above, certain positions of the Fc molecule can be altered. By "position" as used herein is meant a location in the sequence of a protein. Positions may be numbered sequentially, or according to an established format, for example the EU index as in Kabat. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or $V_H$ genes that make up the kappa, lambda, and heavy chain immunoglobulin genetic loci respectively.

By "variant polypeptide" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "Fc variant" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it.

The Fc variants of the present invention are defined according to the amino acid modifications that compose them. Thus, for example, I332E is an Fc variant with the substitution I332E relative to the parent Fc polypeptide. Likewise, S239D/A330L/I332E (also referred to as 239D/330L/332E) defines an Fc variant with the substitutions S239D, A330L, and I332E (239D, 330L, and 332E) relative to the parent Fc polypeptide. It is noted that the order in which substitutions are provided is arbitrary, that is to say that, for example, S239D/A330L/I332E is the same Fc variant as S239D/I332E/A330L, and so on. For all positions discussed in the present invention, numbering is according to the EU index or EU numbering scheme (Kabat et al., 1991, *Sequences of Proteins of Immunological Interest*, 5th Ed., United States Public Health Service, National Institutes of Health, Bethesda, incorporated by reference). The EU index or EU index as in Kabat refers to the numbering of the EU antibody (Edelman et al., 1969, Proc Natl Acad Sci USA 63:78-85, incorporated by reference).

The present invention is directed to optimized Fc variants useful in a variety of contexts. As outlined above, current antibody therapies suffer from a variety of problems. The present invention provides a promising means for enhancing the anti-tumor potency of antibodies is via enhancement of their ability to mediate cytotoxic effector functions such as ADCC, ADCP, and CDC. The present invention shows that antibodies with an Fc region optimized for binding to certain FcγRs may better mediate effector functions and thereby destroy cancer cells more effectively in patients. The balance between activating and inhibiting receptors is an important consideration, and optimal effector function may result from an Fc with enhanced affinity for activation receptors, for example FcγRI, FcγRIIa/c, and FcγRIIIa, yet reduced affinity for the inhibitory receptor FcγRIIb. Furthermore, because FcγRs can mediate antigen uptake and processing by antigen presenting cells, enhanced Fc/FcγR affinity may also improve the capacity of antibody therapeutics to elicit an adaptive immune response. For example, several mutations disclosed in this application, including S298A, E333A, and K334A, show enhanced binding to the activating receptor FcγRIIIa and reduced binding to the inhibitory receptor FcγRIIb. These mutations maybe combined to obtain double and triple mutation variants that show additive improvements in binding. A particular variant is a S298A/E333A/K334A triple mutant with approximately a 1.7-fold increase in binding to F158 FcγRIIIa, a 5-fold decrease in binding to FcγRIIb, and a 2.1-fold enhancement in ADCC.

Although there is a need for greater effector function, for some antibody therapeutics reduced or eliminated effector function may be desired. This is often the case for therapeutic antibodies whose mechanism of action involves blocking or antagonism but not killing of the cells bearing target antigen. In these cases depletion of target cells is undesirable and can be considered a side effect. For example, the ability of anti-CD4 antibodies to block CD4 receptors on T cells makes them effective anti-inflammatories, yet their ability to recruit FcγR receptors also directs immune attack against the target cells, resulting in T cell depletion (Reddy et al., 2000, *J Immunol* 164:1925-1933, incorporated by reference). Effector function can also be a problem for radiolabeled antibodies, referred to as radioconjugates, and antibodies conjugated to toxins, referred to as immunotoxins. These drugs can be used to destroy cancer cells, but the recruitment of immune cells via Fc interaction with FcγRs brings healthy immune cells in proximity to the deadly payload (radiation or toxin), resulting in depletion of normal lymphoid tissue along with targeted cancer cells (Hutchins et al., 1995, *Proc Natl Acad Sci USA* 92:11980-11984; White et al., 2001, *Annu Rev Med* 52:125-145, incorporated by reference). This problem can potentially be circumvented by using IgG isotypes that poorly recruit complement or effector cells, for example IgG2 and IgG4. An alternate solution is to develop Fc variants that reduce or ablate binding (Alegre et al., 1994, *Transplantation* 57:1537-1543; Hutchins et al., 1995, *Proc Natl Acad Sci USA* 92:11980-11984; Armour et al., 1999, *Eur J Immunol* 29:2613-2624; Reddy et al., 2000, *J Immunol* 164:1925-1933; Xu et al., 2000, *Cell Immunol* 200:16-26; Shields et al., 2001, *J Biol Chem* 276:6591-6604) (U.S. Pat. No. 6,194,551; U.S. Pat. No. 5,885,573; PCT WO 99/58572), all incorporated by reference. A critical consideration for the reduction or elimination of effector function is that other important antibody properties not be perturbed. Fc variants should be engineered that not only ablate binding to FcγRs and/or C1q, but also maintain antibody stability, solubility, and structural integrity, as well as ability to interact with other important Fc ligands such as FcRn and proteins A and G.

In addition, the invention utilizes engineered glycoforms that can enhance Fc/FcγR affinity and effector function. An aglycosylated Fc with favorable solution properties and the capacity to mediate effector functions would be significantly enabling for the alternate production methods described above. By overcoming the structural and functional shortcomings of aglycosylated Fc, antibodies can be produced in bacteria and transgenic plants and animals with reduced risk of immunogenicity, and with effector function for clinical applications in which cytotoxicity is desired such as cancer. The present invention describes the utilization of protein engineering methods to develop stable, soluble Fc variants with effector function. Currently, such Fc variants do not exist in the art.

Fc Variants of the Present Invention

The Fc variants of the present invention may find use in a variety of Fc polypeptides. An Fc polypeptide that comprises an Fc variant of the present invention is herein referred to as an "Fc polypeptide of the present invention". Fc polypeptides of the present invention include polypeptides that comprise the Fc variants of the present invention in the context of a larger polypeptide, such as an antibody or Fc fusion. That is, Fc polypeptides of the present invention include antibodies and Fc fusions that comprise Fc variants of the present invention. By "antibody of the present invention" as used herein is meant an antibody that comprises an Fc variant of the present invention. By "Fc fusion of the present invention" as used herein refers to an Fc fusion that comprises an Fc variant of the present invention. Fc polypeptides of the present invention also include polypeptides that comprise little or no additional polypeptide sequence other than the Fc region, referred to as an isolated Fc. By "isolated Fc of the present invention" used herein is meant an Fc polypeptide that comprises an Fc variant of the present invention, and comprises little or no additional polypeptide sequence other than the Fc region. Fc polypeptides of the present invention also include fragments of the Fc region. By "Fc fragment of the present invention" as used herein is meant an Fc fragment that comprises an Fc variant of the present invention. As described below, any of the aforementioned Fc polypeptides of the present invention may be fused to one or more fusion partners or conjugate partners to provide desired functional properties.

Fc variants may be constructed in a parent Fc polypeptide irrespective of its context. That is to say that, the sole criteria for a parent Fc polypeptide is that it comprise an Fc region. The parent Fc polypeptides described herein may be derived from a wide range of sources, and may be substantially encoded by one or more Fc genes from any organism, including but not limited to humans, rodents including but not limited to mice and rats, lagomorpha such as rabbits and hares, camelidae such as camels, llamas, and dromedaries, and non-human primates, including but not limited to Prosimians, Platyrrhini (New World monkeys), Cercopithecoidea (Old World monkeys), and Hominoidea include the Gibbons, Lesser and Great Apes, with humans most preferred. The parent Fc polypeptides of the present invention may be substantially encoded by immunoglobulin genes belonging to any of the antibody classes, including but not limited to sequences belonging to the IgG (including human subclasses IgG1, IgG2, IgG3, or IgG4), IgA (including human subclasses IgA1 and IgA2), IgD, IgE, IgG, or IgM classes of antibodies. Most preferably the parent Fc polypeptides of the present invention comprise sequences belonging to the human IgG class of antibodies. For example, the parent Fc polypeptide may be a parent antibody, for example a human IgG1 antibody, a human IgA antibody, or a mouse IgG2a or IgG2b antibody. Said parent antibody may be nonhuman, chimeric, humanized, or fully human as described in detail below. The parent Fc polypeptide may be modified or engineered in some way, for example a parent antibody may be affinity matured, or may possess engineered glycoforms, all as described more fully below. Alternatively, the parent Fc polypeptide may be an Fc fusion, for example an Fc fusion wherein the fusion partner targets a cell surface receptor. Alternatively, the parent Fc polypeptide may be an isolated Fc region, comprising little or no other polypeptide sequence outside the Fc region. The parent Fc polypeptide may be a naturally existing Fc region, or may be an existing engineered variant of an Fc polypeptide. What is important is that the parent Fc polypeptide comprise an Fc region, which can then be mutated to generate an Fc variant.

The Fc variants of the present invention may be an antibody, referred to herein as an "antibody of the present invention". Antibodies of the present invention may comprise immunoglobulin sequences that are substantially encoded by immunoglobulin genes belonging to any of the antibody classes, including but not limited to IgG (including human subclasses IgG1, IgG2, IgG3, or IgG4), IgA (including human subclasses IgA1 and IgA2), IgD, IgE, IgG, and IgM classes of antibodies. Most preferably the antibodies of the present invention comprise sequences belonging to the human IgG class of antibodies. Antibodies of the present invention may be nonhuman, chimeric, humanized, or fully human. As will be appreciated by one skilled in the art, these different types of antibodies reflect the degree of "humanness" or potential level of immunogenicity in a human. For a description of these concepts, see Clark et al., 2000 and references cited therein (Clark, 2000, *Immunol Today* 21:397-402, incorporated by reference). Chimeric antibodies comprise the variable region of a nonhuman antibody, for example $V_H$ and $V_L$ domains of mouse or rat origin, operably linked to the constant region of a human antibody (see for example U.S. Pat. No. 4,816,567, incorporated by reference). Said nonhuman variable region may be derived from any organism as described above, preferably mammals and most preferably rodents or primates. In one embodiment, the antibody of the present invention comprises monkey variable domains, for example as described in Newman et al., 1992, Biotechnology 10:1455-1460, U.S. Pat. No. 5,658,570, and U.S. Pat. No. 5,750,105, incorporated by reference. In a preferred embodiment, the variable region is derived from a nonhuman source, but its immunogenicity has been reduced using protein engineering. In a preferred embodiment, the antibodies of the present invention are humanized (Tsurushita & Vasquez, 2004, Humanization of Monoclonal Antibodies, Molecular Biology of B Cells, 533-545, Elsevier Science (USA), incorporated by reference). By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) $V_L$ and $V_H$ frameworks (Winter U.S. Pat. No. 5,225,539, incorporated by reference). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, incorporated by reference). A large number of other methods for humanization are known in the art (Tsurushita & Vasquez, 2004, Humanization of Monoclonal Antibodies, Molecular Biology of B Cells, 533-545, Elsevier Science (USA), incorporated by reference), and any of such methods may find use in the present invention for modifying Fc variants for reduced immunogenicity. The humanized antibody optimally also will comprise at least a portion of an immunoglobulin constant region, typically that of a human immunoglobulin, and thus will typically comprise a human Fc region. In a most preferred embodiment, the immunogenicity of an Fc variant of the present invention is reduced using a method described in U.S. Ser. No. 11/004,590, filed Dec. 3, 2004, entitled "Methods of Generating Variant Proteins with Increased Host String Content and Compositions Thereof," incorporated by reference. In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, *Curr Opin Biotechnol* 8:455-458, incorporated by reference) or human antibody libraries coupled with selection methods (Griffiths et al., 1998, *Curr Opin Biotechnol* 9:102-108, incorporated by reference).

The Fc variants of the present invention may be an Fc fusion, referred to herein as an "Fc fusion of the present invention". Fc fusions of the present invention comprise an Fc polypeptide operably linked to one or more fusion partners. The role of the fusion partner typically, but not always, is to mediate binding of the Fc fusion to a target antigen. (Chamow et al., 1996, *Trends Biotechnol* 14:52-60; Ashkenazi et al., 1997, *Curr Opin Immunol* 9:195-200, incorporated by reference). For example, the approved drug alefacept (marketed as AMEVIVE®) is an immunosuppressive Fc fusion that consists of the extracellular CD2-binding portion of the human leukocyte function antigen-3 (LFA-3) linked to the Fc region of human IgG1. The approved drug etanercept (marketed as ENBREL®) is an Fc fusion comprising the extracellular ligand-binding portion of human tumor necrosis factor receptor (TNFR) linked to human IgG1 Fc. Virtually any protein, polypeptide, peptide, or small molecule may be linked to Fc to generate an Fc fusion. Fusion partners include but are not limited to receptors and extracellular receptor domains, adhesion molecules, ligands, enzymes, cytokines, chemokines, or some other protein or protein domain. The fusion partner may also play a role as a chemoattractant. Undiscovered ligands or receptors may serve as fusion partners for the Fc variants of the present invention. Small molecules may serve as fusion partners, and may include any therapeutic agent that directs the Fc fusion to a therapeutic target. Such targets may be any molecule, preferably an extracellular receptor, that is implicated in disease. Two families of surface receptors that are targets of a number of approved small molecule drugs are G-Protein Coupled Receptors (GPCRs), and ion channels, including K+, Na+, Ca+ channels. Nearly 70% of all drugs currently marketed worldwide target GPCRs. Thus the Fc variants of the present invention may be fused to a small molecule that targets, for example, one or more GABA receptors, purinergic receptors, adrenergic receptors, histaminergic receptors, opiod receptors, chemokine receptors, glutamate receptors, nicotinic receptors, the 5HT (serotonin) receptor, and estrogen receptors. A fusion partner may be a small-molecule mimetic of a protein that targets a therapeutically useful target. Specific examples of particular drugs that may serve as Fc fusion partners can be found in L. S. Goodman et al., Eds., *Goodman and Gilman's The Pharmacological Basis of Therapeutics* (McGraw-Hill, New York, ed. 9, 1996, incorporated by reference). Fusion partners include not only small molecules and proteins that bind known targets for existing drugs, but orphan receptors that do not yet exist as drug targets. The completion of the genome and proteome projects are proving to be a driving force in drug discovery, and these projects have yielded a trove of orphan receptors. There is enormous potential to validate these new molecules as drug targets, and develop protein and small molecule therapeutics that target them. Such protein and small molecule therapeutics are contemplated as Fc fusion partners that employ the Fc variants of the present invention. Fc fusions of the invention may comprise immunoglobulin sequences that are substantially encoded by immunoglobulin genes belonging to any of the antibody classes, including but not limited to IgG (including human subclasses IgG1, IgG2, IgG3, or IgG4), IgA (including human subclasses IgA1 and IgA2), IgD, IgE, IgG, and IgM classes of antibodies. Most preferably the Fc fusions of the present invention comprise sequences belonging to the human IgG class of antibodies. A variety of linkers, defined and described below, may be used to covalently link Fc to a fusion partner to generate an Fc fusion.

The Fc variants of the present invention may find use in an isolated Fc, that is an Fc polypeptide that comprises little or no additional polypeptide sequence other than the Fc region and that comprises an Fc variant of the present invention.

Isolated Fc of the present invention are meant as molecules wherein the desired function of the molecule, for example the desired therapeutic function, resides solely in the Fc region. Thus the therapeutic target of an isolated Fc of the present invention is likely to involve one or more Fc ligands. An isolated Fc that comprises the Fc variant may require no additional covalent polypeptide sequence to achieve its desired outcome. In a preferred embodiment, said isolated Fc comprises from 90-100% of the Fc region, with little or no "extra" sequence. Thus, for example, an isolated Fc of the present invention may comprise residues C226 or P230 to the carboxyl-terminus of human IgG1, wherein the numbering is according to the EU index as in Kabat. In one embodiment, the isolated Fc of the present invention may contain no extra sequence outside the Fc region. However it is also contemplated that isolated Fc's may not also comprise additional polypeptide sequences. For example, an isolated Fc may, in addition to comprising an Fc variant Fc region, comprise additional polypeptide sequence tags that enable expression, purification, and the like.

The Fc variants of the present invention may find use in a fragment of the Fc region, that is an Fc polypeptide that comprises an Fc fragment that comprises an Fc variant of the present invention. Clearly a requirement of an Fc fragment of the present invention is that it contains the position(s) at which the amino acid modifications of the Fc variant are made. An Fc fragment of the present invention may comprise from 1-90% of the Fc region, with 10-90% being preferred, and 30-90% being most preferred. Thus for example, an Fc fragment of the present invention may comprise an Fc variant IgG1 Cγ2 domain, an Fc variant IgG1 Cγ2 domain and hinge region, an Fc variant IgG1 Cγ3 domain, and so forth. In one embodiment, an Fc fragment of the present invention additionally comprises a fusion partner, effectively making it an Fc fragment fusion. As with isolated Fcs, Fc fragments may or may not contain extra polypeptide sequence.

Fc variants of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a most preferred embodiment, the Fc variants of the present invention are substantially human. The Fc variants of the present invention may be substantially encoded by immunoglobulin genes belonging to any of the antibody classes. In a most preferred embodiment, the Fc variants of the present invention comprise sequences belonging to the IgG class of antibodies, including human subclasses IgG1, IgG2, IgG3, and IgG4. In an alternate embodiment, the Fc variants of the present invention comprise sequences belonging to the IgA (including human subclasses IgA1 and IgA2), IgD, IgE, IgG, or IgM classes of antibodies. The Fc variants of the present invention may comprise more than one protein chain. That is, the present invention may find use in an Fc variant that is a monomer or an oligomer, including a homo- or hetero-oligomer.

In the most preferred embodiment, the Fc polypeptides of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgGD, IgGM, and the like. It is contemplated that, although the Fc variants of the present invention are engineered in the context of one parent Fc variant, the variants may be engineered in or "transferred" to the context of another, second parent Fc variant. This is done by determining the "equivalent" or "corresponding" residues and substitutions between the first and second Fc variants, typically based on sequence or structural homology between the sequences of the two Fc variants. In order to establish homology, the amino acid sequence of a first Fc variant outlined herein is directly compared to the sequence of a second Fc variant. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first Fc variant are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second Fc variant that is at the level of tertiary structure for Fc variants whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent Fc variant in which the Fc variants are made, what is meant to be conveyed is that the Fc variants discovered by the present invention may be engineered into any second parent Fc variant that has significant sequence or structural homology with said Fc variant. Thus for example, if a variant antibody is generated wherein the parent antibody is human IgG1, by using the methods described above or other methods for determining equivalent residues, said variant antibody may be engineered in a human IgG2 parent antibody, a human IgA parent antibody, a mouse IgG2a or IgG2b parent antibody, and the like. Again, as described above, the context of the parent Fc variant does not affect the ability to transfer the Fc variants of the present invention to other parent Fc variants. For example, the variant antibodies that are engineered in a human IgG1 antibody that targets one epitope may be transferred into a human IgG2 antibody that targets a different epitope, into an Fc fusion that comprises a human IgG1 Fc region that targets yet a different epitope, and so forth.

The Fc variants of the present invention may find use in a wide range of products. In one embodiment the Fc variant of the invention is a therapeutic, a diagnostic, or a research reagent, preferably a therapeutic. Alternatively, the Fc variant of the present invention may be used for agricultural or industrial uses. An antibody of the present invention may find use in an antibody composition that is monoclonal or polyclonal. The Fc variants of the present invention may be agonists, antagonists, neutralizing, inhibitory, or stimulatory. In a preferred embodiment, the Fc variants of the present invention are used to kill target cells that bear the target antigen, for example cancer cells. In an alternate embodiment, the Fc variants of the present invention are used to block, antagonize, or agonize the target antigen. In an alternately preferred embodiment, the Fc variants of the present invention are used to block, antagonize, or agonize the target antigen and kill the target cells that bear the target antigen.

Targets

Virtually any antigen may be targeted by the Fc variants of the present invention, including but not limited to proteins, subunits, domains, motifs, and/or epitopes belonging to the following list of targets: 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, AxI, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, BcI, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NCAD, N-Cadherin, NCA 90, NCAM, NCAM, Neprilysin, Neurotrophin-3,-4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc variants of the present invention in order to generate an Fc fusion. Thus for example, an Fc fusion that targets EGFR could be constructed by operably linking an Fc variant to EGF, TGF-β, or any other ligand, discovered or undiscovered, that binds EGFR. Accordingly, an Fc variant of the present invention could be operably linked to EGFR in order to generate an Fc fusion that binds EGF, TGF-β, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc variants of the present invention to develop an Fc fusion.

Choosing the right target antigen for antibody therapy is a complex process and encompasses many variables. For anticancer treatment it is desirable to have a target whose expression is restricted to the cancerous cells. Some targets that have proven especially amenable to antibody therapy are those with signaling functions. Other therapeutic antibodies exert their effects by blocking signaling of the receptor by inhibiting the binding between a receptor and it's cognate ligand. Another mechanism of action of therapeutic antibodies is to cause receptor down regulation. Although many therapeutically effective antibodies work in part by signaling through their target antigen, this is not always the case. For example, some target classes such as cell surface glycoforms do not generate any biological signal. However, altered glycoforms are often associated with disease states such as cancer. Another significant target type are those that internalize either as a normal function or in response to antibody binding. In the case of targets that are soluble rather than cell surface bound the recruitment of effector functions would not result in any cell death.

Some targets that have proven especially amenable to antibody therapy are those with signalling functions. For example, antibody cross-linking of the Her2/neu antigen may generate an apoptotic signal that results in cancer cell death. In some cases such as the CD30 antigen, this clustering with free antibody may be insufficient to cause apoptosis in vitro. For in vitro assays sufficient clustering can be mediated by crosslinking the antibody or by immobilizing it at high density to a surface such as the well of a microtiter plate. However, in vivo this effect may be mediated by binding of the antibody to the Fc ligands, for example FcγRs expressed on a nearby cell. Antibody Fc variants that bind more tightly to Fc ligands may thus more effectively cluster the signaling target and lead to enhanced induction of apoptosis. Such a mechanism could be tested experimentally by adding antibody with and without enhanced Fc ligand binding to cells expressing the desired target that signals, and/or adding an Fc receptor and a corresponding antibody that will cluster the Fc receptor. Alternative means for clustering Fc receptor include immobilization on beads, and overexpression in a non-effector cell line. After allowing apoptosis to occur, measurement of the relative apoptosis of target expressing cells would enable a quantitative determination of the effect.

Antibodies that cause cell death through their interaction with targets may have an additional benefit. The signals released by such dying cells attract macrophages and other cells of the immune system. These cells can then takeup the dead or dying cells in an antibody mediated manner. This has been shown to result in cross-presentation of antigen and the potential for a host immune response against the target cells. Such auto-antibodies in response to antibody therapy have been reported for the antigen targets Her2 and CD20. For this reason it may be advantageous to have Fc variants with altered receptor specificities to specifically stimulate cross-presentation and an immune response rather than the undesired effect of tolerance induction.

Other therapeutic antibodies exert their effects by inhibiting interaction between a receptor and it's cognate ligand, ultimately blocking signaling of the receptor. Such antibodies are used to treat many disease states. In this case it may be advantageous to utilize antibodies that do not recruit any host immune functions. A secondary effect of such an antibody may be actually inducing signalling itself through receptor clustering. In this case the desired therapeutic effect of blocking signaling would be abrogated by antibody mediated signaling. As discussed above, this clustering may be enhanced by antibody interaction with cells containing an Fc receptor. In this case, use of an Fc variant that binds less tightly or not at all to the Fc receptor would be preferable. Such an antibody would not mediate signaling, and its mechanism of action would thereby be restricted to blockage of receptor/ligand interactions. Signaling receptors for which this would be most appropriate would likely be monomeric receptors which can only be dimerized but not substantially clustered by a primary antibody. Mulitimeric receptors may be significantly clustered by the primary antibody and may not require additional clustering by Fc receptor binding.

Another potential mechanism of action of therapeutic antibodies is receptor downregulation. Such may be the case, for example, with the insulin-like growth factor receptor. Cell growth depends on continued signaling through the receptor, whereas in its absence cells cease to grow. One effect of antibodies directed against this receptor is to downregulate its expression and thereby ablate signaling. Cell recovery from cytotoxic therapy requires stimulation of this receptor. Downregulation of this receptor prevents these cells from recovery and renders the cytotoxic therapy substantially more effective. For antibodies for which this is the primary mechanism of action, decreased Fc receptor binding may prevent the sequestration of antibody by nontarget binding to Fc receptors.

Although many therapeutically effective antibodies work in part by signaling through their target antigen, this is not always the case. For example, some target classes such as cell surface glycoforms do not generate any biological signal. However, altered glycoforms are often associated with disease states such as cancer. In other cases, interaction of antibodies with different epitopes of the same target antigen may confer different signaling effects. In such cases where this is little or no elicited signaling by binding of antibody or Fc fusion to target antigen, Fc polypeptides of the present invention may find utility in providing novel mechanisms of efficacy for otherwise non-efficacious molecules.

One approach that has been taken in generating therapeutic antibodies to such nonsignaling targets is to couple the antibody to a cytotoxic agent such as a radio-isotope, toxin, or an enzyme that will process a substrate to produce a cytotoxic agent in the vicinity of the tumor. As an alternative to a cytotoxic moiety, Fc variants of the present invention may provide increased recruitment of immune functions that are inherently less toxic to the host while still effective at destroying target cancer cells. Such Fc variants may, for example, be more efficient at recruiting NK cells or at activating phagocytosis or initiating CDC. Alternatively, if a cytotoxic agent is utilized, it may be advantageous to use an Fc variant that provides reduced or altered Fc ligand binding. This may reduce or ablate the cytotoxic effects of the agent on immune cells that express Fc receptors, thereby reducing toxicity to the patient. Furthermore, reduction of Fc ligand binding may help to minimize the generation of an immune response to the toxic agent or enzyme. As mentioned above, cell death may result in recruitment of host immune cells; antibody mediated cross-presentation in such a case may be increased with immune response rather than immune tolerance if in addition to a cytotoxic moiety the therapeutic antibody has increased Fc receptor binding affinity or altered receptor specificity.

Another significant target type are those targets that internalize, either as a normal part of their biological function or in response to antibody binding. For such targets, many efforts have been made to couple cytotoxic agents such as RNase, ricin and calicheamicin, which can only exert their effect after internalization. For such reagents, Fc ligand binding may reduce efficacy due to nonproductive sequestration of the therapeutic by Fc ligands. In this case it may be advantageous to utilize Fc variants that provide decreased Fc ligand affinity. Conversely, antibody pre-association with Fc ligands prior to their binding to target antigen presented on cells may serve to inhibit internalization of the target. In this case, increased Fc ligand affinity may serve to improve pre-association and thereby recruitment of effector cells and the host immune response.

In the case of targets that are soluble rather than cell surface bound, recruitment of effector functions would not result directly in cell death. However, there may be utility in stimulating the generation of host antibodies to the target. For some disease states, successful treatment may require administration of the therapeutic antibody for extremely long periods of time. Such therapy may be prohibitively costly or cumbersome. In these cases, stimulation of the host immune response and the generation of antibodies may result in improved efficacy of the therapeutic. This may be applicable as an adjuvant to vaccine therapy. Antibody Fc variants that mediate such an effect may have increased affinity for Fc ligands or altered Fc ligand specificity.

A number of antibodies and Fc fusions that are approved for use, in clinical trials, or in development may benefit from the Fc variants of the present invention. These antibodies and Fc fusions are herein referred to as "clinical products and candidates". Thus in a preferred embodiment, the Fc polypeptides of the present invention may find use in a range of clinical products and candidates. For example, a number of antibodies that target CD20 may benefit from the Fc polypeptides of the present invention. For example the Fc polypeptides of the present invention may find use in an antibody that is substantially similar to rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), Huma-LYM (Intracel), and PRO70769 (PCT/US2003/040426, entitled "Immunoglobulin Variants and Uses Thereof"). A number of antibodies that target members of the family of epidermal growth factor receptors, including EGFR (ErbB-1), Her2/neu (ErbB-2), Her3 (ErbB-3), Her4 (ErbB-4), may benefit from the Fc polypeptides of the present invention. For example the Fc polypeptides of the present invention may find use in an antibody that is substantially similar to trastuzumab (Herceptin®, Genentech) (see for example U.S. Pat. No. 5,677,171), a humanized anti-Her2/neu antibody approved to treat breast cancer; pertuzumab (rhuMab-2C4, Omnitarg™), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, *Arch Biochem Biophys.* 252(2):549-60; Rodeck et al., 1987, *J Cell Biochem.* 35(4):315-20; Kettleborough et al., 1991, *Protein Eng.* 4(7):773-83); ICR62 (Institute of Cancer Research) (PCT WO 95/20045; Modjtahedi et al., 1993, *J. Cell Biophys.* 1993, 22(1-3):129-46; Modjtahedi et al., 1993, *Br J Cancer.* 1993, 67(2):247-53; Modjtahedi et al, 1996, *Br J Cancer*, 73(2):228-35; Modjtahedi et al, 2003, *Int J Cancer*, 105(2):273-80); TheraCIM hR3 (YM Biosciences, Canada and Centro de Immunologia Molecular, Cuba (U.S. Pat. No. 5,891,996; U.S. Pat. No. 6,506,883; Mateo et al, 1997, *Immunotechnology*, 3(1):71-81); mAb-806 (Ludwig Institute for Cancer Research, Memorial Sloan-Kettering) (Jungbluth et al. 2003, *Proc Natl Acad Sci USA.* 100 (2):639-44); KSB-102 (KS Biomedix); MR1-1 (IVAX, National Cancer Institute) (PCT WO 0162931A2); and SC100 (Scancell) (PCT WO 01/88138). In another preferred embodiment, the Fc polypeptides of the present invention may find use in alemtuzumab (Campath®, Millenium), a humanized monoclonal antibody currently approved for treatment of B-cell chronic lymphocytic leukemia. The Fc polypeptides of the present invention may find use in a variety of antibodies or Fc fusions that are substantially similar to other clinical products and candidates, including but not limited to muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by MedImmune, infliximab (Remicade®), an anti-TNFalpha antibody developed by Centocor, adalimumab (Humira®), an anti-TNFalpha antibody developed by Abbott, Humicade™, an anti-TNFalpha antibody developed by Celltech, etanercept (Enbrel®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, $^{90}$Y-muHMFG1), an anti-MUC1 In development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β2 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B™ an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin™ (bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair™ (Omalizumab), an anti-IgE antibody being developed by Genentech, Raptiva™ (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide™ (labetuzumab), an anti-carcinoembryonic antigen (CEA) antibody being developed by Immunomedics, LymphoCide™ (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem™ (IDM-1), and anti-Her2 antibody being developed by Medarex and Immuno-Designed Molecules, HuMax™-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF™, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, and MLN01, an anti-Beta2 integrin antibody being developed by Xoma, all references incorporated by reference.

Application of the Fc polypeptides to the aforementioned antibody and Fc fusion clinical products and candidates is not meant to be constrained to their precise composition. The Fc polypeptides of the present invention may be incorporated into the aforementioned clinical candidates and products, or into antibodies and Fc fusions that are substantially similar to them. The Fc polypeptides of the present invention may be incorporated into versions of the aforementioned clinical candidates and products that are humanized, affinity matured, engineered, or modified in some other way. Furthermore, the entire polypeptide of the aforementioned clinical products and candidates need not be used to construct a new antibody or Fc fusion that incorporates the Fc polypeptides of the present invention; for example only the variable region of a clinical product or candidate antibody, a substantially similar variable region, or a humanized, affinity matured, engineered, or modified version of the variable region may be used. In another embodiment, the Fc polypeptides of the present invention may find use in an antibody or Fc fusion that binds to the same epitope, antigen, ligand, or receptor as one of the aforementioned clinical products and candidates.

In one embodiment, the Fc polypeptides of the present invention are used for the treatment of autoimmune, inflammatory, or transplant indications. Target antigens and clinical products and candidates that are relevant for such diseases include but are not limited to anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFα, TNFα, TNF-alpha) antibodies such as CDP571, CDP870, D2E7, Infliximab, MAK-195F, and anti-VLA-4 antibodies such as Antegren.

Fc variants of the present invention may be utilized in TNF inhibitor molecules to provide enhanced properties. It has been shown that the effector function associated with FcγRIIIa may negatively impact the effectiveness of certain TNF inhibitor molecules used in the treatment of rheumatoid arthritis or psoriatic arthritis patients that have a high-affinity polymorphism (158 F:V discussed herein elsewhere) and vice-versa (Z. Tutuncu et al., 2004, "FcR Polymorphisms and Treatment Outcomes in Patients with Inflammatory Arthritis Treated with TNF Blocking Agents", oral presentation on Oct. 18, 2004 at the 2004 ACR Meeting, San Antonio, Tex.; abstract published in Arthritis & Rheumatism, September 2004, incorporated by reference). In general for autoimmune conditions such as rheumatoid arthritis or psoriatic arthritis, combining a TNF inhibitor with an Fc variant that provides reduced binding to one or more FcγRs as compared to the parent enhances the effectiveness of therapy. Ideally, reduced or even ablated binding to one or more FcγRs, for example FcγRIIIa, with a TNF inhibitor molecule would produce the best results.

Useful TNF inhibitor molecules include any molecule that inhibits the action of TNF-alpha in a mammal. Suitable examples include the Fc fusion Enbrel® (etanercept) and the antibodies Humira® (adalimumab) and Remicade® (infliximab). Monoclonal antibodies (such as Remicade and Humira) engineered using the Fc variants of the present invention to reduce Fc binding, may translate to better efficacy. Effector function of Humira, Remicade, and Enbrel was not considered in the development of these drugs, let alone modulation of effector function. By using an Fc variant of the present invention that reduces binding to one or more FcγRs in the context of an antibody or Fc fusion that acts on autoimmune conditions, efficacy may be enhanced as compared to the currently commercialized products. Useful TNF inhibitor molecules preferably include Dominant Negative TNF molecules (as defined in U.S. Ser. No. 09/798,789, filed Mar. 2, 2000; 09/981,289, filed Oct. 15, 2001; 10/262,630, filed Sep. 30, 2002; and 10/963,994, filed Oct. 12, 2004, all incorporated by reference). The Dominant Negative TNF molecules (DN-TNF) have no intrinsic effector activity, and act to "save" transmembrane TNF (tmTNF) (i.e., if the killing of cells that contain tmTNF has a negative effect on disease outcome for rheumatoid or psoriatic arthritis). A DN-TNF molecule associated with an Fc variant that reduces or ablates FcγR binding to the receptor is preferred.

In one embodiment, the Fc polypeptides of the present invention function therapeutically, in whole or in part, through ADCC activity. Target antigens and clinical products and candidates that are relevant for such application may include but are not limited to: anti-CD20 antibodies such as Bexocar, Rituxan®, Zevalin®, and PRO70769, anti-CD33 antibodies such as Smart M195, anti-CD22 antibodies such as Lymphocide™, anti-CD30 antibodies such as AC-10 and SGN-30, anti-EGFR antibodies such as ABX-EGF, Cetuximab, IMC-C225, Merck Mab 425, anti-EpCAM antibodies such as Crucell's anti-EpCAM, anti-HER2 antibodies such as Herceptin and MDX-210, and anti-CEA antibodies such as cantumab and Pentacea.

In one embodiment, the Fc polypeptides of the present invention function therapeutically, in whole or in part, through CDC activity. Target antigens and clinical products and candidates that are relevant for such application may include but are not limited to: anti-CEA antibodies such as cantumab and Pentacea, anti-CD20 antibodies such as Bexocar, Rituxan®, Zevalin®, and PRO70769, anti-EpCAM antibodies such as Crucell's anti-EpCAM and Edrecolomab, and anti-CD52 antibodies such as Campath® (alemtuzumab).

In one embodiment, the Fc polypeptides of the present invention are directed against antigens expressed in the hematological lineage. Target antigens and clinical products and candidates that are relevant for such application may include but are not limited to: anti-CD33 antibodies such as Smart M195, anti-CD40L antibodies such as Antova™, IDEC-131, anti-CD44 antibodies such as Blvatuzumab, anti-CD52 antibodies such as Campath® (alemtuzumab), anti-CD80 antibodies such as IDEC-114, anti-CTLA-4 antibodies such as MDX-101, anti-CD20 antibodies such as Bexocar, Rituxan®, Zevalin®, and PRO70769, anti-CD22 antibodies such as Lymphocide™, anti-CD23 antibodies such as IDEC-152, anti-CD25 antibodies such as Zenapax® (daclizumab), and anti-MHC (HLA-DR) antibodies such as apolizumab.

In one embodiment, the Fc polypeptides of the present invention are directed against antigens expressed in solid tumors. Target antigens and clinical products and candidates that are relevant for such application may include but are not limited to: anti-EpCAM antibodies such as Crucell's anti-EpCAM and Edrecolomab, anti-CEA antibodies such as cantumab and Pentacea, anti-EGFR antibodies such as ABX-EGF, Cetuximab, IMC-C225, Merck Mab 425, anti-Mucl antibodies such as BravaRex, TriAb, anti-Her2 antibodies such as Herceptin®, MDX-210, anti-GD-2 ganglioside antibodies such as 3F8 and TriGem, anti-GD-3 ganglioside antibodies such as mitumomab, anti-PSMA antibodies such as MDX-070, anti-CA125 antibodies such as oregovomab, anti-TAG-72 antibodies such as MDX-220, and anti-MUC-1 antibodies such as cantuzumab.

In a preferred embodiment, the target of the Fc variants of the present invention is itself one or more Fc ligands. Fc polypeptides of the invention can be utilized to modulate the activity of the immune system, and in some cases to mimic the effects of IVIg therapy in a more controlled, specific, and efficient manner. IVIg is effectively a high dose of immunoglobulins delivered intravenously. In general, IVIg has been used to downregulate autoimmune conditions. It has been hypothesized that the therapeutic mechanism of action of IVIg involves ligation of Fc receptors at high frequency (J. Bayry et al., 2003, Transfusion Clinique et Biologique 10: 165-169; Binstadt et al., 2003, J. Allergy Clin. Immunol, 697-704). Indeed animal models of Ithrombocytopenia purpura (ITP) show that the isolated Fc are the active portion of IVIg (Samuelsson et al, 2001, Pediatric Research 50(5), 551). For use in therapy, immunoglobulins are harvested from thousands of donors, with all of the concomitant problems associated with non-recombinant biotherapeutics collected from humans. An Fc variant of the present invention should serve all of the roles of IVIg while being manufactured as a recombinant protein rather than harvested from donors.

The immunomodulatory effects of IVIg may be dependent on productive interaction with one or more Fc ligands, including but not limited to FcγRs, complement proteins, and FcRn. In some embodiments, Fc variants of the invention with enhanced affinity for FcγRIIb can be used to promote anti-inflammatory activity (Samuelsson et al., 2001, *Science* 291: 484-486) and or to reduce autoimmunity (Hogarth, 2002, *Current Opinion in Immunology*, 14:798-802). In other embodiments, Fc polypeptides of the invention with enhanced affinity for one or more FcγRs can be utilized by themselves or in combination with additional modifications to reduce autoimmunity (Hogarth, 2002, *Current Opinion in Immunology*, 14:798-802). In alternative embodiments, Fc variants of the invention with enhanced affinity for FcγRIIIa but reduced capacity for intracellular signaling can be used to reduce immune system activation by competitively interfering with FcγRIIIa binding. The context of the Fc variant dramatically impacts the desired specificity. For example, Fc variants that provide enhanced binding to one or more activating FcγRs may provide optimal immunomodulatory effects in the context of an antibody, Fc fusion, isolated Fc, or Fc fragment by acting as an FcγR antagonist (van Mirre et al., 2004, J. Immunol. 173:332-339). However, fusion or conjugation of two or more Fc variants may provide different effects, and for such an Fc polypeptide it may be optimal to utilize Fc variants that provide enhanced affinity for an inhibitory receptor.

The Fc variants of the present invention may be used as immunomodulatory therapeutics. Binding to or blocking Fc receptors on immune system cells may be used to influence immune response in immunological conditions including but not limited to idiopathic thrombocytopenia purpura (ITP) and rheumatoid arthritis (RA) among others. By use of the affinity enhanced Fc variants of the present invention, the dosages required in typical IVIg applications may be reduced while obtaining a substantially similar therapeutic effect. The Fc variants may provide enhanced binding to an FcγR, including but not limited to FcγRIIa, FcγRIIb, FcγRIIIa, FcγRIIIb, and/or FcγRI. In particular, binding enhancements to FcγRIIb would increase expression or inhibitory activity, as needed, of that receptor and improve efficacy. Alternatively, blocking binding to activation receptors such as FcγRIIIb or FcγRI may improve efficacy. In addition, modulated affinity of the Fc variants for FcRn and/or also complement may also provide benefits.

In one embodiment, Fc variants that provide enhanced binding to the inhibitory receptor FcγRIIb provide an enhancement to the IVIg therapeutic approach. In particular, the Fc variants of the present invention that bind with greater affinity to the FcγRIIb receptor than parent Fc polypeptide may be used. Such Fc variants would thus function as FcγRIIb agonists, and would be expected to enhance the beneficial effects of IVIg as an autoimmune disease therapeutic and also as a modulator of B-cell proliferation. In addition, such FcγRIIb-enhanced Fc variants may also be further modified to have the same or limited binding to other receptors. In additional embodiments, the Fc variants with enhanced FcγRIIb affinity may be combined with mutations that reduce or ablate to other receptors, thereby potentially further minimizing side effects during therapeutic use.

Such immunomodulatory applications of the Fc variants of the present invention may also be utilized in the treatment of oncological indications, especially those for which antibody therapy involves antibody-dependant cytotoxic mechanisms. For example, an Fc variant that enhances affinity to FcγRIIb may be used to antagonize this inhibitory receptor, for example by binding to the Fc/FcγRIIb binding site but failing to trigger, or reducing cell signaling, potentially enhancing the effect of antibody-based anti-cancer therapy. Such Fc variants, functioning as FcγRIIb antagonists, may either block the inhibitory properties of FcγRIIb, or induce its inhibitory function as in the case of IVIg. An FcγRIIb antagonist may be used as co-therapy in combination with any other therapeutic, including but not limited to antibodies, acting on the basis of ADCC related cytotoxicity. FcγRIIb antagonistic Fc variants of this type are preferably isolated Fc or Fc fragments, although in alternate embodiments antibodies and Fc fusions may be used.

Optimized Properties

The present invention provides Fc variants that are optimized for a number of therapeutically relevant properties. An Fc variant comprises one or more amino acid modifications relative to a parent Fc polypeptide, wherein said amino acid modification(s) provide one or more optimized properties. An Fc variant of the present invention differs in amino acid sequence from its parent Fc polypeptide by virtue of at least one amino acid modification. Thus Fc variants of the present invention have at least one amino acid modification compared to the parent. Alternatively, the Fc variants of the present invention may have more than one amino acid modification as compared to the parent, for example from about one to fifty amino acid modifications, preferably from about one to ten amino acid modifications, and most preferably from about one to about five amino acid modifications compared to the parent. Thus the sequences of the Fc variants and those of the parent Fc polypeptide are substantially homologous. For example, the variant Fc variant sequences herein will possess about 80% homology with the parent Fc variant sequence, preferably at least about 90% homology, and most preferably at least about 95% homology.

The Fc variants of the present invention may be optimized for a variety of properties. An Fc variant that is engineered or predicted to display one or more optimized properties is herein referred to as an "optimized Fc variant". Properties that may be optimized include but are not limited to enhanced or reduced affinity for an FcγR. In a preferred embodiment, the Fc variants of the present invention are optimized to possess enhanced affinity for a human activating FcγR, preferably FcγRI, FcγRIIa, FcγRIIc, FcγRIIIa, and FcγRIIIb, most preferably FcγRIIIa. In an alternately preferred embodiment, the Fc variants are optimized to possess reduced affinity for the human inhibitory receptor FcγRIIb. These preferred embodiments are anticipated to provide Fc polypeptides with enhanced therapeutic properties in humans, for example enhanced effector function and greater anti-cancer potency. In an alternate embodiment, the Fc variants of the present invention are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide Fc polypeptides with enhanced therapeutic properties in humans, for example reduced effector function and reduced toxicity. In other embodiments, Fc variants of the present invention provide enhanced affinity for one or more FcγRs, yet reduced affinity for one or more other FcγRs. For example, an Fc variant of the present invention may have enhanced binding to FcγRIIIa, yet reduced binding to FcγRIIb. Alternately, an Fc variant of the present invention may have enhanced binding to FcγRIIa and FcγRI, yet reduced binding to FcγRIIb. In yet another embodiment, an Fc variant of the present invention may have enhanced affinity for FcγRIIb, yet reduced affinity to one or more activating FcγRs.

Preferred embodiments comprise optimization of Fc binding to a human FcγR, however in alternate embodiments the Fc variants of the present invention possess enhanced or reduced affinity for FcγRs from nonhuman organisms, including but not limited to rodents and non-human primates. Fc variants that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of Fc variants that comprise Fc variants that are optimized for one or more mouse FcγRs, may provide valuable information with regard to the efficacy of the protein, its mechanism of action, and the like. The Fc variants of the present invention may also be optimized for enhanced functionality and/or solution properties in aglycosylated form. In a preferred embodiment, the aglycosylated Fc variants of the present invention bind an Fc ligand with greater affinity than the aglycosylated form of the parent Fc variant. Said Fc ligands include but are not limited to FcγRs, C1q, FcRn, and proteins A and G, and may be from any source including but not limited to human, mouse, rat, rabbit, or monkey, preferably human. In an alternately preferred embodiment, the Fc variants are optimized to be more stable and/or more soluble than the aglycosylated form of the parent Fc variant.

Fc variants of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

Preferably, the Fc ligand specificity of the Fc variant of the present invention will determine its therapeutic utility. The utility of a given Fc variant for therapeutic purposes will depend on the epitope or form of the Target antigen and the disease or indication being treated. For some targets and indications, enhanced FcγR-mediated effector functions may be preferable. This may be particularly favorable for anti-cancer Fc variants. Thus Fc variants may be used that comprise Fc variants that provide enhanced affinity for activating FcγRs and/or reduced affinity for inhibitory FcγRs. For some targets and indications, it may be further beneficial to utilize Fc variants that provide differential selectivity for different activating FcγRs; for example, in some cases enhanced binding to FcγRIIa and FcγRIIIa may be desired, but not FcγRI, whereas in other cases, enhanced binding only to FcγRIIa may be preferred. For certain targets and indications, it may be preferable to utilize Fc variants that enhance both FcγR-mediated and complement-mediated effector functions, whereas for other cases it may be advantageous to utilize Fc variants that enhance either FcγR-mediated or complement-mediated effector functions. For some Targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize Fc variants that provide enhanced binding to the inhibitory FcγRIIb, yet WT level, reduced, or ablated binding to activating FcγRs. This may be particularly useful, for example, when the goal of an Fc variant is to inhibit inflammation or auto-immune disease, or modulate the immune system in some way.

Clearly an important parameter that determines the most beneficial selectivity of a given Fc variant to treat a given disease is the context of the Fc variant, that is what type of Fc variant is being used. Thus the Fc ligand selectivity or specificity of a given Fc variant will provide different properties depending on whether it composes an antibody, Fc fusion, or an Fc variants with a coupled fusion or conjugate partner. For example, toxin, radionucleotide, or other conjugates may be less toxic to normal cells if the Fc variant that comprises them has reduced or ablated binding to one or more Fc ligands. As another example, in order to inhibit inflammation or auto-immune disease, it may be preferable to utilize an Fc variant with enhanced affinity for activating FcγRs, such as to bind these FcγRs and prevent their activation. Conversely, an Fc variant that comprises two or more Fc regions with enhanced FcγRIIb affinity may co-engage this receptor on the surface of immune cells, thereby inhibiting proliferation of these cells. Whereas in some cases an Fc variants may engage its target antigen on one cell type yet engage FcγRs on separate cells from the target antigen, in other cases it may be advantageous to engage FcγRs on the surface of the same cells as the target antigen. For example, if an antibody targets an antigen on a cell that also expresses one or more FcγRs, it may be beneficial to utilize an Fc variant that enhances or reduces binding to the FcγRs on the surface of that cell. This may be the case, for example when the Fc variant is being used as an anti-cancer agent, and co-engagement of target antigen and FcγR on the surface of the same cell promote signaling events within the cell that result in growth inhibition, apoptosis, or other anti-proliferative effect. Alternatively, antigen and FcγR co-engagement on the same cell may be advantageous when the Fc variant is being used to modulate the immune system in some way, wherein co-engagement of target antigen and FcγR provides some proliferative or anti-proliferative effect. Likewise, Fc variants that comprise two or more Fc regions may benefit from Fc variants that modulate FcγR selectivity or specificity to co-engage FcγRs on the surface of the same cell.

The Fc ligand specificity of the Fc variants of the present invention can be modulated to create different effector function profiles that may be suited for particular target antigens, indications, or patient populations. Table 1 describes several preferred embodiments of receptor binding profiles that include improvements to, reductions to or no effect to the binding to various receptors, where such changes may be beneficial in certain contexts. The receptor binding profiles in the table could be varied by degree of increase or decrease to the specified receptors. Additionally, the binding changes specified could be in the context of additional binding changes to other receptors such as C1q or FcRn, for example by combining with ablation of binding to C1q to shut off complement activation, or by combining with enhanced binding to C1q to increase complement activation. Other embodiments with other receptor binding profiles are possible, the listed receptor binding profiles are exemplary.

TABLE 1

| Affinity Enhancement | Affinity Reduction | Cell Activity | Therapeutic Activity |
|---|---|---|---|
| FcγRI only | — | Enhanced dendritic cell activity and uptake, and subsequent presentation of antigens Enhanced monocyte and macrophage response to antibody | Enhanced cell-based immune response against target |
| FcγRIIIa | — | Enhanced ADCC and phagocytosis of broad range of cell types | Increased target cell lysis |
| FcγRIIIa | FcγRIIb | Enhanced ADCC and phagocytosis of broad range of cell types | Increased target cell lysis |
| FcγRIIb FcγRIIc | — | Reduced activity of all FcγR bearing cell types except NK cells Possible activation of NK cells via FcγRIIc receptor signaling | Enhancement of target cell lysis selective for NK cell accessible target cells |
| FcγRIIb FcγRIIIa | — | Possible NK cell specific activation and enhancement of NK cell mediated ADCC | Enhanced target cell lysis selective for NK cell accessible target cells |
| FcγRIIIb | — | Neutrophil mediated phagocytosis enhancement | Enhanced target cell destruction for neutrophil accessible cells |
| FcαR | — | Neutrophil mediated phagocytosis enhancement | Enhanced target cell destruction for neutrophil accessible cells |
| FcγRI FcγRIIa FcγRIIIa | FcγRIIb | Enhanced dendritic cell activity and uptake, and subsequent presentation of antigens to T cells Enhanced monocyte and macrophage response to antibody | Enhanced cell-based immune response against target |
| FcγRIIb | FcγRI FcγRIIa FcγRIIIa | Reduced activity of monocytes, macrophages, neutrophils, NK, dendritic and other gamma receptor bearing cells | Eliminated or reduced cell-mediated cytotoxicity against target bearing cells |

The presence of different polymorphic forms of FcγRs provides yet another parameter that impacts the therapeutic utility of the Fc variants of the present invention. Whereas the specificity and selectivity of a given Fc variant for the different classes of FcγRs significantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selectivity of Fc variants of the present invention to Fc ligand polymorphisms, including but not limited to FcγR, C1q, FcRn, and FcRH polymorphisms, may be used to guide the selection of valid research and pre-clinical experiments, clinical trial design, patient selection, dosing dependence, and/or other aspects concerning clinical trials.

Additional Modifications

In addition to comprising an Fc variant of the present invention, the Fc polypeptides of the present invention may comprise one or more additional modifications. Said modifications may be amino acid modifications, or may modifications that are not amino acid modifications such as modifications that are made enzymatically or chemically. Combinations of additional amino acid modifications and modifications that are not amino acid modifications are contemplated. Such additional modification(s) likely provide some improvement in the Fc polypeptide, for example an enhancement in its stability, solubility, function, or clinical use. The present invention contemplates a variety of improvements that made be made by coupling the Fc variants of the present invention with additional modifications.

The Fc variants of the present invention may be combined with other amino acid modifications in the Fc region that provide altered or optimized interaction with one or more Fc ligands, including but not limited to FcγRs, C1q or other complement proteins, FcRn, FcR homologues (FcRHs), and/or as yet undiscovered Fc ligands. It is noted that Fc polypeptides of the present invention may themselves have as yet unknown useful interaction properties with one or more Fc ligands, for example FcRHs. Additional modifications may provide altered or optimized affinity and/or specificity to the Fc ligands. Additional modifications may provide altered or optimized effector functions, including but not limited to ADCC, ADCP, CDC, and/or serum half-life. Such combination may provide additive, synergistic, or novel properties. In one embodiment, the Fc variants of the present invention may be combined with known Fc variants (Duncan et al., 1988, Nature 332:563-564; Lund et al., 1991, J Immunol 147:2657-2662; Lund et al., 1992, Mol Immunol 29:53-59; Alegre et al., 1994, Transplantation 57:1537-1543; Hutchins et al., 1995, Proc Natl Acad Sci USA 92:11980-11984; Jefferis et al., 1995, Immunol Lett 44:111-117; Lund et al., 1995, Faseb J 9:115-119; Jefferis et al., 1996, Immunol Lett 54:101-104; Lund et al., 1996, J Immunol 157:4963-4969; Armour et al., 1999, Eur J Immunol 29:2613-2624; Idusogie et al., 2000, J Immunol 164:4178-4184; Reddy et al., 2000, J Immunol 164: 1925-1933; Xu et al., 2000, Cell Immunol 200:16-26; Idusogie et al., 2001, J Immunol 166:2571-2575; Shields et al., 2001, J Biol Chem 276:6591-6604; Jefferis et al., 2002, Immunol Lett 82:57-65; Presta et al., 2002, Biochem Soc Trans 30:487-490; Hinton et al., 2004, J Biol Chem 279: 6213-6216) (U.S. Pat. No. 5,624,821; U.S. Pat. No. 5,885, 573; U.S. Pat. No. 6,194,551; PCT WO 00/42072; PCT WO 99/58572; US 2004/0002587 A1), U.S. Pat. No. 6,737,056, PCT US2004/000643, U.S. Ser. No. 10/370,749, and PCT/US2004/005112), all incorporated by reference. For example, as described in U.S. Pat. No. 6,737,056, PCT US2004/000643, U.S. Ser. No. 10/370,749, and PCT/US2004/005112, the substitutions S298A, S298D, K326E, K326D, E333A, K334A, and P396L provide optimized FcγR binding and/or enhanced ADCC. Furthermore, as disclosed in Idusogie et al., 2001, J. Immunology 166:2571-2572, incorporated by reference, substitutions K326W, K326Y, and E333S provide enhanced binding to the complement protein C1q and enhanced CDC. Finally, as described in Hinton et al., 2004, J. Biol. Chem. 279(8): 6213-6216, incorporated by reference, substitutions T250Q, T250E, M428L, and M428F provide enhanced binding to FcRn and improved pharmacokinetics.

Because the binding sites for FcγRs, C1q, and FcRn reside in the Fc region, the differences between the IgGs in the Fc region are likely to contribute to differences in FcγR- and C1q-mediated effector functions. It is also possible that the modifications can be made in other non-Fc regions of an Fc variant, including for example the Fab and hinge regions of an antibody, or the Fc fusion partner of an Fc fusion. For example, as disclosed in U.S. Ser. No. 11/090,981, hereby incorporated by reference, the Fab and hinge regions of an antibody may impact effector functions such as antibody dependent cell-mediated cytotoxicity (ADCC), antibody dependent cell-mediated phagocytosis (ADCP), and complement dependent cytotoxicity (CDC). Thus modifications outside the Fc region of an Fc variant of the present invention are contemplated. For example, antibodies of the present invention may comprise one or more amino acid modifications in the $V_L$, $C_L$, $V_H$, $C_H1$, and/or hinge regions of an antibody.

Other modifications may provide additional or novel binding determinants into an Fc variant, for example additional or novel Fc receptor binding sites, for example as described in U.S. Ser. No. 60/531,752, filed Dec. 22, 2003, entitled "Fc variants with novel Fc receptor binding sites". In one embodiment, an Fc variant of one antibody isotype may be engineered such that it binds to an Fc receptor of a different isotype. This may be particularly applicable when the Fc binding sites for the respective Fc receptors do not significantly overlap. For example, the structural determinants of IgA binding to FcγRI may be engineered into an IgG Fc variant.

The Fc variants of the present invention may comprise modifications that modulate the in vivo pharmacokinetic properties of an Fc variant. These include, but are not limited to, modifications that enhance affinity for the neonatal Fc receptor FcRn (U.S. Ser. No. 10/020,354; WO2001US0048432; EP2001000997063; U.S. Pat. No. 6,277,375; U.S. Ser. No. 09/933,497; WO1997US0003321; U.S. Pat. No. 6,737,056; WO2000US0000973; Shields et al., 2001, J Biol Chem 276(9): 6591-6604; Zhou et al., 2003, J Mol Biol., 332: 901-913). These further include modifications that modify FcRn affinity in a pH-specific manner. In some embodiments, where enhanced in vivo half-life is desired, modifications that specifically enhance FcRn affinity at lower pH (5.5-6) relative to higher pH (7-8) are preferred (Hinton et al., 2004, J Biol Chem 279(8): 6213-6216; Dall' Acqua et al., 2002 J Immuno 169: 5171-5180; Ghetie et al., 1997, Nat Biotechnol 15(7): 637-640; WO2003US0033037; WO2004US0011213). For example, as described in Hinton et al., 2004, "Engineered Human IgG Antibodies with Longer Serum Half-lives in Primates" J Biol Chem 279(8): 6213-6216, substitutions T250Q, T250E, M428L, and M428F provide enhanced binding to FcRn and improved pharmacokinetics. Additionally preferred modifications are those that maintain the wild-type Fc's improved binding at lower pH relative to the higher pH. In alternative embodiments, where rapid in vivo clearance is desired, modifications that reduce affinity for FcRn are preferred. (U.S. Pat. No. 6,165,745; WO1993US0003895; EP1993000910800; WO1997US0021437; Medesan et al., 1997, J Immunol 158 (5): 2211-2217; Ghetie & Ward, 2000, Annu Rev Immunol 18: 739-766; Martin et al. 2001, Molecular Cell 7: 867-877; Kim et al. 1999, Eur J Immunol 29: 2819-2825). Preferred variants that enhance FcRn are described in U.S. Ser. No. 60/627,763, filed Nov. 12, 2004; 60/642,886, filed Jan. 11, 2005; 60/649,508, filed Feb. 2, 2005; 60/662,468, filed Mar. 15, 2005, and 60/669,311 filed Apr. 6, 2005, entitled "Fc Variants with Altered Binding to FcRn", all hereby incorporated by reference.

Additional modifications may comprise amino acid modifications wherein residues in an Fc polypeptide are modified to the corresponding residue in a homologous Fc polypeptide. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (references—Michaelsen et al., 1992, Molecular Immunology 29(3): 319-326). Human IgG1 is the most commonly used antibody for therapeutic purposes, and engineering studies wherein variants have been constructed that show enhanced effector function have been carried out predominantly in this context. As described above, it is possible to determine corresponding or equivalent residues in Fc polypeptides that have significant sequence or structural homology with each other. By the same token, it is possible to use such methods to engineer additional amino acid modifications in an Fc polypeptide to provide additional optimized properties, for example as described in U.S. Ser. No. 60/621,387, filed Oct. 21, 2004. In one embodiment, amino acid modifications can be made that replace one or more residues in an Fc polypeptide of the present invention with one or more residues in another homologous Fc polypeptide. In an alternate embodiment, hybrid Fc polypeptides are constructed, such that one or more regions of an Fc polypeptide of the present invention are replace with the corresponding regions of a homolous Fc polypeptide. For example, some studies have explored IgG1, IgG2, IgG3, and IgG4 variants in order to investigate the determinants of the effector function differences between them. See for example Canfield & Morrison, 1991, J Exp Med 173: 1483-1491; Chappel et al., 1991, Proc Natl Acad Sci USA 88(20): 9036-9040; Chappel et al., 1993, J Biol Chem 268: 25124-25131; Tao, Canfield, and Morrison, 1991, J Exp Med 173: 1025-1028; Tao et al., 1993, J Exp Med 178: 661-667; Redpath et al., 1998, Human Immunology, 59, 720-727.

In one embodiment, the Fc variants of the present invention comprise one or more engineered glycoforms. By "engineered glycoform" as used herein is meant a carbohydrate composition that is covalently attached to an Fc variant, wherein said carbohydrate composition differs chemically from that of a parent Fc variant. Engineered glycoforms may be useful for a variety of purposes, including but not limited to enhancing or reducing effector function. Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]). Many of these techniques are based on controlling the level of fucosylated and/or bisecting oligosaccharides that are covalently attached to the Fc region, for example by expressing an Fc variant in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the Fc variant has been expressed. Engineered glycoform typically refers to the different carbohydrate or oligosaccharide; thus an Fc variant, for example an antibody or Fc fusion, may comprise an engineered glycoform. Alternatively, engineered glycoform may refer to the Fc variant that comprises the different carbohydrate or oligosaccharide.

Fc variants of the present invention may comprise one or more modifications that provide optimized properties that are not specifically related to effector function per se. Said modifications may be amino acid modifications, or may be modifications that are made enzymatically or chemically. Such modification(s) likely provide some improvement in the Fc variant, for example an enhancement in its stability, solubility, function, or clinical use. The present invention contemplates a variety of improvements that made be made by coupling the Fc variants of the present invention with additional modifications.

In a preferred embodiment, the Fc variants of the present invention may comprise modifications to reduce immunogenicity in humans. In a most preferred embodiment, the immunogenicity of an Fc variant of the present invention is reduced using a method described in U.S. Ser. No. 11/004,590, filed Dec. 3, 2004, entitled "Methods of Generating Variant Proteins with Increased Host String Content and Compositions Thereof". In alternate embodiments, the antibodies of the present invention are humanized (Clark, 2000, *Immunol Today* 21:397-402). By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) $V_L$ and $V_H$ frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, *Nature* 321:522-525; Riechmann et al., 1988; Nature 332:323-329; Verhoeyen et al., 1988, *Science*, 239:1534-1536; Queen et al., 1989, *Proc Natl Acad Sci, USA* 86:10029-33; He et al., 1998, *J Immunol* 160: 1029-1035; Carter et al., 1992, *Proc Natl Acad Sci USA* 89:4285-9, Presta et al., 1997, Cancer Res 57(20):4593-9; Gorman et al., 1991, Proc Natl Acad Sci USA 88:4181-4185; O'Connor et al., 1998, *Protein Eng* 11:321-8. Humanization or other methods of reducing the immunogenicity of nonhuman antibody variable regions may include resurfacing methods, as described for example in Roguska et al., 1994, Proc Natl Acad Sci USA 91:969-973. In one embodiment, selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084. Structure-based methods may be employed for humanization and affinity maturation, for example as described in U.S. Ser. No. 10/153,159 and related applications.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an Fc variant of the present invention. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/339,788; PCT WO 01/21823; and PCT WO 02/00165; Mallios, 1999, *Bioinformatics* 15: 432-439; Mallios, 2001, *Bioinformatics* 17: 942-948; Sturniolo et al., 1999, *Nature Biotech.* 17: 555-561; WO 98/59244; WO 02/069232; WO 02/77187; Marshall et al., 1995, *J. Immunol.* 154: 5927-5933; and Hammer et al., 1994, *J. Exp. Med.* 180: 2353-2358. Sequence-based information can be used to determine a binding score for a given peptide—MHC interaction (see for example Mallios, 1999, *Bioinformatics* 15: 432-439; Mallios, 2001, *Bioinformatics* 17: p942-948; Sturniolo et. al., 1999, *Nature Biotech.* 17: 555-561). It is possible to use structure-based methods in which a given peptide is computationally placed in the peptide-binding groove of a given MHC molecule and the interaction energy is determined (for example, see WO 98/59244 and WO 02/069232). Such methods may be referred to as "threading" methods. Alternatively, purely experimental methods can be used; for example a set of overlapping peptides derived from the protein of interest can be experimentally tested for the ability to induce T-cell activation and/or other aspects of an immune response. (see for example WO 02/77187). In a preferred embodiment, MHC-binding propensity scores are calculated for each 9-residue frame along the protein sequence using a matrix method (see Sturniolo et. al., supra; Marshall et. al., 1995, *J. Immunol.* 154: 5927-5933, and Hammer et. al., 1994, *J. Exp. Med.* 180: 2353-2358). It is also possible to consider scores for only a subset of these residues, or to consider also the identities of the peptide residues before and after the 9-residue frame of interest. The matrix comprises binding scores for specific amino acids interacting with the peptide binding pockets in different human class II MHC molecule. In the most preferred embodiment, the scores in the matrix are obtained from experimental peptide binding studies. In an alternate preferred embodiment, scores for a given amino acid binding to a given pocket are extrapolated from experimentally characterized alleles to additional alleles with identical or similar residues lining that pocket. Matrices that are produced by extrapolation are referred to as "virtual matrices". In an alternate embodiment, additional amino acid modifications may be engineered to reduce the propensity of the intact molecule to interact with B cell receptors and circulating antibodies.

Antibodies and Fc fusions of the present invention may comprise amino acid modifications in one or more regions outside the Fc region, for example the antibody Fab region or the Fc fusion partner, that provide optimal properties. In one embodiment, the variable region of an antibody of the present invention may be affinity matured, that is to say that amino acid modifications have been made in the $V_H$ and/or $V_L$ domains of the antibody to enhance binding of the antibody to its target antigen. Likewise, modifications may be made in the Fc fusion partner to enhance affinity of the Fc fusion for its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, aberrant forms of antigens that are expressed only on certain cell types such as tumor cells, cell-surface vs. soluble forms, selectivity for various polymorphic variants, or selectivity for specific conformational forms of the target.

Fc variants of the invention may comprise one or more modifications that provide reduced or enhanced internalization of an Fc variant. In one embodiment, Fc variants of the present invention can be utilized or combined with additional modifications in order to reduce the cellular internalization of an Fc variant that occurs via interaction with one or more Fc ligands. This property might be expected to enhance effector function, and potentially reduce immunogenicity of the Fc variants of the invention. Alternatively, Fc variants of the present Fc variants of the present invention can be utilized directly or combined with additional modifications in order to enhance the cellular internalization of an Fc variant that occurs via interaction with one or more Fc ligands. For example, in a preferred embodiment, an Fc variant is used that provides enhanced binding to FcγRI, which is expressed on dendritic cells and active early in immune response. This strategy could be further enhanced by combination with additional modifications, either within the Fc variant or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, *Immunol Rev.* 172: 279-84), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In a preferred embodiment, modifications are made to improve biophysical properties of the Fc variants of the present invention, including but not limited to stability, solubility, and oligomeric state. Modifications can include, for example, substitutions that provide more favorable intramolecular interactions in the Fc variant such as to provide greater stability, or substitution of exposed nonpolar amino acids with polar amino acids for higher solubility. A number of optimization goals and methods are described in U.S. Ser. No. 10/379,392 that may find use for engineering additional modifications to further optimize the Fc variants of the present invention. The Fc variants of the present invention can also be combined with additional modifications that reduce oligomeric state or size, such that tumor penetration is enhanced, or in vivo clearance rates are increased as desired.

Other modifications to the Fc variants of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, J Exp Med 176:1191-1195, and Shopes, 1992, J Immunol 148(9): 2918-22. Additional modifications to the variants of the present invention include those that enable the specific formation or heterodimeric, heteromultimeric, bifunctional, and/or multifunctional molecules. Such modifications include, but are not limited to, one or more amino acid substitutions in the $C_H3$ domain, in which the substitutions reduce homodimer formation and increase heterodimer formation. For example, methods of engineering and compositions of such molecules are described in Atwell et al., 1997, J Mol Biol 270(1):26-35, and Carter et al., 2001, J Immunol Methods 248:7-15. Additional modifications include modifications in the hinge and CH3 domains, in which the modifications reduce the propensity to form dimers.

In further embodiments, the Fc variants of the present invention comprise modifications that remove proteolytic degradation sites. These may include, for example, protease sites that reduce production yields, as well as protease sites that degrade the administered protein in vivo. In a preferred embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The Fc variants of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101(2):7566-71, Zhang et al., 2003, 303(5656):371-3, and Chin et al., 2003, Science 301(5635):964-7. In some embodiments, these modifications enable manipulation of various functional, biophysical, immunological, or manufacturing properties discussed above. In additional embodiments, these modifications enable additional chemical modification for other purposes. Other modifications are contemplated herein. For example, the Fc variant may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the Fc variants. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the Fc variants of the present invention.

The Fc variants of the present invention may be fused or conjugated to one or more other molecules or polypeptides. Conjugate and fusion partners may be any molecule, including small molecule chemical compounds and polypeptides. For example, a variety of antibody conjugates and methods are described in Trail et al., 1999, Curr. Opin. Immunol. 11:584-588. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the Fc variant. Thus, for example, the conjugation of a toxin to an antibody or Fc fusion targets the delivery of said toxin to cells expressing the target antigen.

In one embodiment, the Fc variants of the present invention are fused or conjugated to a cytokine. By "cytokine" as used herein is meant a generic term for proteins released by one cell population that act on another cell as intercellular mediators. For example, as described in Penichet et al., 2001, J Immunol Methods 248:91-101, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the Fc polypeptides of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71. Small molecule toxins include but are not limited to calicheamicin, maytansine (U.S. Pat. No. 5,208,020), trichothene, and CC1065. In one embodiment of the invention, the Fc polypeptide is conjugated to one or more maytansine molecules (e.g. about 1 to about 10 maytansine molecules per antibody molecule). Maytansine may, for example, be converted to May-SS-Me which may be reduced to May-SH3 and reacted with modified Fc polypeptide (Chari et al., 1992, Cancer Research 52: 127-131) to generate a maytansinoid-antibody or maytansinoid-Fc fusion conjugate. Another conjugate of interest comprises an Fc polypeptide, for example an antibody or Fc fusion, conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma_1^1$, PSAG, and $\Theta^1_1$, (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773,001). Dolastatin 10 analogs such as auristatin E (AE) and monomethylauristatin E (MMAE) may find use as conjugates for the Fc variants of the present invention (Doronina et al., 2003, Nat Biotechnol 21(7):778-84; Francisco et al., 2003 Blood 102(4):1458-65). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232, hereby incorporated by reference. The present invention further contemplates a conjugate between an Fc variant of the present invention and a compound with nucleolytic activity, for example a ribonuclease or DNA endonuclease such as a deoxyribonuclease (Dnase).

In an alternate embodiment, an Fc variant of the present invention may be fused, conjugated, or operably linked to a radioisotope to form a radioconjugate. A variety of radioactive isotopes are available for the production of radioconjugate antibodies and Fc fusions. Examples include, but are not limited to, At211, I131, I125, Y90, Re186, Re188, Sm153, Bi212, P32, and radioactive isotopes of Lu. See for example, reference.

In yet another embodiment, an Fc variant of the present invention may be conjugated to a "receptor" (e.g., streptavidin) for utilization in tumor pretargeting wherein the Fc variant-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the Fc variant is conjugated or operably linked to an enzyme in order to employ Antibody Dependent Enzyme Mediated Prodrug Therapy (ADEPT). ADEPT may be used by conjugating or operably linking the Fc variant to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, *Nature* 328: 457-458). Fc variant-abzyme conjugates can be prepared for delivery of the abzyme to a tumor cell population. A variety of additional conjugates are contemplated for the Fc variants of the present invention. A variety of chemotherapeutic agents, anti-angiogenic agents, tyrosine kinase inhibitors, and other therapeutic agents are described below, which may find use as Fc variant conjugates.

Also contemplated as fusion and conjugate partners are Fc polypeptides. Thus an Fc variant may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab' s and Fc's may be linked by thioether bonds originating at cysteine residues in the hinges, generating molecules such as FabFc$_2$ (Kan et al., 2001, *J. Immunol.*, 2001, 166: 1320-1326; Stevenson et al., 2002, *Recent Results Cancer Res.* 159: 104-12; U.S. Pat. No. 5,681,566). Fc regions may be linked using disulfide engineering and/or chemical cross-linking, for example as described in Caron et al., 1992, J. Exp. Med. 176:1191-1195, and Shopes, 1992, J. Immunol. 148(9):2918-22. In a preferred embodiment, Fc regions may be linked genetically. For example multiple Cγ2 domains have been fused between the Fab and Fc regions of an antibody (White et al., 2001, *Protein Expression and Purification* 21: 446-455). In a preferred embodiment, Fc regions in an Fc variant are linked genetically to generated tandemly linked Fc regions as described in U.S. Ser. No. 60/531,752, filed Dec. 22, 2003, entitled "Fc polypeptides with novel Fc receptor binding sites". Tandemly linked Fc polypeptides may comprise two or more Fc regions, preferably one to three, most preferably two Fc regions. It may be advantageous to explore a number of engineering constructs in order to obtain homo- or hetero-tandemly linked Fc variants with the most favorable structural and functional properties. Tandemly linked Fc variants may be homo-tandemly linked Fc variants, that is an Fc variant of one isotype is fused genetically to another Fc variant of the same isotype. It is anticipated that because there are multiple FcγR, C1q, and/or FcRn binding sites on tandemly linked Fc polypeptides, effector functions and/or pharmacokinetics may be enhanced. In an alternate embodiment, Fc variants from different isotypes may be tandemly linked, referred to as hetero-tandemly linked Fc variants. For example, because of the capacity to target FcγR and FcαRI receptors, an Fc variant that binds both FcγRs and FcαRI may provide a significant clinical improvement.

As will be appreciated by one skilled in the art, in reality the concepts and definitions of fusion and conjugate are overlapping. The designation of an Fc variant as a fusion or conjugate is not meant to constrain it to any particular embodiment of the present invention. Rather, these terms are used loosely to convey the broad concept that any Fc variant of the present invention may be linked genetically, chemically, or otherwise, to one or more polypeptides or molecules to provide some desirable property.

Fusion and conjugate partners may be linked to any region of an Fc variant of the present invention, including at the N- or C-termini, or at some residue in-between the termini. In a preferred embodiment, a fusion or conjugate partner is linked at the N- or C-terminus of the Fc variant, most preferably the N-terminus. A variety of linkers may find use in the present invention to covalently link Fc variants to a fusion or conjuate partner or generate an Fc fusion. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 30 amino acids in length, with linkers of 1 to 20 amino acids in length being most preferred. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n SEQ ID NO:9, (GGGGS)n SEQ ID NO:10, and (GGGS)n SEQ ID NO:11, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains. In a preferred embodiment, the linker is not immunogenic when administered in a human patient. Thus linkers may be chosen such that they have low immunogenicity or are thought to have low immunogenicity. For example, a linker may be chosen that exists naturally in a human. In a most preferred embodiment, the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n SEQ ID NO:10, through random mutagenesis. Alternatively, once a suitable polypeptide linker is defined, additional linker polypeptides can be created to select amino acids that more optimally interact with the domains being linked. Other types of linkers that may be used in the present invention include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, Science 238:1098. Chemical linkers may enable chelation of an isotope. For example, Carbon-14-labeled 1-isothiocyanatobenzyl-3-methyldiethylene triaminepentaacetic acid (MX-DTPA) is an exemplary chelating agent for conjugation of radionucleotide to the antibody (see PCT WO 94/11026). The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the Fc variants of the present invention to a fusion or conjugate partner to generate an Fc fusion, or to link the Fc variants of the present invention to a conjugate.

Engineering Methods

Design strategies, computational screening methods, and library generation methods are described in U.S. Ser. No. 10/672,280 and U.S. Ser. No. 10/822,231, entitled "Optimized Fc Variants and Methods for their Generation", herein expressly incorporated by reference. These strategies, approaches, techniques, and methods may be applied individually or in various combinations to generate optimized Fc variants.

Experimental Production of Fc Variants

The present invention provides methods for producing and experimentally testing Fc variants. The described methods are not meant to constrain the present invention to any particular application or theory of operation. Rather, the provided methods are meant to illustrate generally that one or more Fc variants may be produced and experimentally tested to obtain variant Fc variants. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988.

In one embodiment of the present invention, nucleic acids are created that encode the Fc variants, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons). As will be appreciated by those skilled in the art, the generation of exact sequences for a library comprising a large number of sequences is potentially expensive and time consuming. Accordingly, there are a variety of techniques that may be used to efficiently generate libraries of the present invention. Such methods that may find use in the present invention are described or referenced in U.S. Pat. No. 6,403,312; U.S. Ser. No. 09/782,004; U.S. Ser. No. 09/927,790; U.S. Ser. No. 10/218,102; PCT WO 01/40091; and PCT WO 02/25588. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode Fc variants.

The Fc variants of the present invention may be produced by culturing a host cell transformed with nucleic acid, preferably an expression vector, containing nucleic acid encoding the Fc variants, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In a preferred embodiment, the Fc variants are expressed in mammalian expression systems, including systems in which the expression constructs are introduced into the mammalian cells using virus such as retrovirus or adenovirus. Any mammalian cells may be used, with human, mouse, rat, hamster, and primate cells being particularly preferred. Suitable cells also include known research cells, including but not limited to Jurkat T cells, NIH3T3, CHO, BHK, COS, HEK293, PER C.6, HeLa, Sp2/0, NS0 cells and variants thereof. In an alternately preferred embodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, Fc variants are produced in insect cells (e.g. Sf21/Sf9, *Trichoplusia ni* Bti-Tn5b1-4) or yeast cells (e.g. *S. cerevisiae, Pichia*, etc). In an alternate embodiment, Fc variants are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the Fc variants may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the Fc variants of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing Fc variants.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Fc variants may be operably linked to a fusion partner to enable targeting of the expressed protein, purification, screening, display, and the like. Fusion partners may be linked to the Fc variant sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS SEQ ID NO. 10. A fusion partner may be a targeting or signal sequence that directs Fc variant and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an Fc variant may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen Fc variants (see below). Fusion partners that enable a variety of selection methods are well-known in the art, and all of these find use in the present invention. For example, by fusing the members of an Fc variant library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317). Fusion partners may enable Fc variants to be labeled. Alternatively, a fusion partner may bind to a specific sequence on the expression vector, enabling the fusion partner and associated Fc variant to be linked covalently or noncovalently with the nucleic acid that encodes them. For example, U.S. Ser. No. 09/642,574; U.S. Ser. No. 10/080,376; U.S. Ser. No. 09/792,630; U.S. Ser. No. 10/023,208; U.S. Ser. No. 09/792,626; U.S. Ser. No. 10/082, 671; U.S. Ser. No. 09/953,351; U.S. Ser. No. 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466 describe such a fusion partner and technique that may find use in the present invention.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In a preferred embodiment, Fc variants are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of Fc variants. For example, the bacterial proteins A and G bind to the Fc region. Likewise, the bacterial protein L binds to the Fab region of some antibodies, as of course does the antibody's target antigen. Purification can often be enabled by a particular fusion partner. For example, Fc variants may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Protein Purification Principles and Practice, $3^{rd}$ Ed., Scopes, Springer-Verlag, NY, 1994. The degree of purification necessary will vary depending on the screen or use of the Fc variants. In some instances no purification is necessary. For example in one embodiment, if the Fc variants are secreted, screening may take place directly from the media. As is well known in the art, some methods of selection do not involve purification of proteins. Thus, for example, if a library of Fc variants is made into a phage display library, protein purification may not be performed.

Experimental Assays

Fc variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the Fc variants of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In a preferred embodiment, the functional and/or biophysical properties of Fc variants are screened in an in vitro assay. In vitro assays may allow a broad dynamic range for screening properties of interest. Properties of Fc variants that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of Fc variants to a protein or nonprotein molecule that is known or thought to bind the Fc variant. In a preferred embodiment, the screen is a binding assay for measuring binding to the Target antigen. In an alternately preferred embodiment, the screen is an assay for binding of Fc variants to an Fc ligand, including but are not limited to the family of FcγRs, the neonatal receptor FcRn, the complement protein C1q, and the bacterial proteins A and G. Said Fc ligands may be from any organism, with humans, mice, rats, rabbits, and monkeys preferred. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the Fc variant. Assays may employ a variety of detection methods including but not limited to chromogenic, fluorescent, luminescent, or isotopic labels.

The biophysical properties of Fc variants, for example stability and solubility, may be screened using a variety of methods known in the art. Protein stability may be determined by measuring the thermodynamic equilibrium between folded and unfolded states. For example, Fc variants of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an Fc variant may be quantitatively or qualitatively determined using a wide range of methods that are known in the art. Methods which may find use in the present invention for characterizing the biophysical properties of Fc variants include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an Fc variant could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the Fc variant's stability and solubility.

In a preferred embodiment, the library is screened using one or more cell-based or in vitro assays. For such assays, Fc variants, purified or unpurified, are typically added exogenously such that cells are exposed to individual variants or groups of variants belonging to a library. These assays are typically, but not always, based on the biology of the ability of the antibody or Fc fusion to bind to the target antigen and mediate some biochemical event, for example effector functions like cellular lysis, phagocytosis, ligand/receptor binding inhibition, inhibition of growth and/or proliferation, apoptosis and the like. Such assays often involve monitoring the response of cells to Fc variant, for example cell survival, cell death, cellular phagocytosis, cell lysis, change in cellular morphology, or transcriptional activation such as cellular expression of a natural gene or reporter gene. For example, such assays may measure the ability of Fc variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Crosslinked or monomeric antibodies and Fc fusions may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In a preferred embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an Fc variant. Cell types for such assays may be prokaryotic or eukaryotic, and a variety of cell lines that are known in the art may be employed. Alternatively, cell-based screens are performed using cells that have been transformed or transfected with nucleic acids encoding the Fc variants.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

Pre-Clinical Experiments and Animal Models

The biological properties of the Fc variants of the present invention may be characterized in cell, tissue, and whole organism experiments. As is know in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the Fc variants of the present invention, a particular challenge arises when using animal models to evaluate the potential for in-human efficacy of candidate polypeptides—this is due, at least in part, to the fact that Fc variants that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics*, 2002 54:463-468), and the fact that some orthologues simply do not exist in the animal (for example, humans possess an FcγRIIa whereas mice do not). Therapeutics are often tested in mice, including but not limited to nude mice, SCID mice, xenograft mice, and transgenic mice (including knockins and knockouts). For example, an antibody or Fc fusion of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the antibody or Fc fusion to reduce or inhibit cancer growth and metastasis. An alternative approach is the use of a SCID murine model in which immune-deficient mice are injected with human PBLs, conferring a semi-functional and human immune system—with an appropriate array of human FcγRs—to the mice that have subsequently been injected with antibodies or Fc polypeptides that target injected human tumor cells. In such a model, the Fc polypeptides that target the desired antigen (such as her2/neu on SkOV3 ovarian cancer cells) interact with human PBLs within the mice to engage tumoricidal effector functions. Such experimentation may provide meaningful data for determination of the potential of said Fc variant to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the Fc polypeptides of the present invention. Tests of the Fc variants of the present invention in humans are ultimately required for approval as drugs, and thus of course these experiments are contemplated. Thus the Fc variants of the present invention may be tested in humans to determine their therapeutic efficacy, toxicity, pharmacokinetics, and/or other clinical properties.

The Fc variants of the present invention may confer superior performance on Fc polypeptides therapeutics in animal models or in humans. The receptor binding profiles of such Fc variants, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc polypeptide drugs. For example, an Fc variant with reduced binding to FcγRIIIa, FcγRI and FcγRIIa can be selected to eliminate most cell-mediated effector function, or an Fc variant with reduced binding to C1q may be selected to limit complement-mediated effector functions. In some contexts, such effector functions are known to have potential toxic effects, therefore eliminating them may increase the safety of the Fc polypeptide drug, and such improved safety may be characterized in animal models. In some contexts, such effector functions are known to mediate the desirable therapeutic activity, therefore enhancing them may increase the activity or potency of the Fc polypeptide drug and such improved activity or potency may be characterized in animal models.

Optimized Fc variants can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intraorgan (e.g. pancreas, prostate or mammary gland) injection of human tumor cells or fragments of donor patients.

In preferred embodiments, Fc variants of the present invention may be assessed for efficacy in clinically relevant animal models of various human diseases. In many cases, relevant models include various transgenic animals for specific tumor antigens. Relevant transgenic models such as those that express human Fc receptors (e.g., FcγRIIIa including the gamma chain, FcγRI, FcγRIIa, FcγRIIb, and others) could be used to evaluate and test the efficacy of Fc polypeptides of the present invention. Evaluation of Fc variants by the introduction of human genes which directly or indirectly mediate effector function in mice or other rodents, may enable physiological studies of efficacy in tumor toxicity or other diseases such as autoimmune disorders and RA. Human Fc receptors such as FcγRIIIa may possess polymorphisms, such as that at position 158 (V or F as described) which would further enable the introduction of specific and combinations of human polymorphisms into rodents. The various studies involving polymorphism-specific FcγRs is not limited to this section, however, and encompasses all discussions and applications of FcγRs in general as specified in throughout this application. Fc variants of the present invention may confer superior activity on Fc polypeptides in such transgenic models. In particular, variants with binding profiles optimized for human FcγRIIIa mediated activity may show superior activity in transgenic CD16 (FcγRIII) mice. Similar improvements in efficacy in mice transgenic for the other human Fc receptors, e.g. FcγRIIa, FcγRI, etc., may be observed for Fc variants with binding profiles optimized for the respective receptors. Mice transgenic for multiple human receptors would show improved activity for Fc variants with binding profiles optimized for the corresponding multiple receptors, for example as outlined in Table 1.

The introduction of target tumor antigens such as human CD20 into rodent B-cells in the form of a transgenic animal model can be used to provide a more relevant evaluation of efficacy. As such, the target antigen need not be limited to a fully human construct but could be a fusion protein containing the relevant human epitope of the target antigen. In a preferred embodiment, the testing of Fc polypeptides may include transgenic model systems, which include the combination of but not limited to both human target antigen and human Fc receptors (e.g. CD16 and other related receptors mediating effector functions) to evaluate efficacy and tumoricidal activity.

In a preferred embodiment, Fc polypeptides of the present invention that target the Her2 antigen (e.g. Fc variants of mu4D5 or its humanized analogues) may be assessed for efficacy in a clinically relevant mouse model of breast cancer. Examples of relevant models include, but are not limited to: 1) the HER2/neu (neu-N)-transgenic mice, which are derived from the parental FVB/N mouse strain and are transgenic for the rat form of the proto-oncogene HER2/neu (neu); and 2) transgenic mice that overexpress human HER2 under the murine mammary tumor virus promoter (Finkle et al., 2004, Clin Cancer Res. 10 (7):2499-511). Fc polypeptides of the present invention that show superior efficacy in these models represent likely candidates for further development.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules would preferably mimic, in the animal system, the FcγR and/or complement biology of a corresponding candidate human Fc variant. This mimicry is most likely to be manifested by relative association affinities between specific Fc variants and animal vs. human receptors. For example, if one were using a mouse model to assess the potential in-human efficacy of an Fc variant that has enhanced affinity for human FcγRIIIa, an appropriate proxy variant would have enhanced affinity for mouse FcγRIII-2 (mouse CD16-2). Alternatively if one were using a mouse model to assess the potential in-human efficacy of an Fc variant that has reduced affinity for the human inhibitory receptor FcγRIIb, an appropriate proxy variant would have reduced affinity for mouse FcγRII. It should also be noted that the proxy Fc variants could be created in the context of a human Fc variant, an animal Fc variant, or both.

In a preferred embodiment, the testing of Fc variants may include study of efficacy in primates (e.g. cynomolgus monkey model) to facilitate the evaluation of depletion of specific target cells harboring target antigen. Additional primate models include but not limited to that of the rhesus monkey and Fc polypeptides in therapeutic studies of autoimmune, transplantation and cancer.

Toxicity studies are performed to determine the Fc polypeptide related effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into humans. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therepeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/ contaminants have been removed, that the test material is comparable throughout development, and GLP compliance.

The pharmacokinetics (PK) of the Fc variants of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax(Tmax), the area under the plasma concentration-time curve from time 0 to infinity [AUC(0-inf] and apparent elimination half-life (T½). Additional measured parameters could include compartmental analysis of concentration-time data obtained following i.v. administration and bioavailability. Examples of pharmacological/toxicological studies using cynomolgus have been established for Rituxan and Zevalin in which monoclonal antibodies to CD20 are cross-reactive. Biodistribution, dosimetry (for radiolabeled antibodies or Fc fusions), and PK studies can also be done in rodent models. Such studies would evaluate tolerance at all doses administered, toxicity to local tissues, preferential localization to rodent xenograft animal models, depletion of target cells (e.g. CD20 positive cells).

The Fc variants of the present invention may confer superior pharmacokinetics on Fc polypeptide therapeutics in animal systems or in humans. For example, increased binding to FcRn may increase the half-life and exposure of the Fc polypeptide. Alternatively, decreased binding to FcRn may decrease the half-life and exposure of the Fc polypeptide in cases where reduced exposure is favorable, such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of Fc variants of the present invention. Because Fc variants of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The Fc variants of the present invention may target particular effector cell populations and thereby direct Fc polypeptides to recruit certain activities to improve potency or to increase penetration into a particularly favorable physiological compartment. For example, neutrophil activity and localization can be targeted by an Fc variant that preferentially targets FcγRIIIb. Such pharmacodynamic effects may be demonstrated in animal models or in humans.

Therapeutic Use of Fc Variants

The Fc variants of the present invention may be used for various therapeutic purposes. As will be appreciated by those in the art, the Fc variants of the present invention may be used for any therapeutic purpose for which antibodies, Fc fusions, and the like may be used. In a preferred embodiment, the Fc variants are administered to a patient to treat disorders including but not limited to autoimmune and inflammatory diseases, infectious diseases, and cancer.

A "patient" for the purposes of the present invention includes both humans and other animals, preferably mammals and most preferably humans. Thus the Fc variants of the present invention have both human therapy and veterinary applications. The term "treatment" in the present invention is meant to include therapeutic treatment, as well as prophylactic, or suppressive measures for a disease or disorder. Thus, for example, successful administration of an Fc variant prior to onset of the disease results in treatment of the disease. As another example, successful administration of an optimized Fc variant after clinical manifestation of the disease to combat the symptoms of the disease comprises treatment of the disease. "Treatment" also encompasses administration of an optimized Fc variant after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an Fc variant of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the Fc variants of the present invention.

"Cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophagael cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

"Autoimmune diseases" herein include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

"Inflammatory disorders" herein include acute respiratory distress syndrome (ARDS), acute septic arthritis, allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

"Infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibria cholerae, Yersinia pestis,* and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei,* and the like. Infectious diseases may also be caused by protozoa and parasites such as chlamydia, kokzidioa, *leishmania*, malaria, *rickettsia, trypanosoma,* and the like.

Furthermore, Fc variants of the present invention may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

Formulation, Administration, and Dosing

Pharmaceutical compositions are contemplated wherein an Fc variant of the present invention and one or more therapeutically active agents are formulated. Formulations of the Fc variants of the present invention are prepared for storage by mixing said Fc variant having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins;

hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the Fc variant of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The Fc variants disclosed herein may also be formulated as immunoliposomes. A liposome is a small vesicle comprising various types of lipids, phospholipids and/or surfactant that is useful for delivery of a therapeutic agent to a mammal. Liposomes containing the Fc variant are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. No. 4,485,045; U.S. Pat. No. 4,544,545; and PCT WO 97/38731. Liposomes with enhanced circulation time are disclosed in U.S. Pat. No. 5,013,556. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484).

The Fc variant and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the LUPRON DEPOT® (which are injectable microspheres composed of lactic acid-glycolic acid copolymer and leuprolide acetate), poly-D-(−)-3-hydroxybutyric acid, and Pro-Lease® (commercially available from Alkermes), which is a microsphere-based delivery system composed of the desired bioactive molecule incorporated into a matrix of poly-DL-lactide-co-glycolide (PLG).

Administration of the pharmaceutical composition comprising an Fc variant of the present invention, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the Fc variant may be directly applied as a solution or spray. As is known in the art, the pharmaceutical composition may be formulated accordingly depending upon the manner of introduction.

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658). Fc polypeptides of the present invention may be more amenable to subcutaneous administration due to, for example, increased potency, improved serum half-life, or enhanced solubility.

As is known in the art, protein therapeutics are often delivered by IV infusion or bolus. The Fc variants of the present invention may also be delivered using such methods. For example, administration may venious be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Fc variants of the present invention may be more amenable to intrapulmonary delivery. FcRn is present in the lung, and may promote transport from the lung to the bloodstream (e.g. Syntonix WO 04004798, Bitonti et. al. (2004) Proc. Nat. Acad. Sci. 101:9763-8). Accordingly, antibodies or Fc fusions that bind FcRn more effectively in the lung or that are released more efficiently in the bloodstream may have improved bioavailability following intrapulmonary administration. Fc variants of the present invention may also be more amenable to intrapulmonary administration due to, for example, improved solubility or altered isoelectric point.

Furthermore, Fc polypeptides of the present invention may be more amenable to oral delivery due to, for example, improved stability at gastric pH and increased resistance to proteolysis. Furthermore, FcRn appears to be expressed in the intestinal epithelia of adults (Dickinson et al., 1999, J Clin Invest 104:903-11), so Fc polypeptides of the present invention, for example antibodies or Fc fusions, with improved FcRn interaction profiles may show enhanced bioavailability following oral administration. FcRn mediated transport of Fc variants may also occur at other mucus membranes such as those in the gastrointestinal, respiratory, and genital tracts (Yoshida et al., 2004, Immunity 20:769-83).

In addition, any of a number of delivery systems are known in the art and may be used to administer the Fc variants of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the LUPRON DEPOT®, and poly-D-(−)-3-hydroxyburyric acid. It is also possible to administer a nucleic acid encoding the Fc variant of the current invention, for example by retroviral infection, direct injection, or coating with lipids, cell surface receptors, or other transfection agents. In all cases, controlled release systems may be used to release the Fc variant at or close to the desired location of action.

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active Fc variant in the formulation may vary from about 0.1 to 100 weight %. In a preferred embodiment, the concentration of the Fc variant is in the range of 0.003 to 1.0 molar. In order to treat a patient, a therapeutically effective dose of the Fc variant of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, with 1 to 10 mg/kg being preferred.

In some embodiments, only a single dose of the Fc variant is used. In other embodiments, multiple doses of the Fc variant are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the Fc variants of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the Fc variant of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination- and Co-Therapies

The Fc variants of the present invention may be administered concomitantly with one or more other therapeutic regimens or agents. The additional therapeutic regimes or agents may be used to improve the efficacy or safety of the Fc variant. Also, the additional therapeutic regimes or agents may be used to treat the same disease or a comorbidity rather than to alter the action of the Fc variant. For example, an Fc variant of the present invention may be administered to the patient along with chemotherapy, radiation therapy, or both chemotherapy and radiation therapy. The Fc variant of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional Fc variants, FcγRIIb or other Fc receptor inhibitors, or other therapeutic agents.

The terms "in combination with" and "co-administration" are not limited to the administration of said prophylactic or therapeutic agents at exactly the same time. Instead, it is meant that the Fc variant of the present invention and the other agent or agents are administered in a sequence and within a time interval such that they may act together to provide a benefit that is increased versus treatment with only either the Fc variant of the present invention or the other agent or agents. It is preferred that the Fc variant and the other agent or agents act additively, and especially preferred that they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the Fc variants of the present invention are administered with one or more additional molecules comprising antibodies or Fc. The Fc variants of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti 17-IA cell surface antigen antibodies such as Panorex™ (edrecolomab); anti-4-1BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-αVβ1 integrin antibodies such as F-200, M-200, and SJ-749; anti-aVIβ3 integrin antibodies such as abciximab, CNTO-95, Mab-17E6, and Vitaxin™; anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab), Rituxan® (rituximab), Zevalin® (Ibritumomab tiuxetan), and PRO70769; anti-CD22 antibodies such as Lymphocide™ (epratuzumab); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™, and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, Iabetuzumab, and Pentacea™; anti-CTLA-4 antibodies such as MDX-101; anti-CXCR4 antibodies; antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Mucl antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antibodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the Fc variants of the present invention may be co-administered or with one or more other molecules that compete for binding to one or more Fc receptors. For example, co-administering inhibitors of the inhibitory receptor FcγRIIb may result in increased effector function. Similarly, co-administering inhibitors of activating receptors, for example FcγRIIIa, may minimize unwanted effector function. Fc receptor inhibitors include but are not limited to Fc variants that are engineered to act as competitive FcγR inhibitors, as well as other immunoglobulins and specifically intravenous immunoglobulin (IVIg). In one embodiment, the inhibitor is administered and allowed to act before the Fc variant is administered. An alternative way of achieving the effect of sequential dosing would be to provide an immediate release dosage form of the Fc receptor inhibitor and then a sustained release formulation of the Fc variant of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the Fc variants of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclophosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the Fc variants of the present invention include but are not limited to any of the aforementioned chemotherapeutic agents.

A variety of other therapeutic agents may find use for administration with the Fc variants of the present invention. In one embodiment, the Fc variant is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the Fc variant is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

In a preferred embodiment, the Fc variant is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)-phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI57I, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech).

In another embodiment, the Fc variant is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but not limited to: non-steroidal anti-inflammatory drugs (NSAIDs) such as asprin, ibuprofed, celecoxib, diclofenac, etodolac, fenoprofen, indomethacin, ketorolac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, Fc variants of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In a preferred embodiment, cytokines or other agents that stimulate cells of the immune system are co-administered with an Fc variant of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et. al. (2003) Scand. J. Immunol. 57: 221-8), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions. In an alternate embodiment, cytokines or other agents that inhibit effector cell function are co-administered with an Fc variant of the present invention. Such a mode of treatment may limit unwanted effector function.

In an additional embodiment, the Fc variant is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefinetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetracyclenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The Fc variants of the present invention may be combined with other therapeutic regimens. For example, in one embodiment, the patient to be treated with an antibody or Fc fusion of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the Fc variant of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with Fc variant and one or more other anti-cancer therapies, such as described above, can be employed to deplete or substantially deplete the cancer cells prior to transplantation in a recipient patient.

Radiation therapy may also comprise treatment with an isotopically labeled molecule, such as an antibody. Examples of radioimmunotherapeutics include but Zevalin™ (Y-90 labeled anti-CD20), LymphoCide™ (Y-90 labeled anti-CD22) and Bexxar™ (1-131 labeled anti-CD20)

It is of course contemplated that the Fc variants of the invention may employ in combination with still other therapeutic techniques such as surgery or phototherapy.

Clinical Trial Design and Post-Approval Treatment Strategies

Pharmacogenomic approaches to clinical trials and therapy are embodiments of the present invention. A number of the receptors that may interact with the Fc variants of the present invention are polymorphic in the human population. For a given patient or population of patients, the efficacy of the Fc variants of the present invention may be affected by the presence or absence of specific polymorphisms in proteins. For example, FcγRIIIs is polymorphic at position 158, which is commonly either V (high affinity) or F (low affinity). Patients with the V/V homozygous genotype are observed to have a better clinical response to treatment with the anti-CD20 antibody Rituxan® (rituximab) (Carton et al., 2002, Blood 99:754-758; Weng et al., 2003, J Clin Oncol 21:3940-3947; Dall'Ozzo et al., 2004, Cancer Res 64:4664-9). Additional polymorphisms include but are not limited to FcγRIIa R131 or H131, and such polymorphisms are known to either increase or decrease Fc binding and subsequent biological activity, depending on the polymorphism. Fc variants of the present invention may bind preferentially to a particular polymorphic form of a receptor, for example F158 FcγRIIIa, or to bind with equivalent affinity to all of the polymorphisms at a particular position in the receptor, for example both the V158 and F158 polymorphisms of FcγRIIIa. In a preferred embodiment, Fc variants of the present invention that provide equivalent binding to polymorphisms may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In a preferred embodiment, Fc variants of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing an FcγRIIb polymorphism that binds with higher affinity to Fc, could receive a drug containing an Fc variant with reduced binding to such polymorphic form of the receptor, creating a more efficacious drug.

In a preferred embodiment, patients are screened for one or more polymorphisms in order to predict the efficacy of the Fc variants of the present invention. This information may be used, for example, to select patients to include or exclude from clinical trials or, post-approval, to provide guidance to physicians and patients regarding appropriate dosages and treatment options. For example, the anti-CD20 antibody rituximab is minimally effective in patients that are homozygous or heterozygous for F158 FcγRIIIa (Carton et al., 2002, Blood 99:754-758; Weng et al., 2003, J Clin Oncol 21:3940-3947; Dall'Ozzo et al., 2004, Cancer Res 64:4664-9). Such patients may show an improved clinical response to antibodies comprising an Fc variant of the present invention. In one embodiment, patients are selected for inclusion in clinical trials if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an Fc variant engineered to be specifically efficacious for such population, or alternatively where such therapy contains an Fc variant that does not show differential activity to the different forms of the polymorphism.

Included in the present invention are diagnostic tests to identify patients who are likely to show a favorable clinical response to an Fc variant of the present invention, or who are likely to exhibit a significantly better response when treated with an Fc variant of the present invention versus one or more currently used antibody therapeutics. Any of a number of methods for determining FcγR polymorphisms in humans known in the art may be used.

In a preferred embodiment, patients are screened to predict the efficacy of the Fc polypeptides of the present invention. This information may be used, for example, to select patients to include or exclude from clinical trials or, post-approval, to provide guidance to physicians and patients regarding appropriate dosages and treatment options. Screening may involve the determination of the expression level or distribution of the target antigen. For example, the level of Her2/neu expression is currently used to select which patients will most favorably respond to trastuzumab therapy. Screening may also involve determination of genetic polymorphisms, for example polymorphisms related to FcγRs or FcαRs. For example, patients who are homozygous or heterozygous for the F158 polymorphic form of FcγRIIIa may respond clinically more favorably to the Fc polypeptides of the present invention. Information obtained from patient screening may be used to select patients for inclusion in clinical trials, to determine appropriate dosages and treatment regimens, or for other clinical applications. Included in the present invention are diagnostic tests to identify patients who are likely to show a favorable clinical response to an Fc polypeptide of the present invention, or who are likely to exhibit a significantly better response when treated with an Fc polypeptide of the present invention versus one or more currently used biotherapeutics. Any of a number of methods for determining antigen expression levels, antigen distribution, and/or genetic polymorphisms in humans known in the art may be used.

Furthermore, the present invention comprises prognostic tests performed on clinical samples such as blood and tissue samples. Such tests may assay for effector function activity, including but not limited to opsonization, ADCC, CDC, ADCP, or for killing, regardless of mechanism, of cancerous or otherwise pathogenic cells. In a preferred embodiment, ADCC assays, such as those described herein, are used to predict, for a specific patient, the efficacy of a given Fc polypeptide of the present invention. Such information may be used to identify patients for inclusion or exclusion in clinical trials, or to inform decisions regarding appropriate dosages and treatment regemins. Such information may also be used to select a drug that contains a particular Fc variant that shows superior activity in such an assay.

EXAMPLES

Examples are provided below to illustrate the present invention. These examples are not meant to constrain the present invention to any particular application or theory of operation.

For all positions discussed in the present invention, numbering is according to the EU index or EU numbering scheme (Kabat et al., 1991, *Sequences of Proteins of Immunological Interest*, 5th Ed., United States Public Health Service, National Institutes of Health, Bethesda), which refers to the numbering of the EU antibody (Edelman et al., 1969, Proc Natl Acad Sci USA 63:78-85). Those skilled in the art of antibodies will appreciate that these conventions consist of nonsequential numbering in specific regions of an immunoglobulin sequence, enabling a normalized reference to conserved positions in immunoglobulin families. Accordingly, the positions of any given immunoglobulin as defined by EU index will not necessarily correspond to its sequential sequence. FIG. 3 shows the sequential and EU index numbering schemes for the antibody alemtuzumab in order to illustrate this principal more clearly. It should also be noted that polymorphisms have been observed at a number of Fc positions, including but not limited to Kabat 270, 272, 312, 315, 356, and 358, and thus slight differences between the presented sequence and sequences in the scientific literature may exist.

Figure 4:
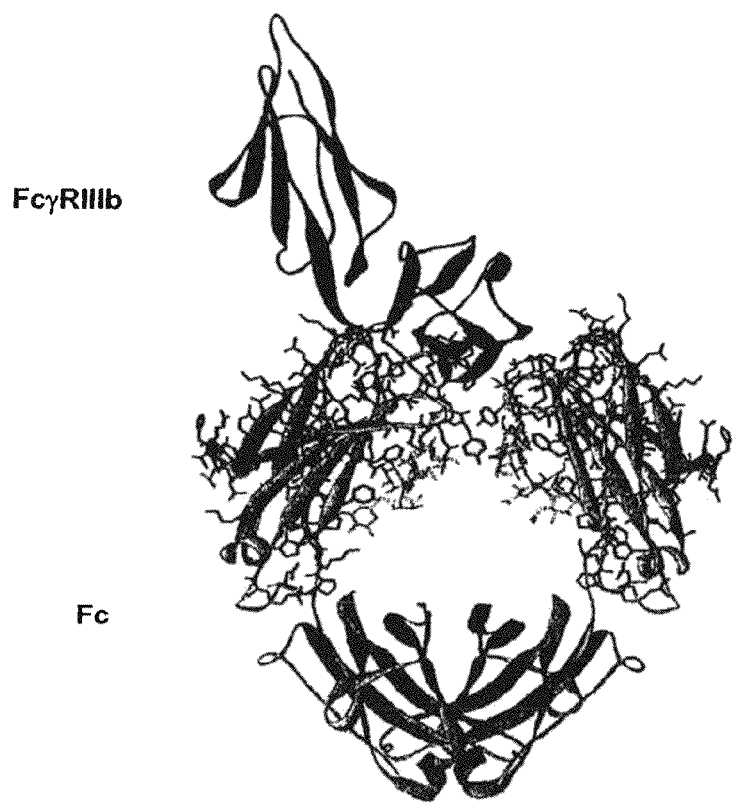
FIG. 4. Residues at which amino acid modifications were made in the Fc variants of the present invention, mapped onto the Fc/FcγRIIIb complex structure 1IIS. Fc is shown as a gray ribbon diagram, and FcγRIIIb is shown as a black ribbon. Experimental library residues are shown in black, the N297 carbohydrate is shown in grey.
Figure 41M:
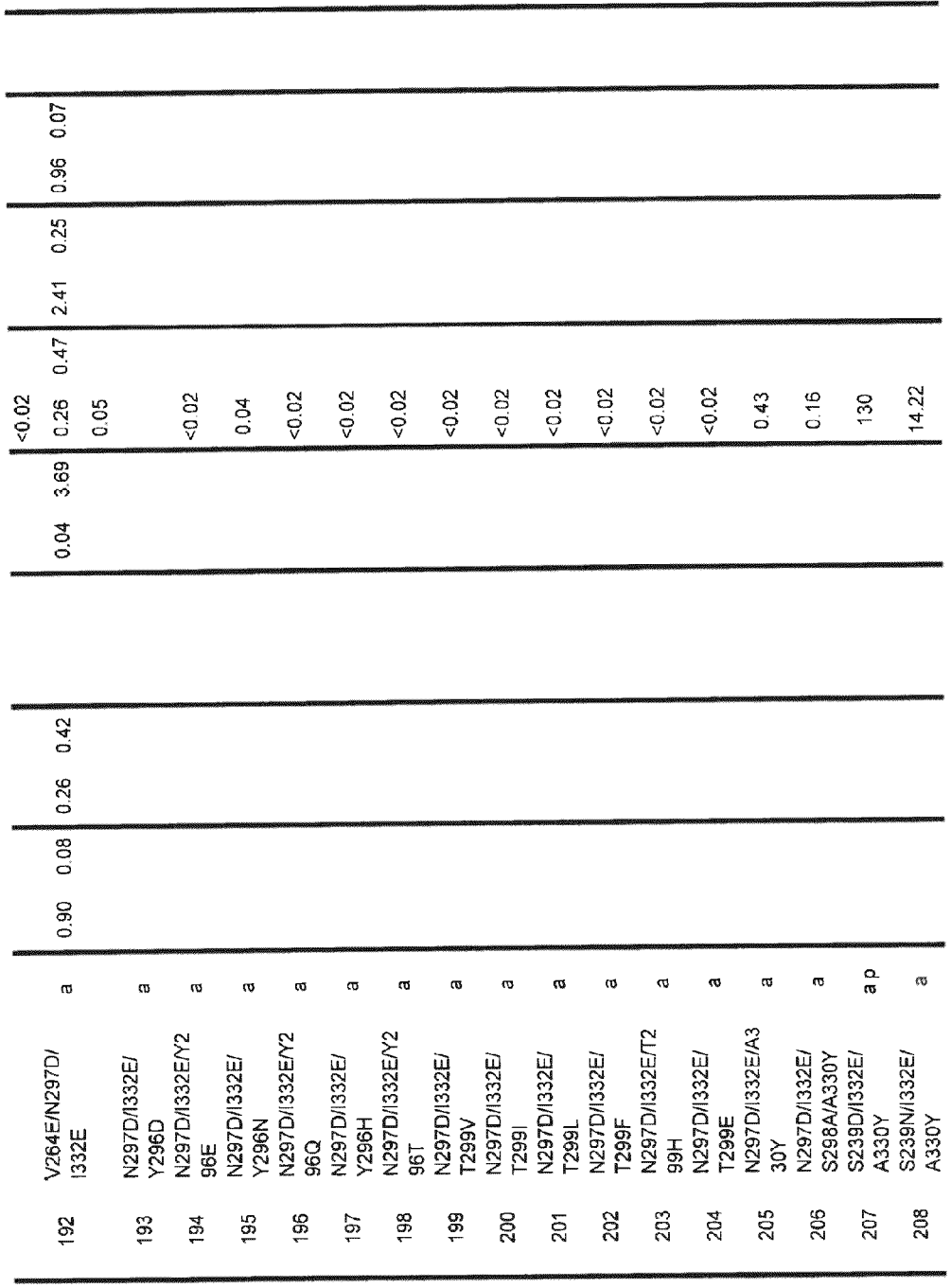
FIGS. 41A-41PP depicts the set of Fc variants that were constructed and experimentally tested.

Fc variants and Fc variant libraries were designed using computational- and sequence-based methods as described in U.S. Ser. No. 10/672,280 and U.S. Ser. No. 10/822,231. Experimental libraries were designed in successive rounds of computational and experimental screening. Design of subsequent Fc libraries benefitted from feedback from prior libraries, and thus typically comprised combinations of Fc variants that showed favorable properties in the previous screen. FIG. 4 shows residues at which amino acid modifications were made in the Fc variants of the present invention, mapped onto the human Fc/FcγRIIIb structure. The entire set of Fc variants that were constructed and experimentally tested is shown in FIG. 41.

Example 1

Molecular Biology and Protein Expression/Purification

The majority of experimentation on the Fc variants was carried out in the context of the anti-cancer antibody alemtuzumab (Campath®, a registered trademark of Ilex Pharmaceuticals LP). Alemtuzumab binds a short linear epitope within its target antigen CD52 (Hale et al., 1990, *Tissue Antigens* 35:118-127; Hale, 1995, *Immunotechnology* 1:175-187). Alemtuzumab has been chosen as the primary engineering template because its efficacy is due in part to its ability to recruit effector cells (Dyer et al., 1989, *Blood* 73:1431-1439; Friend et al., 1991, *Transplant Proc* 23:2253-2254; Hale et al., 1998, *Blood* 92:4581-4590; Glennie et al., 2000, *Immunol Today* 21:403-410), and because production and use of its antigen in binding assays are relatively straightforward. In order to evaluate the optimized Fc variants of the present invention in the context of other antibodies, select Fc variants were evaluated in the anti-Her2 antibody trastuzumab (Herceptin®, a registered trademark of Genentech), the anti-CD20 antibody rituximab (Rituxan®, a registered trademark of IDEC Pharmaceuticals Corporation), the anti-EGFR antibody cetuximab (Erbitux®, a registered trademark of Imclone), and the anti-CD20 antibody PRO70769 (PCT/US2003/040426, entitled "Immunoglobulin Variants and Uses Thereof"). The use of alemtuzumab, trastuzumab, rituximab, cetuximab, and PRO70769 for screening purposes is not meant to constrain the present invention to any particular antibody.

Figure 5:
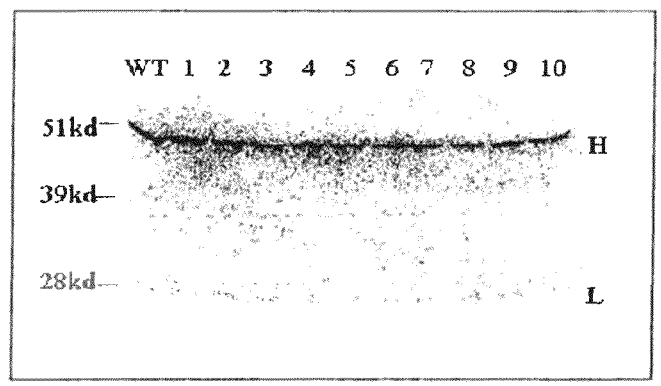
FIG. 5. Expression of Fc variant and wild type (WT) proteins of alemtuzumab in 293T cells. Plasmids containing alemtuzumab heavy chain genes (WT or variants) were co-transfected with plasmid containing the alemtuzumab light chain gene. Media were harvested 5 days after transfection. For each transfected sample, 10 ul medium was loaded on a SDS-PAGE gel for Western analysis. The probe for Western was peroxidase-conjugated goat-anti human IgG (Jackson Immuno-Research, catalog #109-035-088). WT: wild type alemtuzumab; 1-10: alemtuzumab variants. H and L indicate antibody heavy chain and light chain, respectively.
Figure 6:
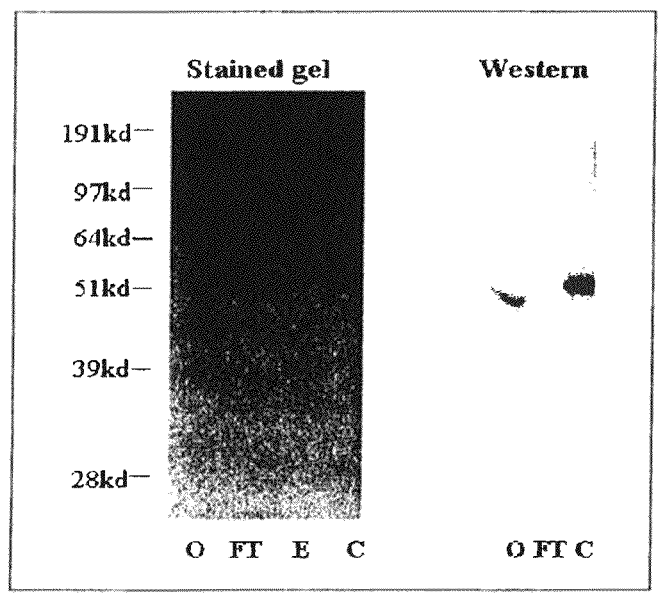
FIG. 6. Purification of alemtuzumab using protein A chromatography. WT alemtuzumab proteins was expressed in 293T cells and the media was harvested 5 days after transfection. The media were diluted 1:1 with PBS and purified with protein A (Pierce, Catalog #20334). O: original sample before purification; FT: flow through; E: elution; C: concentrated final sample. The left picture shows a Simple Blue-stained SDS-PAGE gel, and the right shows a western blot labeled using peroxidase-conjugated goat-anti human IgG.
Figure 7:
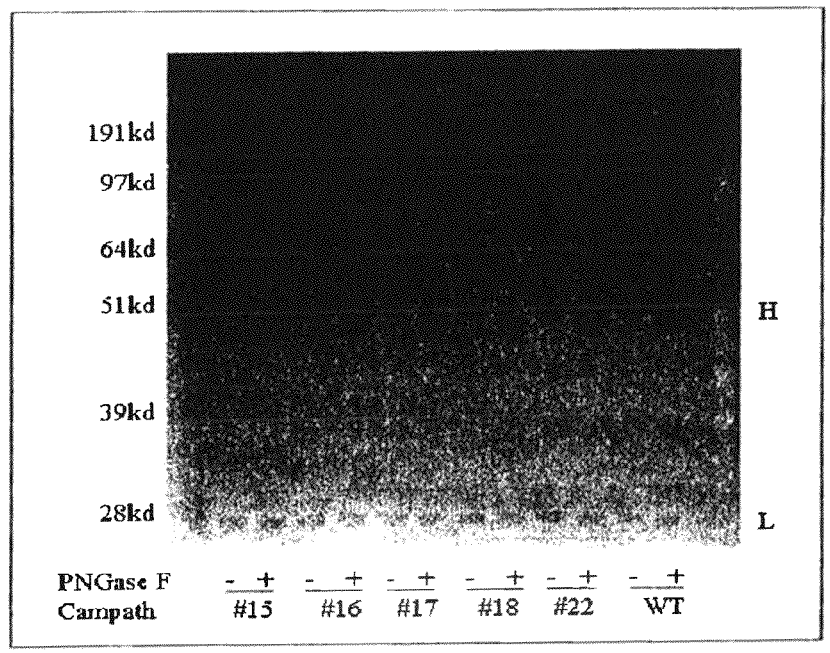
FIG. 7. Production of deglycosylated antibodies. Wild type and variants of alemtuzumab were expressed in 293T cells and purified with protein A chromatography. Antibodies were incubated with peptide-N-glycosidase (PNGase F) at 37° C. for 24 h. For each antibody, a mock treated sample (−PNGase F) was done in parallel. WT: wild-type alemtuzumab; #15, #16, #17, #18, #22: alemtuzumab variants F241E/F243R/V262E/V264R, F241E/F243Q/V262T/V264E, F241R/F243Q/V262T/V264R, F241E/F243Y/V262T/V264R, and I332E respectively. The faster migration of the PNGase F treated versus the mock treated samples represents the deglycosylated heavy chains.

The IgG1 full length light ($V_L$-$C_L$) and heavy ($V_H$-Cγ1-Cγ2-Cγ3) chain antibody genes for alemtuzumab (campath-1H, James et al., 1999, *J Mol Biol* 289: 293-301), trastuzumab (hu4D5-8; Carter et al., 1992, *Proc Natl Acad Sci USA* 89:4285-4289; Gerstner et al., 2002, *J. Mol. Biol.,* 321: 851-862), rituximab (C2B8, U.S. Pat. No. 6,399,061), and cetuximab (C225, PCT US96/09847) were constructed using recursive PCR with convenient end restriction sites to facilitate subcloning. The genes were ligated into the mammalian expression vector pcDNA3.1Zeo (Invitrogen), comprising the full length light kappa (Cκ) and heavy chain IgG1 constant regions. The $V_H$-Cγ1-Cγ2-Cγ3 clone in pcDNA3.1zeo was used as a template for mutagenesis of the Fc region. Mutations were introduced into this clone using PCR-based mutagenesis or quick-change mutagenesis (Stratagene) techniques. Fc variants were sequenced to confirm the fidelity of the sequence. Plasmids containing heavy chain gene ($V_H$-Cγ1-Cγ2-Cγ3) (wild-type or variants) were co-transfected with plasmid containing light chain gene ($V_L$-$C_L$) into 293T cells. Media were harvested 5 days after transfection. Expression of immunoglobulin was monitored by screening the culture supernatant of transfectomas by western using peroxidase-conjugated goat-anti human IgG (Jackson ImmunoResearch, catalog #109-035-088). FIG. 5 shows expression of wild-type alemtuzumab and variants 1 through 10 in 293T cells. Antibodies were purified from the supernatant using protein A affinity chromatography (Pierce, Catalog #20334. FIG. 6 shows results of the protein purification for WT alemtuzumab. Antibody Fc variants showed similar expression and purification results to WT. Some Fc variants were deglycosylated in order to determine their solution and functional properties in the absence of carbohydrate. To obtain deglycosylated antibodies, purified alemtuzumab antibodies were incubated with peptide-N-glycosidase (PNGase F) at 37° C. for 24 h. FIG. 7 presents an SDS PAGE gel confirming deglycosylation for several Fc variants and WT alemtuzumab.

Figure 8:
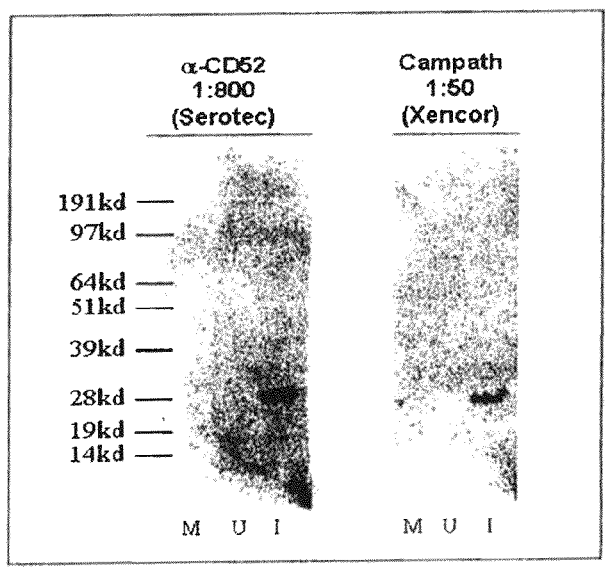
FIG. 8. Alemtuzumab expressed from 293T cells binds its antigen. The antigenic CD52 peptide, fused to GST, was expressed in $E.\ coli$ BL21 (DE3) under IPTG induction. Both uninduced and induced samples were run on a SDS-PAGE gel, and transferred to PVDF membrane. For western analysis, either alemtuzumab from Sotec (a-CD52, Sotec) (final concentration 2.5 ng/ul) or media of transfected 293T cells (Campath, Xencor) (final alemtuzumab concentration approximately 0.1-0.2 ng/ul) were used as primary antibody, and peroxidase-conjugated goat-anti human IgG was used as secondary antibody. M: pre-stained marker; U: un-induced sample for GST-CD52; I: induced sample for GST-CD52.

In order to confirm the functional fidelity of alemtuzumab produced under these conditions, the antigenic CD52 peptide, fused to GST, was expressed in *E. coli* BL21 (DE3) under IPTG induction. Both un-induced and induced samples were run on a SDS PAGE gel, and transferred to PVDF membrane. For western analysis, either alemtuzumab from Sotec (final concentration 2.5 ng/ul) or media of transfected 293T cells (final alemtuzumab concentration about 0.1-0.2 ng/ul) were used as primary antibody, and peroxidase-conjugated goat-anti human IgG was used as secondary antibody. FIG. 8 presents these results. The ability to bind target antigen confirms the structural and functional fidelity of the expressed alemtuzumab. Fc variants that have the same variable region as WT alemtuzumab are anticipated to maintain a comparable binding affinity for antigen.

Figure 9:
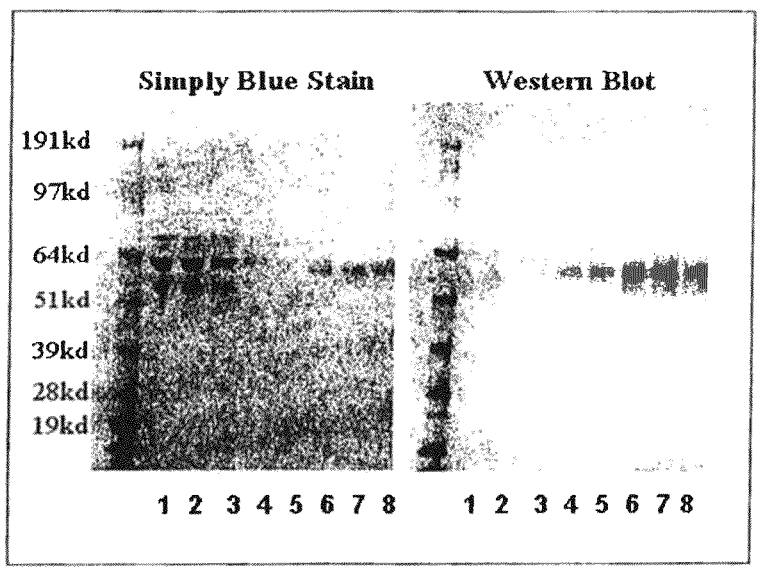
FIG. 9. Expression and purification of extracellular region of human V158 FcγRIIIa. Tagged FcγRIIIa was transfected in 293T cells, and media containing secreted FcγRIIIa were harvested 3 days later and purified using affinity chromatography. 1: media; 2: flow through; 3: wash; 4-8: serial elutions. Both simple blue-stained SDS-PAGE gel and western result are shown. For the western blot, membrane was probed with anti-GST antibody.

The gene encoding the extracellular region of human V158 FcγRIIIa was obtained by PCR from a clone obtained from the Mammalian Gene Collection (MGC:22630). F158 FcγRIIIa was constructed by mutagenesis of the V158 FcγRIIIa gene. The genes encoding the extracellular regions of human FcγRI, human FcγRIIa, human FcγRIIb, human FcγRIIc, mouse FcγRIII, and human FcRn α chain and β-microglobulin chain were constructed using recursive PCR. FcγRs and FcRn α chain were fused at the C-terminus with a 6×His-tag and a GST-tag. All genes were subcloned into the pcDNA3.1zeo vector. For expression, vectors containing human FcγRs were transfected into 293T cells, FcRn α chain and β-microglobulin chain were co-transfected into 293T cells, and mouse FcγRIII was transfected into NIH3T3 cells. Media containing secreted receptors were harvested 3 days later and purified using Nickel affinity chromatography. For western analysis, membrane was probed with an anti-GST antibody. FIG. 9 presents an SDS PAGE gel that shows the results of expression and purification of human V158 FcγRIIIa. Purified human C1q protein complex was purchased commercially (Quidel Corp., San Diego).

Example 2

Fc Ligand Binding Assays

Binding to the human Fc ligands FcγRI, FcγRIIa, FcγRIIb, FcγRIIc, FcγRIIIa, C1q, and FcRn was measured for the designed Fc variants. Binding affinities were measured using an AlphaScreen™ assay (Amplified Luminescent Proximity Homogeneous Assay (ALPHA), PerkinElmer, Wellesley, Mass.), a bead-based luminescent proximity assay. Laser excitation of a donor bead excites oxygen, which if sufficiently close to the acceptor bead generates a cascade of chemiluminescent events, ultimately leading to fluorescence emission at 520-620 nm. WT alemtuzumab antibody was biotinylated by standard methods for attachment to streptavidin donor beads, and GST-tagged FcγRs and FcRn were bound to glutathione chelate acceptor beads. For the C1q binding assay, untagged C1q protein was conjugated with Digoxygenin (DIG, Roche) using N-hydrosuccinimide (NHS) chemistry and bound to DIG acceptor beads. For the protein A binding assay, protein A acceptor beads were purchased directly from PerkinElmer. The AlphaScreen assay was applied as a competition assay for screening Fc variants. In the absence of competing Fc variants, WT antibody and FcγR interact and produce a signal at 520-620 nm. Addition of untagged Fc variant competes with the WT Fc/FcγR interaction, reducing fluorescence quantitatively to enable determination of relative binding affinities. Fc variants were screened in the context of either alemtuzumab or trastuzumab, and select Fc variants were also screened in the context of rituximab and cetuximab.

Figure 10:
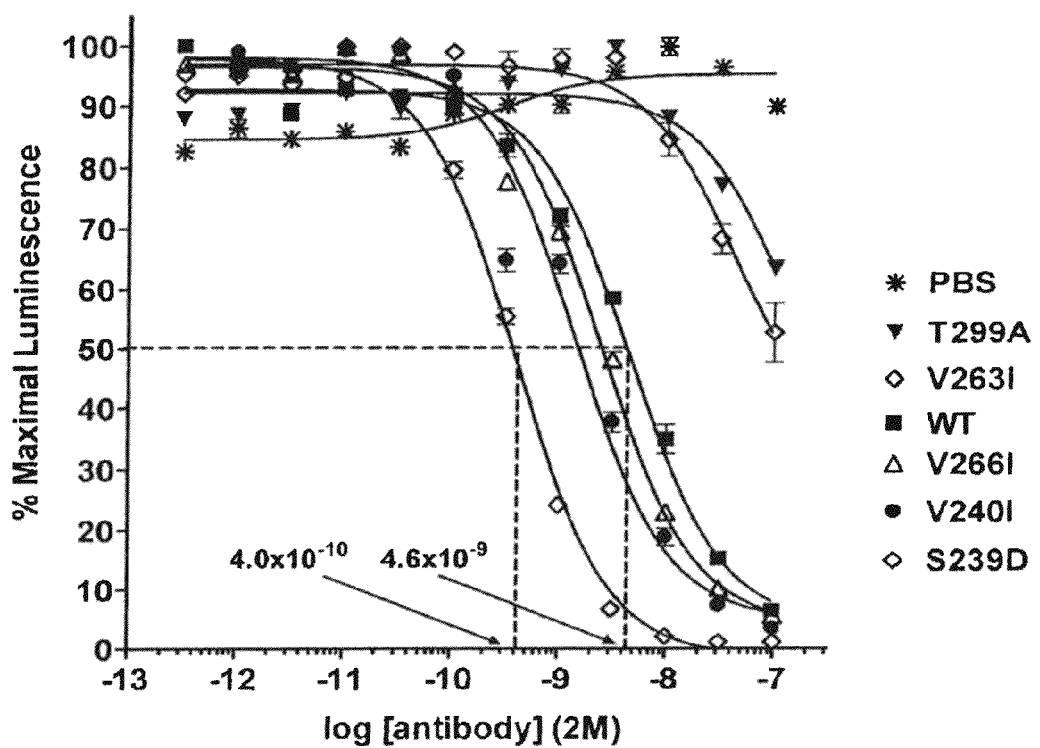
FIG. 10. Binding to human V158 FcγRIIIa by select alemtuzumab Fc variants from the experimental library as determined by the AlphaScreen™ assay, described in Example 2. In the presence of competitor antibody (Fc variant or WT alemtuzumab) a characteristic inhibition curve is observed as a decrease in luminescence signal. Phosphate buffer saline (PBS) alone was used as the negative control. The binding data were normalized to the maximum and minimum luminescence signal for each particular curve, provided by the baselines at low and high antibody concentrations respectively. The curves represent the fits of the data to a one site competition model using nonlinear regression. These fits provide IC50s for each antibody, illustrated for WT and S239D by the dotted lines.
Figure 11A:
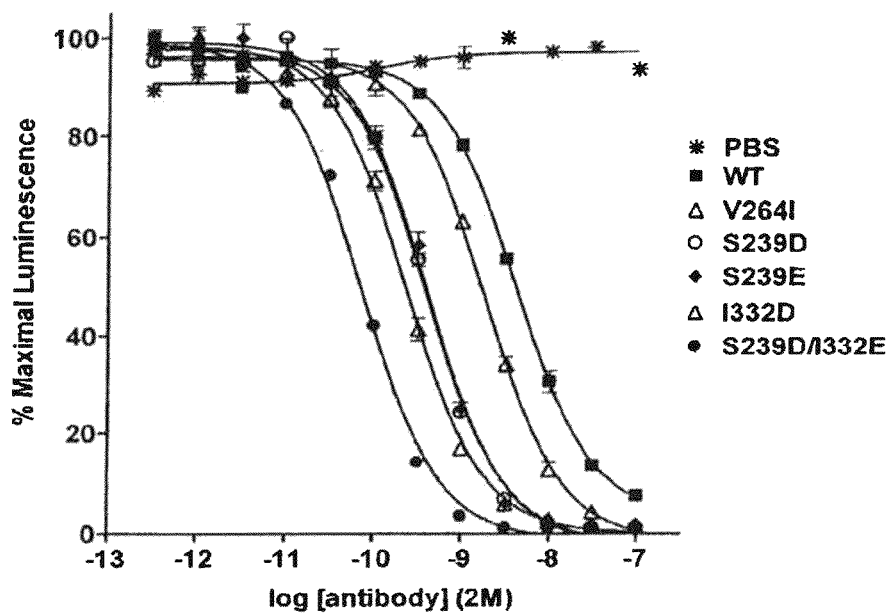
FIGS. 11a and 11b. AlphaScreen assay showing binding of select alemtuzumab (FIG. 11a) and trastuzumab (FIG. 11b) Fc variants to human Val158 FcγRIIIa. The binding data were normalized to the upper and lower baselines for each particular antibody, and the curves represent the fits of the data to a one site competition model. PBS was used as a negative control.
Figure 11B:
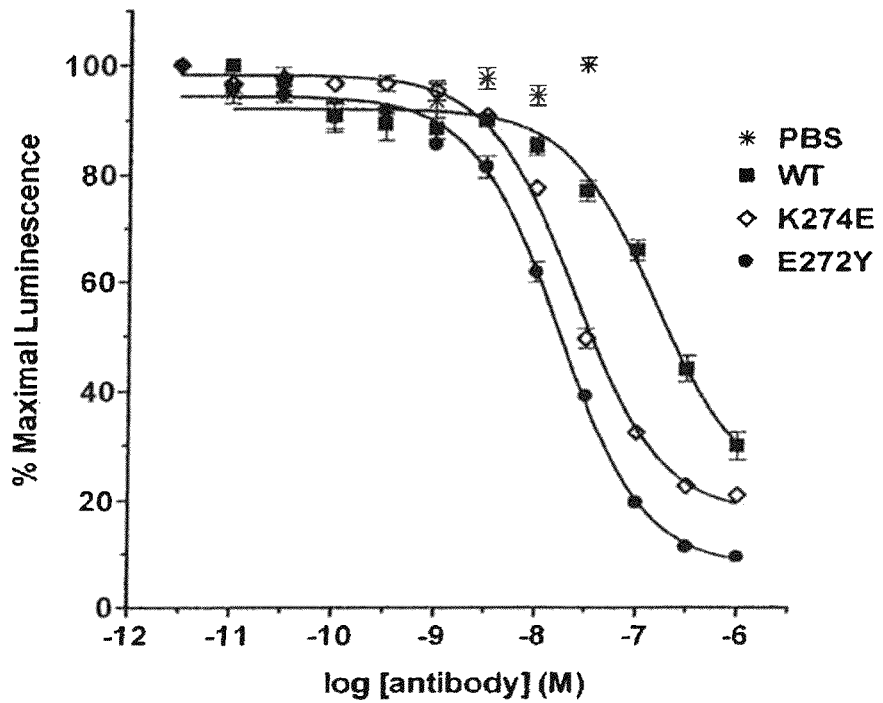

FIG. 10 shows AlphaScreen data for binding to human V158 FcγRIIIa by select Fc variants. The binding data were normalized to the maximum and minimum luminescence signal for each particular curve, provided by the baselines at low and high antibody concentrations respectively. The data were fit to a one site competition model using nonlinear regression, and these fits are represented by the curves in the figure. These fits provide the inhibitory concentration 50% (IC50) (i.e. the concentration required for 50% inhibition) for each antibody, illustrated by the dotted lines in FIG. 10, thus enabling the relative binding affinities of Fc variants to be quantitatively determined. By dividing the IC50 for each variant by that of WT alemtuzumab, the fold-enhancement or reduction relative to WT Herceptin (Fold WT) are obtained. Here, WT alemtuzumab has an IC50 of $(4.63 \times 10^{-9}) \times (2) = 9.2$ nM, whereas S239D has an IC50 of $(3.98 \times 10^{-10}) \times (2) = 0.8$ nM. Thus S239D alemtuzumab binds 9.2 nM/0.8 nM=11.64-fold more tightly than WT alemtuzumab to human V158 FcγRIIIa. FIGS. 11*a* and 11*b* provide AlphaScreen data showing additional Fc variants, with substitutions at positions 239, 264, 272, 274, and 332, that bind more tightly to FcγRIIIa, and thus are candidates for improving the effector function of Fc polypeptides.

Figure 12:
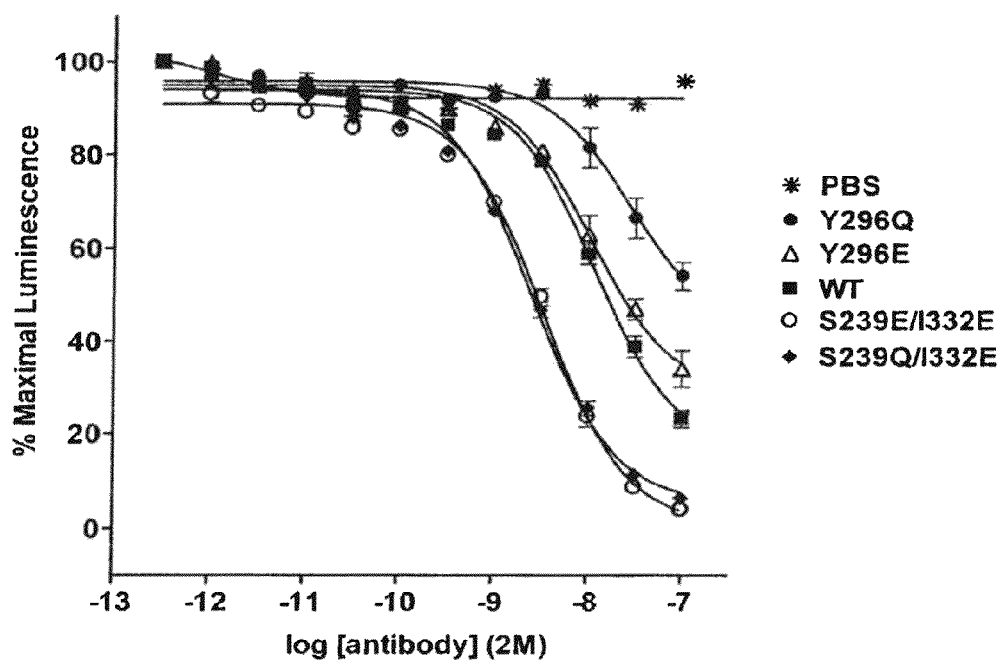
FIG. 12. AlphaScreen assay showing binding of select alemtuzumab Fc variants to human FcγRIIb. The binding data were normalized to the upper and lower baselines for each particular antibody, and the curves represent the fits of the data to a one site competition model. PBS was used as a negative control.
Figure 13:
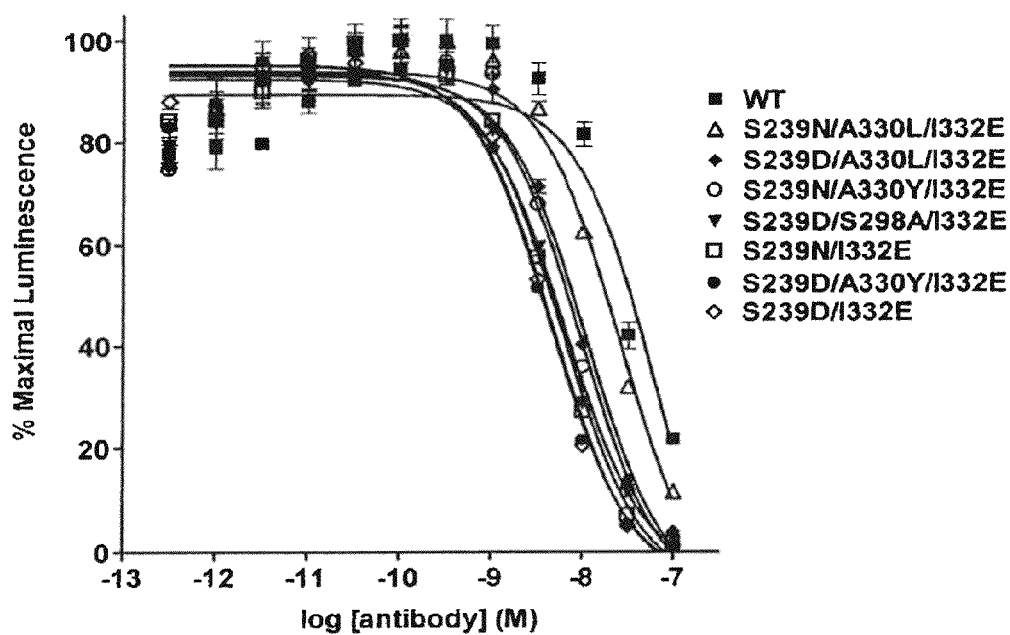
FIG. 13. AlphaScreen assay showing binding of select alemtuzumab Fc variants to human R131FcγRIIa. The binding data were normalized to the upper and lower baselines for each particular antibody, and the curves represent the fits of the data to a one site competition model.
Figure 14:
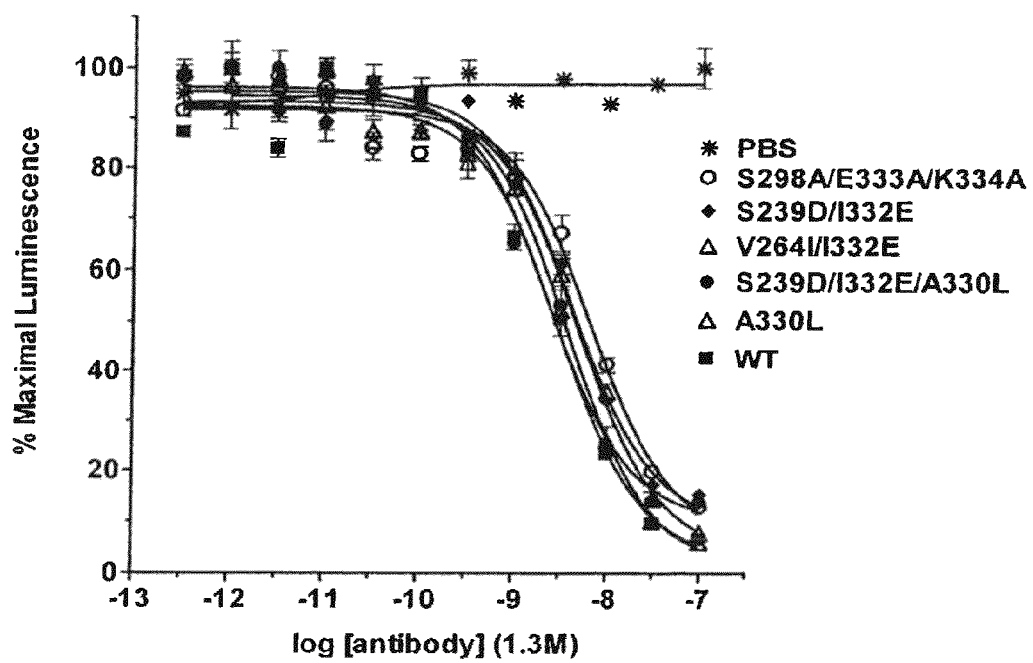
FIG. 14. AlphaScreen assay measuring binding of select alemtuzumab Fc variants to human FcRn, as described in Example 2. The binding data were normalized to the upper and lower baselines for each particular antibody, and the curves represent the fits of the data to a one site competition model. PBS was used as a negative control.
Figure 15:
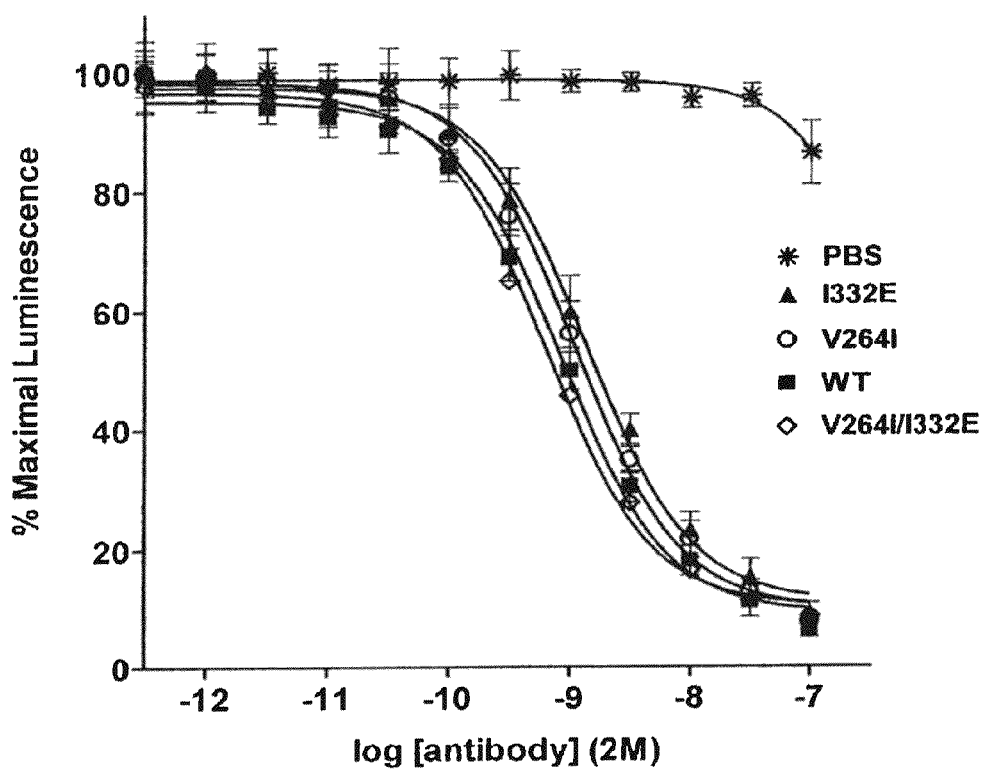
FIG. 15. AlphaScreen assay measuring binding of select alemtuzumab Fc variants to bacterial protein A, as described in Example 2. The binding data were normalized to the upper and lower baselines for each particular antibody, and the curves represent the fits of the data to a one site competition model. PBS was used as a negative control.

Fc variants were also screened in parrallel for other Fc ligands. As discussed, the inhibitory receptor FcγRIIb plays an important role in effector function. Exemplary data for binding of select Fc variants of the invention to human FcγRIIb, as measured by the AlphaScreen, are provided in FIG. 12. FcγRIIa is an activating receptor that is highly homologous to FcγRIIb. Exemplary data for binding of select Fc variants to the R131 polymorphic form of human FcγRIIa are provided in FIG. 13. Another important Fc ligand is the neonatal Fc receptor FcRn. As discussed, this receptor binds to the Fc region between the Cγ2 and Cγ3 domains; because binding mediates endosomal recycling, affinity of Fc for FcRn is a key determinant of antibody and Fc fusion pharmacokinetics. Exemplary data showing binding of select Fc variants to FcRn, as measured by the AlphaScreen, are provided in FIG. 14. The binding site for FcRn on Fc, between the Cγ2 and Cγ3 domains, is overlapping with the binding site for bacterial proteins A and G. Because protein A is frequently employed for antibody purification, select variants were tested for binding to this Fc ligand. FIG. 15 provides these AlphaScreen data. Although protein A was not included in the parrallel screen for all variants, the ability of the Fc variants to be purified using protein A chromatography (see Example 1) implies that for the majority of Fc variants the capacity to bind protein A, and moreover the integrity of the Cγ2-Cγ3 hinge region, are unaffected by the Fc substitutions.

The data for binding of Fc variants to FcγRI, FcγRIIa, FcγRIIb, FcγRIIc, FcγRIIIa, C1q, and FcRn were analyzed as described above for FIG. 11. The fold-enhancement or reduction relative to WT for binding of each variant to each Fc ligand, as measured by the AlphaScreen, are provided in FIG. 41. The table presents for each variant the variant number (Variant), the substitution(s) of the variant, the antibody context (Context), the fold affinity relative to WT (Fold) and the confidence (Conf) in the fold affinity for binding to each Fc ligand, and the IIIa:IIb specificity ratio (IIIa:IIb) (see below). Multiple data sets were acquired for many of the variants, and all data for a given variant are grouped together. The context of the antibody indicates which antibodies have been constructed with the particular Fc variant; a=alemtuzumab, t=trastuzumab, r=rituximab, c=cetuximab, and p=PRO70769. The data provided were acquired in the context of the first antibody listed, typically alemtuzumab, although in some cases trastuzumab. An asterix (*) indicates that the data for the given Fc ligand was acquired in the context of trastuzumab. A fold (Fold) above 1 indicates an enhancement in binding affinity, and a fold below 1 indicates a reduction in binding affinity relative to the parent antibody for the given Fc ligand. Confidence values (Conf) correspond to the log confidence levels, provided from the fits of the data to a sigmoidal dose response curve. As is known in the art, a lower Conf value indicates lower error and greater confidence in the Fold value. The lack of data for a given variant and Fc ligand indicates either that the fits to the data did not provide a meaningful value, or that the variant was not tested for that Fc ligand.

FIG. 41 shows that a number of Fc variants have been obtained with enhanced affinities and altered specificities for the various Fc ligands. Some Fc variants of the present invention provide selective enhancement in binding affinity to different Fc ligands, whereas other provide selective reduction in binding affinity to different Fc ligands. By "selective enhancement" as used herein is meant an improvement in or a greater improvement in binding affinity of an Fc variant to one or more Fc ligands relative to one or more other Fc ligands. For example, for a given variant, the Fold WT for binding to, say FcγRIIa, may be greater than the Fold WT for binding to, say FcγRIIb. By "selective reduction" as used herein is meant a reduction in or a greater reduction in binding affinity of an Fc variant to one or more Fc ligands relative to one or more other Fc ligands. For example, for a given variant, the Fold WT for binding to, say FcγRI, may be lower than the Fold WT for binding to, say FcγRIIb. As an example of such selectivity, G236S provides a selective enhancement to FcγRII's (IIa, IIb, and IIc) relative to FcγRI and FcγRIIIa, with a somewhat greater enhancement to FcγRIIa relative to FcγRIIb and FcγRIIc. G236A, however, is highly selectively enhanced for FcγRIIa, not only with respect to FcγRI and FcγRIIIa, but also over FcγRIIb and FcγRIIc. Selective enhancements and reductions are observed for a number of Fc variants, including but not limited to variants comprising substitutions at residues L234, L235, G236, S267, H268, R292, E293, Q295, Y300, S324, A327, L328, A330, and T335. Overall, the data provided in FIG. 41 show that it is indeed possible to tune the Fc region for Fc ligand specificity, often by using very subtle mutational differences, despite the fact that a number of highly homologous receptors bind to the same FcγR binding site. The present invention provides a number of Fc variants that may be used to selectively enhance, as well as selectively reduce, affinity of an Fc polypeptide for certain Fc ligands relative to others. Collections of Fc variants such as these will not only enable the generation of antibodies and Fc fusions that have effector function tailored for the desired outcome, but they also provide a unique set of reagents with which to experimentally investigate and characterize effector function biology.

Figure 16A:
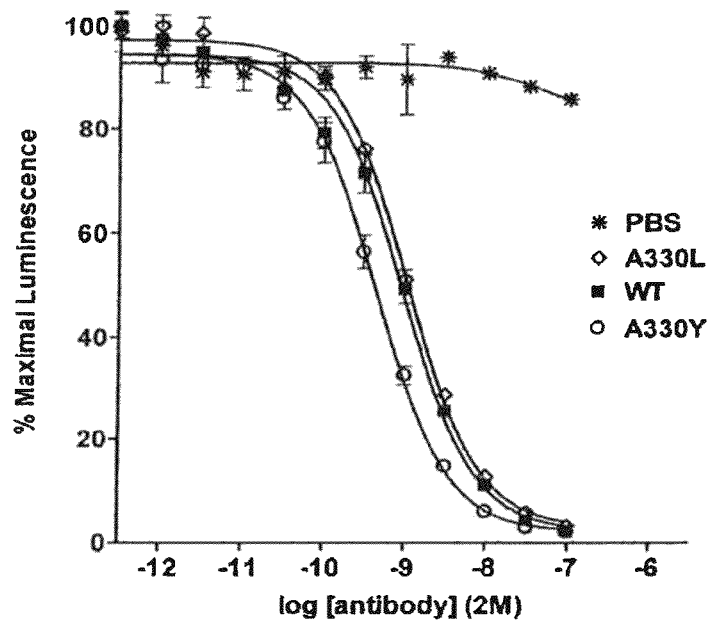
FIGS. 16a-16b. AlphaScreen assay comparing binding of select alemtuzumab Fc variants to human V158 FcγRIIIa (FIG. 16a) and human FcγRIIb (FIG. 16b). The binding data were normalized to the upper and lower baselines for each particular antibody, and the curves represent the fits of the data to a one site competition model. PBS was used as a negative control.
Figure 16B:
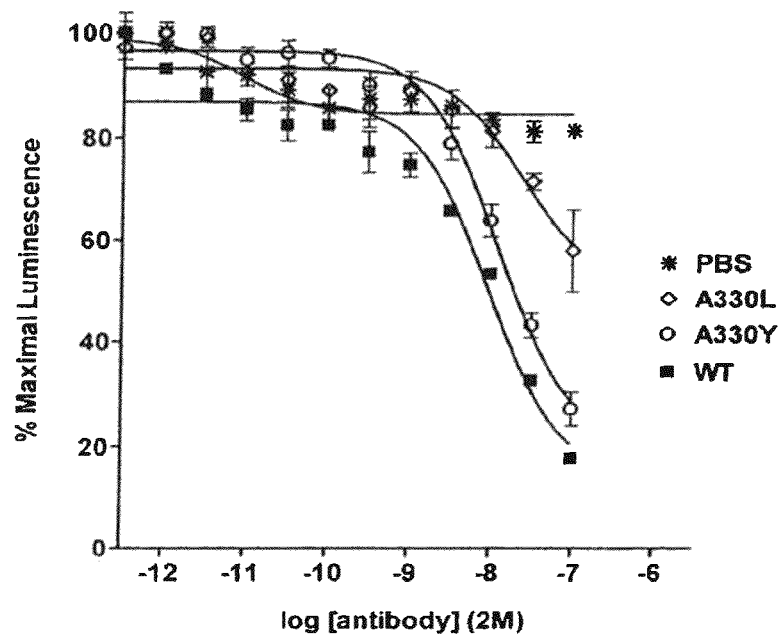

As discussed, optimal effector function may result from Fc variants wherein affinity for activating FcγRs is greater than affinity for the inhibitory FcγRIIb. Indeed a number of Fc variants have been obtained that show differentially enhanced binding to FcγRIIIa over FcγRIIb. AlphaScreen data directly comparing binding to FcγRIIIa and FcγRIIb for two Fc variants with this specificity profile, A330L and A330Y, are shown in FIGS. 16a and 16b. This concept can be defined quantitatively as the fold-enhancement or -reduction of the activating FcγRIIIa (FIG. 41, column 12) divided by the fold-enhancement or -reduction of the inhibitory FcγRIIb (FIG. 41, column 8), herein referred to as the "FcγRIIIa-fold:FcγRIIb-fold ratio" or "IIIa:IIb ratio". This value is provided in column 18 of FIG. 41 (as IIIa:IIb). Combination of A330L and A330Y with other variants, for example A330L/I332E, A330Y/I332, and S239D/A330L/I332E, provide very favorable IIIa:IIb ratios. FIG. 41 shows that a number of Fc variants provide a positive, favorable FcγRIIIa to FcγRIIb specificity profile, with a IIIa:IIb ratio as high as 86:1.

Figure 17A:
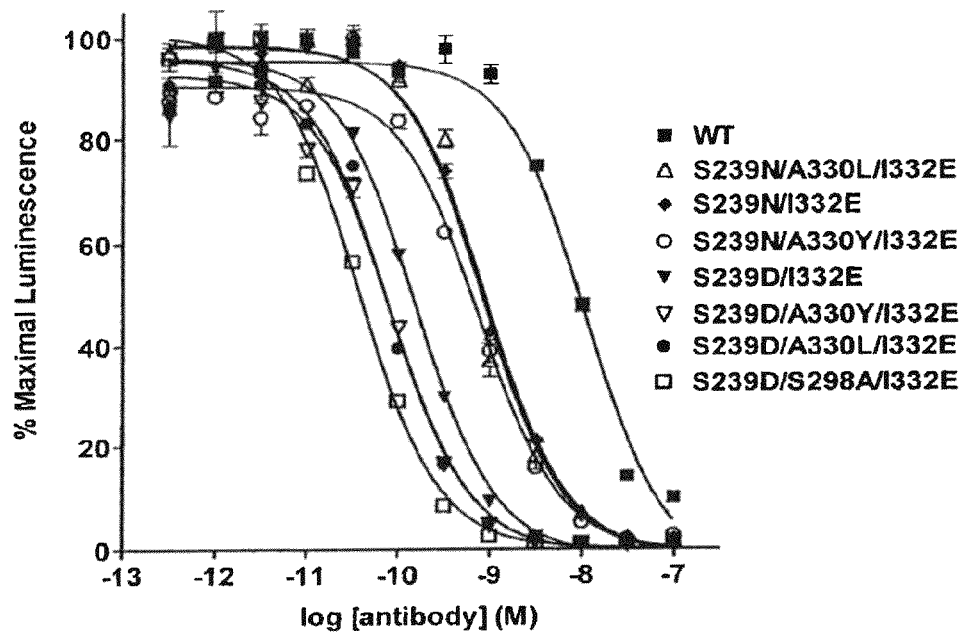
FIGS. 17a-17c. AlphaScreen assay measuring binding to human V158 FcγRIIIa (FIGS. 17a and 17b) and human FcγRIIb (FIG. 17c) by select Fc variants in the context of trastuzumab. The binding data were normalized to the upper and lower baselines for each particular antibody, and the curves represent the fits of the data to a one site competition model. PBS was used as a negative control.
Figure 17B:
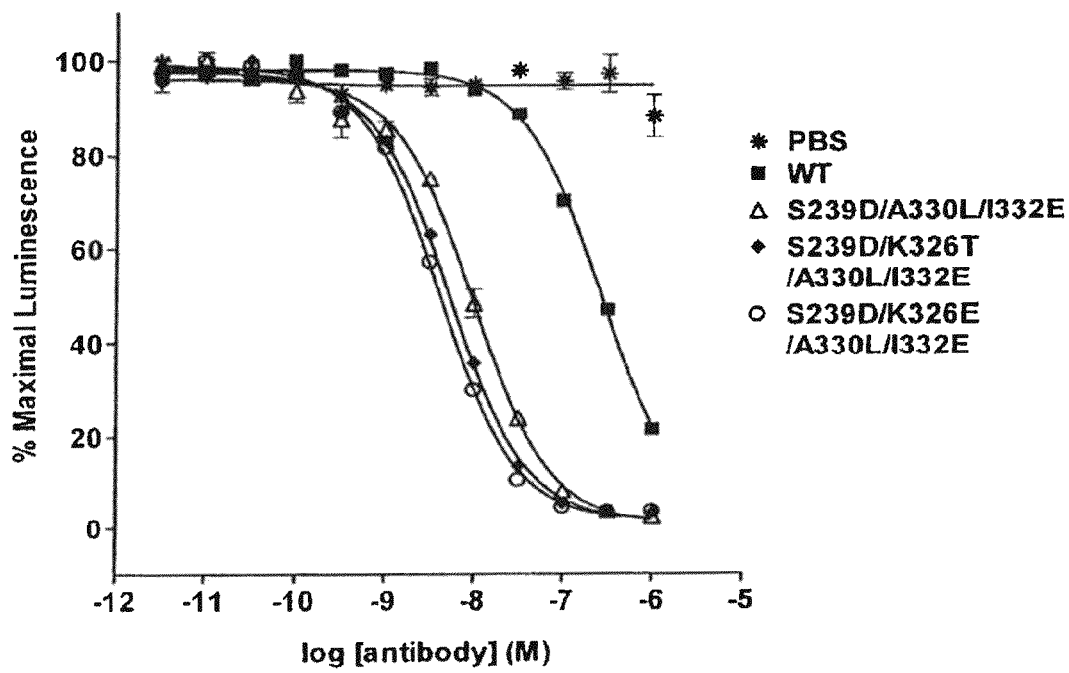
Figure 17C:
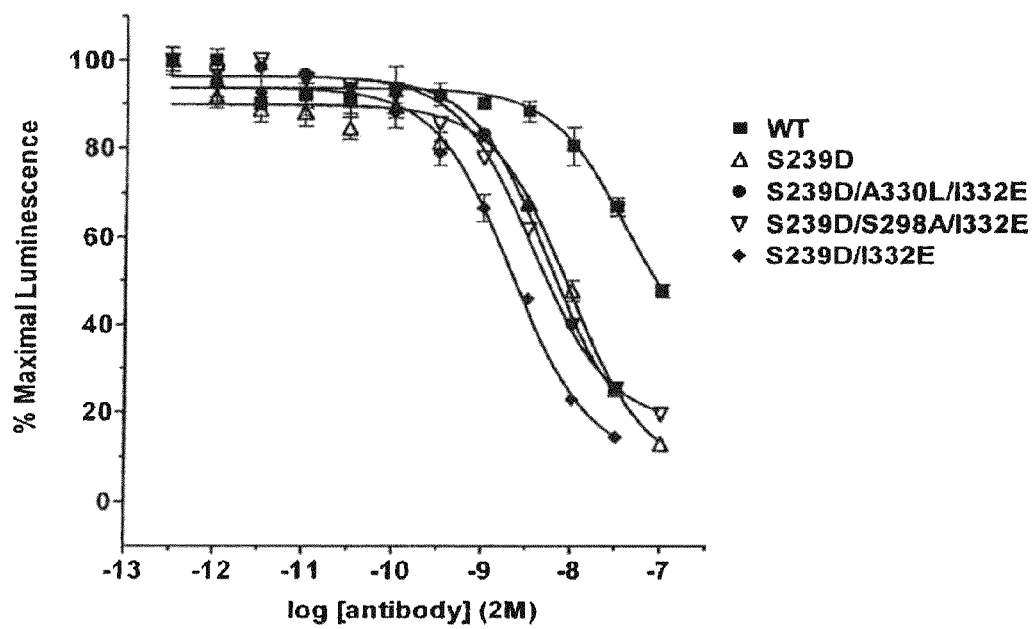

Some of the most promising Fc variants of the present invention for enhancing effector function have both substantial increases in affinity for FcγRIIIa and favorable FcγRIIIa-fold:FcγRIIb-fold ratios. These include, for example, S239D/I332E (FcγRIIIa-fold=56-192, FcγRIIIa-fold:FcγRIIb-fold=3), S239D/A330Y/I332E (FcγRIIIa-fold=130), S239D/A330L/I332E (FcγRIIIa-fold=139, FcγRIIIa-fold:FcγRIIb-fold=18), and S239D/S298A/I332E (FcγRIIIa-fold=295, FcγRIIIa-fold:FcγRIIb-fold=48). FIGS. 17a-17c show AlphaScreen data monitoring binding of these and other Fc variants in the context of trastuzumab to human V158 FcγRIIIa and human FcγRIIb.

Figure 18:
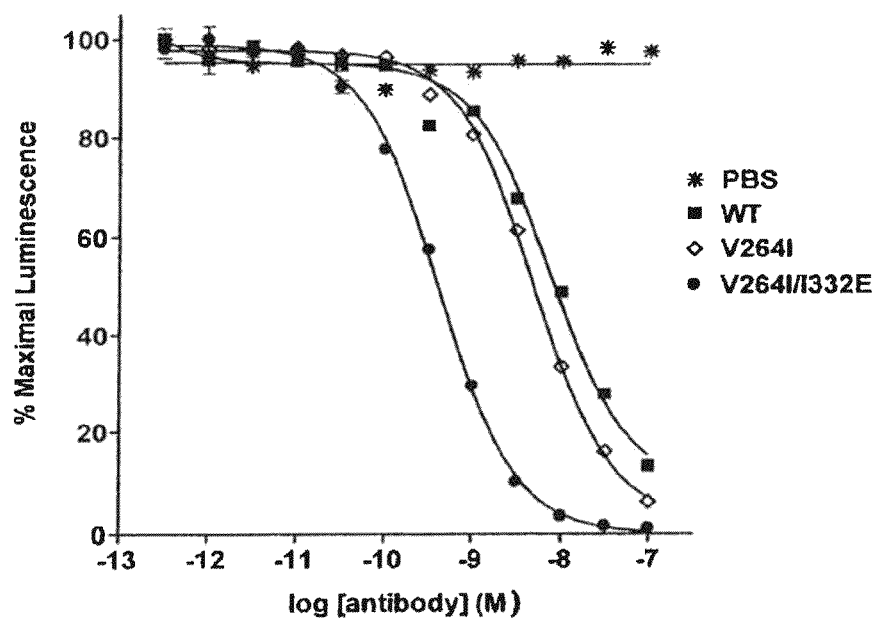
FIG. 18. AlphaScreen assay measuring binding to human V158 FcγRIIa by select Fc variants in the context of rituximab. The binding data were normalized to the upper and lower baselines for each particular antibody, and the curves represent the fits of the data to a one site competition model. PBS was used as a negative control.
Figure 19:
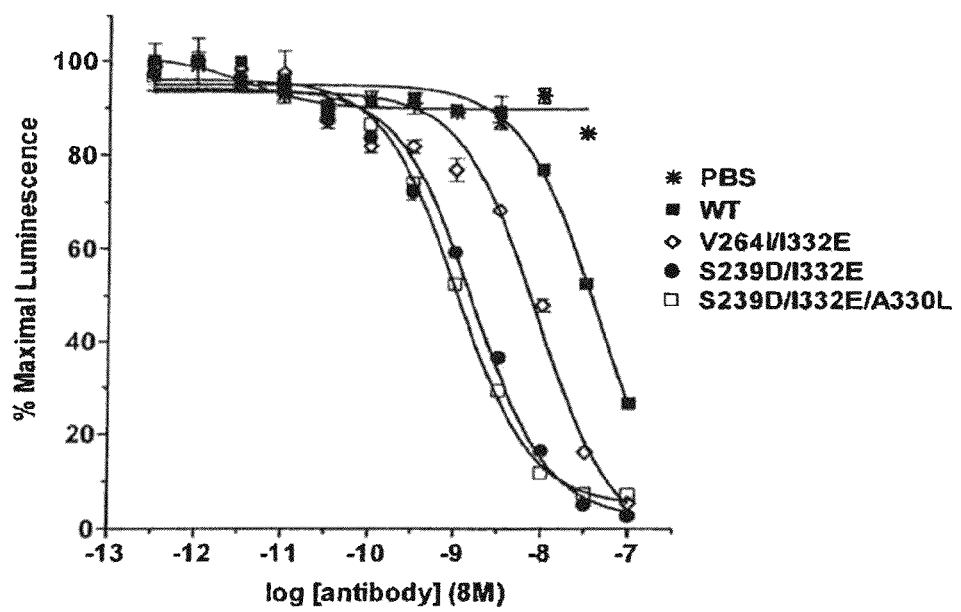
FIG. 19. AlphaScreen assay measuring binding to human V158 FcγRIIIa by select Fc variants in the context of cetuximab. The binding data were normalized to the upper and lower baselines for each particular antibody, and the curves represent the fits of the data to a one site competition model. PBS was used as a negative control.

In addition to alemtuzumab and trastuzumab, select Fc variants were screened in the context of other antibodies in order to investigate the breadth of their applicability. AlphaScreen data measuring binding of select Fc variants to human V158 FcγRIIIa in the context of rituximab and cetuximab are shown in FIG. 18 and FIG. 19 respectively. Together with the data shown previously for alemtuzumab and trastuzumab, the results indicate consistent binding enhancements regardless of the antibody context, and thus that the Fc variants of the present invention are broadly applicable to antibodies and Fc fusions.

Figure 20A:
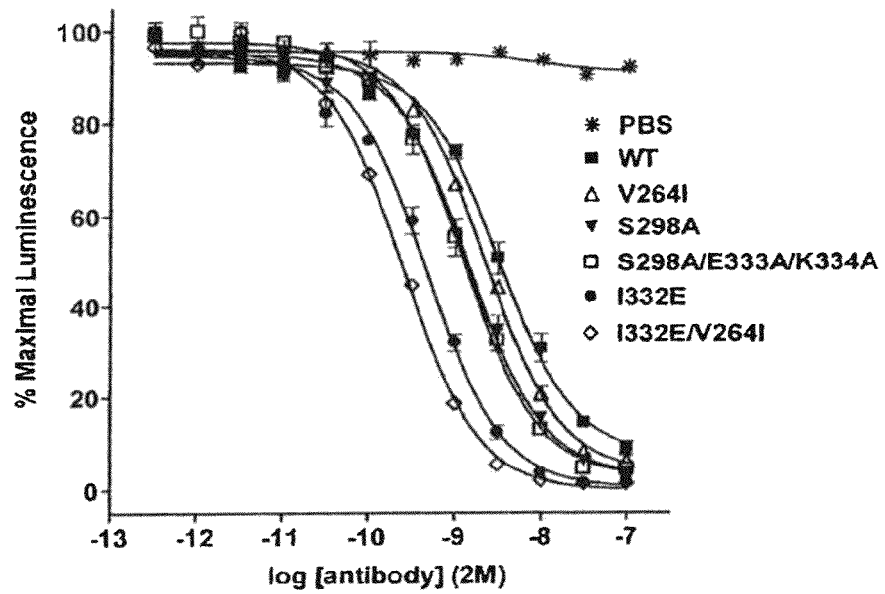
FIGS. 20a-20b. AlphaScreen assay showing binding of select alemtuzumab Fc variants to the V158 (FIG. 20a) and F158 (FIG. 20b) allotypes of human FcγRIIIa. The binding data were normalized to the upper and lower baselines for each particular antibody, and the curves represent the fits of the data to a one site competition model. PBS was used as a negative control.
Figure 20B:
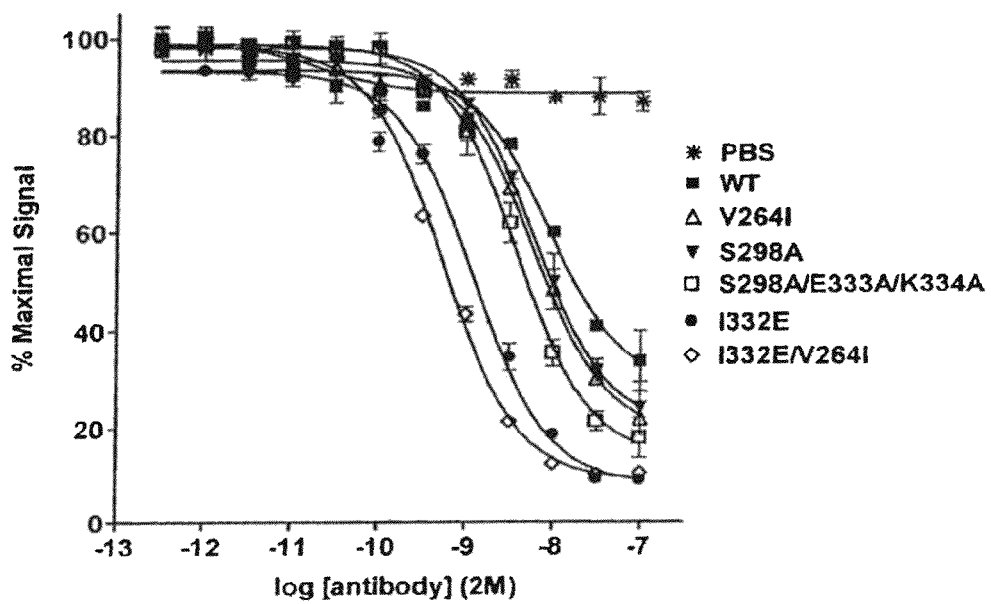

As discussed above, an important parameter of Fc-mediated effector function is the affinity of Fc for both V158 and F158 polymorphic forms of FcγRIIIa. AlphaScreen data comparing binding of select variants to the two receptor allotypes are shown in FIG. 20a (V158 FcγRIIIa) and FIG. 20b (F158 FcγRIIIa). As can be seen, all variants improve binding to both FcγRIIIa allotypes. These data indicate that those Fc variants of the present invention with enhanced effector function will be broadly applicable to the entire patient population, and that enhancement to clinical efficacy will potentially be greatest for the low responsive patient population who need it most.

The FcγR binding affinities of these Fc variants were further investigated using Surface Plasmon Resonance (SPR) (Biacore, Uppsala, Sweden). SPR is a sensitive and extremely quantitative method that allows for the measurement of binding affinities of protein-protein interactions, and has been used to effectively measure Fc/FcγR binding (Radaev et al., 2001, *J Biol Chem* 276:16478-16483). SPR thus provides an excellent complementary binding assay to the AlphaScreen assay. His-tagged V158 FcγRIIIa was immobilized to an SPR chip, and WT and Fc variant alemtuzumab antibodies were flowed over the chip at a range of concentrations. Binding constants were obtained from fitting the data using standard curve-fitting methods. Table 3 presents dissociation constants (Kd) for binding of select Fc variants to V158 FcγRIIIa and F158 FcγRIIIa obtained using SPR, and compares these with IC50s obtained from the AlphaScreen assay. By dividing the Kd and IC50 for each variant by that of WT alemtuzumab, the fold-improvements over WT (Fold WT) are obtained.

TABLE 3

| | SPR V158 FcγRIIIa | | SPR F158 FcγRIIIa | | AlphaScreen V158 FcγRIIIa | | AlphaScreen F158 FcγRIIIa | |
|---|---|---|---|---|---|---|---|---|
| | Kd (nM) | Fold WT | Kd (nM) | Fold WT | IC50 (nM) | Fold WT | IC50 (nM) | Fold WT |
| WT | 68 | | 730 | | 6.4 | | 17.2 | |
| V264I | 64 | 1.1 | 550 | 1.3 | 4.5 | 1.4 | 11.5 | 1.5 |
| I332E | 31 | 2.2 | 72 | 10.1 | 1.0 | 6.4 | 2.5 | 6.9 |
| V264I/I332E | 17 | 4.0 | 52 | 14.0 | 0.5 | 12.8 | 1.1 | 15.6 |
| S298A | 52 | 1.3 | 285 | 2.6 | 2.9 | 2.2 | 12.0 | 1.4 |
| S298A/E333A/K334A | 39 | 1.7 | 156 | 4.7 | 2.5 | 2.6 | 7.5 | 2.3 |

Figure 21A:
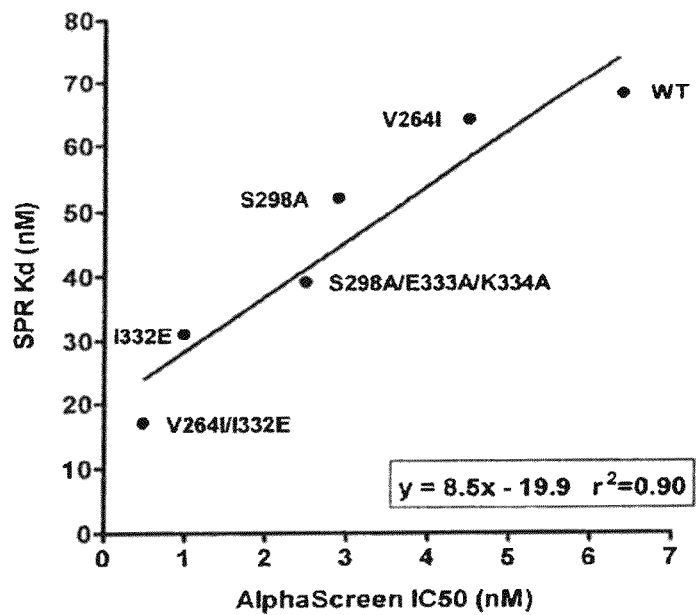
FIGS. 21a-21d.
Figure 21B:
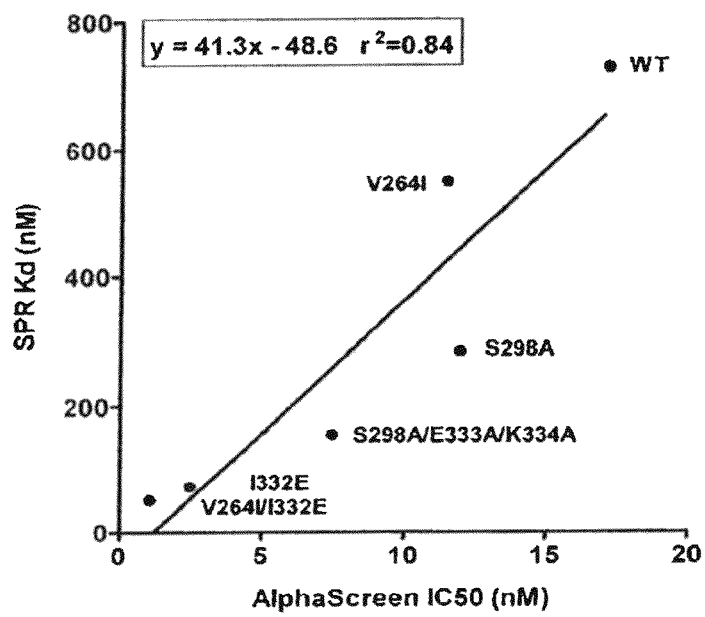
Figure 21C:
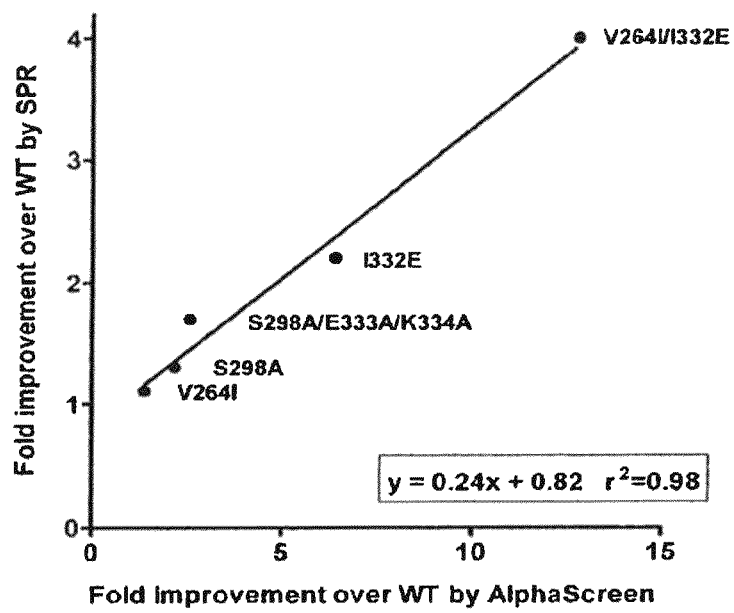
Figure 21D:
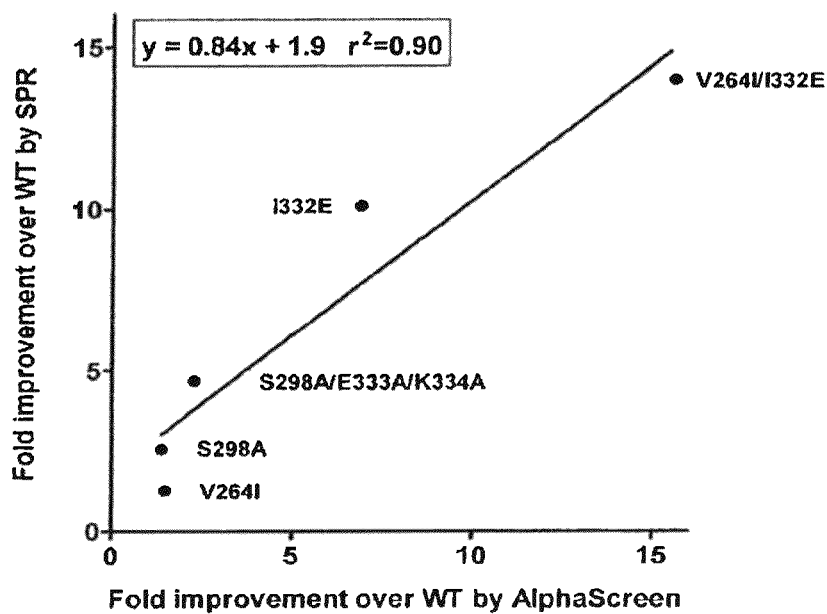

The SPR data corroborate the improvements to FcγRIIIa affinity observed by AlphaScreen assay. Table 3 further indicates the superiority of V264I/I332E and I332E over S298A and S298A/E333A/K334A; whereas S298A/E333A/K334A improves Fc binding to V158 and F158 FcγRIIIa by 1.7-fold and 4.7-fold respectively, I332E shows binding enhancements of 2.2-fold and 10.1-fold respectively, and V264I/I332E shows binding enhancements of 4.0-fold and 14-fold respectively. Also worth noting is that the affinity of V264I/I332E for F158 FcγRIIIa (52 nM) is better than that of WT for the V158 allotype (68 nM), suggesting that this Fc variant, as well as those with even greater improvements in binding, may enable the clinical efficacy of antibodies for the low responsive patient population to achieve that currently possible for high responders. The correlation between the SPR and AlphaScreen binding measurements are shown in FIGS. 21a-21d. FIGS. 21a and 21b show the Kd—IC50 correlations for binding to V158 FcγRIIIa and F158 FcγRIIIa respectively, and FIGS. 21c and 21d show the fold-improvement correlations for binding to V158 FcγRIIIa and F158 FcγRIIIa respectively. The good fits of these data to straight lines ($r^2$=0.9, $r^2$=0.84, $r^2$=0.98, and $r^2$=0.90) support the accuracy the AlphaScreen measurements, and validate its use for determining the relative FcγR binding affinities of Fc variants.

SPR data were also acquired for binding of select trastuzumab Fc variants to human V158 FcγRIIIa, F158 FcγRIIIa, and FcγRIIb. These data are shown in Table 4. The Fc variants tested show substantial binding enhancements to the activating receptor FcγRIIIa, with over 100-fold tighter binding observed for interaction of S239D/I332E/S298A with F158 FcγRIIIa. Furthermore, for the best FcγRIIIa binders, F158 FcγRIIIa/FcγRIIb ratios of 3-4 are observed.

TABLE 4

| | SPR V158 FcγRIIIa | | SPR F158 FcγRIIIa | | SPR FcγRIIb | |
|---|---|---|---|---|---|---|
| | Kd (nM) | Fold WT | Kd (nM) | Fold WT | IC50 (nM) | Fold WT |
| WT | 363.5 | | 503 | | 769 | |
| V264I/I332E | 76.9 | 4.7 | 252 | 2.0 | 756 | 1.0 |
| V264I/I332E/A330L | 113.0 | 3.2 | 88 | 5.7 | 353 | 2.2 |
| S239D/I332E/A330L | 8.2 | 44.3 | 8.9 | 56.5 | 46 | 16.7 |
| S239D/I332E/S298A | 8.7 | 41.8 | 4.9 | 102.7 | 32 | 24.0 |
| S239D/I332E/V264I/A330L | 12.7 | 28.6 | 6.3 | 79.8 | 35 | 22.0 |

Figure 22A:
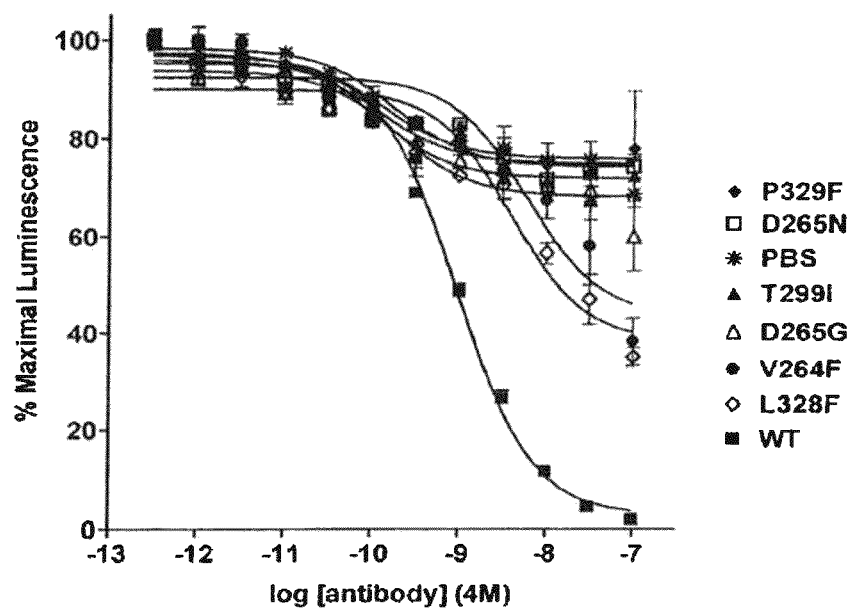
FIGS. 22a and 22b. AlphaScreen assay showing binding of select alemtuzumab Fc variants to human V158 FcγRIIIa. The binding data were normalized to the upper and lower baselines for each particular antibody, and the curves represent the fits of the data to a one site competition model. PBS was used as a negative control.
Figure 22B:
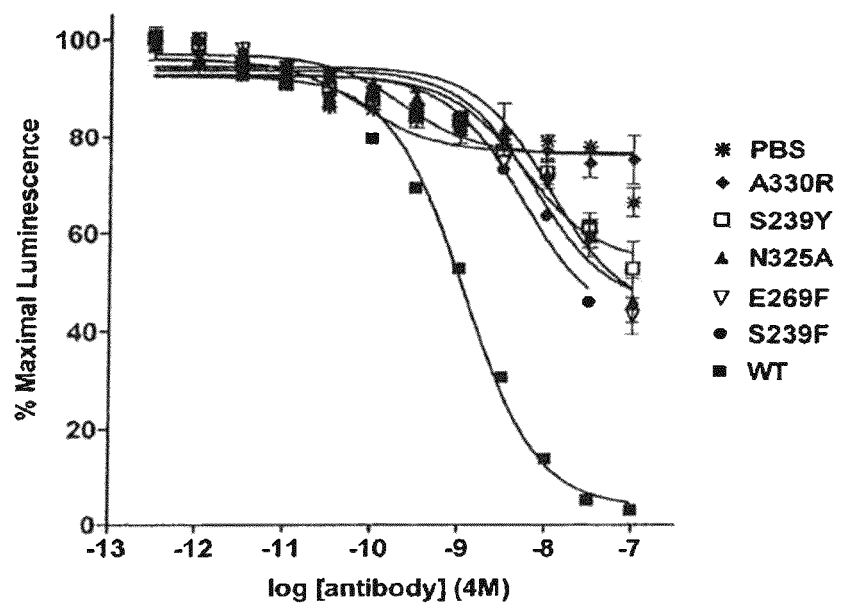

As discussed, although there is a need for greater effector function, for some antibody therapeutics, reduced or eliminated effector function may be desired. Several Fc variants in FIG. 41 substantially reduce or ablate FcγR binding, and thus may find use in antibodies and Fc fusions wherein effector function is undesirable. AlphaScreen data measuring binding of some exemplary Fc variants to human V158 FcγRIIIa are shown in FIGS. 22a and 22b. These Fc variants, as well as their use in combination, may find use for eliminating effector function when desired, for example in antibodies and Fc fusions whose mechanism of action involves blocking or antagonism but not killing of the cells bearing target antigen. Based on the data provided in FIG. 41, preferred positions for reducing Fc ligand binding and/or effector function, that is positions that may be modified to reduce binding to one or more Fc ligands and/or reduce effector function, include but are not limited to positions 232, 234, 235, 236, 237, 239, 264, 265, 267, 269, 270, 299, 325, 328, 329, and 330.

Example 3

ADCC of Fc Variants

In order to determine the effect on effector function, cell-based ADCC assays were performed on select Fc variants. ADCC was measured using the DELFIA® EuTDA-based cytotoxicity assay (Perkin Elmer, Mass.) with purified human peripheral blood monocytes (PBMCs) as effector cells. Target cells were loaded with BATDA at $1\times10^6$ cells/ml, washed 4 times and seeded into 96-well plate at 10,000 cells/well. The target cells were then opsonized using Fc variant or WT antibodies at the indicated final concentration. Human PBMCs, isolated from buffy-coat were added at the indicated fold-excess of target cells and the plate was incubated at 37° C. for 4 hrs. The co-cultured cells were centrifuged at 500×g, supernatants were transferred to a separate plate and incubated with Eu solution, and relative fluorescence units were measured using a Packard Fusion™ α-FP HT reader (Packard Biosciences, IL). Samples were run in triplicate to provide error estimates (n=3, +/−S.D.). PBMCs were allotyped for the V158 or F158 FcγRIIIa allotype using PCR.

Figure 23A:
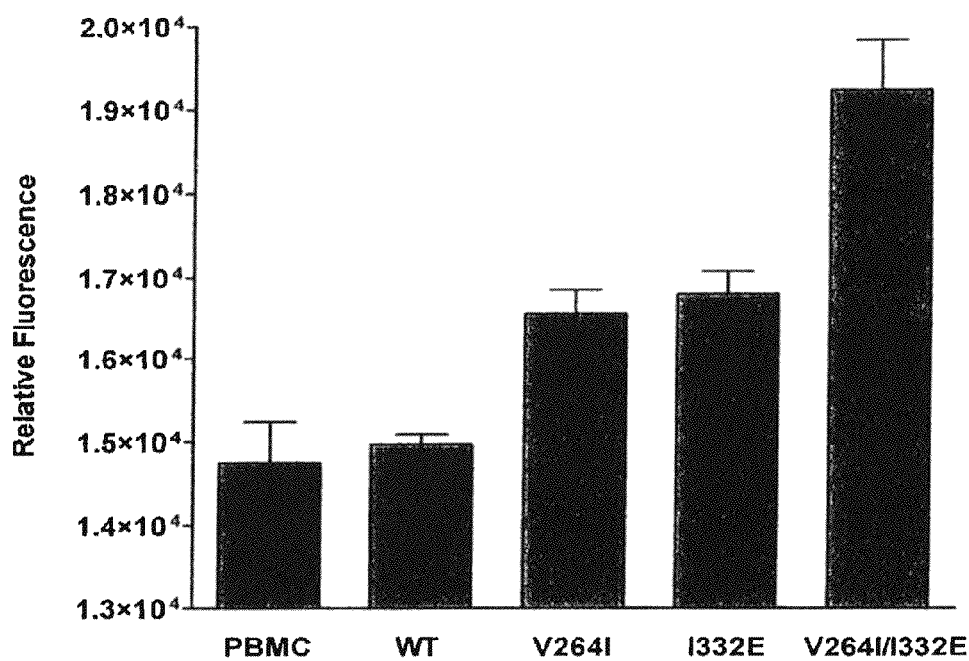
FIGS. 23a-23b. Cell-based ADCC assays of select Fc variants in the context of alemtuzumab. ADCC was measured using the DELFIA® EuTDA-based cytotoxicity assay (Perkin Elmer, Mass.), as described in Example 3, using DoHH-2 lymphoma target cells and 50-fold excess human PBMCs.
Figure 23B:
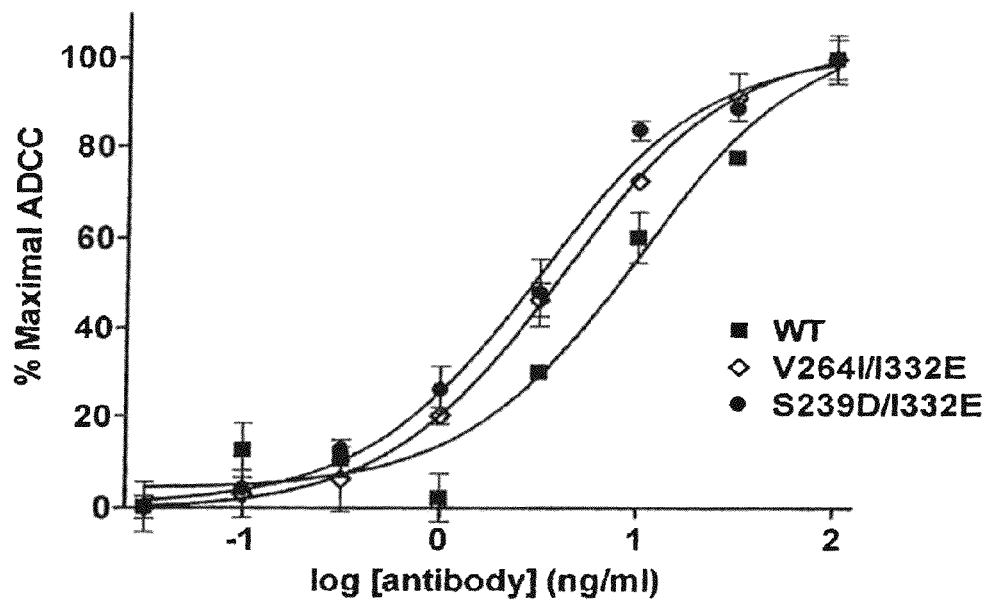

ADCC assays were run on Fc variant and WT alemtuzumab using DoHH-2 lymphoma target cells. FIG. 23a is a bar graph showing the ADCC of these proteins at 10 ng/ml antibody. Results show that alemtuzumab Fc variants I332E, V264I, and I332E/V264I have substantially enhanced ADCC compared to WT alemtuzumab, with the relative ADCC enhancements proportional to their binding improvements to FcγRIIIa as indicated by AlphaScreen assay and SPR. The dose dependence of ADCC on antibody concentration is shown in FIG. 23b. The binding data were normalized to the minimum and maximum fluorescence signal for each particular curve, provided by the baselines at low and high antibody concentrations respectively. The data were fit to a sigmoidal dose-response model using nonlinear regression, represented by the curve in the figure. The fits enable determination of the effective concentration 50% (EC50) (i.e. the concentration required for 50% effectiveness), which provides the relative enhancements to ADCC for each Fc variant. The EC50s for these binding data are analogous to the IC50s obtained from the AlphaScreen competition data, and derivation of these values is thus analogous to that described in Example 2 and FIG. 11. In FIG. 23b, the log(EC50)s, obtained from the fits to the data, for WT, V264I/I332E, and S239D/I332E alemtuzumab are 0.99, 0.60, and 0.49 respectively, and therefore their respective EC50s are 9.9, 4.0, and 3.0. Thus V264I/I332E and S239E/I332E provide a 2.5-fold and 3.3-fold enhancement respectively in ADCC over WT alemtuzumab using PBMCs expressing heterozygous V158/F158 FcγRIIIa. These data are summarized in Table 5 below.

TABLE 5

|  | log(EC50) | EC50 (ng/ml) | Fold WT |
| --- | --- | --- | --- |
| WT | 0.99 | 9.9 |  |
| V264I/I332E | 0.60 | 4.0 | 2.5 |
| S239D/I332E | 0.49 | 3.0 | 3.3 |

Figure 24A:
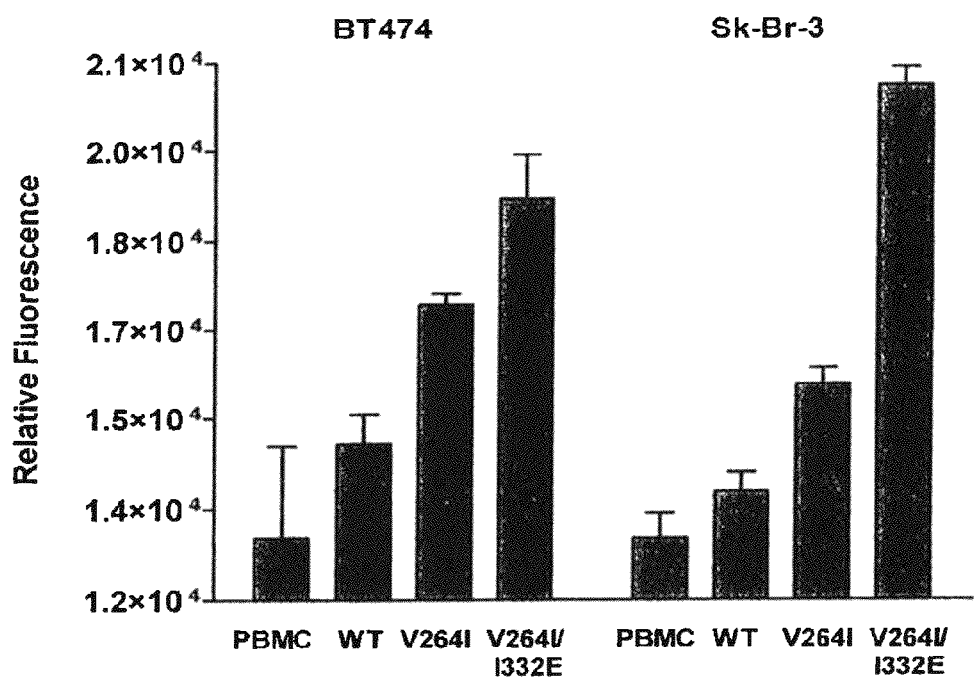
FIGS. 24a-24c. Cell-based ADCC assays of select Fc variants in the context of trastuzumab. ADCC was measured using the DELFIA® EuTDA-based cytotoxicity assay, as described in Example 3, using BT474 and Sk-Br-3 breast carcinoma target cells and 50-fold excess human PBMCs.
Figure 24B:
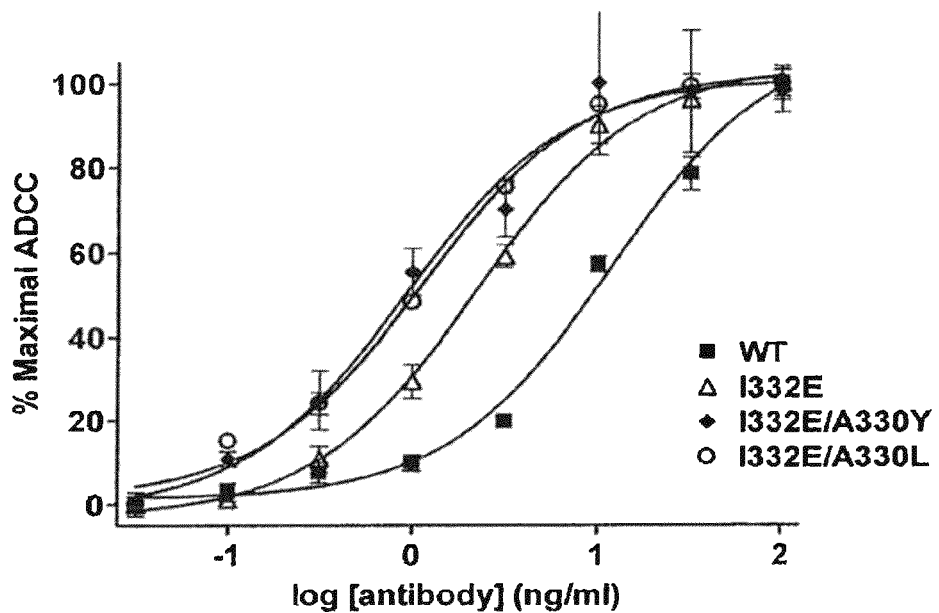
Figure 24C:
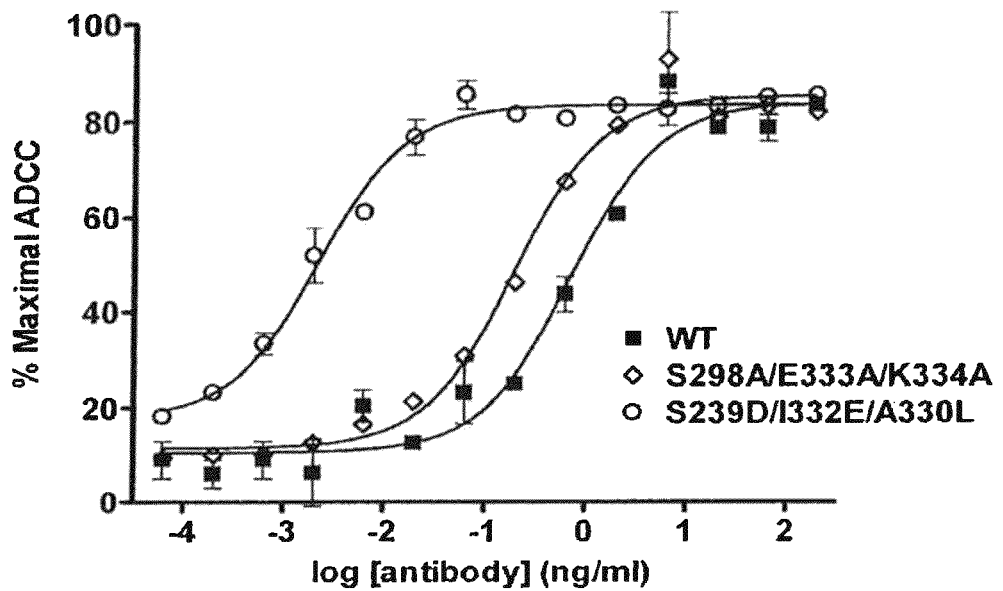

In order to determine whether these ADCC enhancements are broadly applicable to antibodies, select Fc variants were evaluated in the context of trastuzumab and rituximab. ADCC assays were run on Fc variant and WT trastuzumab using two breast carcinoma target cell lines BT474 and Sk-Br-3. FIG. 24a shows a bar graph illustrating ADCC at 1 ng/ml antibody. Results indicate that V264I and V264I/I332E trastuzumab provide substantially enhanced ADCC compared to WT trastuzumab, with the relative ADCC enhancements proportional to their binding improvements to FcγRIIIa as indicated by AlphaScreen assay and SPR. FIGS. 24b and 24c show the dose dependence of ADCC on antibody concentration for select Fc variants. The EC50s obtained from the fits of these data and the relative fold-improvements in ADCC are provided in Table 6 below. Significant ADCC improvements are observed for I332E trastuzumab when combined with A330L and A330Y. Furthermore, S239D/A330L/I332E provides a substantial ADCC enhancement, greater than 300-fold for PBMCs expressing homozygous F158/F158 FcγRIIa, relative to WT trastuzumab and S298A/E333A/K334A, consistent with the FcγR binding data observed by the AlphaScreen assay and SPR.

TABLE 6

|  | log(EC50) | EC50 (ng/ml) | Fold WT |
| --- | --- | --- | --- |
| FIG. 24b |  |  |  |
| WT | 1.1 | 11.5 |  |
| I332E | 0.34 | 2.2 | 5.2 |
| A330Y/I332E | −0.04 | 0.9 | 12.8 |
| A330L/I332E | 0.04 | 1.1 | 10.5 |
| FIG. 24c |  |  |  |
| WT | −0.15 | 0.71 |  |
| S298A/E333A/K334A | −0.72 | 0.20 | 3.6 |
| S239D/A330L/I332E | −2.65 | 0.0022 | 323 |

Figure 25A:
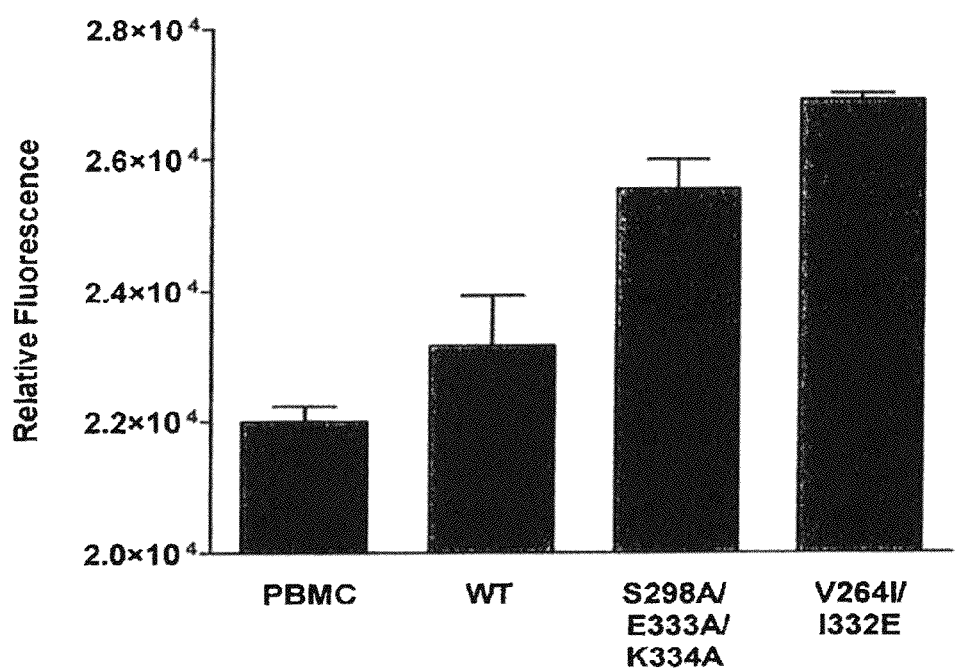
FIGS. 25a-25c. Cell-based ADCC assays of select Fc variants in the context of rituximab. ADCC was measured using the DELFIA® EuTDA-based cytotoxicity assay, as described in Example 3, using WIL2-S lymphoma target cells and 50-fold excess human PBMCs.
Figure 25B:
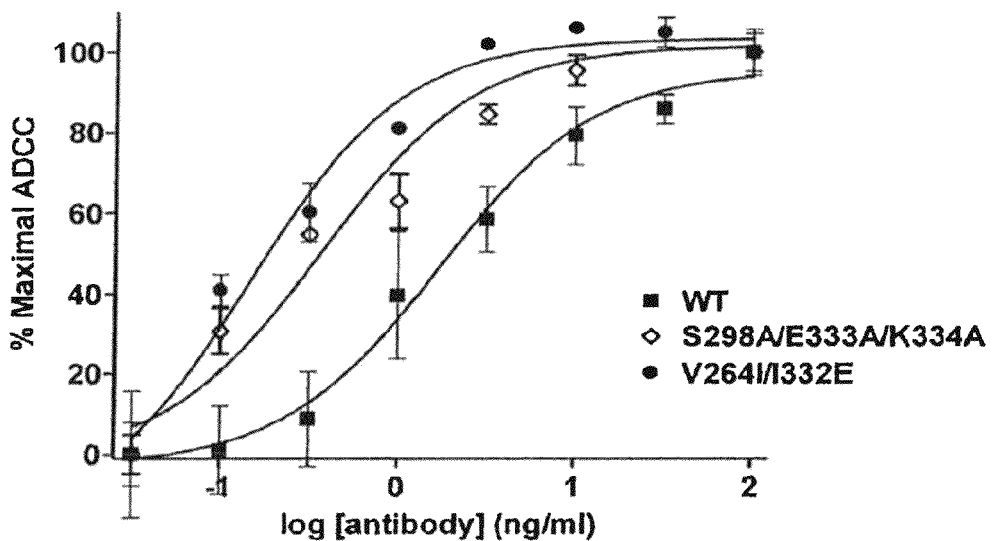
Figure 25C:
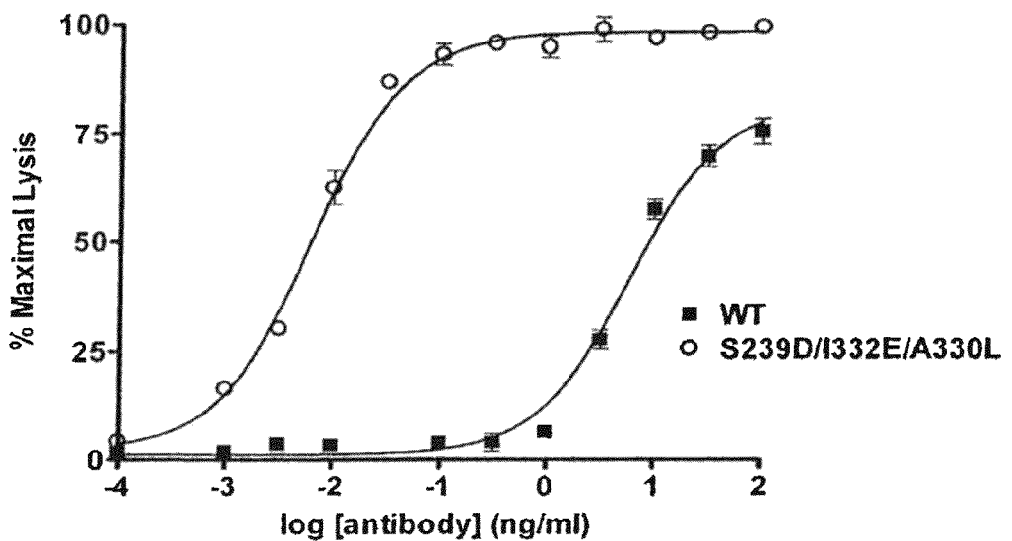

ADCC assays were run on V264I/I332E, WT, and S298A/D333A/K334A rituximab using WIL2-S lymphoma target cells. FIG. 25a presents a bar graph showing the ADCC of these proteins at 1 ng/ml antibody. Results indicate that V264I/I332E rituximab provides substantially enhanced ADCC relative to WT rituximab, as well as superior ADCC to S298A/D333A/K334A, consistent with the FcγRIIIa binding improvements observed by AlphaScreen assay and SPR. FIGS. 25b and 25c show the dose dependence of ADCC on antibody concentration for select Fc variants. The EC50s obtained from the fits of these data and the relative fold-improvements in ADCC are provided in Table 7 below. As can be seen S239D/I332E/A330L rituximab provides greater than 900-fold enhancement in EC50 over WT for PBMCs expressing homozygous F158/F158 FcγRIIIa. The differences in ADCC enhancements observed for alemtuzumab, trastuzumab, and rituximab are likely due to the use of different PBMCs, different antibodies, and different target cell lines.

TABLE 7

|  | log(EC50) | EC50 (ng/ml) | Fold WT |
| --- | --- | --- | --- |
| FIG. 25b |  |  |  |
| WT | 0.23 | 1.7 |  |
| S298A/E333A/K334A | −0.44 | 0.37 | 4.6 |
| V264I/I332E | −0.83 | 0.15 | 11.3 |
| FIG. 25c |  |  |  |
| WT | 0.77 | 5.9 |  |
| S239D/I332E/A330L | −2.20 | 0.0063 | 937 |

Figure 26A:
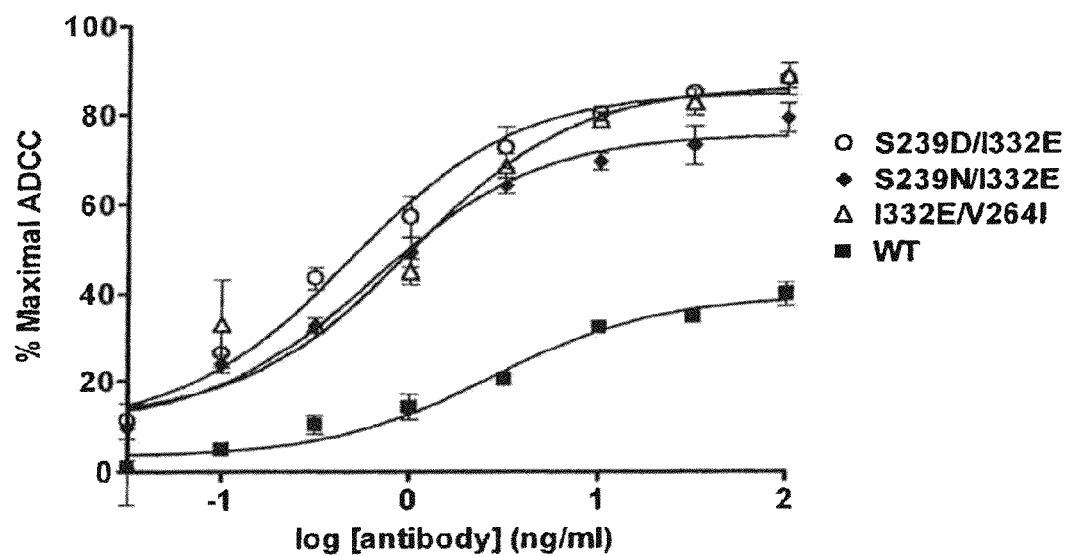
FIGS. 26a-26b. Cell-based ADCC assay of select trastuzumab (FIG. 26a) and rituximab (FIG. 26b) Fc variants showing enhancements in potency and efficacy. Both assays used homozygous F158/F158 FcγRIIIa PBMCs as effector cells at a 25-fold excess to target cells, which were Sk-Br-3 for the trastuzumab assay and WIL2-S for the rituximab assay. Data were normalized according to the absolute minimal lysis for the assay, provided by the fluorescence signal of target cells in the presence of PBMCs alone (no antibody), and the absolute maximal lysis for the assay, provided by the fluorescence signal of target cells in the presence of Triton X1000, as described in Example 3.
Figure 26B:
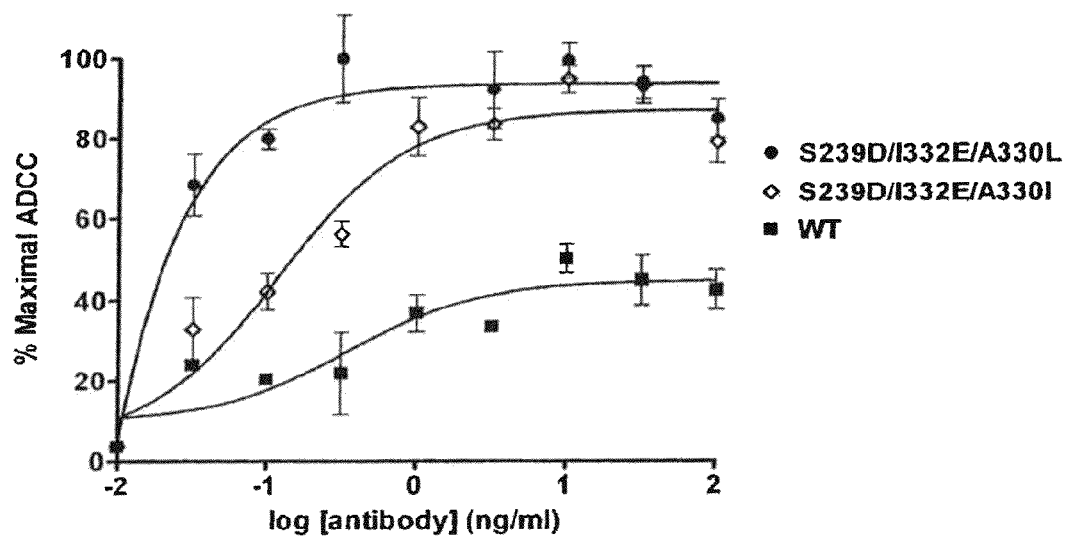
Figure 27:
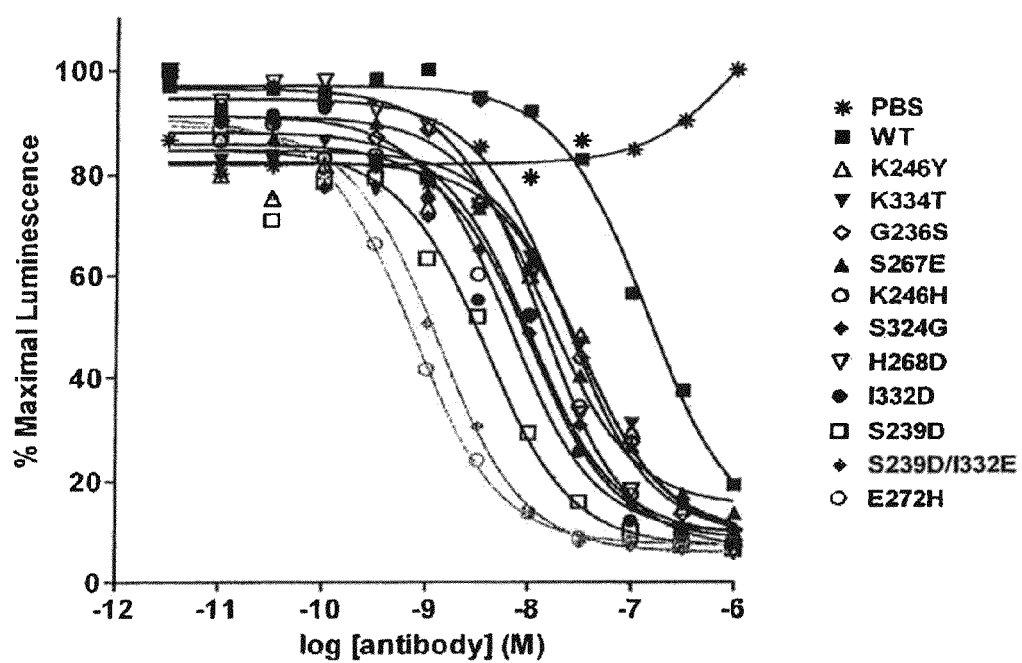
FIG. 27. AlphaScreen assay showing binding of select alemtuzumab Fc variants to human V158 FcγRIIIa. The binding data were normalized to the upper and lower baselines for each particular antibody, and the curves represent the fits of the data to a one site competition model. PBS was used as a negative control.

Thus far, ADCC data has been normalized such that the lower and upper baselines of each Fc polypeptide are set to the minimal and maximal fluorescence signal for that specific Fc polypeptide, typically being the fluorescence signal at the lowest and highest antibody concentrations respectively. Although presenting the data in this matter enables a straightforward visual comparison of the relative EC50s of different antibodies (hence the reason for presenting them in this way), important information regarding the absolute level of effector function achieved by each Fc polypeptide is lost. FIGS. 26a and 27b present cell-based ADCC data for trastuzumab and rituximab respectively that have been normalized according to the absolute minimal lysis for the assay, provided by the fluorescence signal of target cells in the presence of PBMCs alone (no antibody), and the absolute maximal lysis for the assay, provided by the fluorescence signal of target cells in the presence of Triton X1000. The graphs show that the antibodies differ not only in their EC50, reflecting their relative potency, but also in the maximal level of ADCC attainable by the antibodies at saturating concentrations, reflecting their relative efficacy. Thus far these two terms, potency and efficacy, have been used loosely to refer to desired clinical properties. In the current experimental context, however, they are denoted as specific quantities, and therefore are here explicitly defined. By "potency" as used in the current experimental context is meant the EC50 of an Fc polypeptide. By "efficacy" as used in the current experimental context is meant the maximal possible effector function of an Fc polypeptide at saturating levels. In addition to the substantial enhancements to potency described thus far, FIGS. 26a and 26b show that the Fc variants of the present invention provide greater than 100% enhancements in efficacy over WT trastuzumab and rituximab.

Example 4

Cross-Validation of Fc Variants

Figure 28:
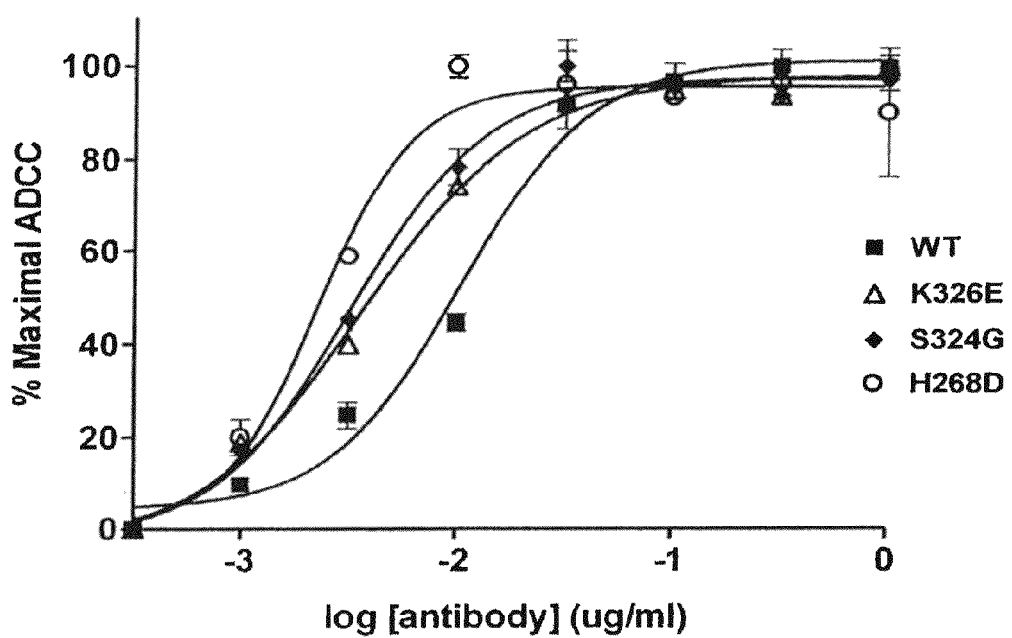
FIG. 28. ADCC. Cell-based ADCC assays of select Fc variant trastuzumab antibodies as compared to WT trastuzumab. Purified human peripheral blood monocytes (PBMCs) were used as effector cells, and Sk-Br-3 breast carcinoma cells were used as target cells. Lysis was monitored by measuring LDH activity using the Cytotoxicity Detection Kit (LDH, Roche Diagnostic Corporation, Indianapolis, Ind.). Samples were run in triplicate to provide error estimates (n=3, +/−S.D.). The figure shows the dose dependence of ADCC at various antibody concentrations, normalized to the minimum and maximum levels of lysis for the assay. The curves represent the fits of the data to a sigmoidal dose-response model using nonlinear regression.

Select Fc variants were validated for their FcγR binding and ADCC improvements in the context of two antibodies—alemtuzumab and trastuzumab. Binding to human V158 FcγRIIIa was measured using both AlphaScreen and SPR as described above. Exemplary AlphaScreen data measuring FcγRIIIa binding are provided in FIG. 27. ADCC was carried out in the context of trastuzumab using Sk-Br-3 target cells and LDH detection as described above. Exemplary ADCC data are provided in FIG. 28. Table 8 provides a summary of the fold FcγRIIIa binding affinities to relative to WT as determined by AlphaScreen and SPR, and the fold ADCC relative to WT for a series of Fc variants in the context of alemtuzumab (alem) and trastuzumab (trast).

TABLE 8

| Variant Substitution | Variant Number | Context | Fold WT V158 FcγRIIIa | | |
|---|---|---|---|---|---|
| | | | AlphaScreen | SPR | ADCC |
| G236S | 719 | trast | 2.78 | 1.34 | 0.37 |
| G236S | 719 | alem | 6.22 | 6.69 | |
| S239E | 43 | trast | 29.99 | 4.17 | 7.6 |
| S239E | 43 | alem | 2.64 | 3.28 | |
| S239D | 86 | trast | 16.9 | 3.5 | 6.1 |
| S239D | 86 | alem | 36.56 | 16.61 | |
| K246H | 812 | trast | 17.91 | 2.67 | 2 |
| K246H | 812 | alem | 13.58 | 22.36 | |
| K246Y | 813 | trast | 17.44 | 2.39 | 1.36 |
| K246Y | 813 | alem | 4.32 | 7.07 | |
| R255Y | 818 | trast | 21.14 | 2.75 | 1.6 |
| R255Y | 818 | alem | 0.92 | 1.41 | |
| E258H | 820 | trast | 1.18 | 0.77 | 0.76 |
| E258H | 820 | alem | 2.35 | 5.5 | |
| E258Y | 821 | trast | 2.82 | 1.69 | 0.92 |
| E258Y | 821 | alem | 0.64 | 1.77 | |
| T260H | 824 | trast | 35.32 | 2.82 | |
| T260H | 824 | alem | 1 | 1.86 | |
| S267E | 338 | alem | 9.33 | 2.62 | |
| H268D | 350 | trast | 45.27 | 4.76 | 4.59 |
| H268D | 350 | alem | 10.55 | 5.66 | |
| E272I | 237 | trast | 5.86 | 1.63 | 1.38 |
| E272I | 237 | alem | 3.24 | 1.99 | |
| E272R | 634 | alem | | 1.38 | |
| E272H | 636 | trast | 1.02 | 0.65 | 1.28 |
| E272H | 636 | alem | 187.1 | 383.88 | |
| E272P | 642 | trast | 0.005 | 0.522 | 0.39 |
| E272P | 642 | alem | 1.46 | 1.41 | |
| E283H | 839 | trast | 0.99 | 0.71 | 1.4 |
| E283H | 839 | alem | | 2.31 | |
| E283L | 840 | trast | 19.88 | 3.68 | 5.2 |
| E283L | 840 | alem | 1.36 | 2.56 | |
| V284E | 844 | trast | 2.82 | 1.26 | 0.84 |
| V284E | 844 | alem | | 1.51 | |
| E293R | 555 | trast | 1.15 | 0.94 | 0.47 |
| S298D | 364 | trast | 3.48 | 1.49 | 0.58 |
| S304T | 879 | trast | 6.33 | 1.65 | 1.02 |

TABLE 8-continued

| Variant Substitution | Variant Number | Context | Fold WT V158 FcγRIIIa | | |
|---|---|---|---|---|---|
| | | | AlphaScreen | SPR | ADCC |
| S304T | 879 | alem | | 12.85 | |
| S324I | 267 | trast | 5.26 | 1.46 | 2.21 |
| S324G | 608 | trast | 3.04 | 1.76 | 3.23 |
| S324G | 608 | alem | 13.62 | 14.17 | |
| K326E | 103 | trast | 6.12 | 2.12 | 2.87 |
| K326E | 103 | alem | 1.86 | 3.13 | |
| A327D | 274 | trast | 2.44 | 1.31 | 1.04 |
| I332E | 22 | trast | | | |
| I332D | 62 | trast | 19 | 2.57 | 5 |
| I332D | 62 | alem | 21.65 | 11.16 | |
| E333Y | 284 | trast | 8.24 | 1.94 | 2.23 |
| K334I | 285 | trast | 15.24 | 7.1 | 1.2 |
| K334T | 286 | trast | 15.73 | 6.79 | 3.14 |
| K334F | 287 | trast | 10.46 | 5.82 | 1.92 |

Example 5

ADCC at Varying Target Antigen Expression Levels

Figure 29A:
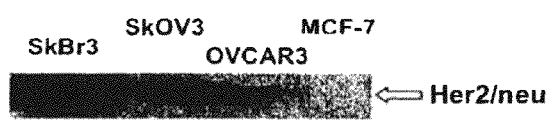
FIGS. 29a-29b. Cell-based ADCC assay of select trastuzumab Fc variants against different cell lines expressing varying levels of the Her2/neu target antigen. ADCC assays were run as described in Example 5, with various cell lines expressing amplified to low levels of Her2/neu receptor, including Sk-Br-3 (1×106 copies), SkOV3 (~1×105), OVCAR3(~1× 104), and MCF-7 (~3×103 copies).
Figure 29B:
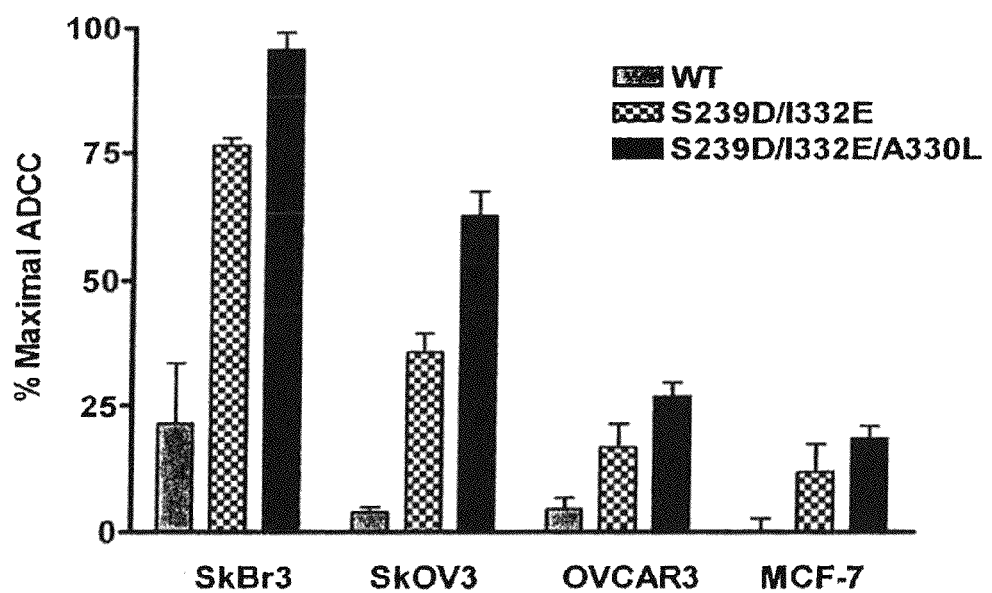

A critical parameter governing the clinical efficacy of anti-cancer antibodies is the expression level of target antigen on the surface of tumor cells. Thus a major clinical advantage of Fc variants that enhance ADCC may be that it enables the targeting of tumors that express lower levels of antigen. In order to test this hypothesis, WT and Fc variant trastuzumab antibodies were tested for their ability to mediate ADCC against different cell lines expressing varying levels of the Her2/neu target antigen using the DELFIA EuTDA method. Four cell lines cell lines expressing amplified to low levels of Her2/neu receptor were used, including Sk-Br-3 ($1\times10^6$ copies), SkOV3 (~$1\times10^5$), OVCAR3 (~$1\times10^4$), and MCF-7 (~$3\times10^3$ copies) (FIG. 29a). Target cells were loaded with BATDA in batch for 25 minutes, washed multiple times with medium and seeded at 10,000 cells per well in 96-well plates. Target cells were opsonized for 15 minutes with various antibodies and concentrations (final conc. ranging from 100 ng/ml to 0.0316 ng/ml in % log steps, including no treatment control). Human PBMCs, isolated from buffy-coat and allotyped as homozygous F158/F158 FcγRIIIa were then added to opsonized cells at 25-fold excess and co-cultured at 37° C. for 4 hrs. Thereafter, plates were centrifuged, supernatants were removed and treated with Eu3+ solution, and relative fluorescence units (correlating to the level of cell lysis) were measured using a Packard Fusion™ α-FP HT reader (PerkinElmer, Boston, Mass.). The experiment was carried out in triplicates. FIG. 29b shows the ADCC data comparing WT and Fc variant trastuzumab against the four different Her2/neu+ cell lines. The S239D/I332E and S239D/I332E/A330L variants provide substantial ADCC enhancements over WT trastuzumab at high, moderate, and low expression levels of target antigen. This result suggests that the Fc variants of the present invention may broaden the therapeutic window of anti-cancer antibodies.

Example 6

ADCC with NK Cells as Effector Cells

Figure 30:
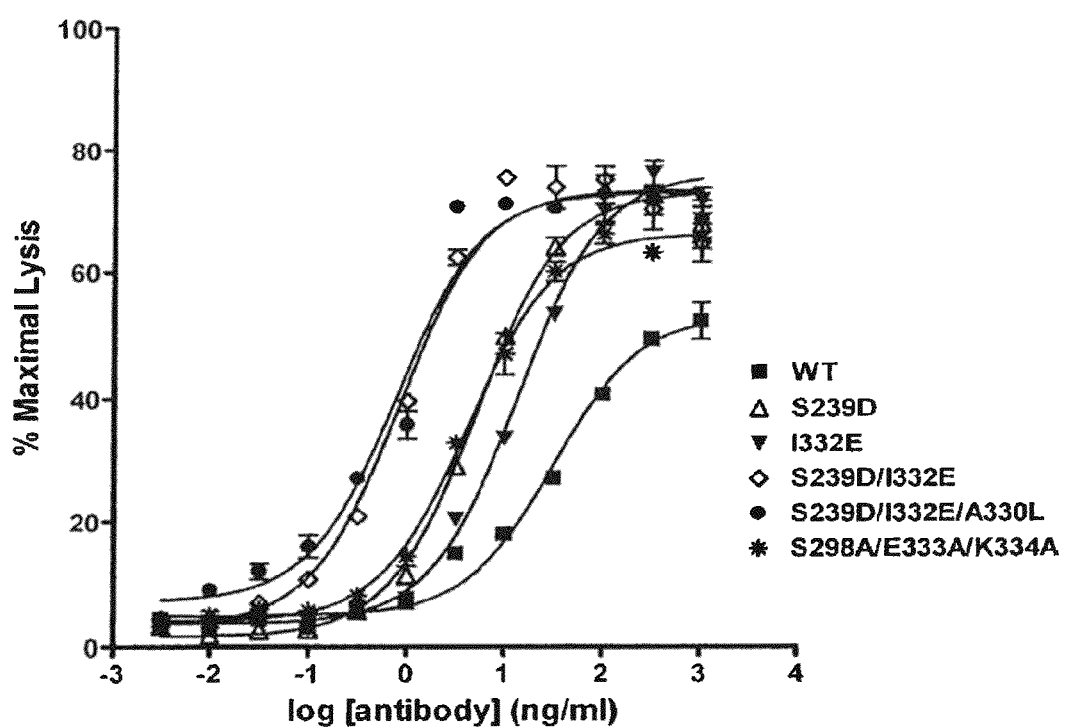
FIG. 30. Cell-based ADCC assays of select Fc variants in the context of trastuzumab using natural killer (NK) cells as effector cells and measuring LDH release to monitor cell lysis. NK cells, allotyped as heterozygous F158/F158 FcγRIIIa, were at an 4-fold excess to Sk-Br-3 breast carcinoma target cells, and the level of cytotoxicity was measured using the LDH Cytotoxicity Detection Kit, according to the manufacturer's protocol (Roche Diagnostics GmbH, Penzberg, Germany). The graph shows the dose-dependence of ADCC on antibody concentration for the indicated trastuzumab antibodies, normalized to the minimum and maximum fluorescence signal for each particular curve, provided by the baselines at low and high antibody concentrations respectively. The curves represent the fits of the data to a sigmoidal dose-response model using nonlinear regression.

Natural killer (NK) cells are a subpopulation of cells present in PBMCs that are thought to play a significant role in ADCC. Select Fc variants were tested in a cell-based ADCC assay in which natural killer (NK) cells rather than PBMCs were used as effector cells. In this assay the release of endogenous lactose dehydrogenase (LDH), rather than EuTDA, was used to monitor cell lysis. FIG. 30 shows that the Fc variants show substantial ADCC enhancement when NK cells are used as effector cells. Furthermore, together with previous assays, the results indicate that the Fc variants of the present invention show substantial ADCC enhancements regardless of the type of effector cell or the detection method used.

Example 7

ADCP of Fc Variants

Figure 31:
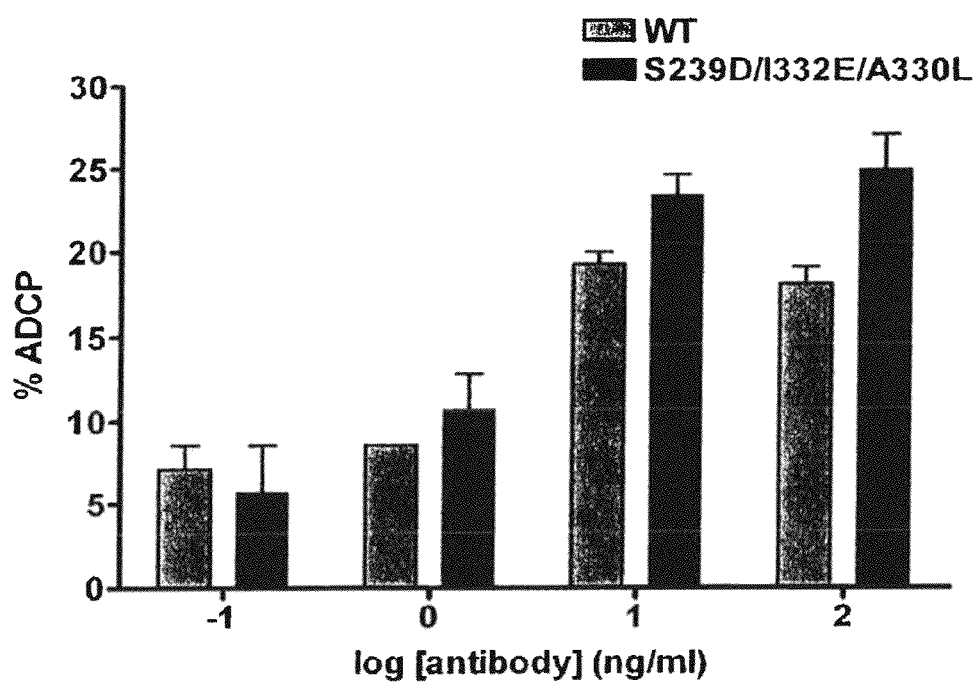
FIG. 31. Cell-based ADCP assay of select variants. The ADCP assay was carried out as described in Example 7, using a co-labeling strategy coupled with flow cytometry. Differentiated macrophages were used as effector cells, and Sk-Br-3 cells were used as target cells. Percent phagocytosis represents the number of co-labeled cells (macrophage+Sk-Br-3) over the total number of Sk-Br-3 in the population (phagocytosed+non-phagocytosed).

Another important FcγR-mediated effector function is ADCP. Phagocytosis of target cancer cells may not only lead to the immediate destruction of target cells, but because phagocytosis is a potential mechanism for antigen uptake and processing by antigen presenting cells, enhanced ADCP may also improve the capacity of the Fc polypeptide to elicit an adaptive immune response. The ability of the Fc variants of the present invention to mediate ADCP was therefore investigated. Monocytes were isolated from heterozygous V158/F158 FcγRIIIa PBMCs using a Percoll gradient. After one week in culture in the presence of 0.1 ng/ml, differentiated macrophages were detached with EDTA/PBS- and labeled with the lipophilic fluorophore, PKH26, according to the manufacturer's protocol (Sigma, St Louis, Mo.). Sk-Br-3 target cells were labeled with PKH67 (Sigma, St Louis, Mo.), seeded in a 96-well plate at 20,000 cells per well, and treated with designated final concentrations of WT or Fc variant trastuzumab. PKH26-labeled macrophages were then added to the opsonized, labeled Sk-Br-3 cells at 20,000 cells per well and the cells were co-cultured for 18 hrs before processing cells for analysis of dual label flow cytometry. Percent phagocytosis was determined as the number of cells co-labeled with PKH76 and PKH26 (macrophage+Sk-Br-3) over the total number of Sk-Br-3 in the population (phagocytosed+ non-phagocytosed) after 10,000 counts. FIG. 31 shows data comparing WT and Fc variant trastuzumab at various antibody concentrations. The results indicate that the S239D/I332E/A330L variant provides a significant enhancement in ADCP over WT trastuzumab.

Example 8

Complement Binding and Activation by Fc Variants

Figure 32B:
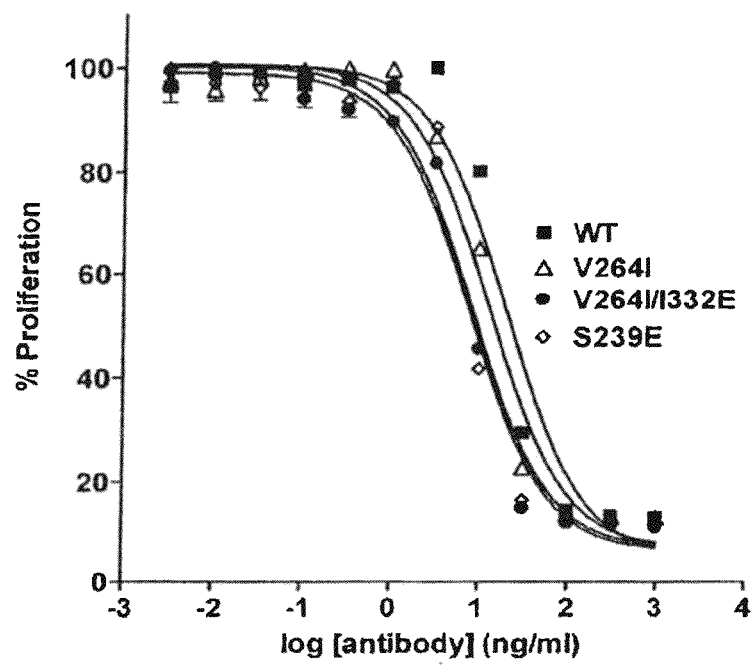
Figure 32C:
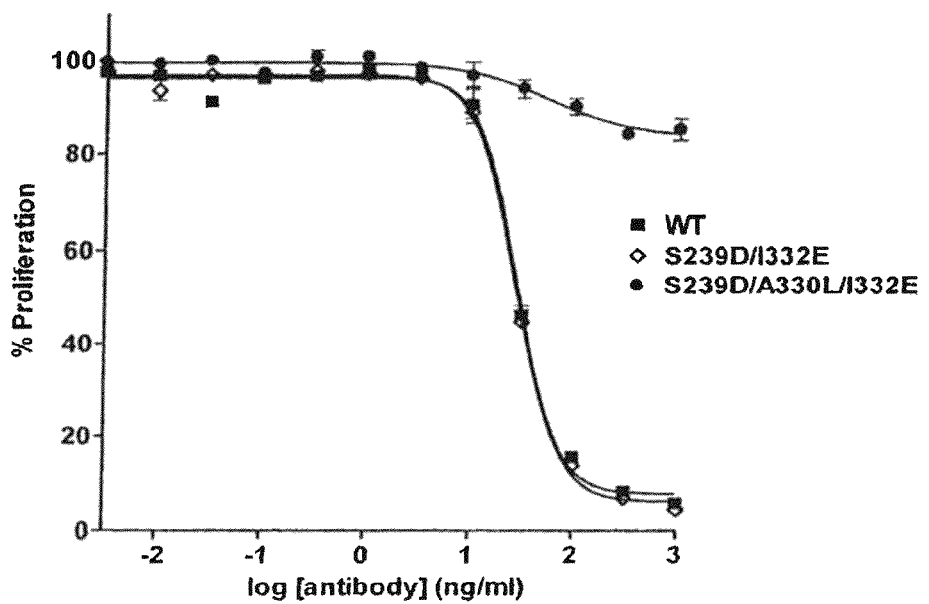

Complement protein C1q binds to a site on Fc that is proximal to the FcγR binding site, and therefore it was prudent to determine whether the Fc variants have maintained their capacity to recruit and activate complement. The AlphaScreen assay was used to measure binding of select Fc variants to the complement protein C1q. The assay was carried out with biotinylated WT alemtuzumab antibody attached to streptavidin donor beads as described in Example 2, and using C1q coupled directly to acceptor beads. Binding data of V264I, I332E, S239E, and V264I/I332E rituximab shown in FIG. 32a indicate that C1q binding is uncompromised. Cell-based CDC assays were also performed on select Fc variants to investigate whether Fc variants maintain the capacity to activate complement. Alamar Blue was used to monitor lysis of Fc variant and WT rituximab-opsonized WIL2-S lymphoma cells by human serum complement (Quidel, San Diego, Calif.). The data in FIG. 32b show that CDC is uncompromised for the Fc variants S239E, V264I, and V264I/I332E rituximab. In contrast, FIG. 32c shows that CDC of the Fc variant S239D/I332E/A330L is completely ablated, whereas the S239D/I332E variant mediates CDC that is comparable to WT rituximab. These results indicate that protein engineering can be used to distinguish between different effector functions. Such control will not only enable the generation of Fc polypeptides, including antibodies and Fc fusions, with properties tailored for a desired clinical outcome, but also provide a unique set of reagents with which to experimentally investigate effector function biology.

Example 9

Enhanced B Cell Depletion in Macaques

In order to evaluate the capacity of the Fc variants to enhance effector function in vivo, a pre-clinical study was carried out wherein B cell depletion was used to measure antibody cytotoxicity in cynomogus monkeys (*Macaca fascicularis*). Three monkeys per sample were injected intravenously with WT or S239D/I332E rituximab antibody, with injections given once daily over days 1-4 in approximate dose ranges of 40 μg/kg (WT control) or 1, 4, 10, or 40 μg/kg (S239D/I332E and/or WT). Actual concentrations were determined experimentally. B cell and natural killer cell levels were monitored from days 5 to 28, and cell populations were counted using flow cytometry using B cell markers CD20+ and CD40+, and natural killer cell markers CD3−/CD16+ and CD3−/CD8+.

Figure 33A:
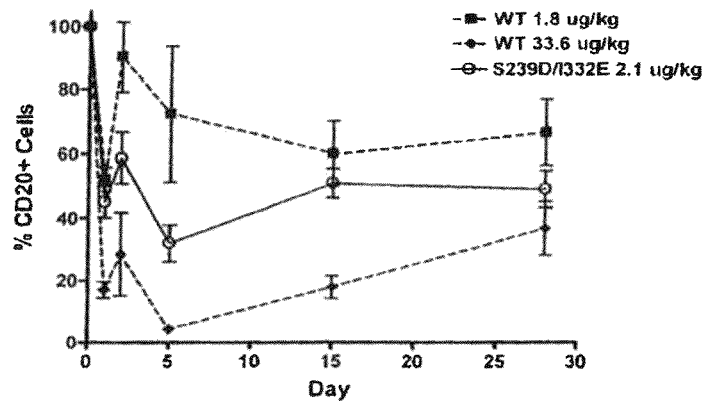
FIGS. 33a-33c. Enhanced B cell depletion by Fc variants in macaques, as described in Example 9.
Figure 33B:
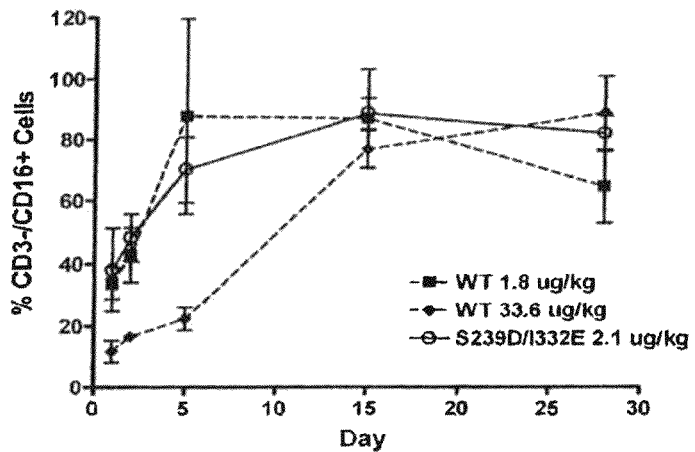
Figure 33C:
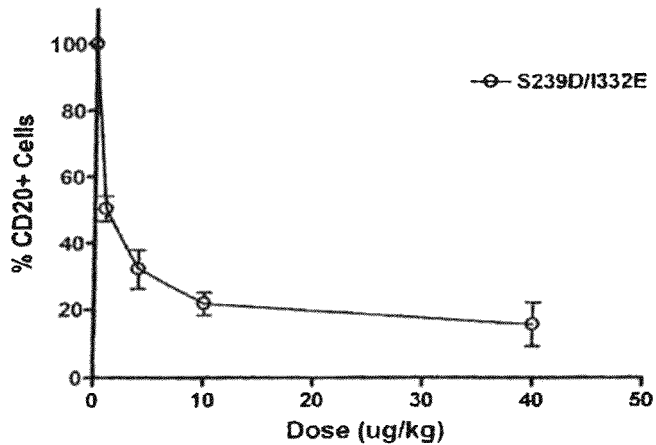

FIG. 33a shows the percent of CD20+ B cells remaining in monkeys dosed with antibodies comprising WT or S239D/I332E rituximab. The S239D/I332E variant and WT control at the lower dosage (1.8 and 2.1 ug/kg) show the greatest difference in B cell counts on day 5. NK cell populations were monitored to evaluate the impact of the effector function enhancement on this cell type; FIG. 33b shows that the increased CD20+ B cell killing of S239D/I332E variant does not affect natural kill cell population. The reduction in B cell level is also dose-dependant, as is shown in FIG. 33c for day 5.

Example 10

Capacity for Testing Fc Variants in Mice

Figure 34A:
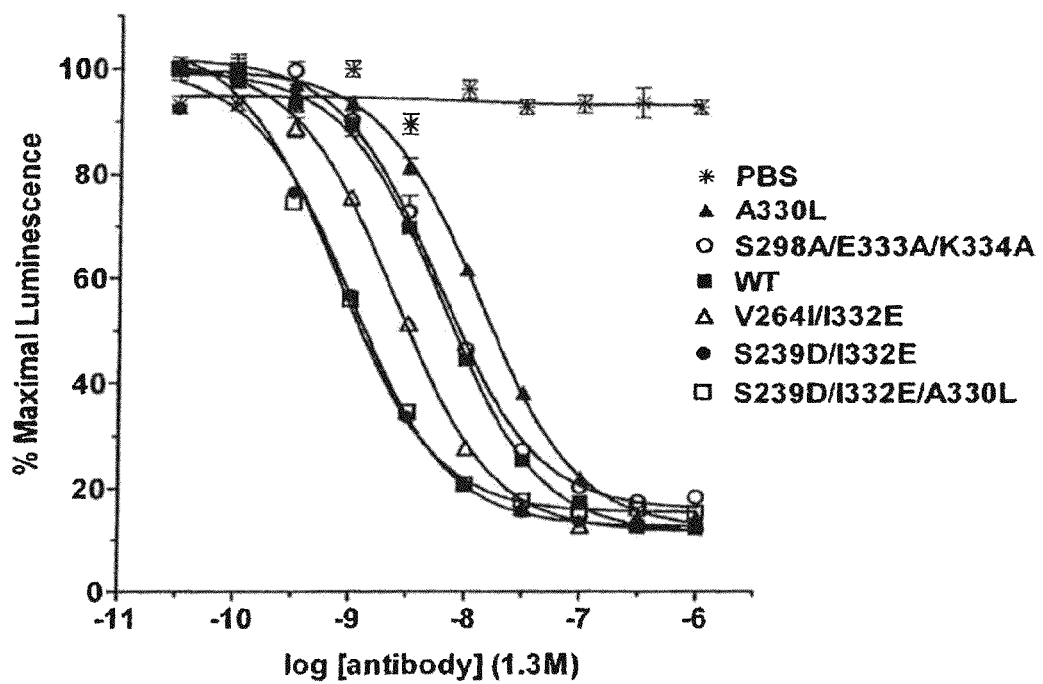
FIGS. 34a-34c. AlphaScreen assay measuring binding of select alemtuzumab (FIG. 34a) and trastuzumab (FIGS. 34b and 34c) Fc variants to mouse FcγRIII, as described in Example 10. The binding data were normalized to the upper and lower baselines for each particular antibody, and the curves represent the fits of the data to a one site competition model. PBS was used as a negative control.
Figure 34B:
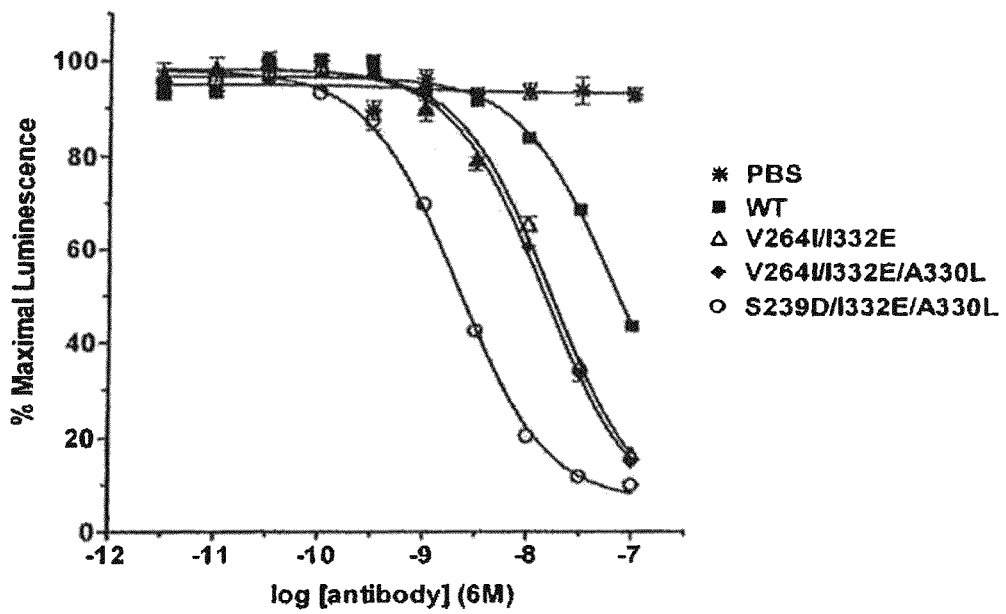
Figure 34C:
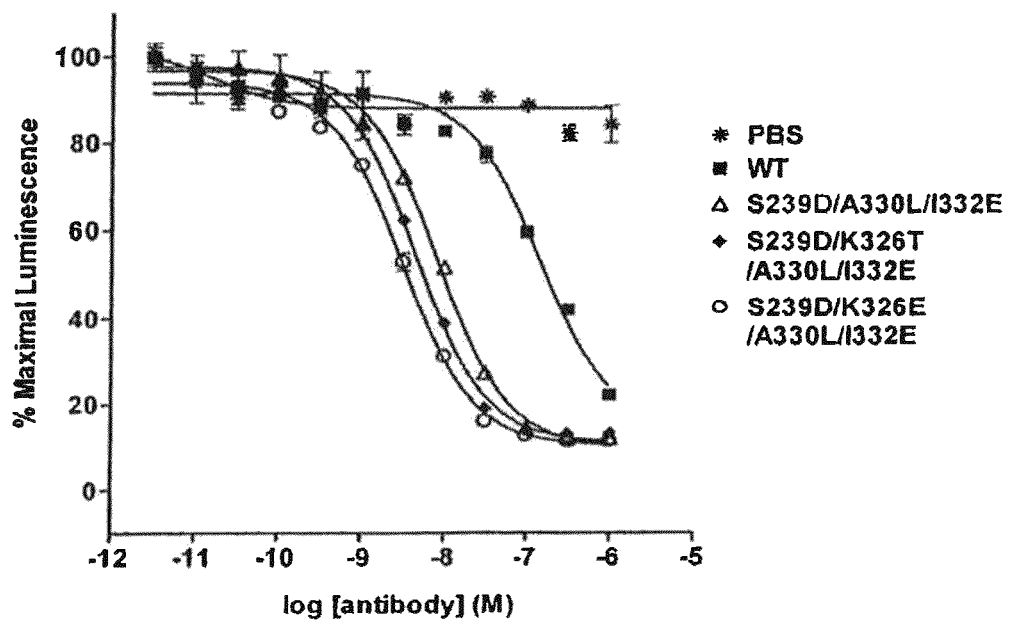
Figure 35:
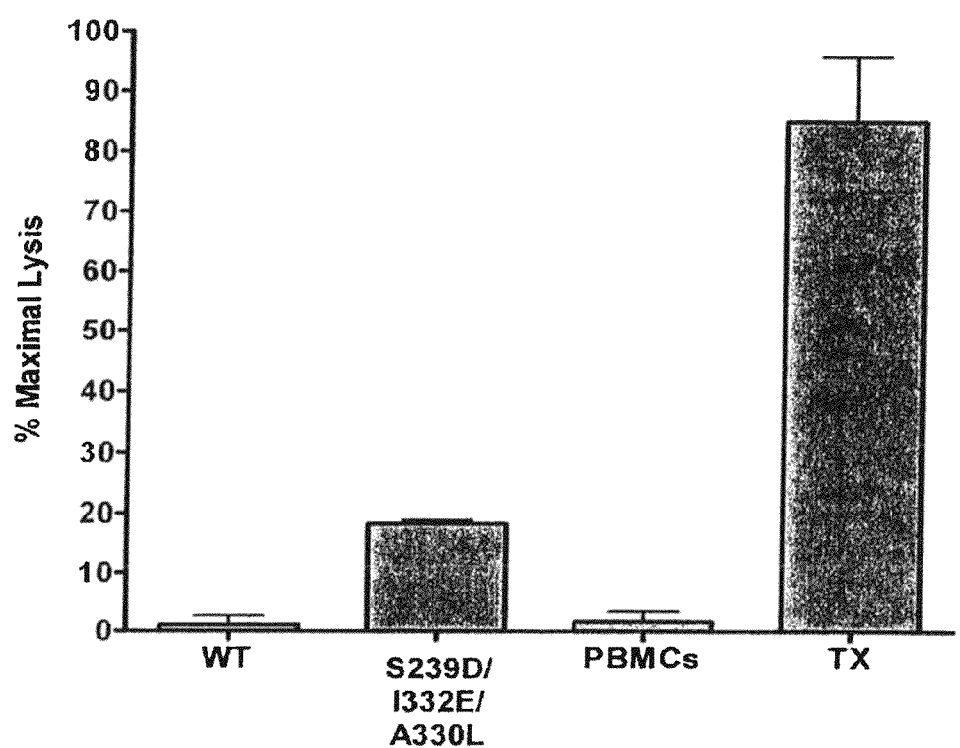
FIG. 35. Cell-based ADCC assays of select Fc variants in the context of trastuzumab using mouse PBMCs as effector cells. ADCC was measured using the DELFIA® EuTDA-based cytotoxicity assay using Sk-Br-3 breast carcinoma target cells and 8-fold excess mouse PBMCs. The bar graph shows the raw fluorescence data for the indicated trastuzumab antibodies at 10 ng/ml. The PBMC bar indicates basal levels of cytotoxicity in the absence of antibody, and TX indicates complete cell lysis in the presence of Triton X1000.

Optimization of Fc to nonhuman FcγRs may be useful for experimentally testing Fc variants in animal models. For example, when tested in mice (for example nude mice, SCID mice, xenograft mice, and/or transgenic mice), antibodies and Fc fusions that comprise Fc variants that are optimized for one or more mouse FcγRs may provide valuable information with regard to clinical efficacy, mechanism of action, and the like. In order to evaluate whether the Fc variants of the present invention may be useful in such experiments, affinity of select Fc variants for mouse FcγRIII was measured using the AlphaScreen assay. The AlphaScreen assay was carried out using biotinylated WT alemtuzumab attached to streptavidin donor beads as described in Example 2, and GST-tagged mouse FcγRIII bound to glutathione chelate acceptor beads, expressed and purified as described in Example 2. These binding data are shown in FIG. 34a for Fc variants in the context of alemtuzumab, and in FIGS. 34b and 34c in the context of trastuzumab. Results show that some Fc variants that enhance binding to human FcγRIIIa also enhance binding to mouse FcγRIII. The enhancement of mouse effector function by the Fc variants was investigated by performing the aforementioned cell-based ADCC assays using mouse rather than human PBMC's. FIG. 35 shows that the S239D/I332E/A330L trastuzumab variant provides substantial ADCC enhancement over WT in the presence of mouse immune cells. This result indicates that the Fc variants of the present invention, or other Fc variants that are optimized for nonhuman FcγRs, may find use in experiments that use animal models.

Example 11

Validation of Fc Variants Expressed in CHO Cells

Figure 36:
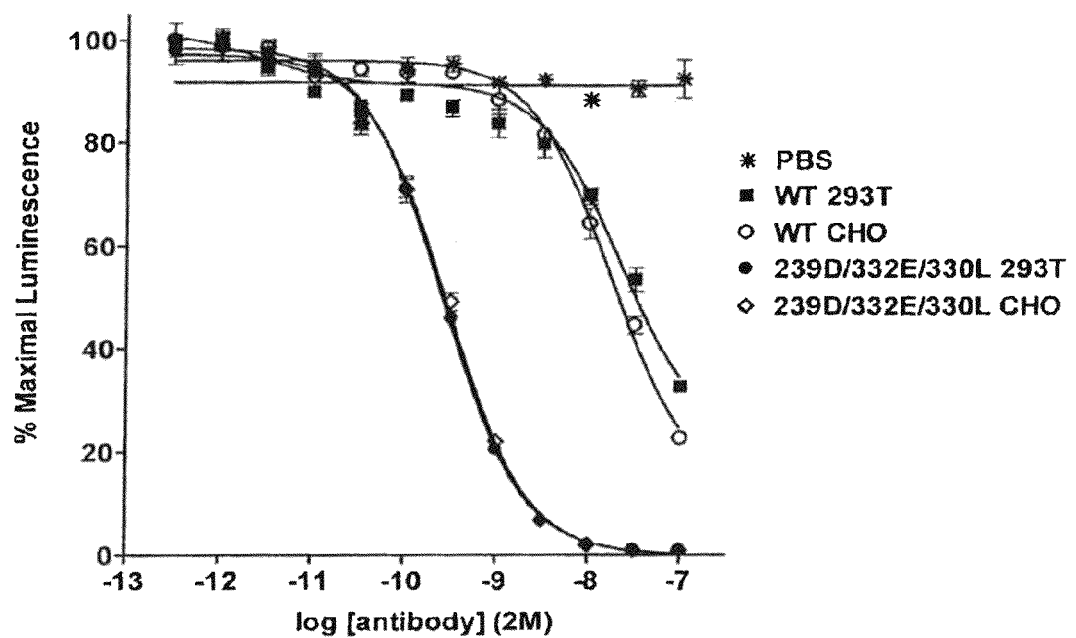
FIG. 36. AlphaScreen assay measuring binding to human V158 FcγRIIIa by select trastuzumab Fc variants expressed in 293T and CHO cells, as described in Example 11. The binding data were normalized to the upper and lower baselines for each particular antibody, and the curves represent the fits of the data to a one site competition model. PBS was used as a negative control.

Whereas the Fc variants of the present invention were expressed in 293T cells for screening purposes, large scale production of antibodies is typically carried out by expression in Chinese Hamster Ovary (CHO) cell lines. In order to evaluate the properties of CHO-expressed Fc variants, select Fc variants and WT alemtuzumab were expressed in CHO cells and purified as described in Example 1. FIG. 36 shows AlphaScreen data comparing binding of CHO- and 293T-expressed Fc variant and WT alemtuzumab to human V158 FcγRIIIa. The results indicate that the Fc variants of the present invention show comparable FcγR binding enhancements whether expressed in 293T or CHO.

Example 12

Enhancement of Fc Variants in Fucose Minus Strain

Figure 37A:
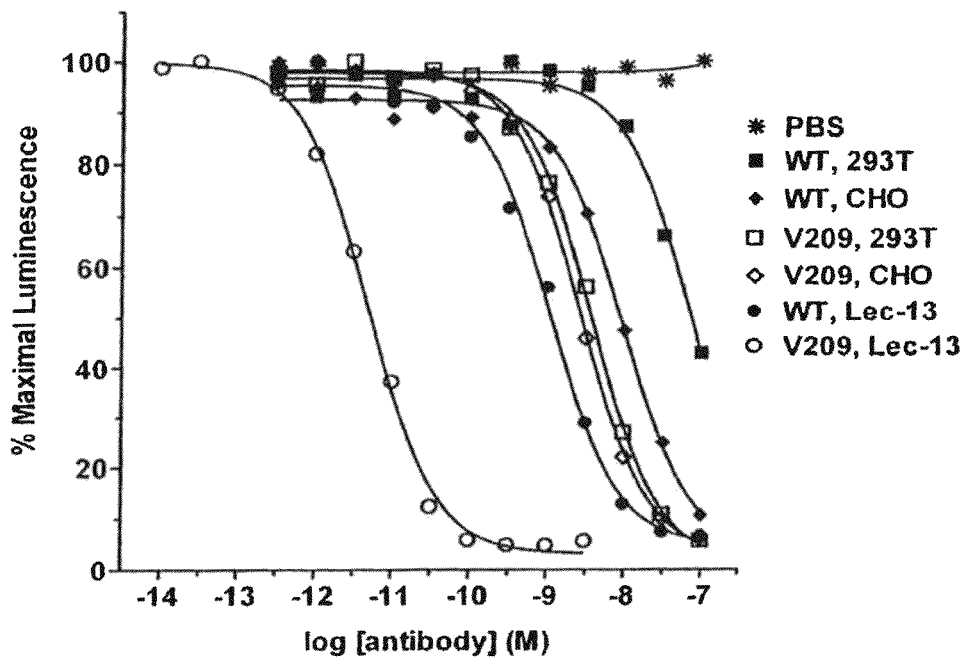
FIGS. 37a-37b. Synergy of Fc variants and engineered glycoforms.
Figure 37B:
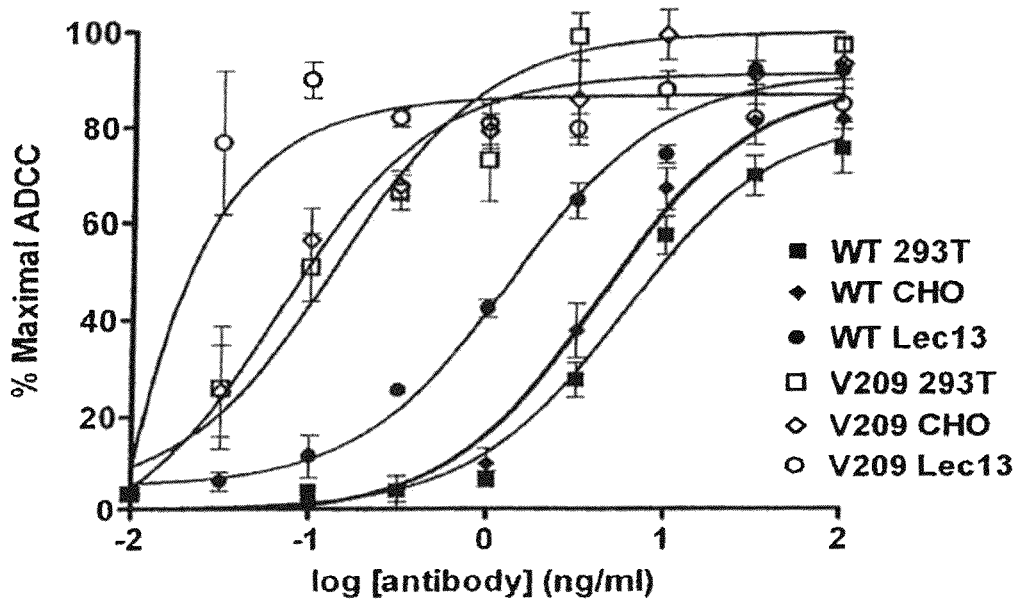

Combinations of the Fc variants of the present invention with other Fc modifications are contemplated with the goal of generating novel Fc polypeptides with optimized properties. It may be beneficial to combine the Fc variants of the present invention with other Fc modifications, including modifications that alter effector function or interaction with one or more Fc ligands. Such combination may provide additive, synergistic, or novel properties in Fc polypeptides. For example, a number of methods exist for engineering different glycoforms of Fc that alter effector function. Engineered glycoforms may be generated by a variety of methods known in the art, many of these techniques are based on controlling the level of fucosylated and/or bisecting oligosaccharides that are covalently attached to the Fc region. One method for engineering Fc glycoforms is to express the Fc polypeptide in a cell line that generates altered glycoforms, for example Lec-13 CHO cells. In order to investigate the properties of Fc variants combined with engineered glycoforms, WT and V209 (S239D/I332E/A330L) trastuzumab were expressed in Lec-13 CHO cells and purified as described above. FIG. 37*a* shows AlphaScreen binding data comparing the binding to human V158 FcγRIIIa by WT and V209 trastuzumab expressed in 293T, CHO, and Lec-13 cells. The results show that there is substantial synergy between the engineered glycoforms produced by this cell line and the Fc variants of the present invention. The cell-based ADCC assay, shown in FIG. 37*b*, supports this result. Together these data indicate that other Fc modifications, particularly engineered glycoforms, may be combined with the Fc variants of the present invention to generate Fc polypeptides, for example antibodies and Fc fusions, with optimized effector functions.

Example 13

Aglycosylated Fc Variants

Figure 38:
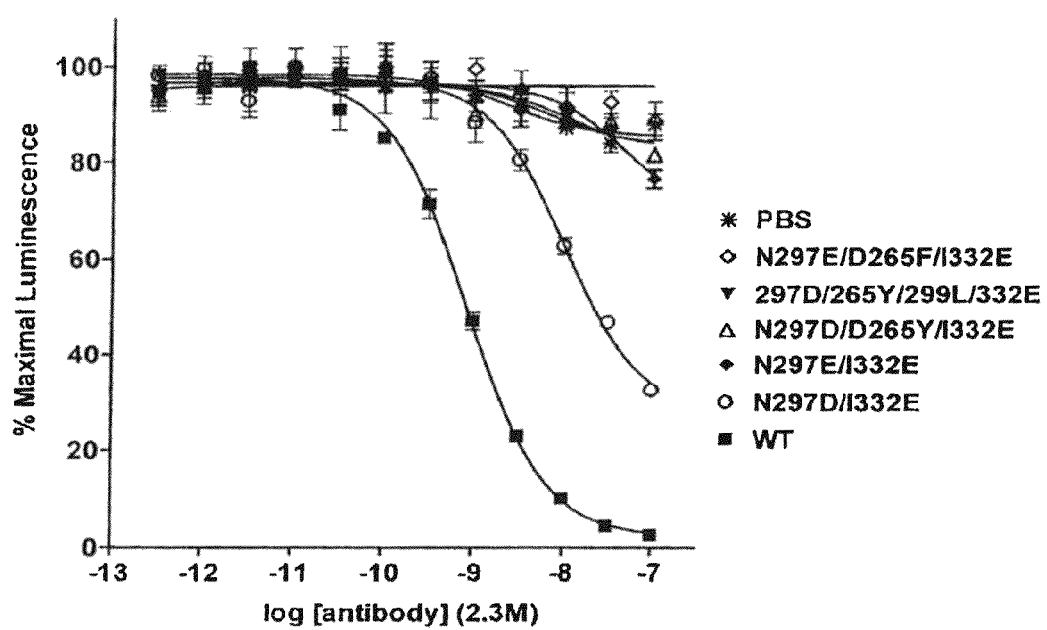
FIG. 38. AlphaScreen assay showing binding of aglycosylated alemtuzumab Fc variants to human V158 FcγRIIIa. The binding data were normalized to the upper and lower baselines for each particular antibody, and the curves represent the fits of the data to a one site competition model. PBS was used as a negative control.

As discussed, one goal of the current experiments was to obtain optimized aglycosylated Fc variants. Several Fc variants provide significant progress towards this goal. Because it is the site of glycosylation, substitution at N297 results in an aglycosylated Fc. Whereas all other Fc variants that comprise a substitution at N297 completely ablate FcγR binding, N297D/I332E has significant binding affinity for FcγRIIIa, shown in FIG. 41 and illustrated in FIG. 38. The exact reason for this result is uncertain in the absence of a high-resolution structure for this variant, although the computational screening predictions suggest that it is potentially due to a combination of new favorable Fc/FcγR interactions and favorable electrostatic properties. Indeed other electrostatic substitutions are envisioned for further optimization of aglycosylated Fc. FIG. 41 shows that other aglycosylated Fc variants such as N297D/A330Y/I332E and S239D/N297D/I332E provide binding enhancements that bring affinity for FcγRIIIa within as much as 0.4- and 0.8-respectively of glycosylated WT alemtuzumab. Combinations of these variants with other Fc variants that enhance FcγR binding are contemplated, with the goal of obtaining aglycosylated Fc variants that bind one or more FcγRs with affinity that is approximately the same as or even better than glycosylated parent Fc. Preferred Fc variants for enhancing Fc ligand binding and/or effector function in an aglycosylated Fc polypeptide include but are not limited to: N297D, N297D/I332E, N297D/I332D, S239D/N297D, S239D/N297D/I332E, N297D/A330Y/I332E, and S239D/N297D/A330Y/I332E. The present invention of course contemplates combinations of these aglycosylated variants with other Fc variants described herein which also enhance Fc ligand binding and/or effector function.

Figure 39:
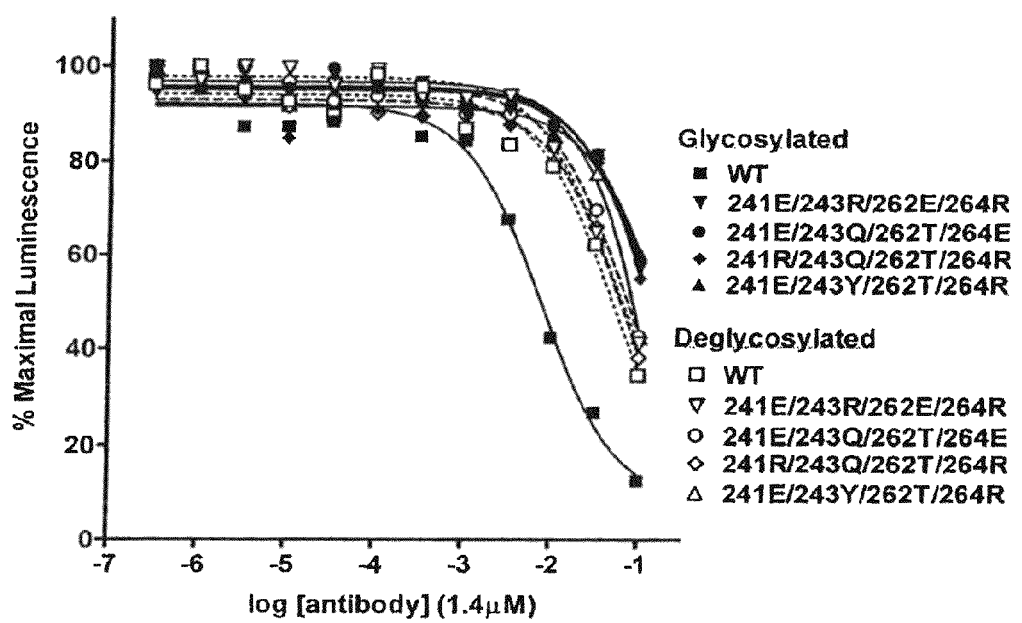
FIG. 39. AlphaScreen assay comparing human V158 FcγRIIIa binding by select alemtuzumab Fc variants in glycosylated (solid symbols, solid lines) and deglycosylated (open symbols, dotted lines). The binding data were normalized to the upper and lower baselines for each particular antibody, and the curves represent the fits of the data to a one site competition model.

An additional set of promising Fc variants provide stability and solubility enhancements in the absence of carbohydrate. Fc variants that comprise substitutions at positions 241, 243, 262, and 264, positions that do not mediate FcγR binding but do determine the interface between the carbohydrate and Fc, ablate FcγR binding, presumably because they perturb the conformation of the carbohydrate. In deglycosylated form, however, Fc variants F241E/F243R/V262E/V264R, F241E/F243Q/V262T/V264E, F241R/F243Q/V262T/V264R, and F241E/F243Y/V262T/V264R show stronger binding to FcγRIIIa than in glycosylated form, as shown by the AlphaScreen data in FIG. 39. This result indicates that these are key positions for optimization of the structure, stability, solubility, and function of aglycosylated Fc. Together these results suggests that protein engineering can be used to restore the favorable functional and solution properties of antibodies and Fc fusions in the absence of carbohydrate, and pave the way for aglycosylated antibodies and Fc fusions with favorable solution properties and full functionality that comprise substitutions at these and other Fc positions.

Example 14

Preferred Variants

Taken together, the data provided in the present invention indicate that Fc variants that provide optimized FcγR binding properties also provide enhanced effector function. Substitutions at a number of positions, including but not limited to 236, 239, 246, 246, 249, 255, 258, 260, 264, 267, 268, 272, 274, 281, 283, 304, 324, 326, 327, 330, 332, 333, 334, and 334 provide promising candidates for improving the effector function and therefore the clinical properties of Fc polypeptides, including antibodies and Fc fusions. Because combinations of Fc variants of the present invention have typically resulted in additive or synergistic binding improvements, and accordingly additive or synergistic enhancements in effector function, it is anticipated that as yet unexplored combinations of the Fc variants provided in FIG. 41 will also provide favorable results. Preferred Fc variants of the present invention for enhancing Fc ligand binding and/or effector function are provided in Table 9.

TABLE 9

| | | | |
|---|---|---|---|
| G236S | S239D/I332E | S239D/K246H/I332E | S239D/K246H/T260H/I332E |
| G236A | S239D/G236A | S239D/V264I/I332E | S239D/K246H/H268D/I332E |
| S239D | S239D/G236S | S239D/S267E/I332E | S239D/K246H/H268E/I332E |
| S239E | S239D/V264I | S239D/H268D/I332E | S239D/H268D/S324G/I332E |
| S239N | S239D/H268D | S239D/H268E/I332E | S239D/H268E/S324G/I332E |
| S239Q | S239D/H268E | S239D/S298A/I332E | S239D/H268D/K326T/I332E |
| S239T | S239D/S298A | S239D/S324G/I332E | S239D/H268E/K326T/I332E |
| K246H | S239D/K326E | S239D/S324I/I332E | S239D/H268D/A330L/I332E |
| K246Y | S239D/A330L | S239D/K326T/I332E | S239D/H268E/A330L/I332E |
| D249Y | S239D/A330Y | S239D/K326E/I332E | S239D/H268D/A330Y/I332E |
| R255Y | S239D/A330I | S239D/K326D/I332E | S239D/H268E/A330Y/I332E |
| E258Y | I332E/V264I | S239D/A327D/I332E | S239D/S298A/S267E/I332E |
| T260H | I332E/H268D | S239D/A330L/I332E | S239D/S298A/H268D/I332E |
| V264I | I332E/H268E | S239D/A330Y/I332E | S239D/S298A/H268E/I332E |
| S267E | I332E/S298A | S239D/A330I/I332E | S239D/S298A/S324G/I332E |
| H268D | I332E/K326E | S239D/K334T/I332E | S239D/S298A/S324I/I332E |
| H268E | I332E/A330L | | S239D/S298A/K326T/I332E |
| E272Y | I332E/A330Y | | S239D/S298A/K326E/I332E |
| E272I | I332E/A330I | | S239D/S298A/A327D/I332E |
| E272H | I332E/G236A | | S239D/S298A/A330L/I332E |
| K274E | I332E/G236S | | S239D/S298A/A330Y/I332E |
| G281D | I332D/V264I | | S239D/K326T/A330Y/I332E |
| E283L | I332D/H268D | | S239D/K326E/A330Y/I332E |
| E283H | I332D/H268E | | S239D/K326E/A330Y/I332E |
| S304T | I332D/S298A | | S239D/K326E/A330L/I332E |
| S324G | I332D/K326E | | |
| S324I | I332D/A330L | | |
| K326T | I332D/A330Y | | |
| A327D | I332D/A330I | | |
| A330Y | I332D/G236A | | |
| A330L | I332D/G236S | | |
| A330I | | | |
| I332D | | | |
| I332E | | | |
| I332N | | | |
| I332Q | | | |
| E333Y | | | |
| K334T | | | |
| K334F | | | |

This list of preferred Fc variants is not meant to constrain the present invention. Indeed all combinations of the any of the Fc variants provided in FIG. 41 are embodiments of the present invention. Furthermore, combinations of any of the Fc variants of the present invention with other discovered or undiscovered Fc variants may also provide favorable properties, and these combinations are also contemplated as embodiments of the present invention. Finally, it is anticipated from these results that other substitutions at positions mutated in present invention may also provide favorable binding enhancements and specificities, and thus substitutions at all positions in FIG. 41 are contemplated.

Example 15

Therapeutic Application of Fc Variants

A number of Fc variants described in the present invention have significant potential for improving the therapeutic efficacy of anticancer antibodies. For illustration purposes, a number of Fc variants of the present invention have been incorporated into the sequence of the antibody rituximab. The WT rituximab light chain and heavy chain, described in U.S. Pat. No. 5,736,137, are provided in FIGS. 40a and 40b. The improved anti-CD20 antibody sequences are provided in FIG. 40c. The improved anti-CD20 antibody sequences comprise at least non-WT amino acid selected from the group consisting of $X_1$, $X_2$, $X_3$, $X_4$, $X_5$, $X_6$, $X_7$, $X_8$, and $X_9$. These improved anti-CD20 antibody sequences may also comprise a substitution $Z_1$ and/or $Z_2$. The use of rituximab here is solely an example, and is not meant to constrain application of the Fc variants to this antibody or any other particular Fc polypeptide.

Table 10 depicts the positions of human Fc, the wild type residue, and the variants (SEQ ID NO: 8) that are included in particular embodiments of the invention. Table 10 is based on IgG1, although as will be appreciated by those in the art, the same thing can be done to any Ig, particularly IgG2, IgG3 and IgG4.

TABLE 10

Figures 2, 3A:
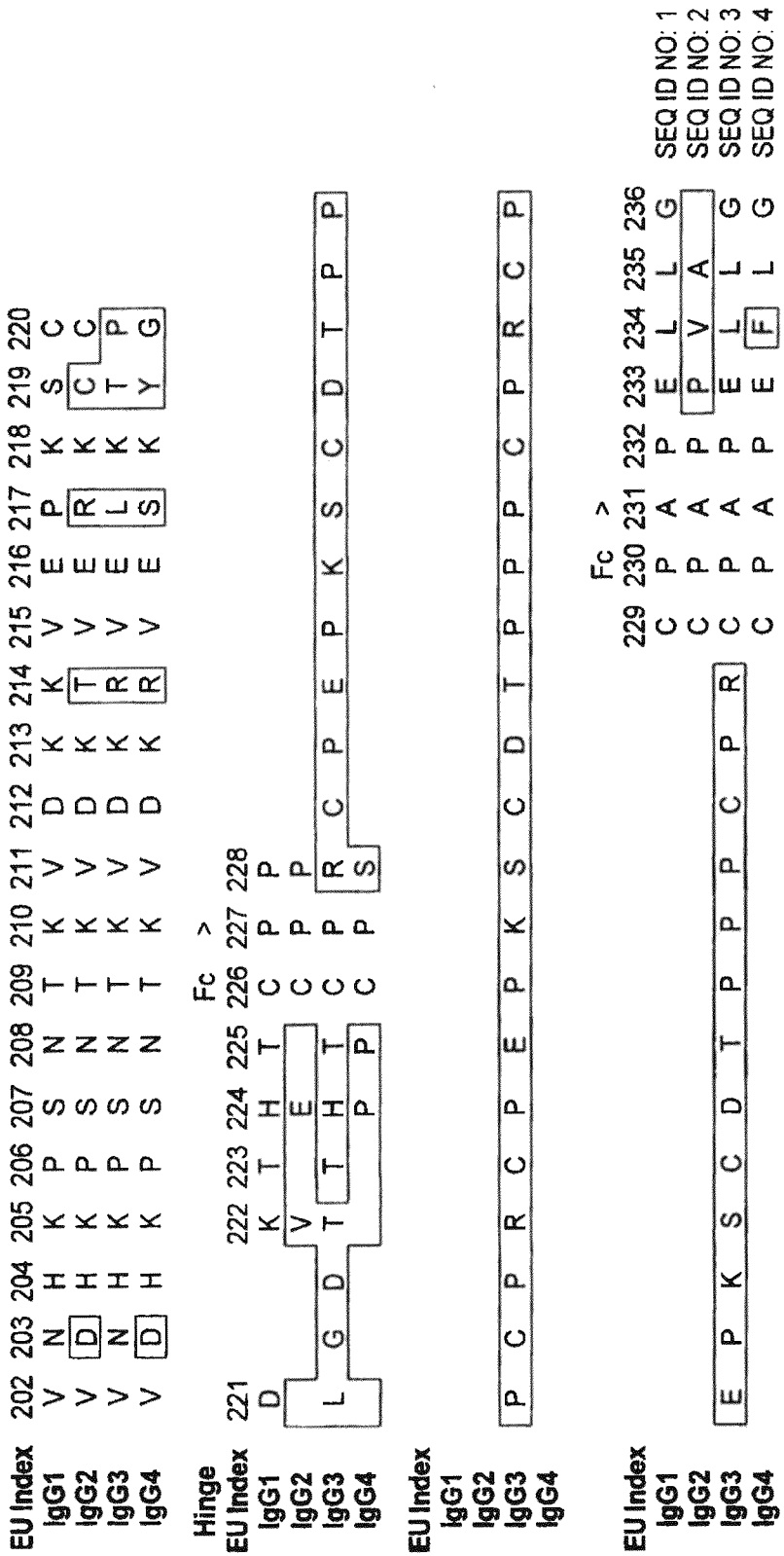

| Position | Wild Type (Human) | Variants including wild type |
|---|---|---|
| 118-220 | FX | see FIG. 3a |
| Vb(221) | D | D, K, Y |
| Vb(222) | K | K, E, Y |
| Vb(223) | T | T, E, K |
| Vb(224) | H | H, E, Y |
| Vb(225) | T | T, E, K, W |
| Fx(226) | WT | C |
| Vb(227) | P | P, E, G, K, Y |
| Vb(228) | P | P, E, G, K, Y |

TABLE 10-continued

| Position | Wild Type (Human) | Variants including wild type |
|---|---|---|
| Fx(229) | (OPEN)(WT) | C |
| Vb(230) | P | P, A, E, G, Y |
| Vb(231) | A | A, E, G, K, P, Y |
| Vb(232) | P | P, E, G, K, Y |
| Vb(233) | E | A, D, F, G, H, I, K, L, M, N, Q, R, S, T, V, W, Y |
| Vb(234) | L | L, A, D, E, F, G, H, I, K, M, N, P, Q, R, S, T, V, W, Y |
| Vb(235) | L | L, A, D, E, F, G, H, I, K, M, N, P, Q, R, S, T, V, W, Y |
| Vb(236) | G | G, A, D, E, F, H, I, K, L, M, N, P, Q, R, S, T, V, W, Y |
| Vb(237) | G | G, D, E, F, H, I, K, L, M, N, P, Q, R, S, T, V, W, Y |
| Vb(238) | P | P, D, E, F, G, H, I, K, L, M, N, Q, R, S, T, V, W, Y |
| Vb(239) | S | S, D, E, F, G, H, I, K, L, M, N, P, Q, R, T, V, W, Y |
| Vb(240) | V | V, A, I, M, T |
| Vb(241) | F | F, D, E, L, R, S, W, Y |
| Fx(242) | WT | L |
| Vb(243) | F | F, E, H, L, Q, R, W, Y |
| Vb(244) | P | P, H |
| Vb(245) | P | P, A |
| Vb(246) | K | K, D, E, H, Y |
| Vb(247) | P | P, G, V |
| Vb(248) | WT | K |
| Vb(249) | D | D, H, Q, Y |
| Fx(250-254) | WT | -(T-L-M-I-S)- |
| Vb(255) | R | R, E, Y |
| Fx(256-257) | WT | -(T-P)- |
| Vb(258) | E | E, H, S, Y |
| Fx(259) | WT | V |
| Vb(260) | T | T, D, E, H, Y |
| Fx(261) | WT | C |
| Vb(262) | V | V, A, E, F, I, T |
| Vb(263) | V | V, A, I, M, T |
| Vb(264) | V | V, A, D, E, F, G, H, I, K, L, M, N, P, Q, R, S, T, W, Y |
| Vb(265) | D | D, F, G, H, I, K, L, M, N, P, Q, R, S, T, V, W, Y |
| Vb(266) | V | V, A, I, M, T |
| Vb(267) | S | S, D, E, F, H, I, K, L, M, N, P, Q, R, T, V, W, Y |
| Vb(268) | H | H, D, E, F, G, I, K, L, M, N, P, Q, R, T, V, W, Y |
| Vb(269) | E | E, F, G, H, I, K, L, M, N, P, R, S, T, V, W, Y |
| Vb(270) | D | D, F, G, H, I, L, M, P, Q, R, S, T, W, Y |
| Vb(271) | A | A, D, E, F, G, H, I, K, L, M, N, P, Q, R, S, T, V, W, Y |
| Vb(272) | E | E, D, F, G, H, I, K, L, M, P, R, S, T, V, W, Y |
| Vb(273) | V | V, I |
| Vb(274) | K | K, D, E, F, G, H, L, M, N, P, R, T, V, W, Y |
| Vb(275) | F | F, L, W |
| Vb(276) | N | N, D, E, F, G, H, I, L, M, P, R, S, T, V, W, Y |
| Fx(277) | WT | W |
| Vb(278) | Y | Y, D, E, G, H, I, K, L, M, N, P, Q, R, S, T, V, W |
| Fx(279) | WT | V |
| Vb(280) | D | D, G, K, L, P, W |
| Vb(281) | G | G, D, E, K, N, P, Q, Y |
| Vb(282) | V | V, E, G, K, P, Y |
| Vb(283) | E | E, G, H, K, L, P, R, Y |
| Vb(284) | V | V, D, E, L, N, Q, T, Y |
| Vb(285) | H | H, D, E, K, Q, W, Y |
| Vb(286) | N | N, E, G, P, Y |
| Fx(287) | WT | A |
| Vb(288) | K | K, D, E, Y |
| Fx(289) | WT | T |
| Vb(290) | K | K, D, H, L, N, W |
| Vb(291) | P | P, D, E, G, H, I, Q, T |
| Vb(292) | R | R, D, E, T, Y |
| Vb(293) | E | E, F, G, H, I, L, M, N, P, R, S, T, V, W, Y |
| Vb(294) | E | E, F, G, H, I, K, L, M, P, R, S, T, V, W, Y |
| Vb(295) | Q | Q, D, E, F, G, H, I, M, N, P, R, S, T, V, W, Y |
| Vb(296) | Y | Y, A, D, E, G, H, I, K, L, M, N, Q, R, S, T, V |
| Vb(297) | N | N, D, E, F, G, H, I, K, L, M, P, Q, R, S, T, V, W, Y |
| Vb(298) | S | S, D, E, F, H, I, K, M, N, Q, R, T, W, Y |
| Vb(299) | T | T, A, D, E, F, G, H, I, K, L, M, N, P, Q, R, S, V, W, Y |
| Vb(300) | Y | Y, A, D, E, G, H, K, M, N, P, Q, R, S, T, V, W |
| Vb(301) | R | R, D, E, H, Y |

TABLE 10-continued

| Position | Wild Type (Human) | Variants including wild type |
| --- | --- | --- |
| Vb(302) | V | V, I |
| Vb(303) | V | V, D, E, Y |
| Vb(304) | S | S, D, H, L, N, T |
| Vb(305) | V | V, E, T, Y |
| Fx(306-312) | WT | -(L-T-V-L-H-Q-D)- * |
| Vb(313) | W | W, F |
| Fx(314-316) | WT | -(L-N-G)- |
| Vb(317) | K | K, E, Q |
| Vb(318) | E | E, H, L, Q, R, Y |
| Fx(319) | WT | Y |
| Vb(320) | K | K, D, F, G, H, I, L, N, P, S, T, V, W, Y |
| Fx(321) | WT | C |
| Vb(322) | K | K, D, F, G, H, I, P, S, T, V, W, Y |
| Vb(323) | V | V, I |
| Vb(324) | S | S, D, F, G, H, I, L, M, P, R, T, V, W, Y |
| Vb(325) | N | N, A, D, E, F, G, H, I, K, L, M, P, Q, R, S, T, V, W, Y |
| Vb(326) | K | K, I, L, P, T |
| Vb(327) | A | A, D, E, F, H, I, K, L, M, N, P, R, S, T, V, W, Y |
| Vb(328) | L | L, A, D, E, F, G, H, I, K, M, N, P, Q, R, S, T, V, W, Y |
| Vb(329) | P | P, D, E, F, G, H, I, K, L, M, N, Q, R, S, T, V, W, Y |
| Vb(330) | A | A, E, F, G, H, I, L, M, N, P, R, S, T, V, W, Y |
| Vb(331) | P | P, D, F, H, I, L, M, Q, R, T, V, W, Y |
| Vb(332) | I | I, A, D, E, F, H, K, L, M, N, P, Q, R, S, T, V, W, Y |
| Vb(333) | E | E, F, H, I, L, M, N, P, T, Y |
| Vb(334) | K | K, F, I, L, P, T |
| Vb(335) | T | T, D, F, G, H, I, L, M, N, P, R, S, V, W, Y |
| Vb(336) | I | I, E, K, Y |
| Vb(337) | S | S, E, H, N |

All references are herein expressly incorporated by reference.

Whereas particular embodiments of the invention have been described above for purposes of illustration, it will be appreciated by those skilled in the art that numerous variations of the details may be made without departing from the invention as described in the appended claims.

We claim:

1. A method of altering effector function in a subject, comprising administering to the subject a polypeptide comprising an Fc variant of a human parent IgG1 Fc polypeptide, wherein said Fc variant comprises an amino acid substitution in the Fc region of said parent Fc polypeptide at position 243, wherein said numbering is according to the EU index in Kabat.

2. The method according to claim 1, wherein said polypeptide is an antibody.

3. The method according to claim 1, wherein said polypeptide comprises an engineered glycoform.

4. The method according to claim 1, wherein said amino acid substitution is 243L.

5. The method according to claim 1, wherein said amino acid substitution is 243L and said Fc variant exhibits decreased binding to FcγRIIIa as compared to the human parent IgG1 Fc polypeptide.

6. The method according to claim 1, wherein said amino acid substitution is 243E.

7. The method according to claim 1, wherein said amino acid substitution is 243E and said Fc variant exhibits decreased binding to FcγRIIIa as compared to the human parent IgG1 Fc polypeptide.

8. The method according to claim 1, wherein said amino acid substitution is 243W.

9. The method according to claim 1, wherein said amino acid substitution is 243W and said Fc variant exhibits increased binding to FcγRIIIa as compared to the human parent IgG1 Fc polypeptide.

10. The method according to claim 2, wherein said antibody has specificity for a target antigen selected from the group consisting of CD19, CD20, CD22, CD30, CD33, CD40, CD40L, CD52, Her2/neu, EGFR, EpCAM, MUC1, GD3, CEA, CA 125, IgE, HLA-DR, TNFalpha, MUC18, prostate specific membrane antigen (PMSA) and VEGF.

11. The method according to claim 2, wherein said antibody has specificity for Her2/neu.

12. The method according to claim 2, wherein said subject has cancer.

13. The method according to claim 1, wherein said subject has an autoimmune disorder.

14. The method according to claim 1, wherein said subject has an inflammatory disorder.

* * * * *

SEQUENCE LISTING

<160> NUMBER OF SEQ ID NOS: 11

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205
```

```
Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                    245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                    325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 451
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (243)..(243)
<223> OTHER INFORMATION: Xaa can be Serine, Aspartic Acid, Glutamic
      Acid, Asparagine, Glutamine or Threonine
<220> FEATURE:
<221> NAME/KEY: misc_feature
<222> LOCATION: (244)..(244)
<223> OTHER INFORMATION: Xaa can be Valine, Isoleucine or Methionine
<220> FEATURE:
<221> NAME/KEY: misc_feature
<222> LOCATION: (268)..(268)
<223> OTHER INFORMATION: Xaa can be Valine, Isoleucine, Threonine or
      Tyrosine
<220> FEATURE:
<221> NAME/KEY: misc_feature
<222> LOCATION: (272)..(272)
<223> OTHER INFORMATION: Xaa can be Histidine, Aspartic Acid or Glutamic
      Acid
<220> FEATURE:
<221> NAME/KEY: misc_feature
<222> LOCATION: (276)..(276)
<223> OTHER INFORMATION: Xaa can be Glutamic Acid or Tyrosine
<220> FEATURE:
<221> NAME/KEY: misc_feature
<222> LOCATION: (278)..(278)
<223> OTHER INFORMATION: Xaa can be Lysine or Glutamic Acid
<220> FEATURE:
<221> NAME/KEY: misc_feature
<222> LOCATION: (301)..(301)
<223> OTHER INFORMATION: Xaa can be Asparagine or Aspartic Acid
<220> FEATURE:
<221> NAME/KEY: misc_feature
<222> LOCATION: (302)..(302)
<223> OTHER INFORMATION: Xaa can be Serine, Alanine or Aspartic Acid
<220> FEATURE:
<221> NAME/KEY: misc_feature
<222> LOCATION: (330)..(330)
<223> OTHER INFORMATION: Xaa can be Lysine, Glutamic Acid or Threonine
<220> FEATURE:
<221> NAME/KEY: misc_feature
<222> LOCATION: (334)..(334)
<223> OTHER INFORMATION: Xaa can be Alanine, Tyrosine, Leucine or
      Isoleucine
<220> FEATURE:
<221> NAME/KEY: misc_feature
<222> LOCATION: (336)..(336)
<223> OTHER INFORMATION: Xaa can be Isoleucine, Aspartic Acid, Glutamic Acid, Asparagine or Glutamine

<400> SEQUENCE: 5

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Xaa Xaa Phe Leu Phe Pro Pro Lys Pro Lys Asp Thr Leu Met
                245                 250                 255

Ile Ser Arg Thr Pro Glu Val Thr Cys Val Val Xaa Asp Val Ser Xaa
            260                 265                 270

Glu Asp Pro Xaa Val Xaa Phe Asn Trp Tyr Val Asp Gly Val Glu Val
        275                 280                 285

His Asn Ala Lys Thr Lys Pro Arg Glu Glu Gln Tyr Xaa Xaa Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Xaa Ala Leu Pro Xaa Pro Xaa
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
```

```
                           405                 410                 415
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 6
<211> LENGTH: 213
<212> TYPE: PRT
<213> ORGANISM: Homo sapiens

<400> SEQUENCE: 6

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 451
<212> TYPE: PRT
<213> ORGANISM: Homo sapiens

<400> SEQUENCE: 7

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60
```

```
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 8
<211> LENGTH: 117
<212> TYPE: PRT
```

```
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Aspartic Acid, Lysine or Tyrosine
<220> FEATURE:
<221> NAME/KEY: misc_feature
<222> LOCATION: (2)..(2)
<223> OTHER INFORMATION: Xaa can be Lysine, Glutamic Acid or Tyrosine
<220> FEATURE:
<221> NAME/KEY: misc_feature
<222> LOCATION: (3)..(3)
<223> OTHER INFORMATION: Xaa can be Threonine, Glutamic Acid or Lysine
<220> FEATURE:
<221> NAME/KEY: misc_feature
<222> LOCATION: (4)..(4)
<223> OTHER INFORMATION: Xaa can be Histidine, Glutamic Acid or Tyrosine
<220> FEATURE:
<221> NAME/KEY: misc_feature
<222> LOCATION: (5)..(5)
<223> OTHER INFORMATION: Xaa can be Threonine, Glutamic Acid, Lysine or
      Tryptophan
<220> FEATURE:
<221> NAME/KEY: misc_feature
<222> LOCATION: (7)..(8)
<223> OTHER INFORMATION: Xaa can be Proline, Glutamic Acid, Glycine,
      Lysine or Tyrosine
<220> FEATURE:
<221> NAME/KEY: misc_feature
<222> LOCATION: (10)..(10)
<223> OTHER INFORMATION: Xaa can be Proline, Alanine, Glutamic Acid,
      Glycine or Tyrosine
<220> FEATURE:
<221> NAME/KEY: misc_feature
<222> LOCATION: (11)..(11)
<223> OTHER INFORMATION: Xaa can be Alanine, Glutamic Acid, Glycine,
      Lysine, Proline or Tyrosine
<220> FEATURE:
<221> NAME/KEY: misc_feature
<222> LOCATION: (12)..(12)
<223> OTHER INFORMATION: Xaa can be Proline, Glutamic Acid, Glycine,
      Lysine or Tyrosine
<220> FEATURE:
<221> NAME/KEY: misc_feature
<222> LOCATION: (13)..(13)
<223> OTHER INFORMATION: Xaa can be any amino acid except Cysteine,
      Lysine and Proline
<220> FEATURE:
<221> NAME/KEY: misc_feature
<222> LOCATION: (14)..(16)
<223> OTHER INFORMATION: Xaa can be any amino acid except Cysteine
<220> FEATURE:
<221> NAME/KEY: misc_feature
<222> LOCATION: (17)..(19)
<223> OTHER INFORMATION: Xaa can be any amino acid except Alanine and
      Cysteine
<220> FEATURE:
<221> NAME/KEY: misc_feature
<222> LOCATION: (20)..(20)
<223> OTHER INFORMATION: Xaa can be Valine, Alanine, Isoleucine,
      Methionine or Threonine
<220> FEATURE:
<221> NAME/KEY: misc_feature
<222> LOCATION: (21)..(21)
<223> OTHER INFORMATION: Xaa can be Phenylalanine, Aspartic Acid,
      Glutamic Acid, Leucine, Arginine, Serine, Tryptophan or Tyrosine
<220> FEATURE:
<221> NAME/KEY: misc_feature
<222> LOCATION: (23)..(23)
<223> OTHER INFORMATION: Xaa can be Phenylalanine, Glutamic Acid,
      Histidine, Leucine, Glutamine, Arginine, Tryptophan or Tyrosine
<220> FEATURE:
<221> NAME/KEY: misc_feature
<222> LOCATION: (24)..(24)
<223> OTHER INFORMATION: Xaa can be Proline or Histidine
<220> FEATURE:
<221> NAME/KEY: misc_feature
<222> LOCATION: (25)..(25)
```

```
<223> OTHER INFORMATION: Xaa can be Proline or Alanine
<220> FEATURE:
<221> NAME/KEY: misc_feature
<222> LOCATION: (26)..(26)
<223> OTHER INFORMATION: Xaa can be Lysine, Aspartic Acid, Glutamic
      Acid, Histidine or Tyrosine
<220> FEATURE:
<221> NAME/KEY: misc_feature
<222> LOCATION: (27)..(27)
<223> OTHER INFORMATION: Xaa can be Proline, Glycine or Valine
<220> FEATURE:
<221> NAME/KEY: misc_feature
<222> LOCATION: (29)..(29)
<223> OTHER INFORMATION: Xaa can be Aspartic Acid, Histidine, Glutamine
      or Tyrosine
<220> FEATURE:
<221> NAME/KEY: misc_feature
<222> LOCATION: (35)..(35)
<223> OTHER INFORMATION: Xaa can be Arginine, Glutamic Acid or Tyrosine
<220> FEATURE:
<221> NAME/KEY: misc_feature
<222> LOCATION: (38)..(38)
<223> OTHER INFORMATION: Xaa can be Glutamic Acid, Histidine, Serine or
      Tyrosine
<220> FEATURE:
<221> NAME/KEY: misc_feature
<222> LOCATION: (40)..(40)
<223> OTHER INFORMATION: Xaa can be Threonine, Aspartic Acid, Glutamic
      Acid, Histidine or Tyrosine
<220> FEATURE:
<221> NAME/KEY: misc_feature
<222> LOCATION: (42)..(42)
<223> OTHER INFORMATION: Xaa can be Valine, Alanine, Glutamic Acid,
      Phenylalanine, Isoleucine or Threonine
<220> FEATURE:
<221> NAME/KEY: misc_feature
<222> LOCATION: (43)..(43)
<223> OTHER INFORMATION: Xaa can be Valine, Alanine, Isoleucine,
      Methionine or Threonine
<220> FEATURE:
<221> NAME/KEY: misc_feature
<222> LOCATION: (44)..(44)
<223> OTHER INFORMATION: Xaa can be any amino acid except Cysteine
<220> FEATURE:
<221> NAME/KEY: misc_feature
<222> LOCATION: (45)..(45)
<223> OTHER INFORMATION: Xaa can be any amino acid except Cysteine,
      Alanine, and Glutamic Acid
<220> FEATURE:
<221> NAME/KEY: misc_feature
<222> LOCATION: (46)..(46)
<223> OTHER INFORMATION: Xaa can be Valine, Alanine, Isoleucine,
      Methionine or Threonine
<220> FEATURE:
<221> NAME/KEY: misc_feature
<222> LOCATION: (47)..(47)
<223> OTHER INFORMATION: Xaa can be any amino acid except Cysteine,
      Alanine, and Glycine
<220> FEATURE:
<221> NAME/KEY: misc_feature
<222> LOCATION: (48)..(48)
<223> OTHER INFORMATION: Xaa can be any amino acid except Cysteine,
      Alanine, and Serine
<220> FEATURE:
<221> NAME/KEY: misc_feature
<222> LOCATION: (49)..(49)
<223> OTHER INFORMATION: Xaa can be any amino acid except Cysteine,
      Alanine, Aspartic Acid and Glutamine
<220> FEATURE:
<221> NAME/KEY: misc_feature
<222> LOCATION: (50)..(50)
<223> OTHER INFORMATION: Xaa can be any amino acid except Cysteine,
      Alanine, Glutamic Acid, Asparagine, Lysine and Valine
<220> FEATURE:
<221> NAME/KEY: misc_feature
<222> LOCATION: (51)..(51)
<223> OTHER INFORMATION: Xaa can be any amino acid except Cysteine and
      Proline
<220> FEATURE:
<221> NAME/KEY: misc_feature
```

```
<222> LOCATION: (52)..(52)
<223> OTHER INFORMATION: Xaa can be any amino acid except Cysteine,
      Alanine, Arginine and Glutamine
<220> FEATURE:
<221> NAME/KEY: misc_feature
<222> LOCATION: (53)..(53)
<223> OTHER INFORMATION: Xaa can be Valine or Isoleucine
<220> FEATURE:
<221> NAME/KEY: misc_feature
<222> LOCATION: (54)..(54)
<223> OTHER INFORMATION: Xaa can be any amino acid except Alanine,
      Cysteine, Glutamine, Isoleucine and Serine
<220> FEATURE:
<221> NAME/KEY: misc_feature
<222> LOCATION: (55)..(55)
<223> OTHER INFORMATION: Xaa can be Phenylalanine, Leucine or Tryptophan
<220> FEATURE:
<221> NAME/KEY: misc_feature
<222> LOCATION: (56)..(56)
<223> OTHER INFORMATION: Xaa can be any amino acid except Alanine,
      Cysteine, Glutamine and Lysine
<220> FEATURE:
<221> NAME/KEY: misc_feature
<222> LOCATION: (58)..(58)
<223> OTHER INFORMATION: Xaa can be any amino acid except Alanine,
      Cysteine and Phenylalanine
<220> FEATURE:
<221> NAME/KEY: misc_feature
<222> LOCATION: (60)..(60)
<223> OTHER INFORMATION: Xaa can be Aspartic Acid, Glycine, Lysine,
      Leucine, Proline or Tryptophan
<220> FEATURE:
<221> NAME/KEY: misc_feature
<222> LOCATION: (61)..(61)
<223> OTHER INFORMATION: Xaa can be Aspartic Acid, Glycine, Glutamic
      Acid, Lysine, Asparagine, Proline, Glutamine or Tyrosine
<220> FEATURE:
<221> NAME/KEY: misc_feature
<222> LOCATION: (62)..(62)
<223> OTHER INFORMATION: Xaa can be Valine, Glutamic Acid, Glycine,
      Lysine, Proline or Tyrosine
<220> FEATURE:
<221> NAME/KEY: misc_feature
<222> LOCATION: (63)..(63)
<223> OTHER INFORMATION: Xaa can be Glutamic Acid, Glycine, Histidine,
      Lysine, Proline, Arginine, Tyrosine or Leucine
<220> FEATURE:
<221> NAME/KEY: misc_feature
<222> LOCATION: (64)..(64)
<223> OTHER INFORMATION: Xaa can be Valine, Aspartic Acid, Glutamic
      Acid, Leucine, Asparagine, Glutamine, Threonine or Tyrosine
<220> FEATURE:
<221> NAME/KEY: misc_feature
<222> LOCATION: (65)..(65)
<223> OTHER INFORMATION: Xaa can be Histidine, Aspartic Acid, Glutamic
      Acid, Lysine, Glutamine, Tryptophan  or Tyrosine
<220> FEATURE:
<221> NAME/KEY: misc_feature
<222> LOCATION: (66)..(66)
<223> OTHER INFORMATION: Xaa can be Asparagine, Glutamic Acid, Glycine,
      Proline or Tyrosine
<220> FEATURE:
<221> NAME/KEY: misc_feature
<222> LOCATION: (68)..(68)
<223> OTHER INFORMATION: Xaa can be Lysine, Aspartic Acid, Glutamic Acid
      or Tyrosine
<220> FEATURE:
<221> NAME/KEY: misc_feature
<222> LOCATION: (70)..(70)
<223> OTHER INFORMATION: Xaa can be Lysine, Aspartic Acid, Histidine,
      Leucine, Asparagine or Tryptophan
<220> FEATURE:
<221> NAME/KEY: misc_feature
<222> LOCATION: (71)..(71)
<223> OTHER INFORMATION: Xaa can be Proline, Aspartic Acid, Glutamic
      Acid, Glycine, Histidinie, Isoleucine, Glutamine or Threonine
<220> FEATURE:
<221> NAME/KEY: misc_feature
<222> LOCATION: (72)..(72)
<223> OTHER INFORMATION: Xaa can be Arginine, Aspartic Acid, Glutamic
```

```
        Acid, Threonine or Tyrosine
<220> FEATURE:
<221> NAME/KEY: misc_feature
<222> LOCATION: (73)..(73)
<223> OTHER INFORMATION: Xaa can be any amino acid except Alanine,
      Cysteine, Aspartic Acid, Glutamine and Lysine
<220> FEATURE:
<221> NAME/KEY: misc_feature
<222> LOCATION: (74)..(74)
<223> OTHER INFORMATION: Xaa can be any amino acid except Alanine,
      Cysteine, Arginine, Aspartic Acid and Glutamine
<220> FEATURE:
<221> NAME/KEY: misc_feature
<222> LOCATION: (75)..(75)
<223> OTHER INFORMATION: Xaa can be any amino acid except Alanine,
      Cysteine, Leucine and Lysine
<220> FEATURE:
<221> NAME/KEY: misc_feature
<222> LOCATION: (76)..(76)
<223> OTHER INFORMATION: Xaa can be any amino acid except Cysteine,
      Phenylalanine, Proline and Tryptophan
<220> FEATURE:
<221> NAME/KEY: misc_feature
<222> LOCATION: (77)..(77)
<223> OTHER INFORMATION: Xaa can be any amino acid except Alanine and
      Cysteine
<220> FEATURE:
<221> NAME/KEY: misc_feature
<222> LOCATION: (78)..(78)
<223> OTHER INFORMATION: Xaa can be any amino acid except Alanine,
      Cysteine, Glycine, Leucine, Proline and Valine
<220> FEATURE:
<221> NAME/KEY: misc_feature
<222> LOCATION: (79)..(79)
<223> OTHER INFORMATION: Xaa can be any amino acid except Cysteine
<220> FEATURE:
<221> NAME/KEY: misc_feature
<222> LOCATION: (80)..(80)
<223> OTHER INFORMATION: Xaa can be any amino acid except Cysteine,
      Isoleucine, Leucine and Phenylalanine
<220> FEATURE:
<221> NAME/KEY: misc_feature
<222> LOCATION: (81)..(81)
<223> OTHER INFORMATION: Xaa can be Arginine, Aspartic Acid, Glutamic
      Acid, Histidine or Tyrosine
<220> FEATURE:
<221> NAME/KEY: misc_feature
<222> LOCATION: (82)..(82)
<223> OTHER INFORMATION: Xaa can be Valine or Isoleucine
<220> FEATURE:
<221> NAME/KEY: misc_feature
<222> LOCATION: (83)..(83)
<223> OTHER INFORMATION: Xaa can be Valine, Aspartic Acid, Glutamic Acid
      or Tyrosine
<220> FEATURE:
<221> NAME/KEY: misc_feature
<222> LOCATION: (84)..(84)
<223> OTHER INFORMATION: Xaa can be Serine, Aspartic Acid, Histidine,
      Leucine, Asparagine or Threonine
<220> FEATURE:
<221> NAME/KEY: misc_feature
<222> LOCATION: (85)..(85)
<223> OTHER INFORMATION: Xaa can be Valine, Gluatmic Acid, Threonine or
      Tyrosine
<220> FEATURE:
<221> NAME/KEY: misc_feature
<222> LOCATION: (93)..(93)
<223> OTHER INFORMATION: Xaa can be Tryptophan or Phenylalanine
<220> FEATURE:
<221> NAME/KEY: misc_feature
<222> LOCATION: (97)..(97)
<223> OTHER INFORMATION: Xaa can be Lysine, Gluatmic Acid, or Glutamine
<220> FEATURE:
<221> NAME/KEY: misc_feature
<222> LOCATION: (98)..(98)
<223> OTHER INFORMATION: Xaa can be Glutamic Acid, Histidine, Leucine,
      Glutamine, Arginine or Tyrosine
<220> FEATURE:
<221> NAME/KEY: misc_feature
<222> LOCATION: (100)..(100)
```

-continued

```
<223> OTHER INFORMATION: Xaa can be any amino acid except Alanine,
      Arginine, Cysteine, Glutamine, Glutamic Acid and Methionine
<220> FEATURE:
<221> NAME/KEY: misc_feature
<222> LOCATION: (102)..(102)
<223> OTHER INFORMATION: Xaa can be any amino acid except Alanine,
      Arginine, Asparagine, Cysteine, Glutamine, Glutamic Acid, Leucine,
      and Methionine
<220> FEATURE:
<221> NAME/KEY: misc_feature
<222> LOCATION: (103)..(103)
<223> OTHER INFORMATION: Xaa can be Valine or Isoleucine
<220> FEATURE:
<221> NAME/KEY: misc_feature
<222> LOCATION: (104)..(104)
<223> OTHER INFORMATION: Xaa can be any amino acid except for Alanine,
      Cysteine, Asparagine, Glutamine, Glutamic Acid and Lysine
<220> FEATURE:
<221> NAME/KEY: misc_feature
<222> LOCATION: (105)..(105)
<223> OTHER INFORMATION: Xaa can be any amino acid except for Cysteine
<220> FEATURE:
<221> NAME/KEY: misc_feature
<222> LOCATION: (106)..(106)
<223> OTHER INFORMATION: Xaa can be Lysine, Isoleucine, Leucine, Proline
      or Threonine
<220> FEATURE:
<221> NAME/KEY: misc_feature
<222> LOCATION: (107)..(107)
<223> OTHER INFORMATION: Xaa can be any amino acid except Cysteine,
      Glutamine and Glycine
<220> FEATURE:
<221> NAME/KEY: misc_feature
<222> LOCATION: (108)..(108)
<223> OTHER INFORMATION: Xaa can be any amino acid except Cysteine
<220> FEATURE:
<221> NAME/KEY: misc_feature
<222> LOCATION: (109)..(109)
<223> OTHER INFORMATION: Xaa can be any amino acid except Alanine and
      Cysteine
<220> FEATURE:
<221> NAME/KEY: misc_feature
<222> LOCATION: (110)..(110)
<223> OTHER INFORMATION: Xaa can be any amino acid except Aspartic Acid,
      Cysteine, Glutamine and Lysine
<220> FEATURE:
<221> NAME/KEY: misc_feature
<222> LOCATION: (111)..(111)
<223> OTHER INFORMATION: Xaa can be any amino acid except Alanine,
      Asparagine, Cysteine, Glutamic Acid, Glycine, Lysine and Serine
<220> FEATURE:
<221> NAME/KEY: misc_feature
<222> LOCATION: (112)..(112)
<223> OTHER INFORMATION: Xaa can be any amino acid except Cysteine and
      Glycine
<220> FEATURE:
<221> NAME/KEY: misc_feature
<222> LOCATION: (113)..(113)
<223> OTHER INFORMATION: Xaa can be Glutamic Acid, Phenylalanine,
      Histidine, Isoleucine, Leucine, Methionine, Asparagine, Proline,
      Threonine or Tyrosine
<220> FEATURE:
<221> NAME/KEY: misc_feature
<222> LOCATION: (114)..(114)
<223> OTHER INFORMATION: Xaa can be Lysine, Phenylalanine, Isoleucine,
      Leucine, Proline or Threonine
<220> FEATURE:
<221> NAME/KEY: misc_feature
<222> LOCATION: (115)..(115)
<223> OTHER INFORMATION: Xaa can be any amino acid except Alanine,
      Cysteine, Glutamine, Glutamic Acid and  Lysine
<220> FEATURE:
<221> NAME/KEY: misc_feature
<222> LOCATION: (116)..(116)
<223> OTHER INFORMATION: Xaa can be Isoleucine, Glutamic Acid, Lysine or
      Tyrosine
<220> FEATURE:
<221> NAME/KEY: misc_feature
<222> LOCATION: (117)..(117)
<223> OTHER INFORMATION: Xaa can be Serine, Glutamic Acid, Histidine or
```

```
                        Asparagine

<400> SEQUENCE: 8

Xaa Xaa Xaa Xaa Xaa Cys Xaa Xaa Cys Xaa Xaa Xaa Xaa Xaa Xaa
1               5                   10                  15

Xaa Xaa Xaa Xaa Xaa Leu Xaa Xaa Xaa Xaa Lys Xaa Thr Leu Met
                20                  25              30

Ile Ser Xaa Thr Pro Xaa Val Xaa Cys Xaa Xaa Xaa Xaa Xaa Xaa
            35              40                  45

Xaa Xaa Xaa Xaa Xaa Xaa Xaa Trp Xaa Val Xaa Xaa Xaa Xaa Xaa
        50                  55              60

Xaa Xaa Ala Xaa Thr Xaa Xaa Xaa Xaa Xaa Xaa Xaa Xaa Xaa Xaa
65              70                  75                  80

Xaa Xaa Xaa Xaa Xaa Leu Thr Val Leu His Gln Asp Xaa Leu Asn Gly
                85                  90                  95

Xaa Xaa Tyr Xaa Cys Xaa Xaa Xaa Xaa Xaa Xaa Xaa Xaa Xaa Xaa
            100                 105                 110

Xaa Xaa Xaa Xaa Xaa
        115

<210> SEQ ID NO 9
<211> LENGTH: 5
<212> TYPE: PRT
<213> ORGANISM: Artificial
<220> FEATURE:
<223> OTHER INFORMATION: Synthetic

<400> SEQUENCE: 9

Gly Ser Gly Gly Ser
1               5

<210> SEQ ID NO 10
<211> LENGTH: 5
<212> TYPE: PRT
<213> ORGANISM: Artificial
<220> FEATURE:
<223> OTHER INFORMATION: Synthetic

<400> SEQUENCE: 10

Gly Gly Gly Gly Ser
1               5

<210> SEQ ID NO 11
<211> LENGTH: 4
<212> TYPE: PRT
<213> ORGANISM: Artificial
<220> FEATURE:
<223> OTHER INFORMATION: Synthetic

<400> SEQUENCE: 11

Gly Gly Gly Ser
1
```